US010092524B2

(12) United States Patent
Macdonald

(10) Patent No.: US 10,092,524 B2
(45) Date of Patent: *Oct. 9, 2018

(54) COMPOSITIONS AND THEIR USE TO TREAT COMPLICATIONS OF ANEURYSMAL SUBARACHNOID HEMORRHAGE

(71) Applicant: EDGE THERAPEUTICS, INC., Berkeley Heights, NJ (US)

(72) Inventor: R. Loch Macdonald, Toronto (CA)

(73) Assignee: EDGE THERAPEUTICS, INC., New Providence, NJ (US)

( * ) Notice: Subject to any disclaimer, the term of this patent is extended or adjusted under 35 U.S.C. 154(b) by 120 days.

This patent is subject to a terminal disclaimer.

(21) Appl. No.: 13/793,767

(22) Filed: Mar. 11, 2013

(65) Prior Publication Data
US 2013/0243864 A1    Sep. 19, 2013

Related U.S. Application Data

(63) Continuation-in-part of application No. 13/440,276, filed on Apr. 5, 2012, which is a continuation-in-part of application No. 12/137,320, filed on Jun. 11, 2008, now Pat. No. 8,303,974.

(51) Int. Cl.
| A61K 9/00 | (2006.01) |
| A61K 31/4418 | (2006.01) |
| A61K 9/70 | (2006.01) |
| A61K 9/14 | (2006.01) |
| A61K 9/50 | (2006.01) |
| A61K 31/4422 | (2006.01) |

(52) U.S. Cl.
CPC .............. *A61K 9/70* (2013.01); *A61K 9/0002* (2013.01); *A61K 9/0019* (2013.01); *A61K 9/0085* (2013.01); *A61K 9/146* (2013.01); *A61K 9/5031* (2013.01); *A61K 31/4418* (2013.01); *A61K 31/4422* (2013.01)

(58) Field of Classification Search
None
See application file for complete search history.

(56) References Cited

U.S. PATENT DOCUMENTS

| 4,757,128 A | 7/1988 | Domb et al. |
| 4,937,270 A | 6/1990 | Hamilton et al. |
| 5,399,665 A | 3/1995 | Barrera et al. |
| 5,407,609 A | 4/1995 | Tice et al. |
| 5,527,893 A | 6/1996 | Burns et al. |
| 5,650,489 A | 7/1997 | Lam et al. |
| 5,712,171 A | 1/1998 | Zambias et al. |
| 5,747,058 A | 5/1998 | Tipton et al. |
| 5,804,159 A | 9/1998 | Eibl et al. |
| 5,968,542 A | 10/1999 | Tipton |
| 5,977,163 A | 11/1999 | Li et al. |
| 5,993,855 A | 11/1999 | Yoshimoto et al. |
| 6,123,956 A * | 9/2000 | Baker et al. ................... 424/426 |
| 6,331,311 B1 | 12/2001 | Brodbeck et al. |
| 6,358,536 B1 | 3/2002 | Thomas et al. |
| 6,495,164 B1 | 12/2002 | Ramstack et al. |
| 6,730,313 B2 | 5/2004 | Helmust et al. |
| 7,608,750 B2 | 10/2009 | Akira et al. |
| 7,713,551 B2 | 5/2010 | McGurk et al. |
| 7,790,140 B2 | 9/2010 | Bolotin et al. |
| 7,923,032 B2 * | 4/2011 | Pratt et al. ................... 424/489 |
| 8,252,302 B2 | 8/2012 | MacDonald et al. |
| 8,288,336 B2 | 10/2012 | Vitek et al. |
| 8,303,974 B2 | 11/2012 | MacDonald et al. |
| 8,703,843 B2 | 4/2014 | Alkinson et al. |
| 8,728,528 B2 | 5/2014 | Biggs et al. |
| 2002/0026236 A1 | 2/2002 | Helmus et al. |
| 2003/0032676 A1 | 2/2003 | Kimelberg et al. |
| 2003/0135196 A1 | 7/2003 | Hesson et al. |
| 2004/0105888 A1 | 6/2004 | Pratt et al. |
| 2004/0235801 A1 | 11/2004 | Julien et al. |
| 2005/0031691 A1 | 2/2005 | McGurk et al. |
| 2005/0164980 A1 | 7/2005 | Shimoboji |
| 2005/0214227 A1 * | 9/2005 | Prestrelski et al. ............. 424/46 |
| 2006/0094643 A1 | 5/2006 | Svirkin et al. |
| 2006/0111282 A1 | 5/2006 | Haaning et al. |
| 2006/0205733 A1 | 9/2006 | Dixon et al. |
| 2006/0217340 A1 | 9/2006 | Braydon et al. |

(Continued)

FOREIGN PATENT DOCUMENTS

| CA | 2296056 | 1/1999 |
| CN | 101873858 A | 10/2010 |

(Continued)

OTHER PUBLICATIONS

Barth et al. "Effect of Nicardipine Prolonged Release Implant on Cerebral Vasospasm and Clinical Outcome After Severe Aneurysmal Subarachnoid Hemorrhage" Stoke 2007, 38:330-336 published online Dec. 2006.

Coplin, W. M. et al., "Cerebrospinal fluid creatine kinase-BB isoenzyme activity and outcome after subarachnoid hemorrhage", Arch. Neurol., Nov. 1999, vol. 56, No. 11, pp. 1348-1352.

Dorhout Mees, S. et al., "Calcium antagonists for aneurysmal subarachnoid haemorrhage," Cochrane Database of Systemic Reviews, (2007), Issue 3, pp. 1-50.

European CGRP in Subarachnoid Haemorrhage Study Group, "Effect of calcitonin-gene-related peptide in patients with delayed postoperative cerebral ischaemia after aneurysmal subarachnoid haemorrhage," Lancet, (1992), vol. 339, pp. 831-834.

(Continued)

*Primary Examiner* — Robert A Wax
*Assistant Examiner* — Danah Al-Awadi
(74) *Attorney, Agent, or Firm* — McCarter & English, LLP; Beverly W. Lubit

(57) ABSTRACT

The described invention provides a method for treating an interruption of a cerebral artery in a subarachnoid space at risk of interruption caused by brain injury in a mammal, which reduces signs or symptoms of at least one delayed complication associated with brain injury using a flowable sustained release particulate composition.

40 Claims, 27 Drawing Sheets

(56) References Cited

U.S. PATENT DOCUMENTS

| | | | |
|---|---|---|---|
| 2006/0229269 A1 | 10/2006 | Wellman et al. | |
| 2007/0092574 A1 | 4/2007 | Cook et al. | |
| 2007/0117851 A1 | 5/2007 | Remenar et al. | |
| 2007/0190154 A1 | 8/2007 | Zeigerson et al. | |
| 2007/0190160 A1* | 8/2007 | Turos et al. | 424/490 |
| 2007/0203079 A1 | 8/2007 | Caldwell et al. | |
| 2007/0207211 A1 | 9/2007 | Zeigerson et al. | |
| 2008/0124400 A1 | 5/2008 | Liggins et al. | |
| 2008/0188400 A1 | 8/2008 | Ropke et al. | |
| 2008/0280811 A1 | 11/2008 | Feener et al. | |
| 2008/0287879 A1 | 11/2008 | Harkins et al. | |
| 2008/0305147 A1 | 12/2008 | Macdonald et al. | |
| 2008/0317855 A1 | 12/2008 | Jolliffe et al. | |
| 2009/0131315 A1 | 5/2009 | Vitek et al. | |
| 2009/0156481 A1 | 6/2009 | Brun et al. | |
| 2009/0162407 A1 | 6/2009 | Biggs et al. | |
| 2010/0008968 A1 | 1/2010 | Lampe et al. | |
| 2010/0063179 A1 | 3/2010 | Atkinson et al. | |
| 2010/0069602 A1 | 3/2010 | Raiche et al. | |
| 2010/0113318 A1 | 5/2010 | Wiedemann et al. | |
| 2010/0185219 A1 | 7/2010 | Gertzman et al. | |
| 2010/0189763 A1 | 7/2010 | Nettles et al. | |
| 2010/0216948 A1 | 8/2010 | Tipton et al. | |
| 2010/0291027 A1 | 11/2010 | Campbell et al. | |
| 2010/0303900 A1 | 12/2010 | Ramstack et al. | |
| 2010/0330184 A1 | 12/2010 | Cleland et al. | |
| 2011/0033463 A1 | 2/2011 | Thakker et al. | |
| 2011/0142937 A1 | 6/2011 | Macdonald et al. | |
| 2011/0201685 A1 | 8/2011 | Campbell | |
| 2011/0204533 A1 | 8/2011 | Winchester et al. | |
| 2011/0236497 A1 | 9/2011 | Tice et al. | |
| 2012/0164226 A1 | 6/2012 | Leuthner et al. | |
| 2012/0245561 A1 | 9/2012 | Macdonald et al. | |
| 2012/0321597 A1 | 12/2012 | Hill et al. | |
| 2013/0059008 A1 | 3/2013 | Atkinson et al. | |
| 2013/0302431 A1* | 11/2013 | Macdonald | A61K 9/1682 424/501 |

FOREIGN PATENT DOCUMENTS

| | | |
|---|---|---|
| EP | 0486959 | 5/1992 |
| JP | 2000070366 A | 3/2000 |
| JP | 2002-003406 | 1/2002 |
| JP | 2002003406 A | 1/2002 |
| JP | 2003512316 A | 4/2003 |
| JP | 2004105234 A | 4/2004 |
| JP | 2006528179 A | 12/2006 |
| JP | 2010529205 A | 8/2010 |
| JP | 20100529205 A | 8/2010 |
| WO | 95/18972 | 7/1995 |
| WO | 96/22529 | 7/1996 |
| WO | 01/28525 | 4/2001 |
| WO | 0147571 A2 | 7/2001 |
| WO | 2004/047768 | 6/2004 |
| WO | 2005/009357 | 2/2005 |
| WO | 2006/026395 | 3/2006 |
| WO | 2006/084005 | 8/2006 |
| WO | 2008/154585 | 12/2008 |
| WO | 2012109664 A1 | 8/2012 |
| WO | 2012138854 A1 | 10/2012 |
| WO | 2014/164904 | 10/2014 |

OTHER PUBLICATIONS

Haley, E.C. Jr. et al., "A randomized trial of two doses of nicardipine in aneurysmal subarachnoid hemorrhage," J. Neurosurg., (1994), vol. 80, pp. 788-796.

http://www.brain-aneurysm.com/cv.html.

Jang, Y.G., et al., "Metaanalysis of Tirilazad Mesylate in Patients with Aneurysmal Subarachnoid Hemorrhage," NeurocritCare, (2009), vol. 10, 141-147.

Kasuya, et al. "Efficacy and Safety of Nicardipine Prolonged-Release Implants for Preventing Vasospasm in Humans". Stroke 2002; 33: 1011-1015.

Langer, R., "New methods of drug delivery", Science, Sep. 28, 1990, vol. 248, No. 4976, pp. 1527-1533.

Llinas, R. et al., "Electrophysiological properties of in vitro Purkinje cell somata in mammalian cerebellar slices", J. Physiol., Aug. 1980, vol. 305, pp. 171-195.

Llinas, R. et al., Blocking and isolation of a calcium channel from neurons in mammals and cephalopods utilizing a toxin fraction (FTX) from funnel-web spider poison, Proc. Natl. Acad. Sci. U.S.A., Mar. 1989, vol. 86, No. 5, pp. 1689-1693.

Mayberg, M. R. et al., "The role of hemoglobin in arterial narrowing after subarachnoid hemorrhage," J. Neurosurg. (1990), vol. 72, pp. 634-640.

Newcomb, R. et al., "Selective peptide antagonist of the class E calcium channel from the venom of the tarantula Hysterocrates gigas", Biochemistry, Nov. 3, 1998, vol. 37, No. 44, pp. 15353-15362.

Nieuwkamp, D.J. et al., "Changes in case fatality of aneurysmal subarachnoid haemorrhage over time, according to age, sex, and region: a meta-analysis," Lancet Neurol, (2009), vol. 8, pp. 635-642.

Pradilla et al. "Pharmacokinetics of controlled-release polymers in the subarachnoid space after subarachnoid hemorrhage in rabbits" J. Neurosurg. Jul. 2004; 101(1) (abstract).

Sawheny, A.S. et al., "Bioerodible hydrogels based on photopclymerized poly(ethylene glycol)-co-poly(.alpha.-hydroxy acid) diacrylate macromers", Macromolecules, 1993, vol. 26, No. 4, pp. 581-587.

Tottene, A. et al., "Alpha(1E) subunits form the pore of three cerebellar R-type calcium channels with different pharmacological and permeation properties", J. Neurosci., Jan. 1, 2000, vol. 20, No. 1, pp. 171-178.

Van Gijn, J. et al., "Subarachnoid haemorrhage: diagnosis, causes and management," Brain, (2001), vol. 124, pp. 249-278.

Vergouwen, M.D.I. et al., "Effect of Statin Treatment on Vasospasm, Delayed Cerebral Ischemia, and Functional Outcome in Patients With Aneurysmal Subarachnoid Hemorrhage: A Systemic Review and Meta-Analysis Update," Stroke, (2010), vol. 41, pp. 2391-2395, e47-e52.

Wang, G. et al., "An R-type Ca(2+) current in neurohypophysial terminals preferentially regulates oxytocin secretion", J. Neuroscience, Nov. 1, 1999, vol. 19, No. 21, pp. 9235-9241.

Wong, G.K.C. et al., "Intravenous Magnesium Sulfate for Aneurysmal Subarachnoid Hemorrhage (IMASH): A Randomized, Double-Blinded, Placebo-Controlled, Multicenter Phase III Trial," Stroke, (2010), vol. 41, pp. 921-926.

Yan, L. et al., "The spider toxin omega-Aga IIIA defines a high affinity site on neuronal high voltage-activated calcium channels", J. Biol. Chem., Jul. 14, 2000, vol. 275, No. 28, pp. 21309-21316.

Aikawa, H. et al., "Experimental chronic subdural hematoma in mice. Gross morphology and light microscopic observations," J. Neurosurg., (Nov. 1987), vol. 67, No. 5, pp. 710-716.

Apfelbaum, R. et al. "Experimental production of subdural hematomas," J. Neurosurg., (Mar. 1974), vol. 40, pp. 336-346.

Beierlein, W. et al., "Forty Years of Clinical Aprotinin Use: A Review of 124 Hypersensitivity Reactions," Ann. Thorac. Surg., (Feb. 2005), vol. 79, pp. 741-748.

Broderick, J.P. et al. "Guidelines for the Management of Spontaneous Intracerebral Hemorrhage: A Statement for Healthcare Professionals From a Special Writing Group of the Stroke Council, American Heart Association." Stroke, 1999; 30:905-915.

Broderick, J.P. et al. "volume of intracerebral hemorrhage. A powerful and easy-to-use predictor of 30-day mortality." Stroke, 1993; 24:987-993.

Camichael, S.T. et al. "Genomic profiles of damage and protection in human intracerebral hemorrhage." J. Cereb. Blood Flow Metab., Nov. 2008; 28(11):1860-1875.

Datta, S. et al. "Neuroradiological aspects of subdural haemorrhages," Arch. Dis. Child, (2005), vol. 90, pp. 947-951.

Diringer, M.N. et al., "Risk of Thromboembolic Events in Controlled Tria;s of rFVIIa in Spontaneous Intracerebral Hemorrhage," Stroke, (Mar. 2008), vol. 39, pp. 850-856.

(56) References Cited

OTHER PUBLICATIONS

Elger, B. et al., "Ancrod reduces intracerebral hemorrhage quantified in vivo by magnetic resonance imaging in rats," J. Stroke Cerebrovasc. Dis., Jan.-Feb. 1998, vol. 7, No. 1, pp. 10-16.
Frati, A. et al., "Inflammation Markers and Risk Factors for Recurrence in 35 Patients with a Postraumatic Chronic Subdural Hematoma: a Prospective Study," J. Neurosurg., (Jan. 2004), vol. 100, No. 1, pp. 24-32.
Glover, D. et al. "Physiopathogenesis of subdural hematomas; Part 2: Inhibition of growth of experimental hematomas with dexamethasone." J. Neurosurg., (Oct. 1976), vol. 45, pp. 393-397.
Goodman & Gillman's The Pharmacological Basis of Therapeutics, Joel G. Hardman and Lee E. Limbird, Eds., McGraw Hill, 2001, pp. 1519-1520, pp. 1531-1532.
Haines, D.E. "On the Question of a Subdural Space." The Anatomical Record, 1991; 230:3-21.
Han, H.J. et al. "One vs. Two Burr Hole Craniostomy in Surgical Treatment of Chronic Subdural Hematoma," J. Korean Neurosurg. Soc., (2009), vol. 46, pp. 87-92.
Kou, J.H. et al. "Bioerosion and biocompatability of poly(d,l-lactic-co-glycolic acid) implants in brain," J. Controlled Release, (1997), vol. 43, pp. 123-130.
Labadie, E. et al. "Physiopathogenesis of subdural hematomas; Part 1: Histological and biochemical comparisons of subcutaneous hematoma in rats with subdural hematomas in man." J. Neurosurg., (Oct. 1976), vol. 45, pp. 382-392.
Maclellan, C. et al. "Intracerebral hemorrhage models in rat: comparing collagenase to blood infusion." J. Cereb. Blood Flow Metab., 2008; 28:516-525.
Mayberg, M. R. et al., "The significance of morphological charges in cerebral arteries after subarachnoid hemorrhage," J. Neurosurg., (1990), vol. 72, pp. 626-633.
Mayer, S.A. et al., "Efficacy and Safety of Recombinant Activated Factor VII for Acute Intracerebral Hemorrhage," The New England Journal of Medicine, (May 15, 2008), vol. 358, No. 20, pp. 2127-2137.
Mayer, S.A., "Intracerebral hemorrhage: natural history and rationale of ultra-early hemostatic therapy," Intensive Care Med., (2002), vol. 28, pp. S235-S240.
Meltzer, M.E. et al., "The Impact of the Fibrinolytic System on he Risk et Venous and Arterial Thrombosis," Seminars Thrombosis Hemostasis, (2005), vol. 35, No. 5, pp. 468-477.
Monroe, D.M. et al., "Platelets and Thrombin Generation," Arterioscler. Thromb. Vasc. Biol., (Sep. 2002), vol. 22, pp. 1381-1389.
Murakami, H. et al. "Why do chronic subdural hematomas continue to grow slowly and not coagulate? Role of thrombomodulin in the mechanism." J. Neurosurg., 2002; 96:877-884.
Nakaguchi, H. et al., "Factors in the Natural History of Chronic Subdural Hematomas that Influence their Postoperative Recurrence," J. Neurosurg., (Aug. 2001), vol. 95, No. 2, pp. 256-262.
Nomura, S. et al., "Characterization of Local Hyperfibrinolysis in Chronic Hematomas by SDS-PAGE and Immunoblot", J. Neurosurg., (Dec. 1994), vol. 81, No. 6, pp. 910-913.
Qureshi, A. et al. "Spontaneous Intracerebral Hemorrhage." N. Engl. J. Med., May 2001; 344(19):1450-1460.
Roos, Y. et al. "Antifibrinolytic therapy for aneurysmal subarachnoid haemorrhage." Cochrane Database of Systematic Reviews, 2003; Issue 2, Art. No. CD001245 (Abstract).
Rosenberg, GA. et al. "Collagenase-induced intracerebral hemorrhage in rats." Stroke, 1990; 21:801-807.
Shim, Y.S. et al. "What are the Causative Factors for a Slow, Progressive Enlargement of a Chronic Subdural Hematoma?" Yonsei Med. J., (2007), vol. 48, No. 2, pp. 210-217.
Starke, R. et al. "Impact of a Protocol for Acute Antifibrinolytic Therapy on Aneurysm Rebleeding After Subarachnoid Hemorrhage," Stroke, (2008), vol. 39, pp. 2617-2621.
Sugiu, K. et al. "Rebleeding From a Vertebral Artery Dissecting Aneurysm After Endovascular Internal Trapping: Adverse Effect of Intrathecal Urokinase Injection or Incomplete Occlusion?" Neurol. Med. Chir. (Tokyo), (Dec. 2009), vol. 49, pp. 597-600.

Tallon, J. et al. "The epidemiology of surgically treated acute subdural and epidural hematomas in patients with head injuries: a population-based study," Can. J. Surg., (Oct. 2008), vol. 51, No. 5, pp. 339-345.
Tokmak, M. et al. "The role of exudation in chronic subdural hematomas." J. Neurosurg., Aug. 2007; 107:290-295.
Vandenabeele, F. et al. "Ultrastructure of the human spinal arachnoid mater and dura mater," J. Anat., (1996), vol. 189, pp. 417-430.
Veziers, J. et al. "Analysis of brain biocompatability of drug-releasing biodegradable microspheres by scanning and transmission electron microscopy," J. Neurosurg., (Sep. 2001), vol. 95, pp. 489-494.
Watanabe S. et al. "Production of clinical form of chronic subdural hematoma in experimental animals," J. Neurosurg., (Nov. 1972), vol. 37, pp. 552-561.
Weigel, R. et al. "Outcome of contemporary surgery for chronic subdural haematoma: evidence based review." J. Neurol. Neurosurg. Psychiatry, 2003; 74:937-943.
Weiss, A. et al., "Signal Transduction by Lymphocyte Antigen Receptors," Cell, (Jan. 28, 1994), vol. 76, No. 2, pp. 263-274.
Catterall, A. W. et al. International Union of Pharmacology. XLVIII. Nomenclature and Structure-Function Relationships of Voltage-Gated Calcium Channels. The American Society for Pharmacology and Experimental Therapeutics; Pharmacol Rev 57: 411-425 (2005).
Dolphin, A. "A short history of voltage-gated calcium channels." British Journal of Pharmacology. Jan. 2006; 147 (Suppl 1): S56-S62.
Dreier, J. P. et al., "Cortical spreading ischaemia is a novel process involved in ischaemic damage inpatients with anaeurysmal subarachnoid haemorrhage." Brain 132: 1866-81 (2009).
Van Petegem, et al. "The structural biology of voltage-gated calcium channel function and regulation". Biochemical Society Transactions; vol. 34 (5) pp. 887-893; 2006.
Sands, Z et al. "Voltage-gated ion channels". Current Biology, vol. 15; No. 2. pp. R44-R47, 2005.
Yamakage, M. and Namiki, A. "Calcium channels—basic aspects of their structure, function and gene encoding; anesthetic action on the channels—a review." Canadian Journal of Anesthesia; Feb. 2002;49 (2):151-64.
Reagan-Shaw S. et al. "Dose translation from animal to human studies revisited." FASEB J. Mar. 2008, 22 (3):659-61. Epub Oct. 17, 2007.
Kandel, E.R. ed., Principles of Neural Science, 2nd ed., Elservier Science Publishing Co., Inc. NY pp. 854-856. and 4th ed. p. 8.
William, E.P. ed., Fundamental Immunology, 4th Ed., Lippincott-Raven Pub, Philadelphia (1999) pp. 1051-1053.
Clozel, M. et al. BQ-123, "A Peptidic Endothelin Eta Receptor Antagonist, Prevents the Early Cerebral Vasospasm, Following Subarachnoid Hemorrhage After Intracisternal But Not Intravenous Injection." Life Sciences. 1993;52(9):825-834.
Sato, S. et al. "Effects of an Endothelin Eta Receptor Antagonist, S-0139 on Cerebral Vasospasm and Behavioral Change in Dogs Intracisternally Administered Endothelin-1." Life Sciences, vol. 62 (13) PL191-PL197 (1998).
Agapitov, A. V. et al., "Role of endothelin in cardiovascular disease," Journal of Renin-Angiotensin-Aldosterone System, 3(1): 1-15 (2002).
Al-Khindi, T. et al., "Cognitive and functional outcome after aneurysmal subarachnoid hemorrhage," Stroke, 41:e519-e536, (2010).
Chou, S H et al., "A randomized, double-blind, placebo-controlled pilot study of simvastatin in aneurysmal subarachnoid hemorrhage," Stroke, 39:2891-2893 (2008).
Dankbaar, J. W. et al., "Effect of different components of triple-H therapy on cerebral perfusion in patients with aneurysmal subarachnoid haemorrhage: a systematic review," Crit. Care, 14:R23 (2010).
Date, Y. et al., "Orexins, orexigenic hypothalamic peptides, interact with autonomic, neuroendocrine and neuroregulatory systems," Peptides, 748-753 (1999).
Day, S. et al., "Blinding in clinical trials," BMJ, 321: 504 (2000).
De Rooij, N. K. et al., "Incidence of subarachnoid hemorrhage: a systematic review with emphasis on region, age, gender and time trends," Journal of Neurology, Neurosurgery, and Psychiatry, 78(12): 1365-1372 (2007).

(56) References Cited

OTHER PUBLICATIONS

Etminan, N. et al., "Effect of pharmaceutical treatment on vasospasm, delayed cerebral ischemia, and clinical outcome in patients with aneurysmal subarachnoid hemorrhage: a systematic review and meta-analysis," J. Cereb. Blood Flow Metab. 31:1443-1451 (2011).
Feigin, V. L. et al., "Risk factors for subarachnoid hemorrhage an updated systematic review of epidemiological studies," Stroke, 36(12): 2773-2780 (2005).
Frontera, J. A. et al., "Defining vasospasm after subarachnoid hemorrhage: what is the most clinically relevant definition?" Stroke, 40:1963-1968 (2009).
Gomis, P. et al., "Randomized, double-blind, placebo-controlled pilot trial of high-dose methylprednisolone in aneurysmal subarachnoid hemorrhage," J. Neurosurg., 112:681-688 (2010).
Granger, C. V. et al., "Measurement of outcome of care for stroke patients," Stroke, 6:34-41 (1975).
Hijdra, A. et al., "Prediction of delayed cerebral ischemia, rebleeding, and outcome after aneurysmal subarachnoid hemorrhage," Stroke 19:1250-1256 (1988).
Hoenderop, J.G.J. et al., "Molecular identification of the apical Ca2+ channel in 1, 25-dihydroxyvitamin D3-responsive epithelia," J. Biol. Chem. 274(13): 8375-8378 (1999).
Hunt, S. A. et al., "ACC/AHA Guidelines for the Evaluation and Management of Chronic Heart Failure in the Adult: Executive Summary a Report of the American College of Cardiology/American Heart Association Task Force on Practice Guidelines (Committee to Revise the 1995 Guidelines for the Evaluation and Management of Heart Failure): Developed in Collaboration With the International Society for Heart and Lung Transplantation; Endorsed by the Heart Failure Society of America," Circulation 104:2996-3007 (2001).
Iiasonos, A. et al., "A comprehensive comparison of the continual reassessment method to the standard 3+3 dose escalation scheme in Phase I dose-finding studies," Clin Trials 5:465-477 (2008).
Kumagai, A. K. et al, J Biol. Chem. 262, 15214 (1987).
Le Tourneau, C. et al., "Dose escalation methods in Phase I cancer clinical trials," J. Natl. Cancer Inst., 101: 708-720 (2009).
Loewen, S. C. et al., "Predictors of stroke outcome using objecive measurement scales," Stroke, 21: 78-81 (1990).
Lovelock, C. E. et al., "Antithrombotic Drug Use, Cerebral Microbleeds, and Intracerebral Hemorrhage. A Systematic Review of Published and Unpublished Studies," Stroke, 41(6): 1222-1228 (2010).
MacDonald, R. L. et al., "Clazosentan to overcome neurological ischemia and infarction occurring after subarachnoid hemorrhage (CONSCIOUS-1): randomized, double-blind, placebo-controlled phase 2 dose-finding trial," Stroke, 39:3015-3021 (2008).
MacDonald, R. L. et al., "Randomized trial of clazosentan in patients with aneurysmal subarachnoid hemorrhage undergoing endovascular coiling," Stroke 43:1463-1469 (2012).
McDonagh, E. M., et al., "From pharmacogenomic knowledge acquisition to clinical applications: the PharmGKB as a clinical pharmacogenomic biomarker resource," Biomark Med.e Dec. 2011; 5(6):795-806).
McGirt, M. J. et al., "Simvastatin increases endothelial nitric oxide synthase and ameliorates cerebral vasospasm resulting from subarachnoid hemorrhage," Stroke, 33(12): 2950-2956 (2002).
Nilius, B. et al., "Transient receptor potential cation channels in disease," Physiol. Rev. 87: 165-217 (2007).
Pickard, J. D. et al., "Effect of oral nimodipine on cerebral infarction and outcome after subarachnoid haemorrhage: British aneurysm nimodipine trial," BMJ, 298:636-642 (1989).
Rosengart, A J, et al. "Prognostic factors for outcome in patients with aneurysmal subarachnoid hemorrhage," Stroke 38:2315-2321 (2007).
Survase, S. et al., "Actions of calcium channel blockers on vascular proteoglycan synthesis: relationship to atherosclerosis," Vasc. Health Risk Manag., 1(3): 199-208 (2005).
Suzuki, M. et al., "Cloning of a stretch-inhibitable nonselective cation channel," J. Biol. Chem. 274: 6330-6335 (1999).
Taylor, T. N. et al., "Lifetime cost of stroke in the United States," Stroke, 27:1459-1466 (1996).
Van Den Bergh, W. M. et al., "Randomized controlled trial of acetylsalicylic acid in aneurysmal subarachnoid hemorrhage: the MASH Study," Stroke 37:2326-2330 (2006).
Van Den Bergh, W. M. et al., "Magnesium sulfate in aneurysrr al subarachnoid hemorrhage: a randomized controlled trial," Stroke, 36(5): 1011-1015 (2005).
Van Swieten, J. C. et al., "Interobserver agreement for the assessment of handicap in stroke patients," Stroke 19:604-607 (1988).
Vergouwen, M. D. et al., "Definition of delayed cerebral ischemia after aneurysmal subarachnoid hemorrhage as an outcome event in clinical trials and observational studies: proposal of a multidisciplinary research group," Stroke 41:2391-2395 (2010).
Vergouwen, M. D. et al., "Lower incidence of cerebral infarction correlates with improved functional outcome after aneurysmal subarachnoid hemorrhage," J. Cereb. Blood Flow Metab., 31:1545-1553 (2011).
Wilby, M. J. et al., "Cost-effective outcome for treating poor-grade subarachnoid hemorrhage," Stroke 34:2508-2511 (2003).
Shibata, S. et al., "Effects of intracisternal methylprednisolone on lipid peroxidation in experimental subarachnoid haemorrhage," Acta neurochirurgica, 1999, vol. 141, No. 5, p. 529-32.
Office Action issued on Sep. 30, 2015 by the Japanese Patent Office for corresponding Japanese Patent Application No. 2013-553640.
Viarbacher S., et al., "Prevention of delayed cerebral vasospasm by continuous intrathecal infusion of glycerol-trinate and nimodipine in the rabbit model in vivo", Intensive Care Medicine, 2008, pp. 932-938, vol. 34, Springer-Vertag.
Hanggi D., et al., "The effect of an intracisternal nimdipine slow-release system on cerebral vasospasm after experimental subarachnoid haemorrhage in the rat", Acta Neurochirugica Supplementum, 2008, pp. 103-107, vol. 104, Springer-Vertag.
Baumann M.D, et al, "Intrathecal delivery of a polymeric nanocomposite hydrogel after spinal cord injury", Biomaterials, 2010, pp. 7631-7639, Elsevier.
Kudo, T, "Postoperative oculomotor palsy due to vasospasm in a patient with a ruptured internal carotid arty aneurysm: A case report", Neurosurgery, 1986, vol. 19, pp. 274-278, Congress of Neurological Surgeons.
Mayberg M.R., et al., "The role of hemoglobin in arterial narrowing after subarachnoid hemorrhage", J. Neurogur., 1990, pp. 634-640, vol. 72.
Wischke C, et al., "Principles of encapsulating hyrdophobic drugs in PLA/PLGA microparticles", International Journal of Pharmaceutics, 2008, pp. 298-327, Elsevier.
Chodobski A., et al., "Blood-brain banier pathophysiology in traumatic brain injury", Transl Stroke Res, 2011, pp. 492-516. National Institute of Health.
Klose D., et al., "PLGA-based drug delivery systems: Importance of the type of drug and device geometry", International Journal of Pharmaceutics, 2008, pp. 95-103, vol. 354, Elsevier.
Kim K.K., et al., "Microspheres for drug delivery", pp. 20-50, University of Illinois at Urbana-Champaign, Springer Publishing.
Hanggi D, et al., "The effect of an intracisternal nimodipine slow-release system on cerebral vasospasm after experimental subarachnoid haemorrhage in the rat", Cerebral Vasospasm. New Strategies in Reseach and Treatment, Acta Neurochirugica Supplementum, 2008, pp. 103-107, vol. 104, Springer.
Lampe K.J., "The administration of BDNF and GDNF to the brain via PLGA microparticles patterned within a legradable PEG-based hydrogel: Protein distribution and the glial response", Journal of Biomedical Materials Research Part A, 2011, pp. 595-607, vol. 96A.
Patterson J., et al., "In situ characterization of the degradation of PLGA microspheres in hyaluronic acid hydrogels by optical coherence tomography", IEEE Transactions on Medical Imaging, IEEE Service Center, 2009, pp. 74-81, vol. 28, Piscataway, NJ.
MacDonald R.L., et al., "Site-specific, sustained-release nimodipine to prevent vasospasm", Edge Therapeutics Website Drug Discovery and Development, 2010, p. 2, www.edgetherapeutics.com/wp-content/uploads/2010/10/Site-specific-Sustained-relevase-Nimodipine-to-Prevent-Vasospasm.pdf.

(56) References Cited

OTHER PUBLICATIONS

Mehta A., et al., "Nimodipine loaded PLGA nanoparticles: Formulation optimization using factorial design, characterization and in vitro evaluation", Current Drug Delivery, 2007, pp. 185-193, Database Biosis [Online] Biosciences Information Service, Philadelphia, PA.

Wartenberg K.E., "Update on the management of subarachnoid hemorrhage", Future Neurology, 2013, pp. 205-224, vol. 8, www.medscape.com.

Beierlein, W., et al., "Forty years of clinical aprotinin use: A review of 124 hypersensitivity reactions," Ann. Thorac. Surg., 2005, pp. 741-748, vol. 79.

Rosenwasser R.H., "Safety of intraventricular sodium nitroprusside and thiosulfate for the treatment of cerebral vasospasm in the intensive care unit setting", Stroke, 2002, p. 1165, http://stroke.ahajournals.org.

Yamaguchi M., et al., "Ras protein contributes to cerebral vasospasm in a canine double-hemorrhage model", Stroke 2004, pp. 1750-1755. vol. 35, http://stroke.ahajournals.org.

Xia, Y., et al., "Uniform biodegradable microparticle systems for controlled release", J Control Release, 2002, vol. 82, pp. 137-147.

Xia Y, et al., "Uniform biodegradable micorpartcle systems for controlled release", J. Control Review, 202, vol. 18, pp. 137-147.

Zou Y., et al., "Patterns of Gelatinase activation induced by injury in the murine femoral artery", J. Surg. Res. 2009, vol. 154, pp. 135-142.

Kyekyoon et al., Microspheres for Drug Delivery, University of Illinois at Urbana-Champaign, 2006, pp. 20-50.

Rosenberg, et al., Inflammation, Fundamental Immunology, Fourth Edition, Chapter 32, 1999, pp. 1051-1055.

Shelke NB et al. "Synthesis and characterization of novel poly(sebacic anhydride-co-Pluronic F68/F127) biopolymeric microspheres for the controlled release of nifedipine." Int J Pharm. Dec. 10, 2007;345(1-2):51-8.

\* cited by examiner

COMPOSITIONS AND THEIR USE TO TREAT COMPLICATIONS OF ANEURYSMAL SUBARACHNOID HEMORRHAGE

CROSS REFERENCE TO RELATED APPLICATIONS

This application is a continuation in part of U.S. application Ser. No. 13/440,276, entitled "Intraventricular drug delivery system for improving outcome after brain injury affecting cerebral blood flow," filed Apr. 5, 2012, which claims the benefit of priority of U.S. Provisional Application No. 61/471,779 filed Apr. 5, 2011, and is a continuation in part of U.S. application Ser. No. 12/137,320, entitled "A Drug Delivery System for the Prevention of Cerebral Vasospasm," filed Jun. 11, 2008, which claims the benefit of priority of U.S. Provisional Application No. 60/976,902 (filed Oct. 29, 2007) and No. 60/943,124 (filed Jun. 11, 2007). The content of each of these applications is incorporated by reference herein in its entirety.

FIELD OF INVENTION

The present invention relates to a system for therapeutic agents delivered locally to the cerebral arteries to prevent or reduce the incidence or severity of adverse consequences of subarachnoid hemorrhage (SAH) resulting from a disease, disorder, condition, or injury.

BACKGROUND OF THE INVENTION

1. Central Nervous System

The central nervous system is a bilateral and essentially symmetrical structure with seven main parts: the spinal cord, medulla oblongata, pons, cerebellum, midbrain, diencephalon, and the cerebral hemispheres. FIG. 1 shows a lateral view of the human brain from Stedman's Medical Dictionary, 27th Edition, plate 7 at A7 (2000).

The spinal cord, the most caudal part of the central nervous system, receives and processes sensory information from the skin, joints, and muscles of the limbs and trunk and controls movement of the limbs and the trunk. It is subdivided into cervical, thoracic, lumbar and sacral regions. The spinal cord continues rostrally as the brainstem, which consists of the medulla, pons, and midbrain. The brainstem receives sensory information from the skin and muscles of the head and provides the motor control for the muscles of the head. It also conveys information from the spinal cord to the brain and from the brain to the spinal cord, and regulates levels of arousal and awareness through the reticular formation. The brainstem contains several collections of cell bodies, the cranial nerve nuclei. Some of these receive information from the skin and muscles of the head; others control motor output to muscles of the face, neck and eyes. Still others are specialized for information from the special senses: hearing, balance and taste. (Kandel, E. et al., Principles of Neural Science, 4th Ed., p. 8, 2000).

The medulla oblongata, which lies directly rostral to the spinal cord, includes several centers responsible for vital autonomic functions, such as digestion, breathing and the control of heart rate (Kandel, E. et al., Principles of Neural Science, 4th Ed., p. 8, 2000).

The pons, which lies rostral to the medulla, conveys information about movement from the cerebral hemispheres to the cerebellum (Kandel, E. et al., Principles of Neural Science, 4th Ed., p. 8, 2000).

The cerebellum lies behind the pons and is connected to the brain stem by several major fiber tracts called peduncles. The cerebellum modulates the force and range of movement, and is involved in the learning of motor skills. It also contributes to learning and cognition (Kandel, E. et al., Principles of Neural Science, 4th Ed., p. 8, 2000).

The midbrain, which lies rostral to the pons, controls many sensory and motor functions, including eye movements and the coordination of visual and auditory reflexes (Kandel, E. et al., Principles of Neural Science, 4th Ed., p. 8, 2000).

The diencephalon lies rostral to the midbrain and contains two structures. One, the thalamus, processes most of the information reaching the cerebral cortex from the rest of the central nervous system and is involved in other functions including motor control, autonomic function and cognition. The other, the hypothalamus, regulates autonomic, endocrine, and visceral function (Kandel, E. et al., Principles of Neural Science, 4th Ed., p. 8, 2000).

The cerebral hemispheres consist of a heavily wrinkled outer layer, the cerebral cortex, and deep-lying gray-matter structures—the basal ganglia, which participate in regulating motor performance; the hippocampus, which is involved with aspects of learning and memory storage; and the amygdaloid nuclei, which coordinate the autonomic and endocrine responses of emotional states (Kandel, E. et al., Principles of Neural Science, 4th Ed., p. 8, 2000).

The cerebral cortex is divided into four lobes: the frontal lobe, parietal lobe, temporal lobe and occipital lobe. The surfaces of the cerebral hemispheres contain many grooves or furrows, known as fissures and sulci. The portions of brain lying between these grooves are called convolutions or gyri. The lateral cerebral fissure (fissure of Sylvius) separates the temporal from the frontal lobe. The central sulcus (Rolandic sulcus) separates the frontal from the parietal lobe (Kandel, E. et al., Principles of Neural Science, 4th Ed., p. 8, 2000).

1.1. Meninges of the Brain, Spinal Cord and their Spaces

The meninges, three distinct connective tissue membranes that enclose and protect the brain and spinal cord, are named (from outer to inner layer) the dura mater, the arachnoid, and the pia mater. FIG. 2 shows an illustrative sagittal view of the human brain (J. G. Chusid, Correlative Neuroanatomy & Functional Neurology, 18th Ed., p. 46, 1982). The meninges are associated with three spaces or potential spaces: the epidural potential space, subdural potential space and the subarachnoid space. FIG. 3 is a drawing of a cross section of the three meningeal layers that cover the brain and the sub-arachnoid space (SAS) between the outer cellular layer of the arachnoid and pia mater. (Haines, D. E., Anatomical Record 230: 3-21, 1991). FIG. 4 is a schematic drawing depicting the meninges and their spaces surrounding the spinal cord. (Kulkarni, N. V., "Clinical anatomy for students: problem solving approach," Jaypee Brothers Medical Publishers (P) Ltd., New Delhi, p. 348-349 (2006)).

The epidural space is a physiological space in the spinal cord; it is not normally present in the brain, but it can develop in response to arterial bleeding, resulting in accumulation of blood between the skull and the dura mater (extradural hemorrhage or epidural hematoma). (Schuenke, M. et al., "Thieme Atlas of Anatomy: Head and Neuroanatomy," Georg Thieme Verlag, Germany, p. 191 (2007); Stedman's Medical Dictionary, Lippincott, Williams & Wilkins, 27th Ed. (2000)). In the spinal cord, the epidural space refers to the space between the dura mater and the lining of the vertebral canal. The spinal epidural space contains loose areolar tissue, internal vertebral venous plexus, roots of spinal nerves, spinal branches of regional arteries, recurrent meningeal branches of spinal nerves and semi fluid fat. Anesthetic agents are commonly administered in the epidural space for pain management associated with surgical procedures to numb the spinal nerves that traverse the space. (Kulkarni, N. V., "Clinical anatomy for students: problem solving approach," Jaypee Brothers Medical Publishers (P) Ltd., New Delhi, p. 348-349 (2006)).

The subdural space refers to the potential space that extends from the dura mater to the arachnoid. It can develop as a result of extravasation of blood from bridging veins that artificially open the subdural space between the meningeal layer of the dura mater and the upper layer of the arachnoid membrane (subdural hematoma or subdural hemorrhage). (Schuenke, M. et al., "Thieme Atlas of Anatomy: Head and Neuroanatomy," Georg Thieme Verlag, Germany, p. 191 (2007); Stedman's Medical Dictionary, Lippincott, Williams & Wilkins, 27$^{th}$ Ed. (2000)).

The subarachnoid space (SAS) or subarachnoid cavity refers to the physiologically normal space that lies between the arachnoid and pia mater. It is filled with cerebrospinal fluid (CSF) and is traversed by blood vessels. (See section titled 1.1.3. "Subarachnoid Cavity" and "Subarachnoid Cisternae"). Spontaneous bleeding into the subarachnoid space (subarachnoid hemorrhage) is usually as a result of arterial bleeding from an aneurysm, although it can occur due to trauma as well. (See section 3 below titled "Subarachnoid hemorrhage"). The subarachnoid space in the spinal cord is of uniform size up to the lower end of the spinal cord beyond which it expands. (Kulkarni, N. V., "Clinical anatomy for students: problem solving approach," Jaypee Brothers Medical Publishers (P) Ltd., New Delhi, p. 348-349 (2006)).

1.1.1. Dura Mater

The dura mater sends inward four processes that divide the cavity of the skull into a series of freely communicating compartments and further provides for the protection of the different parts of the brain. The dura mater is a dense fibrous structure that covers the brain and spinal cord. It has an inner meningeal and an outer periosteal or endosteal layer. The dural layers over the brain generally are fused, except where they separate to provide space for the venous sinuses and where the inner layer forms septa between brain portions. The outer layer attaches firmly to the inner surface of the cranial bones and sends vascular and fibrous extensions into the bone itself. Around the margin of the foramen magnum (the large opening in the base of the skull forming the passage from the cranial cavity to the spinal cavity) it is closely adherent to the bone, and is continuous with the spinal dura mater.

The cranial dura mater consists of fibroblasts, abundant extracellular collagen and a few elastic fibers arranged in flattened laminae which are imperfectly separated by lacunar spaces and blood vessels into two layers: an inner (meningeal) layer and an outer (endosteal) layer, closely connected together, except in certain situations, where they separate to form sinuses for the passages of venous blood or form septae between portions of the brain. The outer surface of the dura mater is rough and fibrillated (composed of fibers), and adheres closely to the inner surfaces of the bones, the adhesions being most marked opposite the cranial sutures (the immovable joints between the bones of the skull or cranium). The endosteal layer is the internal periosteum for the cranial bones, and contains the blood vessels for their supply. The meningeal layer is lined on its inner surface by a layer of unique elongated, flattened fibroblasts that have been called dural border cells. There is no collagen in this layer and the cells are not connected by cell junctions. They are frequently separated by extracellular spaces filled with amorphous nonfilamentous material. The meningeal layer further comprises two lamellas: the compact lamella and the loose lamella; the former generally contains tight fibrous tissue and few blood vessels, but the latter contains some blood vessels.

The processes of the cranial dura mater, which project into the cavity of the skull, are formed by reduplications of the inner (or meningeal) layer of the membrane. These processes include: (1) the falx cerebri, (2) the tentorium cerebelli, (3) the falx cerebelli, and (4) the diaphragma sellae.

The falx cerebri is a strong, arched process with a sickle-like form which descends vertically in the longitudinal fissure between the cerebral hemispheres. It is narrow in front, where it is attached to the ethmoid bone (the bone at the base of the cranium and the root of the nose) at the crista galli (the triangular midline process of the ethmoid bone); and broad behind, where it is connected with the upper surface of the tentorium cerebelli (an arched fold of dura mater that covers the upper surface of the cerebellum). Its upper margin is convex, and attached to the inner surface of the skull in the middle line, as far back as the internal occipital protuberance; it contains the superior sagittal sinus. Its lower margin is free and concave, and contains the inferior sagittal sinus.

The tentorium cerebelli is an arched lamina, elevated in the middle, and inclining downward toward the circumference. It covers the superior surface of the cerebellum, and supports the occipital lobes of the brain. Its anterior border is free and concave, and bounds a large oval opening (the incisura tentorii) for the transmission of the cerebral peduncles (the massive bundle of corticofugal nerve fibers passing longitudinally over the ventral surface of the midbrain on each side of the midline) as well as ascending sensory and autonomic fibers and other fiber tracts. The tentorium cerebelli is attached behind, by its convex border, to the transverse ridges upon the inner surface of the occipital bone, and there encloses the transverse sinuses; and, in front, to the superior angle of the petrous part of the temporal bone on either side, enclosing the superior petrosal sinuses. At the apex of the petrous part of the temporal bone, the free and attached borders meet, and, crossing one another, are continued forward to be fixed to the anterior and posterior clinoid processes respectively. The posterior border of the falx cerebri is attached to the middle line of its upper surface. The straight sinus is placed at the junction of the falx cerebri and the tentorium cerebelli.

The falx cerebelli is a small triangular process of dura mater that separates the two cerebellar hemispheres. Its base is attached, above, to the under and back part of the tentorium; and its posterior margin is attached to the lower division of the vertical crest on the inner surface of the occipital bone. As it descends, it sometimes divides into two smaller folds, which are lost on the sides of the foramen magnum.

The diaphragma sellae is a small circular horizontal fold, which roofs in the sella turcica (a saddlelike prominence on the upper surface of the sphenoid bone of the skull, situated in the middle cranial fossa and dividing it into two halves) and almost completely covers the pituitary gland (hypophysis); a central opening of variable size transmits the infundibulum (a funnel-shaped extension of the hypothalamus connecting the pituitary gland to the base of the brain).

The arteries of the dura mater are numerous. The meningeal branches of the anterior and posterior ethmoidal arteries and of the internal carotid artery, and a branch from the middle meningeal artery supply the dura of the anterior cranial fossa. The middle and accessory meningeal arteries of the internal maxillary artery; a branch from the ascending pharyngeal artery, which enters the skull through the foramen lacerum; branches from the internal carotid artery, and a recurrent branch from the lacrimal artery supply the dura of the middle cranial fossa. Meningeal branches from the occipital artery, one entering the skull through the jugular foramen, and another through the mastoid foramen; the posterior meningeal artery from the vertebral artery; occasional meningeal branches from the ascending pharyngeal artery, entering the skull through the jugular foramen and hypoglossal canal; and a branch from the middle meningeal artery supply the dura of the posterior cranial fossa.

The veins returning the blood from the cranial dura mater anastomose with the diploic veins or end in the various sinuses. Many of the meningeal veins do not open directly into the sinuses, but open indirectly through a series of ampullae, termed venous lacunae. These are found on either side of the superior sagittal sinus, especially near its middle portion, and are often invaginated by arachnoid granulations; they also exist near the transverse and straight sinuses. They communicate with the underlying cerebral veins, and also with the diploic and emissary veins.

The nerves of the cranial dura mater are filaments derived from the trigeminal, glossopharyngeal, vagal, second and third spinal, sphenopalatine, otic, and superior cervical ganglia and supply unmyelinated and myelinated sensory and autonomic fibers.

1.1.2. Arachnoid

The middle meningeal layer, the arachnoid, is a delicate avascular membrane lying between the pia mater and the dura mater. It is separated from the overlying dura mater by the subdural space and from the underlying pia mater by the subarachnoid space, which contains cerebrospinal fluid.

The arachnoid consists of an outer cell layer of low cuboidal mesothelium. There is a space of variable thickness filled with cerebrospinal fluid and traversed by trabeculae and membranes consisting of collagen fibrils and cells resembling fibroblasts. The inner layer and the trabecula are covered by a somewhat low type of cuboidal mesothelium, which in places are flattened to a pavement type and blends on the inner deep layer with the cells of the pia mater. The arachnoid further contains a plexus of nerves derived from the motor root of the trigeminal, the facial, and the accessory cranial nerves.

The cranial part (arachnoidea encephali) of the arachnoid invests the brain loosely, and does not dip into the sulci (depressions or fissures in the surface of the brain) between the gyri (upraised folds or elevations in the surface of the brain), nor into the fissures, with the exception of the longitudinal fissure and several other larger sulci and fissures. On the upper surface of the brain, the arachnoid is thin and transparent; at the base it is thicker. It is slightly opaque toward the central part of the brain, where it extends across between the two temporal lobes in front of the pons so as to leave a considerable space between the pons and the brain.

The arachnoid surrounds the cranial and spinal nerves, and encloses them in loose sheaths as far as their points of exit from the skull.

1.1.3. Subarachnoid Cavity

The subarachnoid cavity or subarachnoid space, which is the space between the outer cellular layer of the arachnoid and the pia mater, is occupied by tissue consisting of trabeculae of delicate connective tissue and intercommunicating channels in which the cerebrospinal fluid is contained. This cavity is small on the surface of the hemispheres of the brain; on the summit of each gyrus, the pia mater and the arachnoid are in close contact, but triangular spaces are left in the sulci between the gyri, in which the subarachnoid trabecular tissue is found, because the pia mater dips into the sulci, whereas the arachnoid bridges across them from gyrus to gyrus. At certain parts of the base of the brain, the arachnoid is separated from the pia mater by wide intervals, which communicate freely with each other and are named subarachnoid cisternae; the subarachnoid tissue in these cisternae is less abundant.

Subarachnoid Cisternae (Cisternae Subarachnoidales)

The cisterna cerebellomedullaris (cisterna magna) is triangular on sagittal section, and results from the arachnoid bridging over the space between the medulla oblongata and the under surfaces of the hemispheres of the cerebellum; it is continuous with the subarachnoid cavity of the spinal cord at the level of the foramen magnum.

The cisterna pontis is a considerable space on the ventral aspect of the pons. It contains the basilar artery, and is continuous caudal to the pons with the subarachnoid cavity of the spinal cord, and with the cisterna cerebellomedullaris; in front of the pons, it is continuous with the cisterna interpeduncularis.

The cisterna interpeduncularis (cisterna basalis) or the basal cistern is a wide cavity where the arachnoid extends across between the two temporal lobes. It encloses the cerebral peduncles and the structures contained in the interpeduncular fossa, and contains part of the arterial circle of Willis. In front, the cisterna interpeduncularis extends forward across the optic chiasma, forming the cisterna chiasmatis, and further on to the upper surface of the corpus callosum. The arachnoid stretches across from one cerebral hemisphere to the other immediately beneath the free border of the falx cerebri, and thus leaves a space in which the anterior cerebral arteries are contained. The cisterna fossae cerebri lateralis is formed in front of either temporal lobe by the arachnoid bridging across the lateral fissure. This cavity contains the middle cerebral artery. The cisterna venae magnae cerebri occupies the interval between the splenium of the corpus callosum and the superior surface of the cerebellum; it extends between the layers of the tela chorioidea of the third ventricle and contains the great cerebral vein.

The subarachnoid cavity communicates with the general ventricular cavity of the brain by three openings; one, the foramen of Majendie, is in the middle line at the inferior part of the roof of the fourth ventricle; the other two (the foramina of Luschka) are at the extremities of the lateral recesses of that ventricle, behind the upper roots of the glossopharyngeal nerves.

The arachnoid villi are tufted prolongations of pia-arachnoid that protrude through the meningeal layer of the dura mater and have a thin limiting membrane. Tufted prolongations of pia-arachnoid composed of numerous arachnoid villi that penetrate dural venous sinuses and effect transfer of cerebrospinal fluid to the venous system are called arachnoid granulations.

An arachnoidal villus represents an invasion of the dura by the arachnoid membrane, whereby arachnoid mesothelial cells come to lie directly beneath the vascular endothelium of the great dural sinuses. Each villus consists of the following parts: (1) in the interior is a core of subarachnoid tissue, continuous with the meshwork of the general subarachnoid tissue through a narrow pedicle, by which the villus is attached to the arachnoid; (2) around this tissue is a layer of arachnoid membrane, limiting and enclosing the subarachnoid tissue; (3) outside this is the thinned wall of the lacuna, which is separated from the arachnoid by a potential space, which corresponds to and is continuous with the potential subdural space; and (4) if the villus projects into the sagittal sinus, it will be covered by the greatly thinned wall of the sinus, which may consist merely of endothelium. Fluid injected into the subarachnoid cavity will find its way into these villi. Such fluid passes from the villi into the venous sinuses into which they project.

1.1.4. Pia Mater

The pia mater is a thin connective tissue membrane that is applied to the surface of the brain and spinal cord. Blood vessels supplying the brain travel through the pia into the brain. The pia mater, which is continuous with the ependyma at the foramen of Majendie and the two foramina of Luschka, is perforated by all the blood vessels as they enter or leave the nervous system, and therefore is considered to be an incomplete membrane. In perivascular spaces, the pia apparently enters as a mesothelial lining of the outer surface of the space; a variable distance from the exterior, these cells become unrecognizable and are apparently lacking, replaced by neuroglia elements. The inner walls of the perivascular spaces likewise seem to be covered for a certain distance by the mesothelial cells, reflected with the vessels from the arachnoid covering of these vascular channels as they traverse the subarachnoid spaces.

The cranial pia mater (pia mater encephali; pia of the brain) invests the entire surface of the brain, dips between the cerebral gyri and cerebellar laminae, and is invaginated to form the tela chorioidea of the third ventricle, and the choroid plexuses of the lateral and third ventricles. As it passes over the roof of the fourth ventricle, it forms the tela chorioidea and the choroid plexuses of the fourth ventricle. On the cerebellum the membrane is more delicate; the vessels from its deep surface are shorter, and its relations to the cortex are not so intimate.

The pia mater forms sheaths for the cranial nerves.

2. Circulation of the Brain

FIGS. 5, 6, 7 and 8 show schematic illustrations of the brain's blood vessels. Each cerebral hemisphere is supplied by an internal carotid artery, which arises from a common carotid artery beneath the angle of the jaw, enters the cranium through the carotid foramen, traverses the cavernous sinus, penetrates the dura (giving off the ophthalmic artery) and divides into the anterior and middle cerebral arteries. The large surface branches of the anterior cerebral artery supply the cortex and white matter of the inferior frontal lobe, the medial surface of the frontal and parietal lobes and the anterior corpus callosum. Smaller penetrating branches supply the deeper cerebrum and diencephalon, including limbic structures, the head of the caudate, and the anterior limb of the internal capsule. The large surface branches of the middle cerebral artery supply most of the cortex and white matter of the hemisphere's convexity, including the frontal, parietal, temporal and occipital lobes, and the insula. Smaller penetrating branches supply the deep white matter and diencephalic structures such as the posterior limb of the internal capsule, the putamen, the outer globus pallidus, and the body of the caudate. After the internal carotid artery emerges from the cavernous sinus, it also gives off the anterior choroidal artery, which supplies the anterior hippocampus and, at a caudal level, the posterior limb of the internal capsule. Each vertebral artery arises from a subclavian artery, enters the cranium through the foramen magnum, and gives off an anterior spinal artery and a posterior inferior cerebellar artery. The vertebral arteries join at the junction of the pons and the medulla to form the basilar artery, which at the level of the pons gives off the anterior inferior cerebellar artery and the internal auditory artery, and, at the midbrain, the superior cerebellar artery. The basilar artery then divides into the two posterior cerebral arteries. The large surface branches of the posterior cerebral arteries supply the inferior temporal and medial occipital lobes and the posterior corpus callosum; the smaller penetrating branches of these arteries supply diencephalic structures, including the thalamus and the subthalamic nuclei, as well as part of the midbrain (see Principles of Neural Sciences, 2d Ed., Eric R. Kandel and James H. Schwartz, Elsevier Science Publishing Co., Inc., New York, pp. 854-56 (1985)).

Interconnections between blood vessels (anastomoses) protect the brain when part of its vascular supply is compromised. At the circle of Willis, the two anterior cerebral arteries are connected by the anterior communicating artery and the posterior cerebral arteries are connected to the internal carotid arteries by the posterior communicating arteries. Other important anastomoses include connections between the ophthalmic artery and branches of the external carotid artery through the orbit, and connections at the brain surface between branches of the middle, anterior, and posterior cerebral arteries (Principles of Neural Sciences, 2d Ed., Eric R. Kandel and James H. Schwartz, Elsevier Science Publishing Co., Inc., New York, pp. 854-56 (1985)).

The circle of Willis at the base of the brain is the principal arterial anastomotic trunk of the brain. Blood reaches it mainly via the vertebral and internal carotid arteries (See FIG. 5); anastomoses occur between arterial branches of the circle of Willis over the cerebral hemispheres and via extracranial arteries that penetrate the skull through various foramina.

The circle of Willis is formed by anastamoses between the internal carotid, basilar, anterior cerebral, anterior communicating, posterior cerebral, and posterior communicating arteries. The internal carotid artery terminates in the anterior cerebral and middle cerebral arteries. Near its termination, the internal carotid artery gives rise to the posterior communicating artery, which joins caudally with the posterior cerebral artery. The anterior cerebral arteries connect via the anterior communicating artery.

2.1. Cerebral Arteries

The blood supply to the cerebral cortex mainly is via cortical branches of the anterior cerebral, middle cerebral, and posterior cerebral arteries, which reach the cortex in the pia mater. FIG. 6 shows an illustrative view of the arterial supply of the cerebral cortex where 1 is the orbitofrontal artery; 2 is the prerolandic artery; 3 is the rolandic artery; 4 is the anterior parietal artery; 5 is the posterior parietal artery; 6 is the angular artery; 7 is the posterior temporal artery; 8 is the anterior temporal artery; 9 is the orbital artery; 10 is the frontopolar artery; 11 is the callosomarginal artery; 12 is the posterior internal frontal artery; and 13 is the pericallosal artery (Correlative Neuroanatomy & Functional Neurology, 18$^{th}$ Ed., p. 50, 1982).

The lateral surface of each cerebral hemisphere is supplied mainly by the middle cerebral artery. The medial and inferior surfaces of the cerebral hemispheres are supplied by the anterior cerebral and posterior cerebral arteries.

The middle cerebral artery, a terminal branch of the internal carotid artery, enters the lateral cerebral fissure and divides into cortical branches that supply the adjacent frontal, temporal, parietal and occipital lobes. Small penetrating arteries, the lenticulostriate arteries, arise from the basal portion of the middle cerebral artery to supply the internal capsule and adjacent structures.

The anterior cerebral artery extends medially from its origin from the internal carotid artery into the longitudinal cerebral fissure to the genu of the corpus callosum, where it turns posteriorly close to the corpus callosum. It gives branches to the medial frontal and parietal lobes and to the adjacent cortex along the medial surface of these lobes.

The posterior cerebral artery arises from the basilar artery at its rostral end usually at the level of the midbrain, curves dorsally around the cerebral peduncle, and sends branches to the medial and inferior surfaces of the temporal lobe and to the medial occipital lobe. Branches include the calcarine artery and perforating branches to the posterior thalamus and subthalamus.

The basilar artery is formed by the junction of the vertebral arteries. It supplies the upper brain stem via short paramedian, short circumferential, and long circumferential branches.

The midbrain is supplied by the basilar, posterior cerebral, and superior cerebellar arteries. The pons is supplied by the basilar, anterior cerebellar, inferior cerebellar, and superior cerebellar arteries. The medulla oblongata is supplied by the vertebral, anterior spinal, posterior spinal, posterior inferior cerebellar, and basilar arteries. The cerebellum is supplied by the cerebellar arteries (superior cerebellar, anterior inferior cerebellar, and posterior inferior cerebellar arteries).

The choroid plexuses of the third and lateral ventricles are supplied by branches of the internal carotid and posterior cerebral arteries. The choroid plexus of the fourth ventricle is supplied by the posterior inferior cerebellar arteries.

Venous drainage from the brain chiefly is into the dural sinuses, vascular channels lying within the tough structure of the dura. The dural sinuses contain no valves and, for the most part, are triangular in shape. The superior longitudinal sinus is in the falx cerebri.

The human brain constitutes only about 2% of the total weight of the body, but it receives about 15% of cardiac output, and its oxygen consumption is approximately 20% of that for the total body. These values indicate the high metabolic rate and oxygen requirement of the brain that are compensated by a correspondingly high rate of blood flow per unit brain weight. Cerebral circulation is supplied by the internal carotid arteries and the vertebral arteries. The total blood flow to the brain is about 750-1000 ml/min; of this amount about 350 ml flows through each internal carotid artery and about 100-200 ml flows through the vertebral basilar system. The venous outflow is drained by the internal jugular veins and the vertebral veins.

The term "stroke" or "cerebrovascular accident" as used herein refers to the neurological symptoms and signs, usually focal and acute, that result from diseases involving blood vessels. Strokes are either occlusive (due to closure of a blood vessel) or hemorrhagic (due to bleeding from a vessel). The term "ischemia" as used herein refers to a lack of blood supply and oxygen that occurs when reduced perfusion pressure distal to an abnormal narrowing (stenosis) of a blood vessel is not compensated by autoregulatory dilation of the resistance vessels. When ischemia is sufficiently severe and prolonged, neurons and other cellular elements die; this condition is referred to as "infarction."

Hemorrhage may occur at the brain surface (extraparenchymal), for example from the rupture of congenital aneurysms at the circle of Willis, causing subarachnoid hemorrhage (SAH). Hemorrhage also may be intraparenchymal, for example from rupture of vessels damaged by long-standing hypertension, and may cause a blood clot (intracerebral hematoma) within the cerebral hemispheres, in the brain stem, or in the cerebellum. Hemorrhage may be accompanied by ischemia or infarction. The mass effect of an intracerebral hematoma may compromise the blood supply of adjacent brain tissue; or SAH may cause reactive vasospasm of cerebral surface vessels, leading to further ischemic brain damage. Infarcted tissue may also become secondarily hemorrhagic. Aneurysms occasionally can rupture into the brain, causing an intracerebral hematoma, and into the cerebral ventricles, causing intraventricular hemorrhage.

Although most occlusive strokes are due to atherosclerosis and thrombosis, and most hemorrhagic strokes are associated with hypertension or aneurysms, strokes of either type may occur at any age from many causes, including, without limitation, cardiac disease, trauma, infection, neoplasm, blood dyscrasia, vascular malformation, immunological disorder, and exogenous toxins.

2.2. Vasoconstriction and Vasodilation

The term "vasoconstriction" as used herein refers to the narrowing of blood vessels resulting from contracting of the muscular wall of the vessels. When blood vessels constrict, the flow of blood is restricted or slowed. The term "vasodilation", which is the opposite of vasoconstriction as used herein, refers to the widening of blood vessels. The terms "vasoconstrictors," "vasopressors," or "pressors" as used herein refer to factors causing vasoconstriction. Vasoconstriction usually results in an increase of blood pressure and may be slight or severe. Vasoconstriction may result from disease, medication, or psychological conditions. Medications that cause vasoconstriction include, but are not limited to, catecholamines, antihistamines, decongestants, methylphenidate, cough and cold combinations, pseudoephedrine, and caffeine.

A vasodilator is a drug or chemical that relaxes the smooth muscle in blood vessels causing them to dilate. Dilation of arterial blood vessels (mainly arterioles) leads to a decrease in blood pressure. The relaxation of smooth muscle relies on removing the stimulus for contraction, which depends predominately on intracellular calcium ion concentrations and phosphorylation of myosin light chain (MLC). Thus, vasodilation predominantly works either 1) by lowering intracellular calcium concentration, or 2) by dephosphorylation of MLC, which includes the stimulation of myosin light chain phosphatase and the induction of calcium symporters and antiporters (which pump calcium ions out of the intracellular compartment). The re-uptake of ions into the sarcoplasmic reticulum of smooth muscle via exchangers and expulsion of ions across the plasma membrane also helps to accomplish vasodilation. The specific mechanisms to accomplish these effects vary from vasodilator to vasodilator and may be grouped as endogenous and exogenous. The term "endogenous" as used herein refers to proceeding from within or derived internally; or resulting from conditions within the organism rather than externally caused. The term "exogenous" as used herein refers to originating from outside; derived externally; or externally caused rather than resulting from conditions within the organism.

Vasodilation directly affects the relationship between mean arterial pressure and cardiac output and total peripheral resistance (TPR). Cardiac output may be computed by multiplying the heart rate (in beats/minute) and the stroke volume (the volume of blood ejected during systole). TPR depends on several factors, including, but not limited to, the length of the vessel, the viscosity of blood (determined by hematocrit), and the diameter of the blood vessel. Blood vessel diameter is the most important variable in determining resistance. An increase in either cardiac output or TPR cause a rise in the mean arterial pressure. Vasodilators work to decrease TPR and blood pressure through relaxation of smooth muscle cells in the tunica media layer of large arteries and smaller arterioles.

Vasodilation occurs in superficial blood vessels of warm-blooded animals when their ambient environment is hot; this process diverts the flow of heated blood to the skin of the animal, where heat may be more easily released into the atmosphere. Vasoconstriction is the opposite physiological process. Vasodilation and vasoconstriction are modulated naturally by local paracrine agents produced by endothelial cells (e.g., bradykinin, adenosine, nitric oxide, endothelins), as well as by an organism's autonomic nervous system and adrenal glands, both of which secrete catecholamines, such as norepinephrine and epinephrine, respectively.

Vasodilators are used to treat conditions such as hypertension, where the patient has an abnormally high blood pressure, as well as angina and congestive heart failure, where maintaining a lower blood pressure reduces the patient's risk of developing other cardiac problems.

Cerebral Ventricles

Cerebral ventricles, which are chambers in the brain that contain cerebrospinal fluid, include two lateral ventricles, one third ventricle, and one fourth ventricle. The lateral ventricles are in the cerebral hemispheres. They drain via the foramen of Monroe into the third ventricle, which is located between the two diencephalic structures of the brain. The third ventricle leads, by way of the aqueduct of Sylvius, to the fourth ventricle. The fourth ventricle is in the posterior fossa between the brainstem and the cerebellum. The cerebrospinal fluid drains out of the fourth ventricle through the foramenae of Luschka and Magendie to the basal cisterns. The cerebrospinal fluid then percolates through subarachnoid cisterns and drains out via arachnoid villi into the venous system.

FIG. 9 is a diagram of the ventricular system of the brain. The system is a series of cavities (ventricles) within the brain and is continuous with both the subarachnoid space and central canal of the spinal cord. There are four cerebral ventricles: the right and left lateral ventricles, and the midline third and fourth ventricles. The two lateral ventricles are located within the cerebrum and each connects to the third ventricle through an interventricular foramen of Monroe. The third ventricle is located in the diencephalon and is connected to the fourth ventricle by the cerebral aqueduct of Sylvius. The fourth ventricle is located in the hind brain and it is continuous with the central canal of the spinal cord, at least embryologically. Three foramina connect the fourth ventricle to the subarachnoid space: the median aperture or foramen of Magendie, and left and right lateral apertures (foramena) of Luschka.

2.4. CSF Flow in the Brain

FIG. 10 shows an illustrative view of CSF flow from the ventricles to the subarachnoid space. Cerebrospinal fluid (CSF) is a clear bodily fluid that occupies the ventricular system, subarachnoid space of the brain, and central canal of the spinal cord. CSF is produced by modified ependymal cells of the choroid plexus found throughout the ventricular system; it is also formed around blood vessels and ventricular walls, presumably from the extracellular space of the brain. CSF flows from the lateral ventricles via interventricular foramina into the third ventricle. CSF then flows into the fourth ventricle through the cerebral aqueduct. CSF flows out in the subarachnoid space via the median aperture and left and right lateral apertures. Finally, the CSF is reabsorbed into the dural venous sinuses through arachnoid granulations and arachnoid villi. Arachnoid granulations consist of collections of villi. The villi are visible herniations of the arachnoid membrane through the dura and into the lumen of the superior sagittal sinus and other venous structures. The granulations appear to function as valves that allow one-way flow of CSF from the subarachnoid spaces into venous blood. All constituents of CSF leave with the fluid, including small molecules, proteins, microorganisms, and red blood cells.

CSF is produced at a rate of approximately 0.3-0.37 ml/minute or 20 ml/hour or 500 ml/day. The volume of the CSF space is about 150 mL and the CSF turns over 3.7 times a day.

The choroid plexus uses capillary filtration and epithelial secretory mechanisms to maintain the chemical stability of the CSF. While the capillaries that traverse the choroid plexus are freely permeable to plasma solutes, a barrier exists at the level of the epithelial cells that make up the choroid plexus, which is responsible for carrier-mediated active transport. CSF and extracellular fluids of the brain are in a steady state and blood plasma and CSF are in osmotic equilibrium under normal physiological conditions.

2.5. Blood Brain Barrier

The blood brain barrier (BBB) prevents entry of blood-borne substances into the brain and maintains a stable environment for neurons to function effectively. It results from specialized properties of brain microvessel endothelial cells, the principal anatomic site of the BBB, their intercellular junctions, and a relative lack of vesicular transport, which makes such cells different from those of general capillaries. Endothelial cells of blood-brain barrier vessels also are not fenestrated; instead they are interconnected by complex arrays of tight junctions, which block diffusion across the vessel wall.

3. Subarachnoid Hemorrhage

The term "subarachnoid hemorrhage" (also referred to as "SAH") refers to bleeding into the subarachnoid space. SAH may occur spontaneously, usually from a cerebral aneurysm, or may result from trauma. A cerebral aneurysm is a weakness in the wall of an artery of the brain that results in circumscribed dilation of the artery, such that the wall(s) of the blood vessel expand outward. Cerebral aneurysms tend to be located in the circle of Willis and its branches. Where SAH is caused by a rupture of an intracranial aneurysm, i.e., aneurysmal SAH ("aSAH"), bleeding is seen in the subarachnoid space, and less commonly in the intraventricular and intracerebral spaces. Bleeding due to SAH may result in brain damage, brain shift, decreased cerebral perfusion and hydrocephalus. Symptoms include an intense headache with a rapid onset (sometimes referred to as a "thunderclap headache"), vomiting, and an altered level of consciousness. Diagnosis generally is made with computed tomography (CT scanning), or occasionally by lumbar puncture. FIG. 11A shows a flow diagram for prognosis following SAH and FIG. 11B shows a flow diagram of pathways proposed to be involved in delayed complications after SAH.

SAH is a medical emergency and may lead to death or severe disability even if recognized and treated at an early stage. About 35% of all SAH cases are fatal, with 10-15% of patients dying before arriving at a hospital. SAH is considered a form of stroke, and causes between 1% and 7% of all strokes. Aneurysmal SAH constitutes on an average about 85% of all cases of spontaneous SAH. While most cases of SAH are due to bleeding from small aneurysms, larger aneurysms (which are rarer) are more likely to rupture. No aneurysm is detected from the first angiogram in 15% of cases of spontaneous SAH. Non-aneurysmal perimesencephalic hemorrhage, in which the blood is limited to the area of the prepontine, interpeduncular and adjacent subarachnoid cisterns, causes 67% of the SAH cases in which no aneurysm is detected. The remaining 33% of cases are due to vasculitic damage to arteries, other disorders affecting the vessels, disorders of the spinal cord blood vessels, bleeding into various tumors, and a number of other causes. Most traumatic SAHs occur near a skull fracture or intracerebral contusion.

In the United States, it is estimated that the incidence of SAH from a ruptured intracranial aneurysm is 1 case per 10,000 persons, yielding approximately 34,000 new cases of SAH each year. These ruptured aneurysms have a 30-day mortality rate of about 35%. About 15% of patients die before reaching hospital and an additional 20% or so die within 30 days of the hemorrhage. (Nieuwkamp D J et al., "Changes in case fatality of aneurysmal subarachnoid hemorrhage over time, according to age, sex, and region: a meta-analysis," Lancet Neurol., 8:635-642 (2009)). An estimated 30% of survivors will have moderate-to-severe disability. The morbidity is substantial in those who survive, with 75% suffering permanent neurological or neurocognitive impairment. (Al-Khindi T. et al., "Cognitive and functional outcome after aneurysmal subarachnoid hemorrhage," Stroke, 41:e519-e536, (2010)). Thus, only about 20% of all patients survive and resume their previous lifestyle by 3 to 6 months after aneurysmal SAH. The burden of aneurysmal SAH is disproportionately high compared to ischemic stroke because of the high likelihood of permanent disability and the relative youth of those affected (51 years of age for aSAH compared to 75-years old for ischemic stroke). (Taylor, T. N. et al., "Lifetime cost of stroke in the United States," Stroke, 27:1459-1466 (1996)). FIG. 12 shows time trends in outcome of SAH in seven population-based studies of SAH, which shows 50% decrease in mortality over 20 years.

A systematic review of the incidence of SAH revealed that the overall incidence of SAH is on average 9.1 per 100,000 annually. Studies from Japan and Finland show higher rates in those countries (22.7 per 100,000 and 19.7 per 100,000, respectively), for reasons that are not entirely understood. South and Central America, in contrast, have a rate of 4.2 per 100,000 on average. The group of people at risk for SAH is younger than the population usually affected by stroke, but the risk still increases with age. Young people are much less likely than middle-aged people (risk ratio 0.1, or 10%) to suffer a SAH. The risk continues to rise with age and is 60% higher in the very elderly (over 85) than in those between 45 and 55. Risk of SAH is about 25% higher in women above 55, possibly reflecting the hormonal changes that result from the menopause (de Rooij, N. K. et al., "Incidence of subarachnoid hemorrhage: a systematic review with emphasis on region, age, gender and time trends," Journal of Neurology, Neurosurgery, and Psychiatry, 2007, 78(12): 1365-1372; Feigin, V. L. et al., "Risk factors for subarachnoid hemorrhage an updated systematic review of epidemiological studies," Stroke, 2005, 36(12): 2773-2780).

Symptoms of SAH

The classic symptom of SAH is thunderclap headache (a headache described as the "worst ever" or an "explosion in the head," developing over seconds to minutes) although it is a symptom in only about a third of all SAH patients. Approximately 10% of patients who seek medical care with this symptom have an underlying SAH. Patients also may present with vomiting, and 1 in 14 have seizures. Neck stiffness and other signs of meningism may be present, as may confusion, decreased level of consciousness, or coma. Intraocular hemorrhage may occur in response to the raised pressure inside the head (intracranial pressure). Subhyaloid (the hyaloid membrane envelopes the vitreous body of the eye) and vitreous hemorrhage may be visible on fundoscopy. This is known as Terson syndrome (occurring in 3-13% of cases), and is more common in more severe SAH. In a patient with thunderclap headache, none of the aforementioned signs are helpful in confirming or ruling out hemorrhage, although seizures are more common if the bleeding is the result of a ruptured aneurysm as opposed to other causes. Oculomotor nerve abnormalities (affected eye movement downward and outward, inability to lift the eyelid on the same side but normal pupillary reflexes) may indicate bleeding from an aneurysm arising near the posterior communicating artery. Isolated dilation of a pupil may also reflect brain herniation as a result of increased intracranial pressure.

The body releases large amounts of adrenaline and similar hormones as a result of the bleeding, which leads to a sudden increase in the blood pressure. The heart comes under substantial strain, and neurogenic pulmonary edema, stunned myocardium, cardiac arrhythmias, electrocardiographic changes (with occasional giant inverted "cerebral" T waves), tsako tsubo cardiomyopathy and cardiac arrest (3%) may rapidly occur after the onset of hemorrhage.

SAH also may occur in people who have suffered a head injury. Symptoms may include headache, decreased level of consciousness or hemiparesis. SAH is regarded as a severe complication of head injury, especially if it is associated with lower Glasgow Coma Scale levels.

Diagnosis of SAH

The initial steps for evaluating a person with a suspected SAH are the steps of obtaining a medical history and performing a physical examination. Since only 10-25% of patients admitted to a hospital with a thunderclap headache are suffering from a SAH, other possible causes usually are considered simultaneously, such as meningitis, migraine, and cerebral venous sinus thrombosis. Intracerebral hemorrhage, which is twice as common as SAH, occasionally is misdiagnosed as SAH.

A diagnosis of SAH cannot be made on clinical grounds alone. Generally, medical imaging [usually computed tomography (CT) scan, which has a high sensitivity (>95% correct identification especially on the first day after the onset of bleeding)] of the brain is required to confirm or exclude bleeding. Magnetic resonance imaging (MRI) may be more sensitive after several days when compared to CT scan. In people with normal CT or MRI scans, lumbar puncture, in which cerebrospinal fluid (CSF) is removed with a needle from the lumbar sac, shows evidence of hemorrhage in 3% of the group in whom the CT was found to be normal; lumbar puncture is therefore regarded as mandatory if imaging is negative. The CSF sample is examined for xanthochromia, the yellow appearance of centrifuged fluid, or by using spectrophotometry for bilirubin, a breakdown product of hemoglobin in the CSF.

After an SAH is confirmed, its origin needs to be determined. CT angiography ("CTA") (visualizing blood vessels with radiocontrast on a CT scan) to identify aneurysms is generally the first step, although the more invasive catheter angiography (injecting radiocontrast through a catheter advanced to the brain arteries) is the gold standard test but has a higher risk of complications. The latter is useful if there are plans to obliterate the source of bleeding, such as an aneurysm, at the same time.

Classification of SAH

Several grading scales available for SAH have been derived by retrospectively matching characteristics of patients with their outcomes.

The Glasgow Coma Scale (GCS) has been used ubiquitously in the clinical assessment of post-traumatic unconsciousness; it assesses 15 points covering three components: eye (E), verbal (V) and motor (M) response to external stimuli. (Teasdale G. et al., "Assessment of coma and impaired consciousness," Lancet, 2(7872): 81084 (1974); Teasdale, G. et al., "Assessment and prognosis of coma after head injury," Acta Neurochir., 34: 45-55 (1976)). Table 1 shows the categorization of the Glasgow Coma Scale.

TABLE 1

Categorization of Glasgow Coma Scale

| COMPONENTS | POINTS OF ASSESSMENT |
|---|---|
| E—Eye Opening | C. Not assessable |
| | 4. Spontaneous |
| | 3. To speech |
| | 2. To pain |
| | 1. None |
| V—Verbal Response | T. Not assessable |
| | 5. Oriented conversation |
| | 4. Confused speech |
| | 3. Inappropriate words |
| | 2. Incomprehensible sounds |
| | 1. None |
| M—Motor Response | 6. Obeys simple commands |
| | 5. Localizes pain |
| | 4. Withdraws (normal flexion) |
| | 3. Stereotyped flexion |
| | 2. Stereotyped extension |
| | 1. None |

The Glasgow Outcome Scale (GOS) and its extended form (eGOS) are global scales measuring functional outcome of patient status. The five categories of the Glasgow outcome scale were extended to eight categories in the extended Glasgow Outcome Scale. (Jennett, B. and Bond, M., "Assessment of outcome after severe brain damage," Lancet, 1: 480-484 (1975); Teasdale, G. M. et al., "Analyzing outcome of treatment of severe head injury: A review and update on advancing the use of the Glasgow Outcome Scale," Journal of Neurotrauma, 15: 587-597 (1998); Wilson, J. T. L. et al., "Structured interviews for the Glasgow Outcome Scale and the Extended Glasgow Outcome Scale," Journal of Neurotrauma, 15(8): 573-585 (1997); Wilson, J. T. et al., "Observer variation in the assessment of outcome in traumatic brain injury: experience from a multicenter, international randomized clinical trial," Neurosurgery, 61(1): 123-128 (2007)). Tables 2 and 3 show the categorization scheme used in the Glasgow Outcome Scale (GOS) and in the extended Glasgow Outcome Scale (eGOS), respectively.

TABLE 2

Categorization of the Glasgow Outcome Scale

| SCORE | CATEGORY | SYMBOL |
|---|---|---|
| 1 | DEAD | D |
| 2 | VEGETATIVE STATE<br>Unable to interact with environment; unresponsive | VS |
| 3 | SEVERE DISABILTY<br>Able to follow commands/unable to live independently | SD− |
| 4 | MODERATE DISABILITY<br>Able to live independently; unable to return to work or school | MD |
| 5 | GOOD RECOVERY<br>Able to return to school | GR |

TABLE 3

Categorization of the Extended Glasgow Outcome Scale

| SCORE | CATEGORY | SYMBOL |
|---|---|---|
| 1 | Death | D |
| 2 | Vegetative State | VS |
| 3 | Lower severe disability | SD− |
| 4 | Uppoer severe disability | SD+ |
| 5 | Lower moderate disability | MD− |
| 6 | Upper moderate disability | MD+ |
| 7 | Lower good recovery | GR− |
| 8 | Upper good recovery | GR+ |

A scale of severity was described by Hunt and Hess in 1968 ("Hunt and Hess scale") and categorizes the clinical condition of the patient. The Fisher Grade classifies the appearance of SAH on CT scan. The Fisher scale has been modified by Claassen and coworkers ("Claassen scale"), reflecting the additive risk from SAH size and accompanying intraventricular hemorrhage. The World Federation of Neurological Surgeons classification uses GCS and focal neurological deficit to gauge severity of symptoms. A comprehensive classification scheme has been suggested by Ogilvy and Carter to predict outcome and gauge therapy. The Ogilvy system has five grades, assigning one point for the presence or absence of each of five factors: (1) age greater than 50; (2) Hunt and Hess grade 4 or 5; (3) Fischer scale 3 or 4; (4) aneurysm size greater than 10 mm; and (5) posterior circulation aneurysm 25 mm or more.

The Barthel index, frequently used in stroke evaluation, is an objective functional scale that measures a patient's independence in activities of daily living (ADL), including feeding, bathing, grooming, dressing, bowel and bladder control, wheelchair management and ascending and descending stairs. (Granger C. V. et al., "Measurement of outcome of care for stroke patients," Stroke, 6:34-41 (1975)). The Montreal Cognitive Assessment (MoCA) test is a screening tool for mild cognitive dysfunction. (Nasreddine Z. S. et al., "The Montreal Cognitive Assessment (MoCA): A brief screening tool for mild cognitive impairment," J. Am. Geriatr. Soc., 53: 695-699 (2005)). The modified Rankin scale is a 7-point scale (0 is the best and 6 is the worst score) that assesses patient condition based on their or their care-givers' response to simple questions about their daily functioning (van Swieten, J. C. et al., "Interobserver agreement for the assessment of handicap in stroke patients," Stroke 19:604-607 (1988)). The National Institutes of Health Stroke Scale (NIHSS) is a 15-item neurological examination stroke scale that is used to evaluate the severity of neurological deficit after a stroke, such as an ischemic stroke or DCI. It assesses level of consciousness, language, neglect, visual field loss, extraocular movement, motor strength, ataxia, dysarthria and sensory loss.

Prognosis of SAH

Early Morbidity and Mortality

The mortality rate for SAH is between 30% and 40%. Of those who survive initial hospitalization, treatment and complications, at least 25% have significant restrictions in their lifestyle, and less than 20% have no residual symptoms whatsoever. Delay in diagnosis of minor SAH without coma (or mistaking the sudden headache for migraine or some other less serious illness) contributes to poor outcome. Risk factors for poor outcome include higher age, poorer neurological grade, more blood and larger aneurysm on the initial CT scan, location of an aneurysm in the posterior circulation, systolic hypertension, and a previous diagnosis of heart attack, hypertension, liver disease or a previous SAH. During the hospital stay, occurrence of delayed ischemia resulting from vasospasm, development of intracerebral hematoma or intraventricular hemorrhage (bleeding into the ventricles of the brain), and presence of fever on the eighth day of admission also worsen the prognosis.

Angiographic vasospasm was suggested to cause death after aneurysmal SAH in up to 35% of patients in the 1970s and in less than 10% currently. However, outcome overall is still poor, and current rescue therapies, such as hemodynamic therapy, endovascular balloon or pharmacological angioplasty, are associated with substantial morbidity, and are expensive and labor intensive. (Clyde B L et al., "The relationship of blood velocity as measured by transcranial doppler ultrasonography to cerebral blood flow as determined by stable xenon computed tomographic studies after aneurysmal subarachnoid hemorrhage," Neurosurgery, 38:896-904 (1996)). Among patients with aneurysmal SAH, the incremental cost for symptomatic vasospasm, which is roughly the same as DCI, was $39,971 in the United States in 2010. (Chou C H et al., "Costs of vasospasm in patients with aneurysmal subarachnoid hemorrhage," Neurosurgery, 67:345-352 (2010)).

SAH that does not show an aneurysm by complete catheter angiography may be referred to as "angiogram-negative SAH." This carries a better prognosis than SAH from an aneurysm; however, it still is associated with a risk of ischemia, rebleeding and hydrocephalus. Perimesencephalic SAH (bleeding around the mesencephalon part of the brain) is a subgroup of angiogram-negative SAH. It has a very low rate of rebleeding or delayed ischemia, and the prognosis of this subtype is better.

Long-Term Outcomes

Symptoms, such as fatigue, mood disturbances, depression, executive dysfunction and related neurocognitive symptoms, are common in people who have suffered SAH. Even in those who have made a good neurological recovery, anxiety, depression, posttraumatic stress disorder and cognitive impairment are common. Over 60% report frequent headaches. Aneurysmal SAH may lead to damage of the hypothalamus and the pituitary gland, two areas of the brain that play a central role in hormonal regulation and production. Studies indicate that at least 25% of people with a previous SAH may develop deficiencies in one or more of the hypothalamic-pituitary hormones, such as growth hormone, prolactin or thyroid-stimulating hormone.

4. Secondary Complications of SAH

Patients who survive SAH also are at risk of secondary complications. Among these complications are, most notably, aneurysmal re-bleeding, angiographic cerebral vasospasm and delayed cerebral ischemia (DCI). (Macdonald R L et al., "Preventing vasospasm improves outcome after aneurysmal subarachnoid hemorrhage: rationale and design of CONSCIOUS-2 and CONSCIOUS-3 trials," Neurocrit. Care, 13:416-424 (2010); Macdonald R L et al., "Factors associated with the development of vasospasm after planned surgical treatment of aneurysmal subarachnoid hemorrhage," J. Neurosurg. 99:644-652 (2003)).

4.1. Delayed Cerebral Ischemia (DCI)

Delayed cerebral ischemia occurs in 30% of patients with aSAH and causes death or permanent disability in half of these patients. (Dorsch N W C, and King M T, "A review of cerebral vasospasm in aneurysmal subarachnoid hemorrhage. Part 1: Incidence and effects," Journal of Clinical Neuroscience, 1:19-26 (1994)). The risk of DCI is not easily predicted; the most important factor is the volume of SAH seen on admission cranial computed tomography (CT). (Harrod C G et al., "Prediction of cerebral vasospasm in patients presenting with aneurysmal subarachnoid hemorrhage: a review," Neurosurgery, 56:633-654 (2005); Reilly C et al., "Clot volume and clearance rate as independent predictors of vasospasm after aneurysmal subarachnoid hemorrhage," J. Neurosurg. 101:255-261 (2004)).

DCI is a delayed neurological deterioration due to ischemia, associated with the occurrence of focal neurological impairment (such as hemiparesis, aphasia, apraxia, hemianopia, or neglect), and/or a decrease in the Glasgow coma scale (either the total score or one of its individual components [eye, motor on either side, verbal]). (Frontera J A et al., "Defining vasospasm after subarachnoid hemorrhage: what is the most clinically relevant definition?" Stroke, 40:1963-1968 (2009); Kassell N F et al., "The International Cooperative Study on the Timing of Aneurysm Surgery. Part 1: Overall management results," J. Neurosurg., 73:18-36 (1990); Vergouwen M D et al., "Effect of statin treatment on vasospasm, delayed cerebral ischemia, and functional outcome in patients with aneurysmal subarachnoid hemorrhage: a systematic review and meta-analysis update," Stroke, 41:e47-e52 (2010)). This may or may not last for at least one hour, is not apparent immediately after aneurysm occlusion and cannot be attributed to other causes by means of clinical assessment, CT or MRI scanning of the brain, and appropriate laboratory studies. DCI and development of delayed cerebral infarction are among the most important causes of poor outcome after SAH.

Cerebral infarction may be a consequence of DCI; infarction due to DCI is defined as the presence of an area of brain cell death resulting from insufficiency of arterial or venous blood supply to the brain. It is detected by CT or MRI scan of the brain within 6 weeks after SAH, or on the latest CT or MRI scan made before death within 6 weeks, or proven at autopsy, not present on the CT or MRI scan between 24 and 48 hours after early aneurysm occlusion, and not attributable to other causes such as surgical clipping or endovascular treatment. Hypodensities on CT imaging resulting from ventricular catheter or intraparenchymal hematoma generally are not regarded as evidence of cerebral infarction from DCI.

Angiographic vasospasm is one process that contributes to DCI. Other processes that may contribute to DCI are cortical spreading ischemia and formation of microthromboemboli. Cortical spreading ischemia, which was described in animal models of SAH as a novel mechanism that may cause DCI, has been detected in humans with SAH and angiographic vasospasm.

4.2. Vasospasm

DCI is usually associated with angiographic cerebral vasospasm. The term "angiographic cerebral vasospasm" refers to the narrowing of the large capacitance arteries at the base of the brain (i.e., cerebral arteries) following hemorrhage into the subarachnoid space, leads to reduced perfusion of distal brain regions, and can be detected by either CT angiography [CTA], MR angiography [MRA] or catheter angiography [CA]). It is the most common cause of focal ischemia after SAH; it adversely affects outcome in patients with SAH as it accounts for up to 23% of SAH-related disability and death. Of all types of ischemic stroke, angiographic vasospasm is unique in that it is, to some degree, preventable and treatable (see Macdonald, R. L. and Weir. B. In Cerebral Vasospasm. Academic Press, Burlington, Mass., USA (2001)).

Generally, angiographic vasospasm of the cerebral arteries begins 3 days after SAH, is maximal 7 to 8 days later and resolves by 14 days. (Weir B. et al., "Time course of vasospasm in man," J. Neurosurg., 48:173-178 (1978)).

About 67% of patients with SAH develop vasospasm, 33% develop DCI and 15% of SAH patients die or sustain permanent disability from DCI.

While angiographic vasospasm is a consequence of SAH, it also can occur after any condition that deposits blood in the subarachnoid space. Vasospasm results in decreased cerebral blood flow and increased cerebral vascular resistance. Without being limited by theory, it generally is believed that vasospasm is caused by local injury to vessels, such as that which results from atherosclerosis and other structural injury including traumatic head injury, aneurysmal subarachnoid hemorrhage and other causes of SAH. Cerebral vasospasm is a naturally occurring vasoconstriction that also may be triggered by the presence of blood in the CSF, a common occurrence after rupture of an aneurysm or following traumatic head injury. Cerebral vasospasm ultimately can lead to brain cell damage, in the form of cerebral ischemia and infarction, due to interrupted blood supply. Potential manifestation of symptoms from vasospasm occurs only in those patients who survive past the first few days.

The incidence of vasospasm is less than the incidence of SAH (since only some patients with SAH develop vasospasm). The incidence of vasospasm will depend on the type of patient a given hospital receives and the methods by which vasospasm is diagnosed.

The unqualified term "vasospasm" is usually used with reference to angiographically determined arterial narrowing as defined above. "Clinical vasospasm" most often is used synonymously with delayed cerebral ischemia (DCI). When used in another fashion, for instance, vasospasm based on increased middle cerebral artery transcranial Doppler velocities, this should be specified (Vergouwen, M. D. et al., "Definition of delayed cerebral ischemia after aneurysmal subarachnoid hemorrhage as an outcome event in clinical trials and observational studies: proposal of a multidisciplinary research group," Stroke 41:2391-2395 (2010)).

Some degree of angiographic narrowing will occur in at least two-thirds of patients having angiography between 4 and 12 days after SAH. The numbers of patients developing neurological deterioration from angiographic vasospasm varies with the diligence with which the patient is monitored and the efficacy of prophylaxis, but it has been estimated at about one-third. Of hospitalized SAH patients, about 5% die from vasospasm. When compared to post-SAH patients of intermediate grade, post-SAH patients in very good condition are less likely to develop vasospasm as they have small volume SAH, while post-SAH patients in very poor condition are more likely to die earlier from the initial episode. The presence of thick, widespread subarachnoid clot which can be visualized on the computerized tomographic (CT) scan done in close proximity to the bleeding episode is a key prognostic factor. The chance of vasospasm and consequently DCI is decreased by factors decreasing the duration of exposure to clot. Conversely, the incidence of vasospasm and DCI is increased by the utilization of antifibrinolytic drugs which prolong the exposure of arteries to clot and possibly cause ischemia by other mechanisms. Poor admission clinical grade is associated with DCI, presumably because they both indicate larger volumes of SAH. A definite relationship between age, hypertension, or sex and DCI has not been established. It is possible that smokers are more prone to vasospasm and DCI. Factors unrelated to the development of vasospasm include season, geography, contrast material, and diabetes.

Patients who develop vasospasm do worse than those who do not. If neurosurgical clipping or endovascular coiling of the ruptured aneurysm is performed earlier (within the first day or so) the outcome tends to be better than if treatment is delayed. When operations were preferentially performed during the peak period for vasospasm, outcomes were generally worse. Vasospasm does not result from early surgery or coiling; early surgery or coiling permits more vigorous treatment should vasospasm develop. If a thick clot is present, an attempt at careful removal of the clot is sometimes made. The amount of residual clot postoperatively is a prognostic factor for DCI. Open operation exposes the patient to retractor pressure, venous sacrifice, temporary clipping ischemia, and arterial injury. Studies have shown post operative decrease in cerebral blood flow, regional cerebral metabolic rate of oxygen, and oxygen extraction ratio. Vasospasm and DCI may be more common in patients who undergo neurosurgical clipping of a ruptured aneurysm as compared to endovascular coiling.

Independent variables, such as admission neurologic grade, increasing age, and massive intracranial or intraventricular hemorrhage, are more closely linked to outcome than vasospasm. Since vasospasm is a graded process, it is expected that only the extreme cases will result in infarction in the absence of systemic hypotension, cardiac dysfunction, anoxia, and intracranial hypertension. Preexisting hypertension and advanced age also strongly influence the vulnerability of the brain to ischemia. The etiological relationship between vasospasm and infarction in fatal cases is not in dispute.

There is evidence that vasospasm may be reduced by clot removal either surgically or pharmacologically. There also are data suggesting that DCI may be lessened by pharmacologically induced hypertension and hypervolemia as well as by calcium antagonists. Vasospasm also may be abolished by mechanical or transiently by pharmacologic angioplasty.

Incidence of Vasospasm

The incidence of angiographic vasospasm depends on the time interval after the SAH. The peak incidence occurs 6-8 days after SAH (range, 3-12 days). In addition to the time after the SAH, other principal factors that affect the prevalence of vasospasm are the volume, density, temporal persistance and distribution of subarachnoid blood.

Prognostic Factors for Vasospasm

Prognostic factors for angiographic vasospasm include: the amount of subarachnoid blood on CT scan; hypertension; anatomical and systemic factors; clinical grade; and whether the patient is receiving antifibrinolytics.

Diagnosis of Vasospasm

The diagnosis of angiographic vasospasm rests on comparison of blood vessel imaging studies. The diagnosis of delayed cerebral ischemia (DCI) is primarily clinical. Angiographic vasospasm can be asymptomatic; however, when the cerebral blood flow is below ischemic threshold, symptoms become apparent, and this is called DCI. Symptoms typically develop subacutely and may fluctuate. Symptoms may include excess sleepiness, lethargy, stupor, hemiparesis or hemiplegia, abulia, language disturbances, visual fields deficits, gaze impairment, and cranial nerve palsies. Although some symptoms are localized, they are not diagnostic of any specific pathological process; therefore alternative diagnoses, such as rebleeding, hydrocephalus, and seizures, should be excluded promptly using radiographic, clinical and laboratory assessments. Cerebral angiography is the gold standard for visualizing and studying cerebral arteries; transcranial Doppler ultrasonography is also utilized.

The pathophysiology of angiographic vasospasm may involve structural changes and biochemical alterations within the vascular endothelium and smooth muscle cells. The presence of blood in the subarachnoid space initiates these changes. In addition, hypovolemia and an impaired cerebral autoregulatory function may concurrently interfere with cerebral perfusion and contribute to DCI due to angiographic vasospasm. The cumulative effects of these processes can lead to reduction in cerebral blood flow so severe as to cause cerebral ischemia leading to infarction. Additionally, a period of severe constriction could lead to morphologic changes in the walls of the cerebral arteries, which may cause them to remain narrowed without the continued presence of vasoactive substances. The area of the brain supplied by the affected artery then would experience ischemia (meaning a restriction in blood supply).

Other Complications

Hydrocephalus (a condition marked by an excessive accumulation of CSF resulting in dilation of the cerebral ventricles and raised intracranial pressure) may complicate SAH in both the short- and long-term, and may be detected on CT scanning. If the level of consciousness is decreased, surgical drainage of the excess fluid (for instance with a ventricular drain or shunt) is occasionally necessary.

Fluctuations in blood pressure and electrolyte disturbances, as well as pneumonia and cardiac decompensation, occur in about 50% of hospitalized patients with SAH, and may worsen prognosis. They are managed symptomatically.

Seizures occur in about a tenth of all cases of SAH.

5. Voltage-Gated Ion Channels

Voltage-gated ion channels are a class of integral membrane proteins that allow the passage of selected inorganic ions across the cell membrane by opening and closing in response to changes in transmembrane voltage. (Sands, Z. et al., "Voltage-gated ion channels," Current Biology, 15(2): R44-R47 (2005)). These types of ion channels are especially critical in neurons, but are common in many types of cells. They have an important role in excitable neuronal and muscle tissues as they allow a rapid and coordinated depolarization in response to triggering voltage change. Positioned along the axon and at the synapse, voltage-gated ion channels directionally propagate electrical signals.

Structure

Voltage-gated potassium, sodium and calcium ion channels are thought to have similar overall architectures. (Sands, Z. et al., "Voltage-gated ion channels," Current Biology, 15(2): R44-R47 (2005)). Voltage-gated ion channels generally are composed of several subunits arranged such that there is a central pore through which ions can travel down their electrochemical gradients. The channels tend to be quite ion-specific, although similarly sized and charged ions may also travel through them to some extent.

Mechanism

Crystallographic structural studies of a potassium channel, assuming that this structure remains intact in the corresponding plasma membrane, suggest that when a potential difference is introduced over the membrane, the associated electromagnetic field induces a conformational change in the potassium channel. The conformational change distorts the shape of the channel proteins sufficiently such that the channel, or cavity, opens to admit ion influx or efflux to occur across the membrane, down its electrochemical gradient. This subsequently generates an electrical current sufficient to depolarize the cell membrane.

Voltage-gated sodium channels and calcium channels are made up of a single polypeptide with four homologous domains. Each domain contains 6 membrane spanning alpha helices. The voltage sensing helix, S4, has multiple positive charges such that a high positive charge outside the cell repels the helix and induces a conformational change such that ions may flow through the channel. Potassium channels function in a similar way, with the exception that they are composed of four separate polypeptide chains, each comprising one domain. The voltage-sensitive protein domain of these channels (the "voltage sensor") generally contains a region composed of S3b and S4 helices, known as the "paddle" due to its shape, which appears to be a conserved sequence.

5.1. Voltage-Dependent Calcium Channels

Voltage-dependent calcium channels (VDCC) are a group of voltage-gated ion channels that control calcium entry into cells in response to membrane potential changes. (Van Petegem F. et al., Biochemical Society Transactions, 34(5): 887-893 (2006)). Voltage-dependent calcium channels are found in excitable cells (e.g., muscle, glial cells, neurons, etc.). At physiologic or resting membrane potential, VDCCs are normally closed. They are activated (i.e., opened) at depolarized membrane potentials. Activation of particular VDCCs allows $Ca^{2+}$ entry into the cell; muscular contraction, excitation of neurons, upregulation of gene expression, or release of hormones or neurotransmitters results, depending upon the cell type. (Catterall W. A. et al., "International Union of Pharmacology. XLVIII. Nomenclature and structure-function relationships of voltage-gated calcium channels," Pharmacol. Rev., 57(4): 411-25 (2005); Yamakage M. et al, "Calcium channels—basic aspects of their structure, function and gene encoding; anesthetic action on the channels—a review," Can. J. Anaesth., 49(2): 151-64 (2002)).

Voltage-dependent calcium channels are formed as a complex of several different subunits: $\alpha_1$, $\alpha_2\delta$, $\beta_{1-4}$, and $\gamma$. The $\alpha$ subunit forms the ion conducting pore while the associated subunits have several functions including modulation of gating. (Dolphin A. C. "A short history of voltage-gated calcium channels," Br. J. Pharmacol., 147 (Suppl 1): S56-62 (2006))

α1 Subunit

The $\alpha_1$ subunit pore (about 190 kDa in molecular mass) is the primary subunit necessary for channel functioning in the VDCC, and consists of the characteristic four homologous I-IV domains containing six transmembrane α-helices each. The α subunit forms the $Ca^{2+}$ selective pore, which contains voltage-sensing machinery and the drug/toxin-binding sites. Ten α subunits that have been identified in humans. (Dolphin A. C. "A short history of voltage-gated calcium channels," Br. J. Pharmacol., 147 (Suppl 1): S56-62 (2006)).

a2δ Subunit

The $\alpha_2\delta$ gene encodes two subunits, $\alpha_2$ and $\delta$. They are linked to each other via a disulfide bond and have a combined molecular weight of 170 kDa. The $\alpha_2$ is the extracellular glycosylated subunit that interacts the most with the α1 subunit. The δ subunit has a single transmembrane region with a short intracellular portion, which serves to anchor the protein in the plasma membrane. There are 4 $\alpha_2\delta$ genes: CACNA2D1 (CACNA2D1), (CACNA2D2), (CACNA2D3), and (CACNA2D4). Co-expression of the $\alpha_2\delta$ enhances the level of expression of the α1 subunit and causes an increase in current amplitude, faster activation and inactivation kinetics and a hyperpolarizing shift in the voltage dependence of inactivation. Some of these effects are observed in the absence of the betα subunit, whereas, in other cases, the co-expression of beta is required. The $\alpha_2\delta$-1 and α2δ-2 subunits are binding sites for at least two anti-convulsant drugs, gabapentin and pregabalin, that also find use in treating chronic neuropathic pain. (Dolphin A. C. "A short history of voltage-gated calcium channels," Br. J. Pharmacol., 147 (Suppl 1): S56-62 (2006))

β Subunit

The intracellular β subunit (55 kDa) is an intracellular membrane-associated guanylate kinase (MAGUK)-like protein containing a guanylate kinase (GK) domain and an SH3 (src homology 3) domain. The guanylate kinase domain of the β subunit binds to the alpha subunit I-II cytoplasmic loop and regulates HVGCC activity. There are four known isoforms of the β subunit: CACNB1, CACNB2, CACNB3, and CACNB4. (Dolphin A. C. "A short history of voltage-gated calcium channels," Br. J. Pharmacol., 147 (Suppl 1): S56-62 (2006))

Without being limited by theory, it is postulated the cytosolic β subunit has a major role in stabilizing the final α subunit conformation and delivering it to the cell membrane by its ability to mask an endoplasmic reticulum retention signal in the α subunit. The endoplasmic retention brake is contained in the I-II loop of the α subunit that becomes masked when the β subunit binds. Therefore the β subunit functions initially to regulate the current density by controlling the amount of α subunit expressed at the cell membrane.

In addition to this potential trafficking role, the β subunit has the added important functions of regulating activation and inactivation kinetics, and hyperpolarizing the voltage-dependence for activation of the α subunit pore, so that more current passes for smaller depolarizations. The β subunit acts as an important modulator of channel electrophysiological properties. The interaction between a highly conserved 18-amino acid region on the α1 subunit intracellular linker between domains I and II (the Alpha Interaction Domain, AIDBP) and a region on the GK domain of the β subunit (Alpha Interaction Domain Binding Pocket) is responsible for the regulatory effects exerted by the β subunit. Additionally, the SH3 domain of the β subunit also gives added regulatory effects on channel function, indicating that the β subunit may have multiple regulatory interactions with the α1 subunit pore. The α interaction domain sequence does not appear to contain an endoplasmic reticulum retention signal; this may be located in other regions of the I-II α1 subunit linker.

γ Subunit

The γ1 subunit is known to be associated with skeletal muscle VDCC complexes, but the evidence is inconclusive regarding other subtypes of calcium channel. The γ1 subunit glycoprotein (33 kDa) is composed of four transmembrane spanning helices. The γ1 subunit does not affect trafficking, and, for the most part, is not required to regulate the channel complex. However, γ2, γ3, γ4 and γ8 also are associated with α-amino-3-hydroxy-5-methyl-4-isoxazolepropionic acid (AMPA) glutamate receptors, non-NMDA-type ionotropic transmembrane receptors for glutamate that mediate fast synaptic transmissions in the CNS. An NMDA-type receptor is a receptor to which NMDA (N-methyl-D-aspartate) binds specifically. There are 8 genes for gamma subunits: γ1 (CACNG1), γ2 (CACNG2), γ3 (CACNG3), γ4 (CACNG4), (CACNG5), (CACNG6), (CACNG7), and (CACNG8). (Chu P. J. et al., "Calcium channel gamma subunits provide insights into the evolution of this gene family," Gene, 280 (1-2): 37-48 (2002)).

Voltage dependent calcium channels vary greatly in structure and form. Calcium channels are classified as L-, N-, P/Q, T- and R-type according to their pharmacological and electrophysiological properties. These channel subtypes have distinct physiological functions. Molecular cloning has clarified the α1 subunit sequence of each channel. The α1 subunit has a specific role in eliciting activity in an individual channel. Nonetheless, selective antagonists for these channel subtypes are required for defining specific channels involved in each activity. The neural N-type channels are blocked by ω-conotoxin GVIA; the R-type channels are resistant to other antagonists and toxins, are blocked by SNX-482, and may be involved in processes in the brain; the closely related P/Q-type channels are blocked by co-agatoxins. The dihydropyridine-sensitive L-type channels are responsible for excitation-contraction coupling of skeletal, smooth, and cardiac muscle and for hormone secretion in endocrine cells and also are antagonized by phenylalkylamines and benzothiazepines.

5.2. Types of Voltage-Dependent Calcium Channels

L-Type Calcium Channels

L-type voltage-gated calcium channels are opened when a smooth muscle cell is depolarized. This depolarization may be brought about by stretching of the cell, by an agonist-binding its G protein-coupled receptor (GPCR), or by autonomic nervous system stimulation. Opening of the L-type calcium channel causes influx of extracellular $Ca^{2+}$, which then binds calmodulin. The activated calmodulin molecule activates myosin light-chain kinase (MLCK), which phosphorylates the myosin in thick filaments. Phosphorylated myosin is able to form cross bridges with actin thin filaments, and the smooth muscle fiber (i.e., cell) contracts via the sliding filament mechanism. (Yamakage M. et al, "Calcium channels—basic aspects of their structure, function and gene encoding; anesthetic action on the channels—a review," Can. J. Anaesth., 49(2): 151-64 (2002))

L-type calcium channels also are enriched in the t-tubules of striated muscle cells, such as, skeletal and cardiac myofibers. As in smooth muscle, L-type calcium channels open when these cells are depolarized. In skeletal muscle, since the L-type calcium channel and the calcium-release channel (ryanodine receptor, or RYR) are mechanically gated to each other with the latter located in the sarcoplasmic reticulum (SR), the opening of the L-type calcium channel causes the opening of the RYR. In cardiac muscle, opening of the L-type calcium channel permits influx of calcium into the cell. The calcium binds to the calcium release channels (RYRs) in the SR, opening them (referred to as "calcium-induced calcium release" or "CICR"). $Ca^{2+}$ is released from the SR and is able to bind to troponin C on the actin filaments regardless of how the RYRs are opened, either through mechanical-gating or CICR. The muscles then contract through the sliding filament mechanism, causing shortening of sarcomeres and muscle contraction.

R-Type Voltage Dependent Calcium Channels

R-type voltage dependent calcium channels (VDCC) are involved in regulating calcium flow. The R-type VDCCs play an important role in decreased cerebral blood flow observed following SAH. Without being limited by theory, R-type voltage-dependent $Ca^{2+}$ channels that may be located within small diameter cerebral arteries may regulate global and local cerebral blood flow, since the concentration of intracellular free calcium ions determines the contractile state of vascular smooth muscle. (Yamakage M. et al, "Calcium channels—basic aspects of their structure, function and gene encoding; anesthetic action on the channels—a review," Can. J. Anaesth., 49(2): 151-64 (2002)).

R-type voltage dependent calcium channel inhibitors are calcium entry blocking drugs whose main pharmacological effect is to prevent or slow the entry of calcium into cells via R-type voltage-gated calcium channels. The gene $Ca_v2.3$ encodes the principal pore-forming unit of R-type voltage-dependent calcium channels being expressed in neurons.

N-Type Calcium Channels

N-type ('N' for "Neural-Type") calcium channels are found primarily at presynaptic terminals and are involved in neurotransmitter release. Strong depolarization by an action potential causes these channels to open and allow influx of $Ca^{2+}$, initiating vesicle fusion and release of stored neurotransmitter. N-type channels are blocked by ω-conotoxin. (Yamakage M. et al, "Calcium channels—basic aspects of their structure, function and gene encoding; anesthetic action on the channels—a review," Can. J. Anaesth., 49(2): 151-64 (2002)).

P/Q-Type Calcium Channels

P-type ('P' for cerebellar Purkinje cells) calcium channels play a similar role to the N-type calcium channel in neurotransmitter release at the presynaptic terminal, and in neuronal integration in many neuronal types. They also are found in Purkinje fibers in the electrical conduction system of the heart (Winds, R., et al., J. Physiol. (Lond.) 305: 171-95 (1980); Llinds, R. et al., Proc. Natl. Acad. Sci. U.S.A. 86 (5): 1689-93 (1989)). Q-type calcium channel antagonists appear to be present in cerebellar granule cells. They have a high threshold of activation and relatively slow kinetics. (Yamakage M. et al, "Calcium channels—basic aspects of their structure, function and gene encoding; anesthetic action on the channels—a review," Can. J. Anaesth., 49(2): 151-64 (2002)).

T-Type Calcium Channels

T-type ('T' for transient) calcium channel antagonists are low voltage-activated. They most often are found in neurons and cells that have pacemaker activity and in osteocytes. Mibefradil shows some selectivity for T-type over other types of VDCC. (Yamakage M. et al, "Calcium channels—basic aspects of their structure, function and gene encoding; anesthetic action on the channels—a review," Can. J. Anaesth., 49(2): 151-64 (2002)).

5.3. Antagonists and Inhibitors of Calcium Channels

Calcium channel antagonists are a class of drugs and natural substances having effects on many excitable cells of the body, such as the muscle of the heart, smooth muscles of the vessels or neuron cells. The primary action of many calcium channel antagonists is to decrease blood pressure, via L-type calcium channel blockade. (Survase, S. et al., "Actions of calcium channel blockers on vascular proteoglycan synthesis: relationship to atherosclerosis," Vasc. Health Risk Manag., 1(3): 199-208 (2005)).

Calcium channel antagonists act upon voltage-dependent calcium channels (VDCCs) in muscle cells of the heart and blood vessels. By blocking the calcium channel they prevent large increases of the calcium levels in the cells when stimulated, which subsequently leads to less muscle contraction. In the heart, a decrease in calcium available for each beat results in a decrease in cardiac contractility. In blood vessels, a decrease in calcium results in less contraction of the vascular smooth muscle and therefore an increase in blood vessel diameter. The resultant vasodilation decreases total peripheral resistance, while a decrease in cardiac contractility decreases cardiac output. Since blood pressure is in part determined by cardiac output and peripheral resistance, blood pressure drops.

Calcium channel antagonists do not decrease the responsiveness of the heart to input from the sympathetic nervous system. Since blood pressure regulation is carried out by the sympathetic nervous system (via the baroreceptor reflex), calcium channel antagonists allow blood pressure to be maintained more effectively than do β-blockers. However, because calcium channel antagonists result in a decrease in blood pressure, the baroreceptor reflex often initiates a reflexive increase in sympathetic activity leading to increased heart rate and contractility. The decrease in blood pressure also likely reflects a direct effect of antagonism of VDCC in vascular smooth muscle, leading to vasodilation. A β-blocker may be combined with a calcium channel antagonist to minimize these effects.

Calcium channel antagonists may decrease the force of myocardial contraction, an effect that depends on the chemical class of antagonist. This is known as the "negative inotropic effect" of calcium channel antagonists. (Bryant, B. et al., "Pharmacology for health professionals," 3rd Ed., Elsevier Australia (2010)). Most calcium channel antagonists are not the preferred choice of treatment in individuals with cardiomyopathy due to their negative inotropic effects. (Lehne, R., "Pharmacology for nursing care," 7th Ed., St. Louis, Mo., Saunders Elsevier., p. 505 (2010)).

Some calcium channel antagonists exhibit a negative dromotropic effect in that they slow the conduction of electrical activity within the heart by blocking the calcium channel during the plateau phase of the action potential of the heart. This effect is known as a "negative dromotropic effect". Some calcium channel antagonists can also cause a lowering of the heart rate and may cause heart block (which is known as the "negative chronotropic effect" of calcium channel antagonists). The negative chronotropic effects of calcium channel antagonists make them a commonly used class of agents for control of the heart rate in individuals with atrial fibrillation or flutter. (See for example, Murphy C. E. et al., "Calcium channel blockers and cardiac surgery," J. Card. Surg., 2(2): 299-325 (1987)).

The antagonists for L, N, and P/Q-types of calcium channels are utilized in distinguishing channel subtypes. For the R-type calcium channel subtype, for example, ω-agatoxin IIIA shows blocking activity, even though its selectivity is rather low. This peptide binds to all of the high voltage-activated channels including L, N, and P/Q subtypes (J. Biol. Chem., 275, 21309 (2000)). A putative R-type (or class α1E) selective blocker, SNX-482, a toxin from the tarantula *Hysterocrates gigas*, is a 41 amino acid residue peptide with 3 disulfide linkages (1-4, 2-5 and 3-6 arrangement) (Biochemistry, 37, 15353 (1998), Peptides 1998, 748 (1999)). This peptide blocks the class E calcium channel (IC50=15 nM to 30 nM) and R-type calcium current in the neurohypophysial nerve endings at 40 nM concentration. R-type (class E) calcium channel blocking activity is highly selective; no effect is observed on $K^+$ and $Na^+$ currents, and L, P/Q and T-type calcium currents. N-type calcium current is blocked only weakly 30-50% at 300 nM to 500 nM. Regionally, different sensitivity of R-type current to SNX-482 is observed; no significant effect on R-type current occurs in preparations of the neuronal cell body, retinal ganglion cells and hippocampal pyramidal cells. Using SNX-482, three a E-calcium subunits with distinct pharmacological properties are recognized in cerebellar R-type calcium channels (J. Neurosci., 20, 171 (2000)). Similarly, it has been shown that secretion of oxytocin, but not vasopressin, is regulated by R-type calcium current in neurohypophysial terminals (J. Neurosci., 19, 9235 (1999)).

Dihydropyridine calcium channel antagonists often are used to reduce systemic vascular resistance and arterial pressure, but are not used to treat angina (with the exception of amlodipine, which carries an indication to treat chronic stable angina as well as vasospastic angina) since the vasodilation and hypotension can lead to reflex tachycardia. This calcium channel antagonist class is easily identified by the suffix "-dipine."

Phenylalkylamine calcium channel antagonists are relatively selective for myocardium. They reduce myocardial oxygen demand and reverse coronary vasospasm. They have minimal vasodilatory effects compared with dihydropyridines. Their action is intracellular.

Benzothiazepine calcium channel antagonists are an intermediate class between phenylalkylamine and dihydropyridines in their selectivity for vascular calcium channels. Benzothiazepines are able to reduce arterial pressure without producing the same degree of reflex cardiac stimulation caused by dihydropyridines due to their cardiac depressant and vasodilator actions.

L-type VDCC inhibitors are calcium entry blocking drugs whose main pharmacological effect is to prevent or slow entry of calcium into cells via L-type voltage-gated calcium channels. Examples of such L-type calcium channel inhibitors include, but are not limited to: dihydropyridine L-type antagonists such as nisoldipine, AHF (such as 4aR,9aS)-(+)-4-a-Amino-1,2,3,4,4a,9a-hexahydro-4a14-fluorene, HCl), isradipine (such as 4-(4-Benzofurazanyl)-1,-4-dihydro-2,6-dimethyl-3,5-pyridinedicarboxylic acid methyl 1-methylethyl ester), calciseptine (such as isolated from (Dendroaspis polylepis ploylepis), H-Arg-Ile-Cys-Tyr-Ile-His-Lys-Ala-Ser-Leu-Pro-Arg-Ala-Thr-Lys-Thr-Cys-Val-Glu-Asn-Thr-Cys-Tyr-Lys-Met- Phe-Ile-Arg-Thr-Gln-Arg- Glu-Tyr-Ile-Ser-Glu-Arg-Gly-Cys-Gly-Cys-Pro-Thr-Ala-Met-Trp-Pro-Tyr-Gl-n-Thr-Glu-Cys-Cys-Lys-Gly-Asp-Arg-Cys-Asn-Lys-OH [SEQ ID NO: 1], Calcicludine (such as isolated from Dendroaspis angusticeps (eastern green mamba)), (H-Trp -Gln-Pro-Pro-Trp-Tyr-Cys-Lys-Glu-Pro-Val-Arg-Ile-Gly-Ser-Cys-Lys-Lys-Gln-Phe-Ser-Ser -Phe-Tyr-Phe-Lys-Trp-Thr-Ala-Lys-Lys-Cys-Leu-Pro-Phe-Leu-Phe-Ser-Gly-Cys-Gly-Gly-Asn -Ala-Asn-Arg-Phe-Gln-Thr-Ile-Gly-Glu-Cys-Arg-Lys-Lys-Cys-Leu-Gly-Lys-OH [SEQ ID NO: 2], Cilnidipine (such as also FRP-8653, a dihydropyridine-type inhibitor), Dilantizem (such as (2S,3S)-(+)-cis-3-Acetoxy-5-(2-dimethylaminoethyl)-2,3-dihydro-2-(4-methoxyphenyl)-1,5-benzothiazepine-4(5H)-one hydrochloride), diltiazem (such as benzothiazepine-4(5H)-one, 3-(acetyloxy)-5-[2-(dimethylamino)ethyl]-2,3-dihydro-2-(4-methoxyphenyl)-(+)-cis-monohydrochloride), Felodipine (such as 4-(2,3-Dichlorophenyl)-1,4-dihydro-2,6-dimethyl-3,5-pyridinecarboxylic acid ethyl methyl ester), FS-2 (such as an isolate from *Dendroaspis polylepis polylepis* venom), FTX-3.3 (such as an isolate from *Agelenopsis aperta*), Neomycin sulfate (such as $C_{23}H_{46}N_6O_{13} \cdot 3H_2SO_4$), Nicardipine (such as 1,4-Dihydro-2,6-dimethyl-4-(3-nitrophenylmethyl-2-[methyl(phenylmethylamino]-3,5-pyridinedicarboxylic acid ethyl ester hydrochloride, also YC-93, Nifedipine (such as 1,4-Dihydro-2,6-dimethyl-4-(2-nitrophenyl)-3,5-pyridinedicarboxylic acid dimethyl ester), Nimodipine (such as 4-Dihydro-2,6-dimethyl-4-(3-nitrophenyl)-3,5-pyridinedicarboxylic acid 2-methoxyethyl 1-methylethyl ester) or (Isopropyl 2-methoxyethyl 1,4-dihydro-2,6-dimethyl-4-(m-nitrophenyl)-3,5-pyridinedicarboxylate), Nitrendipine (such as 1,4-Dihydro-2,6-dimethyl-4-(3-nitrophenyl)-3,5-pyridinedicarboxylic acid ethyl methyl ester), S-Petasin (such as (3S,4aR,5R,6R)-[2,3,4,4a,5,6,7,8-Octahydro-3-(2-propenyl)-4-a,5-dimethyl-2-o-xo-6-naphthyl]Z-3'-methylthio-1'-propenoate), Phloretin (such as 2',4',6'-Trihydroxy-3-(4-hydroxyphenyl)propiophenone, also 3-(4-Hydroxyphenyl)-1-(2,4,6-trihydroxyphenyl)-1-propanone, also b-(4-Hydroxyphenyl)-2,4,6-trihydroxypropiophenone), Protopine (such as $C_{20}H_{19}NO_5Cl$), SKF-96365 (such as 1-[b-[3-(4-Methoxyphenyl)propoxy]-4-methoxyphenethyl]-1H-imidazole, HCl), Tetrandine (such as 6,6',7,12-Tetramethoxy-2,2'-dimethylberbaman), (+/−)-Methoxyverapamil or (+)-Verapamil (such as 54N-(3,4-Dimethoxyphenylethyl)methylamino]-2-(3,4-dimethoxyphenyl)-2-iso-propylvaleronitrile hydrochloride), and (R)-(+)-Bay K8644 (such as R-(+)-1,4-Dihydro-2,6-dimethyl-5-nitro-442-(trifluoromethyl)phenyl]-3-pyridinecarboxylic acid methyl ester). The foregoing examples may be specific to L-type voltage-gated calcium channels or may inhibit a broader range of voltage-gated calcium channels, e.g. N, P/Q, R, and T-type.

6. Endothelins

Endothelins are small vasoconstricting peptides (21 amino acids) produced in vivo primarily in the endothelium that increase blood pressure and vascular tone, and play an important role in vascular homeostasis. This family of peptides includes endothelin-1 (ET-1), endothelin-2 (ET-2) and endothelin-3 (ET-3). ET-1 is secreted mostly by vascular endothelial cells. The predominant ET-1 isoform is expressed in vasculature and is the most potent vasoconstrictor. ET-1 also has inotropic, chemotactic and mitogenic properties. It stimulates the sympathetic nervous system, and influences salt and water homeostasis through its effects on the renin-angiotensin-aldosterone system (RAAS), vasopressin and atrial natriuretic peptide. Endothelins are among the strongest vasoconstrictors known and have been implicated in vascular diseases of several organ systems, including the heart, general circulation and brain.

There are two key endothelin receptor types, ETA and ETB. ETA and ETB have distinct pharmacological characteristics. The ETA-receptor affinity is much higher for ET-1 than for ET-3. ETA-receptors are located in the vascular smooth muscle cells, but not in endothelial cells. The binding of endothelin to ETA increases vasoconstriction and the retention of sodium, leading to increased blood pressure. ETB receptors primarily are located on the endothelial cells that line the interior of the blood vessels. There may be ETB receptors on smooth muscle cells which mediate contraction. Endothelin binding to ETB receptors lowers blood pressure by increasing natriuresis and diuresis, and releasing nitric oxide. ET-1 and ET-3 activate the ETB-receptor equally, which in turn leads to vasodilation via production of NO and prostaglandins. Endothelin-1 (ET-1) also has been demonstrated to cause vascular smooth muscle constriction via ETA-receptor stimulation and to induce nitric oxide (NO) production in endothelial cells via ETB-receptors. Some ETB-receptors are located in vascular smooth muscle, where they may mediate vasoconstriction. A number of endothelin receptors are regulated by various factors. Angiotensin II and phorbol esters down-regulate endothelin receptors whereas ischemia and cyclosporin increase the number of endothelin receptors. (Reviewed in Aapitov, A. V. et al., "Role of endothelin in cardiovascular disease," Journal of Renin-Angiotensin-Aldosterone System, 3(1): 1-15 (2002)).

A number of peptide and nonpeptide ET antagonists have been studied. ETA-receptor antagonists may include, but are not limited to, A-127722 (non-peptide), ABT-627 (non-peptide), BMS 182874 (non-peptide), BQ-123 (peptide), BQ-153 (peptide), BQ-162 (peptide), BQ-485 (peptide), BQ-518 (peptide), BQ-610 (peptide), EMD-122946 (non-peptide), FR 139317 (peptide), IPI-725 (peptide), L-744453 (non-peptide), LU 127043 (non-peptide), LU 135252 (non-peptide), PABSA (non-peptide), PD 147953 (peptide), PD 151242 (peptide), PD 155080 (non-peptide), PD 156707 (non-peptide), RO 611790 (non-peptide), SB-247083 (non-peptide), clazosentan (non-peptide), atrasentan (non-peptide), sitaxsentan sodium (non-peptide), TA-02 01 (non-peptide), TBC 11251 (non-peptide), TTA-386 (peptide), WS-7338B (peptide), ZD-1611 (non-peptide), and aspirin (non-peptide). ETA/B-receptor antagonists may include, but are not limited to, A-182086 (non-peptide), CGS 27830 (non-peptide), CP 170687 (non-peptide), J-104132 (non-peptide), L-751281 (non-peptide), L-754142 (non-peptide), LU 224332 (non-peptide), LU 302872 (non-peptide), PD 142893 (peptide), PD 145065 (peptide), PD 160672 (non-peptide), RO-470203 (bosentan, non-peptide), RO 462005 (non-peptide), RO 470203 (non-peptide), SB 209670 (non-peptide), SB 217242 (non-peptide), and TAK-044 (peptide). ETB-receptor antagonists may include, but are not limited to, A-192621 (non-peptide), A-308165 (non-peptide), BQ-788 (peptide), BQ-017 (peptide), IRL 1038 (peptide), IRL 2500 (peptide), PD-161721 (non-peptide), RES 701-1 (peptide), and RO 468443 (peptide). (Aapitov, A. V. et al., "Role of endothelin in cardiovascular disease," Journal of Renin-Angiotensin-Aldosterone System, 3(1): 1-15 (2002)).

ET-1 is translated initially to a 212 amino-acid peptide (pre-proendothelin-1). It is further converted to proendothelin-1 after removal of the secretory sequence. Proendothelin-1 then is cleaved by furin to generate the biologically-inactive precursor big endothelin-1. Mature ET-1 is formed upon cleavage of big endothelin-1 by one of several endothelin-converting enzymes (ECEs). There are two splice variants of ECE-1; these are ECE-1a and ECE-1b. Each has functionally distinct roles and tissue distribution. ECE-1a is expressed in the Golgi network of endothelin-producing cells and cleaves big endothelin-1 to form ET-1. ECE-1b is localized at the plasma membrane and cleaves extracellular big endothelin-1. Both ECE-1a and ECE-1b are inhibited by metalloprotease inhibitor phosphoramidon. ECEs also are located on α-actin filaments in smooth muscle cells. ECE inhibition by phosphoramidon completely blocks vasoconstriction to big endothelin-1. ECE inhibitors may include, but are not limited to, B-90063 (non-peptide), CGS 26393 (non-peptide), CGS 26303 (non-peptide), CGS 35066 (non peptide), phosphoramidon (peptide), PP-36 (peptide), SM-19712 (non-peptide), and TMC-66 (non-peptide). (Aapitov, A. V. et al., "Role of endothelin in cardiovascular disease," Journal of Renin-Angiotensin-Aldosterone System, 3(1): 1-15 (2002)).

In a healthy individual, a delicate balance between vasoconstriction and vasodilation is maintained by endothelin and other vasoconstrictors on the one hand and nitric oxide, prostacyclin and other vasodilators on the other. Endothelin antagonists may have a role in the treatment of cardiac, vascular and renal diseases associated with regional or systemic vasoconstriction and cell proliferation, such as essential hypertension, pulmonary hypertension, chronic heart failure, chronic renal failure, and SAH.

7. Transient Receptor Potential Channels

The transient receptor potential (TRP) channel family is a member of the calcium channel group. These channels include transient receptor potential protein and homologues thereof, the vanilloid receptor subtype I, stretch-inhibitable non-selective cation channel, olfactory, mechanosensitive channel, insulin-like growth factor I-regulated calcium channel, and vitamin D-responsive apical, epithelial calcium channel (ECaC). (see for example, Montell C. et al., "Molecular characterization of the *Drosophila* trp locus: a putative integral membrane protein required for phototransduction, Neuron, 2(4):1313-1323 (1989); Caterina et al., "The capsaicin receptor: a heat-activated ion channel in the pain pathway," Nature, 389 (6653): 816-824 (1997); Suzuki et al., "Cloning of a stretch-inhibitable nonselective cation channel," J. Biol. Chem. 274: 6330-6335 (1999); Kiselyov et al., "Functional interaction between InsP3 receptors and store-operated Htrp3 channels," Nature 396 (6710): 478-482 (1998); Hoenderop et al., "Molecular identification of the apical Ca2+ channel in 1, 25-dihydroxyvitamin D3-responsive epithelia," J. Biol. Chem. 274(13): 8375-8378 (1999); and Chen et al., "Polycystin-L is a calcium-regulated cation channel permeable to calcium ions," Nature, 401(6751): 383-386 (1999)). Each of these molecules is at least 700 amino acids in length, and shares certain conserved structural features. Predominant among these structural features are six transmembrane domains, with an additional hydrophobic loop present between the fifth and sixth transmembrane domains. It is believed that this loop is integral to the activity of the pore of the channel formed upon membrane insertion. TRP channel proteins also include one or more ankyrin domains and frequently display a proline-rich region at the N-terminus.

Based on amino acid homology, the TRP superfamily can be further subdivided into sub-families. In mammals, these include TRPC (canonical), TRPV (vanilloid), TRPM (melastanin), TRPP (polycystin), TRPML (mucolipin), and TRPA (ankyrin) groups. The TRPC (canonical) subfamily includes 7 TRP channels (TRPC1-7); the TRPM (melastanin) subfamily includes eight different channels (TRPM1-8); the TRPV (vanilloid) subfamily includes six members (TRPV1-6); the TRPA (ankyrin) subfamily includes one member (TRPA1) and the TRPP (polycystin) and TRPML (mucolipin) subfamilies each include three mammalian members. In addition, the TRPN (No mechanopotential) found in hearing assisting sensory neurons have been identified in *Drosophila* and zebrafish. (Nilius, B. et al., "Transient receptor potential cation channels in disease," Physiol. Rev. 87: 165-217 (2007)).

Transient receptor potential (TRP) cation channels are present in vascular smooth muscle and are involved in the smooth muscle depolarizing response to stimuli such as membrane stretch. Uridine triphosphate (UTP) invokes membrane depolarization and constriction of vascular smooth muscle by activating a cation current that exhibits inward rectification, is not rapidly desensitized, and is blocked by gadolinium ions (Gd3+). Canonical transient receptor potential (TRPC) proteins form Ca2+ permeable, non-selective cation channels in a variety of mammalian tissues. Suppression of one member of this family of channels, TRPC6, has been reported to prevent an alpha-adeno-receptor-activated cation current in cultured rabbit portal vein myocytes. However, suppression of TRPC6 channels in cerebral vascular smooth muscle does not attenuate the UTP-induced membrane depolarization and vasoconstriction. In contrast, TRPC3, unlike TRPC6, has been found to mediate the agonist induced depolarization, as observed in rat cerebral artery, following UTP activation of the P2Y receptor. Thus, TRPC3 channels in vascular smooth muscle mediate agonist-induced depolarization which contributes to vasoconstriction in resistance-sized cerebral arteries.

The TRP1 channel family comprises a large group of channels mediating an array of signal and sensory transduction pathways. The proteins of the mammalian TRPC subfamily are the products of at least seven genes coding for cation channels that appear to be activated in response to phospholipase C(PLC)-coupled receptors. The putative ion channel subunits TRPC3, TRPC6, and TRPC7 comprise a structurally related subgroup of the family of mammalian TRPC channels. The ion channels formed by these proteins appear to be activated downstream of phospholipase C (PLC). PLC-dependent activation of TRPC6 and TRPC7 has been shown to involve diacylglycerol and is independent of G proteins or inositol 1,4,5-triphosphate (IP3).

TRPC channels are widely expressed among cell types and may play important roles in receptor-mediated Ca2+ signaling. The TRPC3 channel is known to be a Ca2+-conducting channel activated in response to PLC-coupled receptors. TRPC3 channels have been shown to interact directly with intracellular inositol 1,4,5-trisphosphate receptors (InsP3Rs), i.e., channel activation is mediated through coupling to InsP3Rs.

Agents useful for increasing arterial blood flow, inhibiting vasoconstriction or inducing vasodilation are agents that inhibit TRP channels. These inhibitors embrace compounds that are TRP channel antagonists. Such inhibitors are referred to as activity inhibitors or TRP channel activity inhibitors. As used herein, the term "activity inhibitor" refers to an agent that interferes with or prevents the activity of a TRP channel. An activity inhibitor may interfere with the ability of the TRP channel to bind an agonist such as UTP. An activity inhibitor may be an agent that competes with a naturally occurring activator of TRP channel for interaction with the activation binding site on the TRP channel. Alternatively, an activity inhibitor may bind to the TRP channel at a site distinct from the activation binding site, but in doing so, it may, for example, cause a conformational change in the TRP channel, which is transduced to the activation binding site, thereby precluding binding of the natural activator. Alternatively, an activity inhibitor may interfere with a component upstream or downstream of the TRP channel but which interferes with the activity of the TRP channel. This latter type of activity inhibitor is referred to as a functional antagonist. Non-limiting examples of a TRP channel inhibitor that is an activity inhibitor are gadolinium chloride, lanthanum chloride, SKF 96365 and LOE-908.

8. Regression Analyses for Selection of Eligible Subjects

DCI and cerebral infarction are associated with poor outcome. A systematic review and meta analysis of twenty one randomized, double-blind, placebo-controlled trials that studied the efficacy of pharmaceutical preventive strategies in SAH patients, including 7788 patients, and had both cerebral infarction and clinical outcome as outcome events were performed. (Asano T et al., "Effects of a hydroxyl radical scavenger on delayed ischemic neurological deficits following aneurysmal subarachnoid hemorrhage: results of a multicenter, placebo-controlled double-blind trial," J. Neurosurg., 84:792-803 (1996); Chou S H et al., "A randomized, double-blind, placebo-controlled pilot study of simvastatin in aneurysmal subarachnoid hemorrhage," Stroke, 39:2891-2893 (2008); Fisher C M et al., "Cerebral vasospasm with ruptured saccular aneurysm—the clinical manifestations," Neurosurgery, 1:245-248 (1977); Gomis P et al., "Randomized, double-blind, placebo-controlled, pilot trial of high-dose methylprednisolone in aneurysmal subarachnoid hemorrhage," J. Neurosurg., 112:681-688 (2010); Haley E C, Jr. et al., "A randomized, double-blind, vehicle-controlled trial of tirilazad mesylate in patients with aneurysmal subarachnoid hemorrhage: a cooperative study in North America," J. Neurosurg., 86:467-474 (1997); Haley E C, Jr. et al., "A randomized controlled trial of high-dose intravenous nicardipine in aneurysmal subarachnoid hemorrhage. A report of the Cooperative Aneurysm Study," J. Neurosurg., 78:537-547 (1993); Hop J W et al., "Randomized pilot trial of postoperative aspirin in subarachnoid hemorrhage," Neurology, 54:872-878 (2000); Kassell N F et al., "Randomized, double-blind, vehicle-controlled trial of tirilazad mesylate in patients with aneurysmal subarachnoid hemorrhage: a cooperative study in Europe, Australia, and New Zealand," J. Neurosurg., 84:221-228 (1996); Lanzino G, and Kassell N F, "Double-blind, randomized, vehicle-controlled study of high-dose tirilazad mesylate in women with aneurysmal subarachnoid hemorrhage. Part II. A cooperative study in North America," J. Neurosurg., 90:1018-1024 (1999); Lanzino G et al., "Double-blind, randomized, vehicle-controlled study of high-dose tirilazad mesylate in women with aneurysmal subarachnoid hemorrhage. Part I. A cooperative study in Europe, Australia, New Zealand, and South Africa," J. Neurosurg., 90:1011-1017 (1999); Macdonald R L et al., "Clazosentan to overcome neurological ischemia and infarction occurring after subarachnoid hemorrhage (CONSCIOUS-1): randomized, double-blind, placebo-controlled phase 2 dose-finding trial," Stroke, 39:3015-3021 (2008); Ohman J, and Heiskanen O, "Effect of nimodipine on the outcome of patients after aneurysmal subarachnoid hemorrhage and surgery," J. Neurosurg. 69:683-686 (1988); Pickard J D et al., "Effect of oral nimodipine on cerebral infarction and outcome after subarachnoid haemorrhage: British aneurysm nimodipine trial," BMJ, 298:636-642 (1989); Saito I et al., "Neuroprotective effect of an antioxidant, ebselen, in patients with delayed neurological deficits after aneurysmal subarachnoid hemorrhage," Neurosurgery, 42:269-277 (1998); Shaw M D, et al. "Efficacy and safety of the endothelin, receptor antagonist TAK-044 in treating subarachnoid hemorrhage: a report by the p,"Steering Committee on behalf of the UK/Netherlands/Eire TAK-044 Subarachnoid Haemorrhage Study Grou J. Neurosurg., 93:992-997 (2000); Springborg J B et al., "Erythropoietin in patients with aneurysmal subarachnoid haemorrhage: a double blind randomised clinical trial," Acta Neurochir. (Wien)) 149:1089-1101 (2007); Tseng M Y, et al., "Interaction of Neuroprotective and Hematopoietic Effects of Acute Erythropoietin Therapy with Age, Sepsis, and Statins Following Aneurysmal Subarachnoid Hemorrhage," Presented at the XIV World Congress of Neurological Surgery of the World Federation of Neurosurgical Societies, Boston, Mass., August 30-Sep. 4, 2009 (Abstract); van den Bergh W M et al., "Randomized controlled trial of acetylsalicylic acid in aneurysmal subarachnoid hemorrhage: the MASH Study," Stroke 37:2326-2330 (2006); Westermaier T et al., "Prophylactic intravenous magnesium sulfate for treatment of aneurysmal subarachnoid hemorrhage: a randomized, placebo-controlled, clinical study," Crit. Care Med. 38:1284-1290 (2010); Etminan, N. et al., "Effect of pharmaceutical treatment on vasospasm, delayed cerebral ischemia, and clinical outcome in patients with aneurysmal subarachnoid hemorrhage: a systematic review and meta-analysis," J. Cereb. Blood Flow Metab. 31:1443-1451 (2011)).

Effect sizes were expressed in (pooled) risk ratio estimates with corresponding 95% confidence intervals (CI). Sensitivity analyses were performed for studies with a low risk of bias, and for those who reported outcome at three months after SAH. The risk of bias is assessed for "allocation concealment" and "blinding" (Day, S. et al., "Blinding in clinical trials," BMJ, 321: 504 (2000)). To avoid selection bias, it is a tenet of randomized controlled trials that the treatment allocation for each patient is not revealed until the patient has irrevocably been entered into the trial. This sort of blinding is referred to as "allocation concealment." In controlled trials the term "blinding," and in particular "double blind," usually refers to keeping study participants, those involved with their management and those collecting and analyzing clinical data unaware of the assigned treatment so that they are not influenced by that knowledge.

Pharmaceutical treatments decreased the incidence of both cerebral infarction (Relative Risk ("RR") 0.83; 95% CI ranging from 0.74-0.94) and of poor functional outcome (Relative Risk ("RR") 0.91; 95% CI ranging from 0.85-

0.98). (Vergouwen, M. D. et al., "Lower incidence of cerebral infarction correlates with improved functional outcome after aneurysmal subarachnoid hemorrhage," J. Cereb. Blood Flow Metab., 31:1545-1553 (2011)). Thus, there is an association between infarction, a principle component of the diagnosis of DCI, and outcome. Since the mechanism of action of most of the drugs used is to either reverse angiographic vasospasm or protect the brain, these data suggest that the association between cerebral infarction and functional outcome implies causality.

Logistic regression analysis was performed with randomized clinical trial data with 3,567 patients between 1991 and 1997 to assess the relationships and interactions between admission neurological grade assessed on the WFNS, subarachnoid clot thickness, DCI and clinical outcome. (Haley E C, Jr. et al., "A randomized, double-blind, vehicle-controlled trial of tirilazad mesylate in patients with aneurysmal subarachnoid hemorrhage: a cooperative study in North America," J. Neurosurg., 86:467-474, (1997); Kassell N F et al., "Randomized, double-blind, vehicle-controlled trial of tirilazad mesylate in patients with aneurysmal subarachnoid hemorrhage: a cooperative study in Europe, Australia, and New Zealand," J. Neurosurg., 84:221-228 (1996); Lanzino G, and Kassell N F, "Double-blind, randomized, vehicle-controlled study of high-dose tirilazad mesylate in women with aneurysmal subarachnoid hemorrhage. Part II. A cooperative study in North America," J. Neurosurg., 90:1018-1024 (1999)).

Clinical outcome was the dependent variable and was assessed 3 months after SAH on the Glasgow Outcome Scale (GOS). (Jennett B, and Bond M, "Assessment of outcome after severe brain damage. A practical scale. Lancet 1:480-484, 1975). Independent variables assessed included World Federation of Neurosurgical Surgeons (WFNS) grade, age and subarachnoid clot thickness, factors found to be associated with outcome. (Rosengart A J, et al. "Prognostic factors for outcome in patients with aneurysmal subarachnoid hemorrhage," Stroke 38:2315-2321 (2007)). The other variables present on admission that were of similar importance were intraventricular hemorrhage, intracerebral hemorrhage and history of hypertension. The multivariable logistic regression theoretically selects variables independently associated with poor outcome. Thus, both subarachnoid clot volume and WFNS grade are important. If DCI is the dependent variable, then the variables significantly associated with are age, again showing an inverted U-shaped relationship with a peak incidence among patients 40 to 59-years-old. (Macdonald R L et al., "Factors associated with the development of vasospasm after planned surgical treatment of aneurysmal subarachnoid hemorrhage," J. Neurosurg. 99:644-652 (2003)). Other significant variables were history of hypertension, WFNS grade, subarachnoid clot thickness, aneurysm size and intraventricular hemorrhage. Thus, both neurological grade and subarachnoid clot thickness predict subsequent development of DCI.

The Co-operative Study on Timing of Aneurysm Surgery collected data from 68 centers across Europe, North America, Australia, Japan and South Africa. (Kassell N F et al., "The International Cooperative Study on the Timing of Aneurysm Surgery. Part 1: Overall management results," J. Neurosurg., 73:18-36 (1990)). 3521 patients were enrolled within 3 days of an SAH. At admission 75% of patients had a good neurological grade, defined as having normal speech at admission. Logistic regression analysis showed that the extent of SAH as assessed by clot thickness on the admission CT scan, is an independent risk factor for development of DCI and infarction. The study found that patients who had a normal CT scan had a low risk of developing DCI, and the risk increased progressively with increasing amounts of blood on CT, with patients having thick focal blood being at the highest risk. The study also showed that development of DCI could not be predicted by the presence of focal motor signs, cranial nerve palsies, language defects, impaired responsiveness, nuchal rigidity or severity of headache at admission. Based on the results of this study, the predictive power of CT for DCI exceeds that of clinical neurological examination.

Hijdra, et al., reported on 176 patients admitted within 72 hours of SAH, who were prospectively studied to assess the predictive value of clinical and radiological features for DCI, rebleeding and outcome. (Hijdra A et al., "Prediction of delayed cerebral ischemia, rebleeding, and outcome after aneurysmal subarachnoid hemorrhage," Stroke 19:1250-1256 (1988)). At baseline, 49% of patients were Hunt and Hess grades 1-2, and 51% were Hunt and Hess 3-5. Hunt and Hess grades 1-2 would be roughly equivalent to WFNS grade 1 and Hunt and Hess 3-5 to WFNS grades 2-5.24% of the patients with admission Hunt and Hess grades 1-2 developed DCI and 51% of them died or were vegetative or had severe disability (poor or unfavorable GOS) at 3 months. Stepwise logistic regression analysis showed that death, vegetative state or severe disability was best predicted by the amount of subarachnoid blood on CT scan within 72 hours of rupture (p=0.0001) and admission Glasgow coma score (GCS, p=0.0030). Blood on CT was a stronger predictor than GCS. The analysis also showed that amount of SAH on CT was the most important predictor of DCI, followed by amount of intraventricular hemorrhage, and that the predictive power of these two factors could not be improved further by taking into account the patient's initial neurological condition.

Öhman, et al., prospectively studied 265 good grade patients with aneurysmal SAH to examine which radiological and clinical factors forecast the development of cerebral infarct as a consequence of DCI. (Öhman J et al., "Risk factors for cerebral infarction in good-grade patients after aneurysmal subarachnoid hemorrhage and surgery: a prospective study," J. Neurosurg. 74:14-20 (1991)). Of these, 104 patients were randomized to receive nimodipine, 109 placebo and 52 received no treatment. The 161 patients who received either placebo or no treatment were analyzed together. At admission 31% of patients were Hunt and Hess grade 1, 44% were grade 2, and 25% were grade 3. Baseline CT showed that 21% of patient had no or small amount of blood on CT, 18% had thin layers of blood, 42% had thick layers of blood and 18% had severe bleeding. Patients were followed up at 1-3 years post-hemorrhage at which time CT scans were performed and evaluated for presence or absence of infarction and GOS was assessed at the same time. Logistic regression analysis showed that, in order of importance, the following factor were strongly predictive of infarction: severe bleeding on admission CT, history of hypertension and thick layers of blood in the basal cisterns on admission CT. Post-operative angiograms were done on 213 patients. 78 patients had moderate or severe vasospasm and 65% of them had infarction on follow up CT scans. Clinical grade at admission had no significant effect on cerebral infarction. There was an apparent trend for grade 3 patients to have more infarcts but the differences between neurological grades did not reach significance.

Woertgen and colleagues studied 292 patients with aneurysmal SAH ("aSAH") between 1995 and 2000 with the aim of comparing clinical scales and CT findings to predict DCI. (Woertgen C et al., "Comparison of the Claassen and Fisher C T classification scale to predict ischemia after aneurysmatic SAH?" Zentralbl Neurochir 64:104-108 (2003)). DCI was defined as new cerebral infarction on CT. Correlations between admission Hunt and Hess grade, Fisher grade 39 and Claassen grades 23 with cerebral infarction on CT were analyzed. The outcome at 3 months, based on the GOS, was also analyzed, with unfavorable outcome defined as death, vegetative or severe disability and favorable outcome defined as moderate disability or good recovery. The odds ratio (meaning the ratio of the odds of developing an infarct in one grade to the odds of developing an infarct in the control group) for infarction was calculated at each level of the grading scales. The control group was the grade with the lowest risk of infarction, that is, Hunt and Hess grade 0. In terms of the impact of infarction on outcome at 3 months, 63% of patients (183/292) had favorable outcome and 37% had unfavorable outcome. Of those that had favorable outcome, only 9% had an infarct on CT, whereas of those that had unfavorable outcome, 62% had an infarct on CT (p<0.0001). According to this data, both clinical grade and clot thickness are independently related to risk of infarction, and infarction is associated with poor outcome.

Data from the Cooperative Study on Timing of Aneurysm Surgery was analyzed to assess the prognostic value of various neurological signs and CT parameters for predicting survival and degree of recovery. (Adams H P, Jr. et al., "Usefulness of computed tomography in predicting outcome after aneurysmal subarachnoid hemorrhage: a preliminary report of the Cooperative Aneurysm Study," Neurology 35:1263-1267 (1985)). Baseline CT was graded as normal or having SAH, intraventricular hemorrhage, intracerebral hemorrhage, subdural blood, hydrocephalus, edema, aneurysm or infarct. If SAH was present, clot thickness was graded as diffuse, local thick or local thin. Outcome was assessed by a blinded assessor, at 6 months, using the GOS. The prognostic value of each parameter was evaluated individually. Logistic regression analysis was then used to determine whether CT factors predicted outcome regardless of level of consciousness at admission. 1778 patients were eligible for evaluation. 44 patients were excluded because CT was not done within the prescribed time frame. The remaining 1734 patients were evaluated. Mortality was higher among patients who had blood on CT compared to those who did not (5% versus 27%). Mortality was greater in patients that had diffuse or local thick blood, compared to those who had local thin blood (33% versus 32% versus 10% respectively). Mortality was greater in patients with local thin blood than those with no blood (10% versus 6%). Among 124 alert patients with no blood on CT, mortality was 2.4% at 6 months and good recovery was 93%. Among 684 alert patients with blood on CT, mortality was 12% and good recovery 73%.

In conclusion, the severity of the SAH, as measured semi quantitatively by clot thickness on CT scan, is the most important predictor of the risk for developing DCI and infarction. Since DCI is a well-documented risk factor for poor outcome, it follows that clinical grade at presentation alone cannot adequately predict patients at risk for DCI and poor outcome, and that the volume of the initial hemorrhage must be taken into account when making a judgment about which patients to treat.

9. Drug Delivery to Target Sites in the Brain

The limited permeability of the brain capillary endothelial wall, constituting the blood brain barrier (BBB), poses challenges to the development of methods of drug delivery to target sites in the brain. Such challenges can be overcome by bypassing the BBB and administering a drug locally into the brain near the site of action. Alternatively, the drug can be administered into the subarachnoid space of the spine, i.e., spinal (intrathecal) drug administration, such that the drug is carried from the site of delivery in the spine to the site of action in the brain via the cerebrospinal fluid (CSF). However, such localized intracranial or spinal administrations are invasive and are associated with a risk of CNS infections, which increases if more injections have to be given or if a catheter has to be left in place to repeat the injection. Furthermore, most drugs delivered directly into the cerebrospinal fluid (CSF) are rapidly cleared, exhibiting very short half-lives, thus requiring frequent invasive administrations to maintain therapeutic levels at target sites of the action. This limits the practical applicability of localized drug delivery to the central nervous system (CNS).

In order to overcome such shortcomings, strategies have been developed to circumvent the BBB. These include, for example, osmotic disruption of the BBB, infusion pumps delivering drugs to the CSF, intravenous injection of surface coated nanoparticles, coupling of drugs to a carrier undergoing receptor-mediated transcytosis through the BBB, implantation of tissue or cells, and gene therapy (reviewed in Tamargo, R. J. et al., "Drug delivery to the central nervous system: a review," Neurosurg., Quarterly 2: 259-279 (1992)). Carriers can affect drug level, location, longevity and antigenicity. (Reviewed in Langer, R., "New methods of drug delivery," Science, 249: 1527-1533 (1990); and Langer, R., "Drug delivery and targeting," Nature, 392 (Supp.): 5-10 (1998)). For example, a drug may be chemically modified to selectively alter such properties as biodistribution, pharmacokinetics, solubility, or antigenicity. For example, a drug can be complexed to agents that enables it to cross a normally impermeable barrier, for example, by rendering the drug more lipophilic or coupling it to a molecule that has a specific transport mechanism. (Bodor, N and Simpkins, Science 221 65 (1983); Kumagai et al, J Biol. Chem. 262, 15214 (1987), Jacob et al, J. Med. Chem. 33, 733 (1990)).

9.1. Controlled Release Polymeric Drug Delivery Systems

Biodegradable polymeric drug delivery systems that control the release rate of the contained drug in a predetermined manner can overcome practical limitations to targeted brain delivery. A drug can be attached to soluble macromolecules, such as proteins, polysaccharides, or synthetic polymers via degradable linkages. For example, in animals, antitumor agents such as doxorubicin coupled to N-(2-hydroxypropyl) methacrylamide copolymers showed radically altered pharmacokinetics resulting in reduced toxicity. The half-life of the drug in plasma and the drug levels in the tumor were increased while the concentrations in the periphery decreased. (Kopecek and Duncan, J Controlled Release 6, 315 (1987)). Polymers, such as polyethylene glycol (PEG) can be attached to drugs to either lengthen their lifetime or alter their immunogenicity; drug longevity and immunogenicity also may be affected by biological approaches, including protein engineering and altering glycosylation patterns.

Controlled release systems have been developed both for localized delivery to target sites in the brain, as well as for localized delivery to sites in the spinal cord. (Reviewed in Fournier, E. et al., "Biocompatibility of implantable synthetic polymeric drug carriers: focus on brain compatibility," Biomaterials, 24(19): 331-3331 (2003); Lagarce, F. et al., "Sustained release formulations for spinal drug delivery," J. Drug Del. Sci. Tech., 14(5): 331-343 (2004)).

Controlled release systems deliver a drug at a predetermined rate for a definite time period. (Reviewed in Langer, R., "New methods of drug delivery," Science, 249: 1527-

1533 (1990); and Langer, R., "Drug delivery and targeting," Nature, 392 (Supp.): 5-10 (1998)). Generally, release rates are determined by the design of the system, and are nearly independent of environmental conditions, such as pH. These systems also can deliver drugs for long time periods (days or years). Controlled release systems provide advantages over conventional drug therapies. For example, after ingestion or injection of standard dosage forms, the blood level of the drug rises, peaks and then declines. Since each drug has a therapeutic range above which it is toxic and below which it is ineffective, oscillating drug levels may cause alternating periods of ineffectiveness and toxicity. A controlled release preparation maintains the drug in the desired therapeutic range by a single administration. Other potential advantages of controlled release systems include: (i) localized delivery of the drug to a particular body compartment, thereby lowering the systemic drug level; (ii) preservation of medications that are rapidly destroyed by the body; (iii) reduced need for follow-up care; (iv) increased comfort; and (v) improved compliance. (Langer, R., "New methods of drug delivery," Science, 249: at 1528).

Optimal control is afforded if the drug is placed in a polymeric material or pump. Polymeric materials generally release drugs by the following mechanisms: (i) diffusion; (ii) chemical reaction, or (iii) solvent activation. The most common release mechanism is diffusion. In this approach, the drug is physically entrapped inside a solid polymer that can then be injected or implanted in the body. The drug then migrates from its initial position in the polymeric system to the polymer's outer surface and then to the body. There are two types of diffusion-controlled systems: reservoirs, in which a drug core is surrounded by a polymer film, which produce near-constant release rates, and matrices, where the drug is uniformly distributed through the polymer system. Drugs also can be released by chemical mechanisms, such as degradation of the polymer, or cleavage of the drug from a polymer backbone. Exposure to a solvent also can activate drug release; for example, the drug may be locked into place by polymer chains, and, upon exposure to environmental fluid, the outer polymer regions begin to swell, allowing the drug to move outward, or water may permeate a drug-polymer system as a result of osmotic pressure, causing pores to form and bringing about drug release. Such solvent-controlled systems have release rates independent of pH. Some polymer systems can be externally activated to release more drug when needed. Release rates from polymer systems can be controlled by the nature of the polymeric material (for example, crystallinity or pore structure for diffusion-controlled systems; the lability of the bonds or the hydrophobicity of the monomers for chemically controlled systems) and the design of the system (for example, thickness and shape). (Langer, R., "New methods of drug delivery," Science, 249: at 1529).

Polyesters such as lactic acid-glycolic acid copolymers display bulk (homogeneous) erosion, resulting in significant degradation in the matrix interior. To maximize control over release, it is often desirable for a system to degrade only from its surface. For surface-eroding systems, the drug release rate is proportional to the polymer erosion rate, which eliminates the possibility of dose dumping, improving safety; release rates can be controlled by changes in system thickness and total drug content, facilitating device design. Achieving surface erosion requires that the degradation rate on the polymer matrix surface be much faster than the rate of water penetration into the matrix bulk. Theoretically, the polymer should be hydrophobic but should have water-labile linkages connecting monomers. For example, it was proposed that, because of the lability of anhydride linkages, polyanhydrides would be a promising class of polymers. By varying the monomer ratios in polyanhydride copolymers, surface-eroding polymers lasting from 1 week to several years were designed, synthesized and used to deliver nitrosoureas locally to the brain. ((Langer, R., "New methods of drug delivery," Science, 249: at 1531 citing. Rosen et al, Biomaterials 4, 131 (1983); Leong et al, J. Biomed. Mater. Res. 19, 941 (1985); Domb et al, Macromolecules 22, 3200 (1989); Leong et al, J. Biomed. Mater. Res. 20, 51 (1986), Brem et al, Selective Cancer Ther. 5, 55 (1989); Tamargo et al, J. Biomed. Mater. Res. 23, 253 (1989)).

Several different surface-eroding polyorthoester systems have been synthesized. Additives are placed inside the polymer matrix, which causes the surface to degrade at a different rate than the rest of the matrix. Such a degradation pattern can occur because these polymers erode at very different rates, depending on pH, and the additives maintain the matrix bulk at a pH different from that of the surface. By varying the type and amount of additive, release rates can be controlled. ((Langer, R., "New methods of drug delivery," Science, 249: at 1531 citing. Heller, et al, in Biodegradable Polymers as Drug Delivery Systems, M. Chasin and R. Langer, Eds (Dekker, New York, 1990), pp. 121-161)).

Polymeric materials used in controlled release drug delivery systems described for delivery to the CNS include poly (α-hydroxyacids), acrylic, polyanhydrides and other polymers, such as polycaprolactone, ethylcellulose, polystyrene, etc. A wide range of delivery systems suitable for delivery to the brain and spinal cord have been developed. These include: macroscopic implants, microcapsules, gels and nanogels, microparticles/microspheres, nanoparticles, and composite hydrogel systems. The different types of systems exhibit differences in pharmokinetic and pharmacodynamic profiles of drugs by affecting different physical and chemical processes involved in drug release, such as water penetration, drug dissolution, and degradation of matrix and drug diffusion. (Reviewed in Siepmann, J. et al., "Local controlled drug delivery to the brain: mathematical modeling of the underlying mass transport mechanisms," International Journal of Pharmaceutics, 314: 101-119 (2006).

10. Current Treatment Options 10.1. Treatment of SAH

The management of SAH consists of general measures to stabilize the patient, specific measures to prevent rebleeding by obliterating the bleeding source, prevention of vasospasm, and prevention and treatment of complications.

General Measures

The first priority is to stabilize the patient. Those with a depressed level of consciousness may need to be intubated and mechanically ventilated. Blood pressure, pulse, respiratory rate and Glasgow Coma Scale are monitored frequently. Once the diagnosis is confirmed, admission to an intensive care unit may be preferable, especially given that 15% of such patients have a further episode (rebleeding) in the first hours after admission. Nutrition is an early priority, with oral or nasogastric tube feeding being preferable over parenteral routes. Analgesia (pain control) is important in order to permit good blood pressure control but must be balanced against oversedating patient, which impacts mental status and thus interfere with the ability to monitor the level of consciousness. Deep vein thrombosis is prevented with compression stockings, intermittent pneumatic compression of the calves, pharmacologic agents, or a combination.

Prevention of Rebleeding

Patients with a large intracerebral hematoma associated with depressed level of consciousness or focal neurological symptoms may be candidates for urgent surgical removal of the blood and occlusion of the bleeding aneurysm. A catheter or tube may be inserted into the ventricles to treat hydrocephalus. The remainder are stabilized and undergo a transfemoral catheter angiogram or CT angiogram later. After the first 24 hours, rebleeding risk remains about 20% over the subsequent four weeks, suggesting that interventions should be aimed at reducing this risk.

Rebleeding is hard to predict but may happen at any time and carries a dismal prognosis. Interventions to prevent rebleeding, therefore are performed as early as possible. If a cerebral aneurysm is identified on angiography, two measures are available to reduce the risk of further bleeding from the same aneurysm: neurosurgical clipping and endovascular coiling. Clipping requires a craniotomy (opening of the skull) to locate the aneurysm, followed by the placement of a clip or clips across the neck of the aneurysm. Coiling is performed through the large blood vessels: a catheter is inserted into the femoral artery in the groin, and advanced through the aorta to the arteries (both carotid arteries and both vertebral arteries) that supply the brain. When the aneurysm has been located, metallic coils are deployed that lead to formation of a blood clot in the aneurysm and obliteration. The decision as to which treatment is undertaken typically is made by a multidisciplinary team, often including a neurosurgeon and a neuroradiologist.

Aneurysms of the middle cerebral artery and its related vessels are hard to reach and of less optimal configuration for endovascular coiling and tend to be amenable to clipping, while those of the basilar artery and posterior arteries are hard to reach surgically and tend to be more accessible for endovascular management. The main drawback of coiling is the possibility that the aneurysm may recur; this risk is lower in the surgical approach. Patients who have undergone coiling are typically followed up for many years with angiography or other measures to ensure recurrence of aneurysms is identified early.

10.2. Current Treatment Options for Aneurysmal SAH

Changes in management of patients with aneurysmal SAH, including early neurosurgical aneurysm clipping or endovascular coiling, nimodipine and improved intensive care, are believed to account for the reduction in overall mortality due to aneurysmal SAH, and to a reduction in the contribution of angiographic vasospasm and DCI to death and disability after aneurysmal SAH. (Lovelock C E et al., "Antithrombotic Drug Use, Cerebral Microbleeds, and Intracerebral Hemorrhage. A Systematic Review of Published and Unpublished Studies," Stroke, 41(6): 1222-1228 (2010)).

Rhoney et al. presents a review on the currently available treatment considerations in the management of aneurysmal SAH. (Rhoney, D. H. et al., "Current and future treatment considerations in the management of aneurysmal subarachnoid hemorrhage," J. Pharm. Pract., 23(5): 408-424 (2010)). Treatment is usually divided into three categories: supportive therapy, prevention of complications and treatment of complications. Initial supportive therapy upon diagnosis of aneurysmal hemorrhage can include, but is not limited to, to ensuring adequate oxygenation, prevention of blood pressure fluctuations, isotonic or hypertonic IV fluids in order to maintain normal intracranial pressure, etc. Rebleeding can be reduced by maintaining systolic blood pressure below a threshold value that varies from patient to patient until the aneurysm is secured by endovascular coiling or neurosurgical clipping along with treatment with anti-fibrinolytic agents, such as tranexamic acid or amniocaproic acid. Medical complications, such as stress related mucosal damage prophylaxis is used either with proton pump inhibitors or histamine type 2 blocking agents in patients at risk for stress ulceration. Venous thrombo-embolism (VTE) prophylaxis is implemented either through a mechanical device or chemically with anticoagulants, such as heparin or enoxaparin. Glycemic control is utilized to maintain a serum glucose range between 80-140 mg/dL.

Nicardipine is a short acting dihydropyridine calcium channel antagonist with a more precise effect on cerebral vasculature rather than maintenance of intracranial pressure. Nicardipine has an onset action of 1 to 5 minutes and duration of action up to 3 hours. High blood pressure associated with subarachnoid hemorrhage can alternatively be treated with alpha/beta adrenergic antagonists, such as labetalol. Clevidipine is an alternative dihydropyridine calcium channel antagonist that can lower blood pressure with a quick offset of effect within 5 to 15 minutes. Esmolol is an antihypertensive agent that can be used with in the treatment of hypertension in patients with acute neurological illness. The effect of any antihypertensive agent on cerebral oxygenation is another consideration factor.

10.3. Treatment of Secondary Complications Associated with SAH

Current treatments to prevent or reduce angiographic vasospasm and DCI consist of measures to prevent or minimize secondary brain injury, use of calcium channel antagonists, hemodynamic management and endovascular therapies. Therapy often is initiated prophylactically in patients and may include: (in stage 1) hemodynamic stabilization including maintaining normovolemia, managing blood pressure, and orally-administered L-type voltage-gated calcium channel antagonists; and (in stage 2) further hemodynamic manipulation or infusion of vasodilator drugs into vasospastic arteries or dilating them with balloons. However, the aforementioned treatments are expensive, time consuming and only partially effective.

For over 35 years, physicians have been trying to prevent or reduce the incidence of adverse consequences of SAH, including angiographic vasospasm and DCI, and have had limited effect due to side effects of current agents or lack of efficacy. There currently are no FDA approved agents for the prevention of vasospasm or the reduction of delayed ischemic neurologic deficits also known as delayed cerebral ischemia (DCI). Current methods to prevent vasospasm have failed due to lack of efficacy or to safety issues, primarily hypotension and cerebral edema. Currently, the only FDA-approved available agent is nimodipine, which has minimal effect on angiographic vasospasm in clinically-used doses, although it improved outcome in SAH patients.

Voltage-dependent calcium channel antagonists may be effective in preventing and reversing vasospasm to a certain extent, however, prior art treatments administer doses too low to exert a maximal pharmacologic effect. Endothelin-receptor antagonists also may be effective at preventing and reversing angiographic vasospasm to a certain extent, but this reversal or prevention of angiographic vasospasm does not translate into as marked an improvement in outcome as would be anticipated by the reduction in angiographic vasospasm. Without being limited by theory, it is postulated that the systemic delivery of the voltage-dependent calcium channel antagonists may cause side effects that mitigate the beneficial effects on angiographic vasospasm, such as, for example, systemic hypotension and pulmonary vasodilation with pulmonary edema, which prevent the administration of higher systemic doses. Dilation of blood vessels in the lungs also may cause lung edema and lung injury. Without being limited by theory, it is postulated that systemic delivery of the voltage-dependent calcium channel antagonists may limit other effects of SAH that contribute to DCI, including cortical spreading ischemia and microthromboemboli.

Treatment of DCI

Treatment for DCI that develops after aneurysmal SAH includes oral or intravenous nimodipine in North America and Europe for up to 3 weeks post aneurysmal SAH. Medical management directed at optimizing cerebral blood flow by raising the blood pressure and avoiding factors that adversely affect cerebral blood flow or that increase brain metabolism are believed to be important. If, despite these measures, a patient deteriorates from DCI, rescue therapies are instituted, including induced hypertension, cerebral balloon angioplasty, or local administration of calcium channel antagonists or other vasodilators.

Treatment of Vasospasm

Nimodipine, an oral calcium channel antagonist, has been shown in clinical trials to reduce the chance of a poor outcome, however it may not significantly reduce the amount of angiographic vasospasm detected on angiography. Other calcium channel antagonists and magnesium sulfate have been studied, but are not presently recommended. There is no evidence that shows benefit if nimodipine is given intravenously but the studies conducted have included small numbers of patients. In traumatic SAH, the efficacy of oral nimodipine remains in question.

When administered in the doses used clinically for oral or intravenous administration, nimodipine is associated with dose-limiting hypotension in up to 50% of patients. (Radhakrishnan D, and Menon D K, "Haemodynamic effects of intravenous nimodipine following aneurysmal subarachnoid haemorrhage: implications for monitoring," Anaesthesia, 52:489-491 (1997)). Plasma concentrations exceed those associated with hypotension, yet CSF concentrations are well below therapeutic concentrations. (Allen G. S. et al., "Cerebral arterial spasm—a controlled trial of nimodipine in patients with subarachnoid hemorrhage," N. Engl. J. Med. 308:619-624 (1983)). Hypotension is deleterious to patients with aneurysmal SAH because it may lower cerebral perfusion pressure and worsen DCI. (Dankbaar J W et al., "Effect of different components of triple-H therapy on cerebral perfusion in patients with aneurysmal subarachnoid haemorrhage: a systematic review," Crit. Care, 14:R23 (2010); Darby J. M. et al., "Acute cerebral blood flow response to dopamine-induced hypertension after subarachnoid hemorrhage," J. Neurosurg., 80:857-864 (1994)).

While there is some evidence suggesting that nimodipine can have neuroprotective effects, it is not conclusive. For example, Aslan et al. found that intravenous administration of nimodipine to patients with severe traumatic brain injury resulted in significantly higher cerebral perfusion pressure (CPP), higher jugular venous oxygen saturation, and higher scores on Glasgow Coma Scale, while lower intracranial pressure, jugular lactate and glucose levels, in treated vs. control groups. However, the study was limited to patients who had severe head trauma with a Glasgow Coma Scale≤8 and patients with traumatic or chronic lung pathology or brain lesion who required surgical intervention were excluded from this study. (Aslan, A. et al., "Nimodipine can improve cerebral metabolism and outcome in patients with severe head trauma," Pharmacol. Res., 59(2): 120-124 (2008)). Zhao et al. (1) reported that intravenous administration of nimodipine in a cisterna magna SAH rat model is capable of restoring the regional cerebral blood flow that is significantly reduced as a result of SAH; (2) reported the concomitant nimodipine-induced angiographic dilation of major cerebral arteries that were constricted as a result of SAH, and (3) demonstrated that the integrity of the blood brain barrier, which is disrupted as a result of SAH correlating with poor neurologic grade, can be restored with nimodipine administration. (Zhao, W. J. et al., "Nimodipine attenuation of early brain dysfunctions is partially related to its inverting acute vasospasm in a cisterna magna subarachnoid hemorrhage (SAH) model in rats," Int. J. Neurosci., PMID: 22694164 (2012)). Nimodipine has also been reported to enhance the excitability of hippocampal neurons in a rabbit study. (Disterhot. J. F. et al., "Nimodipine facilitates learning and increases excitability of hippocampal neurons in aging rabbits," Drugs in Development, 2: 395-403; discussion, p. 405, (1993)).

Dreier et al. reported that intravenous administration of nimodipine to rats can reverse cortical spreading ischemia after SAH triggered by hemoglobin in rats to cortical spreading hyperemia, but conceded that no conclusion could be drawn from their study regarding territorial infarctions after SAH, which likely include other pathogenic cascades. (Dreier, J. P. et al., "Ischemia triggered by red blood cell products in the subarachnoid space is inhibited by nimodipine administration or moderate volume expansion/hemodilution in rats," Neurosurgery, 51(6): 1457-1465 (2002)).

Hemodynamic manipulation, previously referred to as "triple H" therapy, often is used as a measure to treat vasospasm. This entails the use of intravenous fluids and vasoconstrictor drugs to achieve a state of hypertension (high blood pressure), hypervolemia (excess fluid in the circulation) and hemodilution (mild dilution of the blood). Induced hypertension is believed to be the most important component of this treatment although evidence for the use of this approach is inconclusive, and no sufficiently large randomized controlled trials ever have been undertaken to demonstrate its benefits.

If symptomatic vasospasm or DCI is resistant to medical treatment, angiography may be attempted to identify the sites of angiographic vasospasm and to administer vasodilator medication (drugs that relax the blood vessel wall) directly into the artery (pharmacological angioplasty), and mechanical angioplasty (opening the constricted area with a balloon) may be performed.

Removal of subarachnoid blood clots with recombinant tissue plasminogen activator (r-t-PA) in patents with aneurysmal SAH has been reported to reduce angiographic vasospasm and DCI but with inconclusive results due to the small number of patients treated and lack of randomized, blinded trials. (Amin-Hanjani, S. et al., "Does intracisternal thrombolysis prevent vasospasm after aneurysmal subarachnoid hemorrhage? A meta-analysis," Neurosurgery, 54(2): 326-334; discussion 334-335 (2004); Kramer A H, Fletcher J J: Locally-administered intrathecal thrombolytics following aneurysmal subarachnoid hemorrhage: a systematic review and meta-analysis. Neurocrit Care 14: 489-499 (2011)). Hydroxymethylglutaryl coenzyme A reductase inhibitors (statins), such as simvastatin, pravastatin, etc. have also become routine practice at some institutions for the prevention of cerebral vasospasm following aneurysmal SAH owing to their pleiotropic effects. In experimental models, statins are associated with increase endothelial nitric oxide (NO) synthase production, anti-inflammatory effects by inhibition of adhesion molecules, free radical scavenging, and inhibition of platelet aggregation. (McGirt, M. J. et al., "Simvastatin increases endothelial nitric oxide synthase and ameliorates cerebral vasospasm resulting from subarachnoid hemorrhage," Stroke, 33(12): 2950-2956 (2002); McGirt, M. J. et al., "Systemic administration of simvastatin after the onset of experimental subarachnoid hemorrhage attenuates cerebral vasospasm," Neurosurgery, 58(5): 945-951; discussion 945-951 (2006)).

Magnesium, acting as an NMDA receptor antagonist and calcium channel blocker leading to smooth muscle relaxation and vessel dilation, has been investigated for the prevention of cerebral vasospasm. (Macdonald, R. L. et al., "Magnesium and experimental vasospasm," J. Neurosurg., 100(1): 106-110 (2004)). Hypomagnesemia is common following aneurysmal SAH and is associated with poor outcome and development of vasospasm. (van den Bergh, W. M. et al., "Magnesium sulfate in aneurysmal subarachnoid hemorrhage: a randomized controlled trial," Stroke, 36(5): 1011-1015 (2005)). A randomized clinical trial that included 1204 patients did not find that intravenous magnesium sulphate improved outcome in patients with SAH (Dorhout Mees, S. M. et al., "Magnesium for aneurysmal subarachnoid haemorrhage (MASH-2): a randomised placebo-controlled trial," Lancet 380:44-49 (2012)). Meta-analysis of the 7 main randomized trials of magnesium in SAH confirmed this so that routine administration of intravenous magnesium to raise serum magnesium concentrations above normal is not recommended.

Clazosentan, a selective endothelin (ET) receptor antagonist, was the subject of investigation in the CONSCIOUS trials. In the CONSCIOUS-1 study, clazosentan significantly reduced the incidence of blood vessel spasms after stroke. (Macdonald, R. L. et al., "Clazosentan to overcome neurological ischemia and infarction occurring after subarachnoid hemorrhage (CONSCIOUS-1): randomized, double-blind, placebo-controlled phase 2 dose-finding trial," Stroke, 39(11): 3015-3021 (2008). CONSCIOUS-2 was a randomized, double-blind, placebo-controlled, phase 3 study that assigned patients with SAH secured by surgical clipping to clazosentan (5 mg/h, n=768) or placebo (n=389) for up to 14 days. The primary composite endpoint (week 6) included all-cause mortality, vasospasm-related new cerebral infarcts, delayed ischemic neurological deficit due to vasospasm, and rescue therapy for vasospasm. In the all-treated dataset, the primary endpoint was met in 161 (21%) of 764 clazosentan-treated patients and 97 (25%) of 383 placebo-treated patients (relative risk reduction 17%, 95% $C_{1-4}$ to 33; p=0.10). Poor functional outcome (GOSE score</=4) occurred in 224 (29%) clazosentan-treated patients and 95 (25%) placebo-treated patients (−18%, −45 to 4; p=0.10). Lung complications, anaemia, and hypotension were more common with clazosentan. Mortality (week 12) was 6% in both groups. Clazosentan at 5 mg/h had no significant effect on mortality and vasospasm-related morbidity or functional outcome. (Macdonald, R. L. et al., "Clazosentan, an endothelin receptor antagonist, in patients with aneurysmal subarachnoid haemorrhage undergoing surgical clipping: a randomised, double-blind, placebo-controlled phase 3 trial (CONSCIOUS-2)," Lancet Neurol. 10:618-625 (2011). CONSCIOUS-3 was a double-blind, placebo-controlled, randomized phase III trial in patients with SAH secured by endovascular coiling and randomized to </=14 days intravenous clazosentan (5 or 15 mg/h) or placebo (Macdonald, R. L. et al., "Randomized trial of clazosentan in patients with aneurysmal subarachnoid hemorrhage undergoing endovascular coiling," Stroke 43:1463-1469 (2012)). The primary composite end point was the same as CONSCIOUS-2. CONSCIOUS-3 was halted prematurely following completion of CONSCIOUS-2; 577/1500 of planned patients (38%) were enrolled and 571 were treated (placebo, n=189; clazosentan 5 mg/h, n=194; clazosentan 15 mg/h, n=188). The primary end point occurred in 50/189 of placebo-treated patients (27%), compared with 47/194 patients (24%) treated with clazosentan 5 mg/h (odds ratio [OR], 0.786; 95% CI, 0.479-1.289; P=0.340), and 28/188 patients (15%) treated with clazosentan 15 mg/h (OR, 0.474; 95% CI, 0.275-0.818; P=0.007). Poor outcome (extended Glasgow Outcome Scale score</=4) occurred in 24% of patients with placebo, 25% of patients with clazosentan 5 mg/h (OR, 0.918; 95% CI, 0.546-1.544; P=0.748), and 28% of patients with clazosentan 15 mg/h (OR, 1.337; 95% CI, 0.802-2.227; P=0.266). Pulmonary complications, anemia, and hypotension were more common in patients who received clazosentan than in those who received placebo. Clazosentan 15 mg/h significantly reduced post aneurysmal SAH vasospasm-related morbidity/all-cause mortality; however, neither dose improved outcome (extended Glasgow Outcome Scale). Clazosentan currently is not approved for use for SAH patients.

Current therapies to prevent or reduce the incidence of secondary complications after aSAH, such as DCI and angiographic vasosparm, are risky, only marginally efficacious, expensive and time-consuming. Thus, there is a large unmet medical need for safe, effective treatments to reduce the need for rescue therapy and improve functional outcome While conventional therapies have been focusing on treating cerebral vasospasms following SAH, accumulating evidence suggests that there are additional complications derived from SAH, which need to be targeted for treatment interventions in order to improve prognosis following SAH treatment. The described invention offers such an approach.

SUMMARY

According to one aspect, the described invention provides a method for treating at least one cerebral artery at risk of interruption due to subarachnoid hemorrhage (SAH) in a human subject, comprising: a) providing a flowable sustained release particulate composition comprising: (i) a microparticle formulation comprising a plurality of particles of uniform size distribution, and a therapeutic amount of at least one first therapeutic agent, wherein the first therapeutic agent is dispersed throughout each particle, adsorbed onto the particles, or in a core surrounded by a coating; (ii) and a pharmaceutical carrier; and b) administering the flowable sustained release particulate composition locally, via an injection apparatus, either intracisternally into the subarachnoid space in a cistern closest to the cerebral artery at risk for interruption; intraventricularly so that the pharmaceutical composition is carried by cerebrospinal flow; or intrathecally into the spinal subarachnoid space so that the pharmaceutical composition is carried by cerebrospinal flow; so as to contact the at least one artery of the subarachnoid space at risk of interruption due to the subarachnoid hemorrhage, without the first therapeutic agent entering systemic circulation in an amount to cause unwanted side effects, wherein interruption of the cerebral artery is associated with at least one delayed complication, wherein the release characteristics of the flowable sustained release particulate composition are as follows: (1) about 50%-100% of the first therapeutic agent is released within 6 days to 14 days; (2) upon release, the concentration of the first therapeutic agent in plasma (PLASMA-$C_{av}$) is less than about 30-40 ng/mL; and (3) upon release, the concentration of the first therapeutic agent in cerebrospinal fluid (CSF) (CSF-$C_{av}$) is at least about 5 ng/mL to about 5000 ng/mL.

According to one embodiment, the delayed complication associated with the interruption of the cerebral artery is at least one of an angiographic vasospasm, a plurality of microthromboemboli, a cortical spreading ischemia, or a delayed cerebral ischemia (DCI). According to another embodiment, the cerebral artery is an anterior cerebral artery, a middle cerebral artery, an internal carotid artery, a basilar cerebral artery, a vertebral cerebral artery, or a combination thereof. According to another embodiment, each microparticle is of a particle size from about 40 µm to about 100 µm. According to another embodiment, the mean size distribution is about 70 µm. According to another embodiment, each microparticle is loaded with at least 65% (wt/wt) of the at least one first therapeutic agent, wherein the first therapeutic agent is a calcium channel antagonist, an endothelin antagonist, a transient receptor potential (TRP) protein antagonist, or a combination thereof. According to another embodiment, the calcium channel antagonist is selected from the group consisting of an L-type voltage dependent calcium channel inhibitor, an R-type voltage dependent calcium channel inhibitor, an N-type voltage dependent calcium channel inhibitor, a P/Q-type voltage dependent calcium channel inhibitor, a T-type voltage dependent calcium channel inhibitor, or a combination thereof. According to another embodiment, the L-type voltage dependent calcium channel inhibitor is a dihydropyridine, selected from the group consisting of amlodipine, aranidipine, azelnidipine, bamidipine, benidipine, cinaldipine, efonidipine, felodipine, isradipine, lacidipine, lemildipine, lercanidipine, nicardipine, nifedipine, nilvadipine, nimodipine, nisoldipine, nitrendipine, manidipine, pranidipine, or a combination thereof. According to another embodiment, the dihydropyridine is nimodipine. According to another embodiment, the pharmaceutical carrier comprises 0% to 5% by weight hyaluronic acid or a derivative thereof, wherein the hyaluronic acid has an average molecular weight of about 500 kDa. According to another embodiment, the injection apparatus is a needle, a cannula, a catheter, or a combination thereof. According to another embodiment, viscosity of the flowable pharmaceutical composition at 20° C., when administered intracisternally, is from about 100 cP to about 1,000 cp. According to another embodiment, viscosity of the flowable pharmaceutical composition at 20° C., when administered intraventricularly, is from about 0.5 cP to about 50 cp. According to another embodiment, viscosity of the flowable pharmaceutical composition at 20° C., when administered intrathecally into the spinal subarachnoid space, is from about 0.5 cP to about 50 cp. According to another embodiment, maximum tolerated dose of the at least one first therapeutic agent when administered intracisternally is from 40 mg to about 1,000 mg. According to another embodiment, maximum tolerated dose of the at least one first therapeutic agent when administered intraventricularly is from 40 mg to about 1,000 mg. According to another embodiment, maximum tolerated dose of the at least one first therapeutic agent when administered intrathecally is from 40 mg to about 1,000 mg. According to another embodiment, the cerebral ventricle is a lateral ventricle, a third ventricle, a fourth ventricle, or a combination thereof. According to another embodiment, the cerebral cistern is a carotid cistern, a chiasmatic cistern, a Sylvian cistern, an interhemispheric cistern, an ambient cistern, a crural cistern, an interpeduncular cistern, a prepontine cistern, a lateral medullary cistern, a cisterna magna, or a combination thereof. According to another embodiment, the particulate formulation comprises a femtoparticle, a picoparticle, a microparticle, or a nanoparticle. According to another embodiment, each particle of the microparticulate formulation is a microparticle. According to another embodiment, each microparticle comprises a matrix. According to another embodiment, the matrix comprises a biodegradable polymer. According to another embodiment, the biodegradable polymer is a poly(lactide-co-glycolide) (PLGA) polymer, wherein the lactide to glycolide ratio is 65:35 or 50:50. According to another embodiment, the pharmaceutically acceptable carrier comprises a matrix. According to another embodiment, the pharmaceutically acceptable carrier comprises nanoparticles. According to another embodiment, the therapeutic agent is dispersed throughout the nanoparticles, adsorbed into the nanoparticles, in a core of the nanoparticles surrounded by a coating, or a combination thereof. According to another embodiment, the pharmaceutically acceptable carrier is a slow release carrier. According to another embodiment, the pharmaceutically acceptable carrier is a localized release carrier. According to another embodiment, the pharmaceutically acceptable carrier is a depot release carrier. According to another embodiment, the pharmaceutically acceptable carrier is a delayed release carrier. According to another embodiment, the pharmaceutically acceptable carrier is a long-term release carrier. According to another embodiment, the pharmaceutically acceptable carrier comprises aqueous channels. According to another embodiment, the pharmaceutically acceptable carrier is a biphasic release carrier. According to another embodiment, the pharmaceutically acceptable carrier is an extended release carrier. According to another embodiment, the concentration of the first therapeutic agent in plasma (PLASMA-$C_{av}$) is from 0.200 ng/ml/day to 30 mg/ml/day for at least 4 days after administration. According to another embodiment, the concentration of the first therapeutic agent in plasma (PLASMA-Cav) is less than 5 ng/ml/day for at least 14 days after administration. According to another embodiment, the concentration of the first therapeutic agent in cerebrospinal fluid (CSF) (CSF-Cav) is from 5 ng/ml/day to 30 mg/ml/day for at least 14 days after administration. According to another embodiment, the therapeutic amount of the first therapeutic agent is effective to decrease angiographic diameter of the cerebral artery at risk of interruption such that percent change in angiographic diameter of at least one cerebral artery is less than 50% compared to baseline. According to another embodiment, the therapeutic amount of the first therapeutic agent is effective to decrease occurrence of delayed cerebral ischemia (DCI) within 14 days of symptom onset of subarachnoid hemorrhage (SAH). According to another embodiment, the therapeutic amount of the first therapeutic agent is effective to decrease occurrence of delayed cerebral infarction on CT within 30 days of symptom onset of subarachnoid hemorrhage (SAH). According to another embodiment, the therapeutic amount of the first therapeutic agent is effective to decrease occurrence of delayed cerebral ischemia. According to another embodiment, occurrence of delayed cerebral ischemia is assessable as a decrease of at least 2 points on the modified glasgow coma score or an increase of at least 2 points on the abbreviated National Institutes of Health Stroke Scale lasting for at least 2 hours. According to another embodiment, the therapeutic amount of the first therapeutic agent is effective to reduce need for rescue therapy.

DETAILED DESCRIPTION OF THE INVENTION

GLOSSARY

Figure 1:
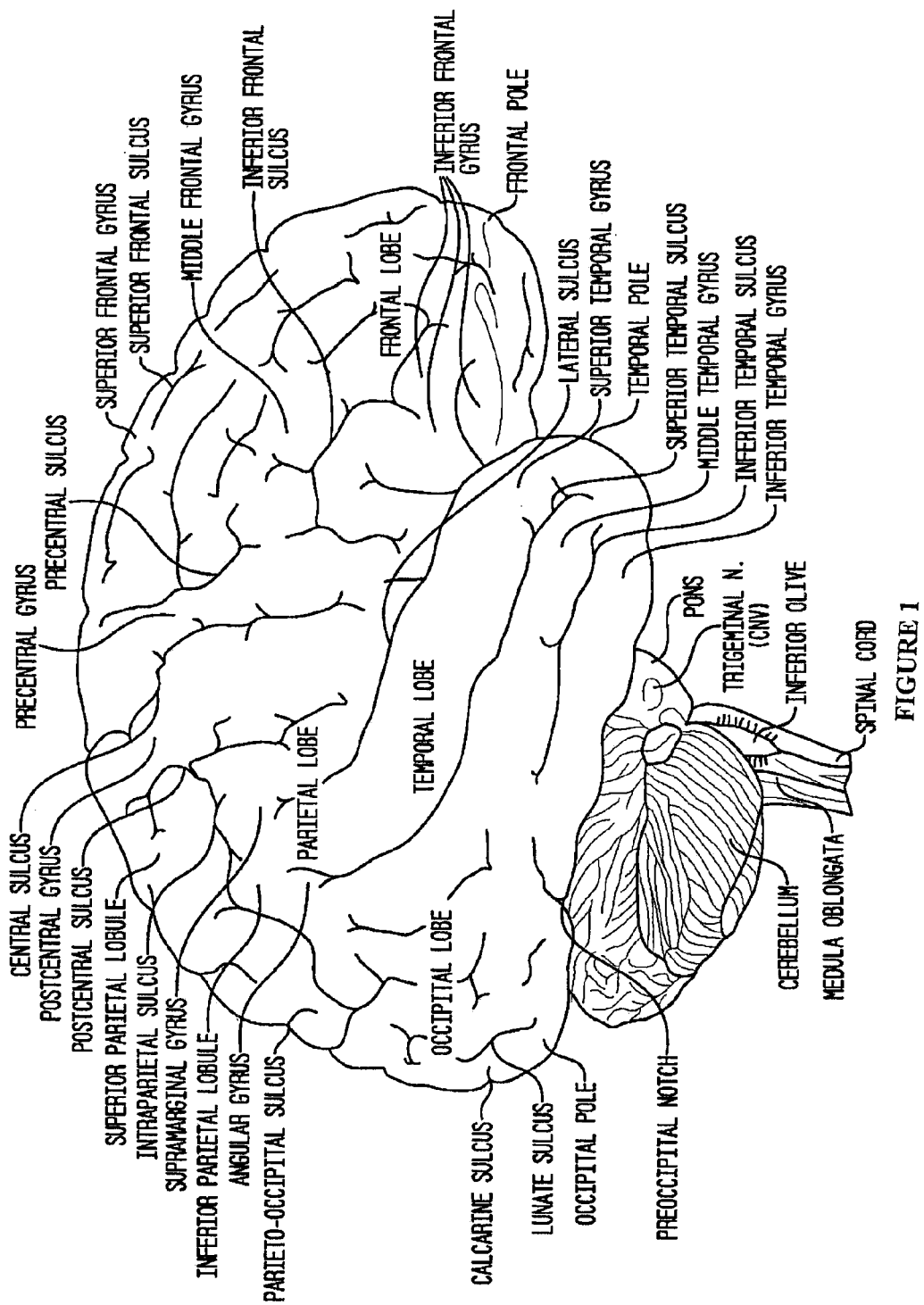
FIG. 1 shows an illustrative lateral view of the human brain (Stedman's Medical Dictionary, 27$^{th}$ Edition, plate 7 at A7 (2000)).
Figure 2:
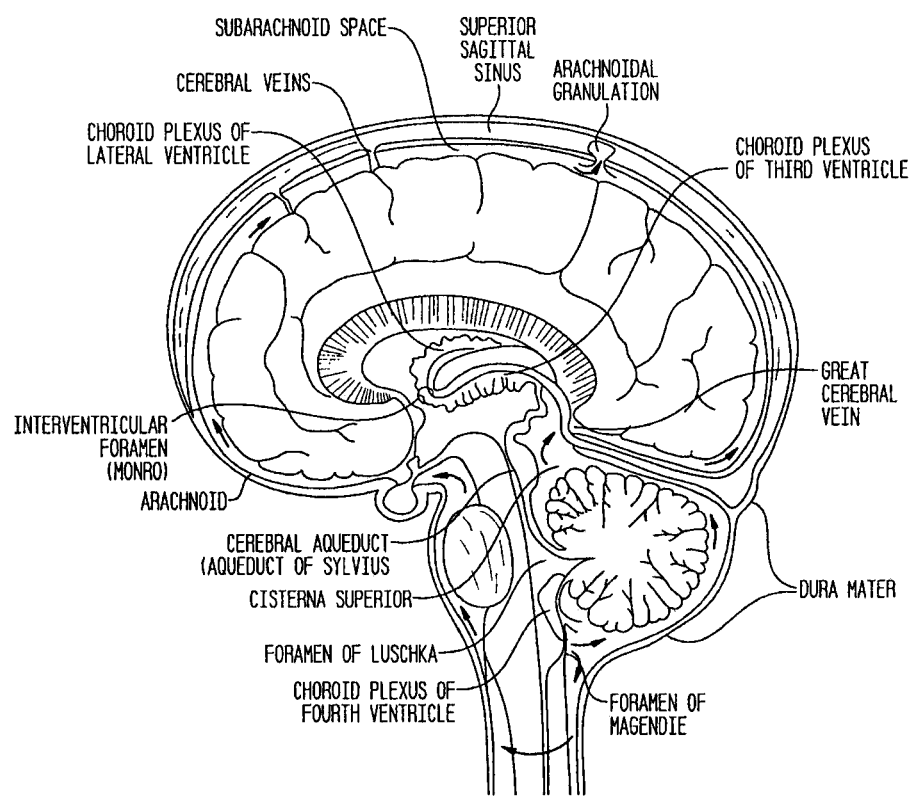
FIG. 2 shows an illustrative sagittal view of the human brain (Correlative Neuroanatomy & Functional Neurology, 18$^{th}$ Ed., p. 46 (1982)).
Figure 3:
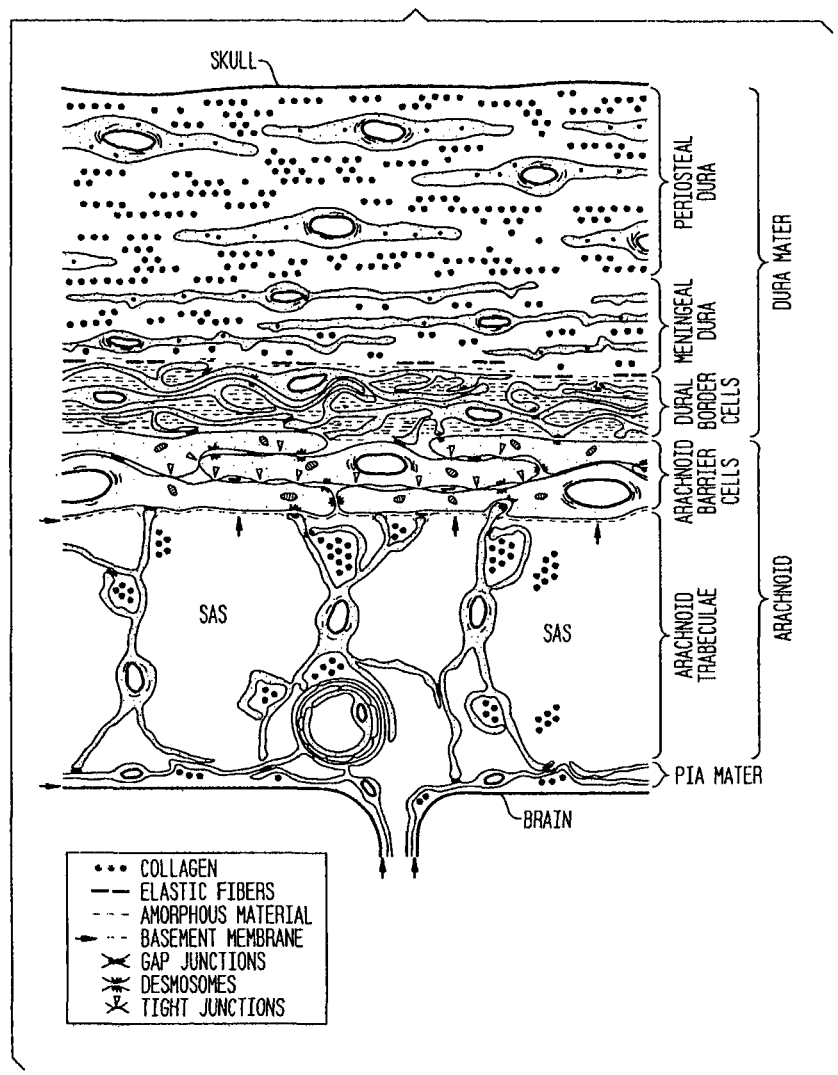
FIG. 3 shows an illustrative view of a cross section of the intact meninges from the inner surface of the skull (upper) to the external surface of the brain (lower). Collagen is present in the periosteal and meningeal dura (large dots, orientation of fibrils not indicated) and in the subarachnoid space (SAS), usually in folds of trabecular cells. The dural border cell layer has no extracellular collagen, few cell junctions, enlarged extracellular spaces (but no basement membrane), and fibroblasts that are distinct from those of the outer portions of the dura. The arachnoid barrier cell layer has essentially no extracellular space, numerous cell junctions, more plump appearing cells, and a comparatively continuous basement membrane on its surface toward the SAS. Note the continuity of cell layers from the arachnoid to the dura (no intervening space), the characteristic appearance of the arachnoid trabeculae, and the relationship of the pia (from Haines D E: On the question of subdural space. Anat Rec 230:3-21, 1991).
Figure 4:
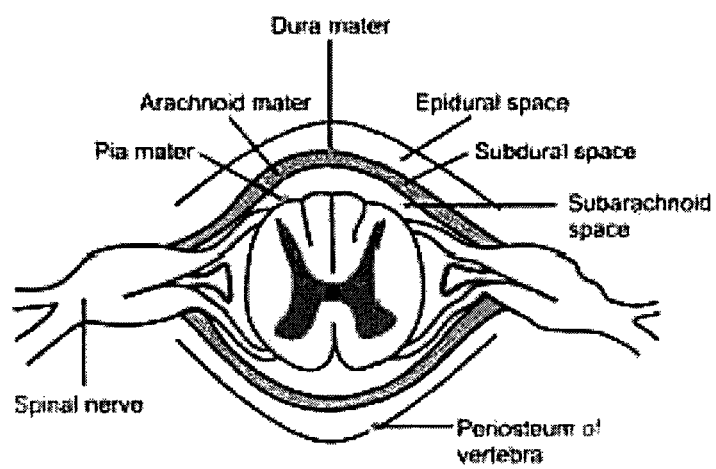
FIG. 4 is a schematic drawing depicting the meninges and their spaces surrounding the spinal cord. (Kulkarni, N. V., "Clinical anatomy for students: problem solving approach," Jaypee Brothers Medical Publishers (P) Ltd., New Delhi, p. 348-349 (2006)). The meninges are associated with three spaces: epidural space, subdural space and subarachnoid space.
Figure 5:
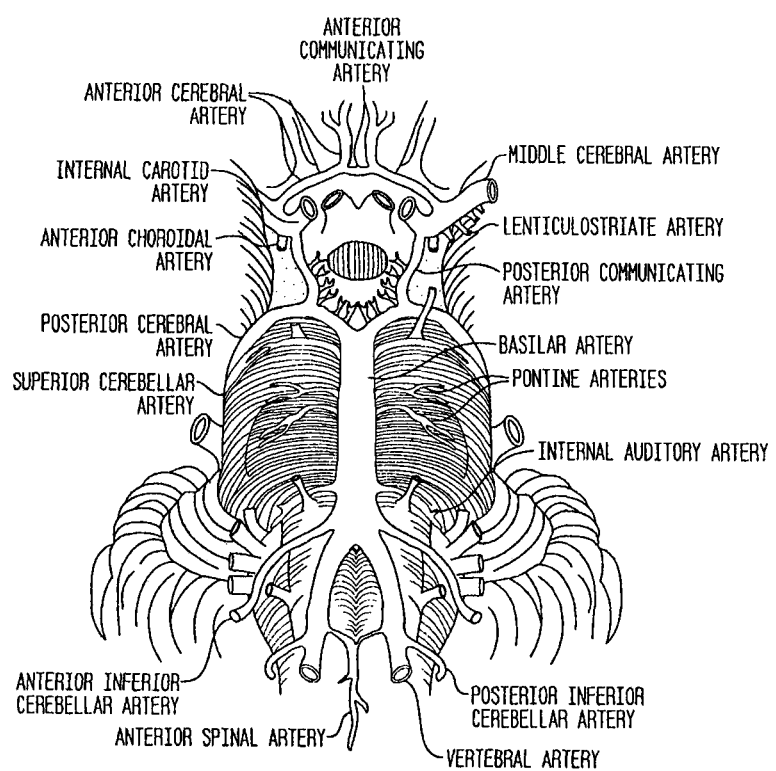
FIG. 5 shows an illustrative view of the circle of Willis and principal arteries of the brain (Correlative Neuroanatomy & Functional Neurology, 18$^{th}$ Ed., p. 48 (1982)).
Figure 6:
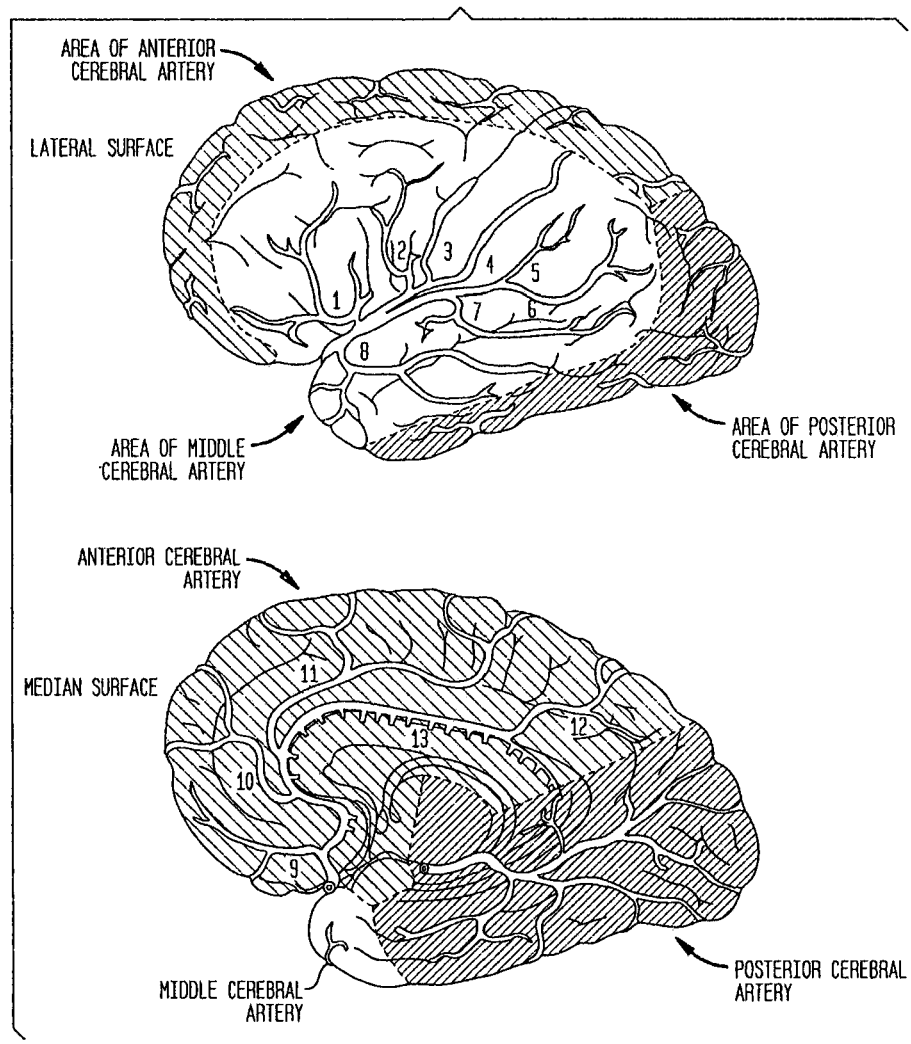
FIG. 6 shows an illustrative view of the arterial supply of the cerebral cortex. 1: orbitofrontal artery; 2: prerolandic artery; 3: rolandic artery; 4: anterior parietal artery; 5: posterior parietal artery; 6: angular artery; 7: posterior temporal artery; 8: anterior temporal artery; 9: orbital artery; 10: frontopolar artery; 11: callosomarginal artery; 12: posterior internal frontal artery; 13: pericallosal artery. (Correlative Neuroanatomy & Functional Neurology, 18$^{th}$ Ed., p. 50 (1982)).
Figure 7:
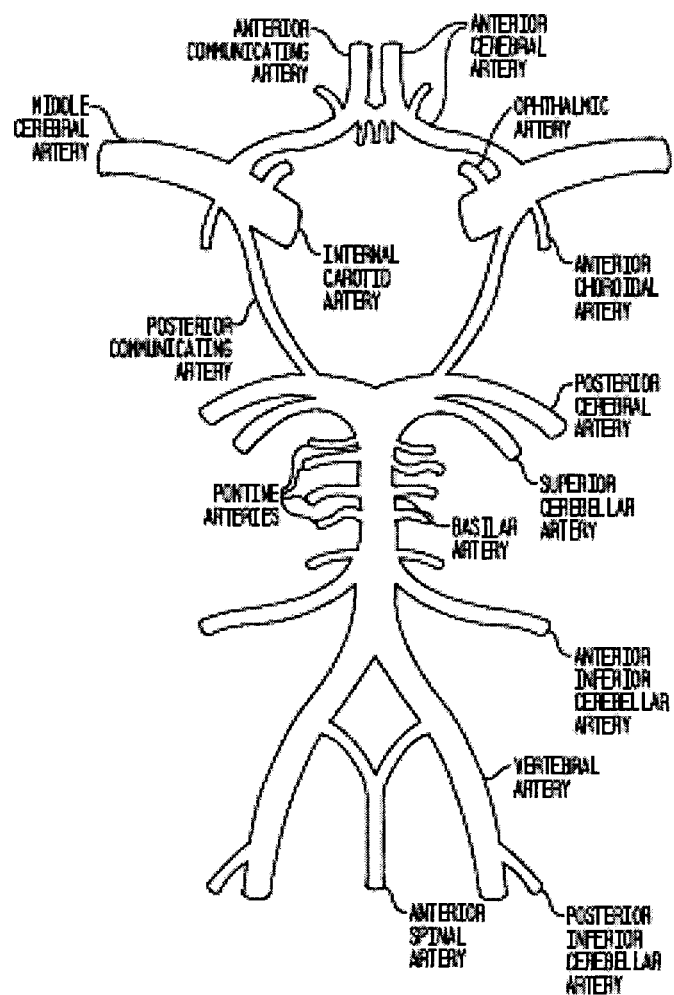
FIG. 7 shows an illustrative view of the cerebral arteries.
Figure 8:
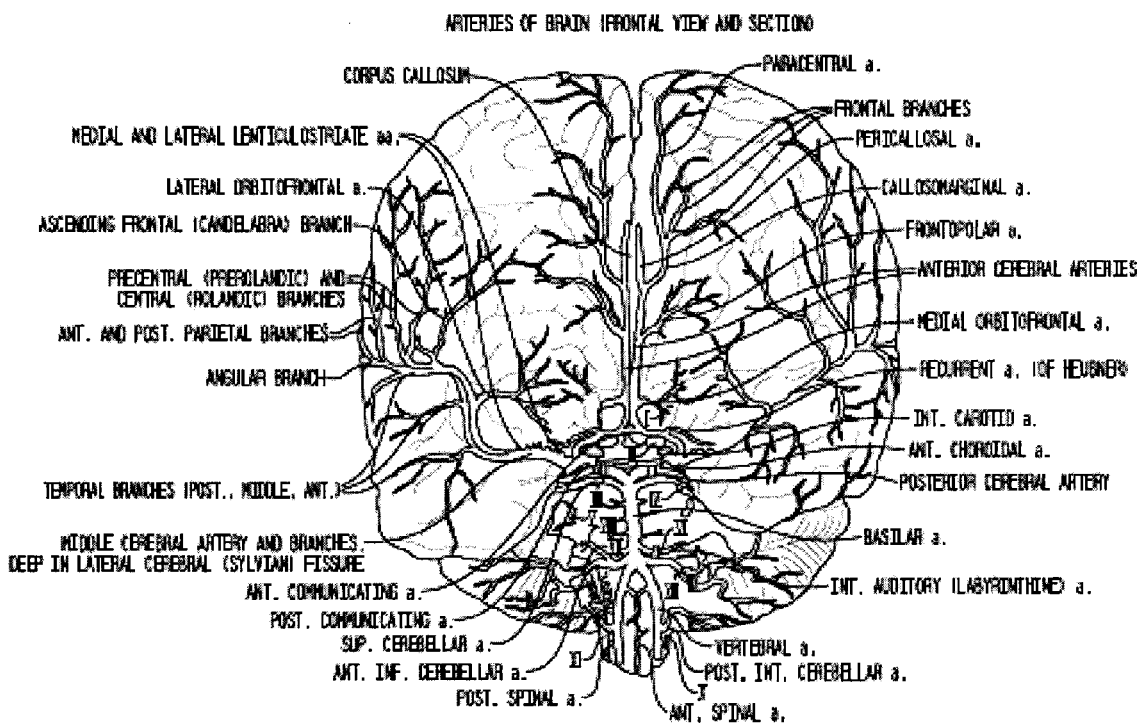
FIG. 8 shows an illustrative view of the cerebral arteries. (from Netter F H. The CIBA Collection of Medical Illustrations: Volumes 1, Nervous System. Vol. 1. Part I. CIBA: USA. 1986. pp. 256).
Figure 9:
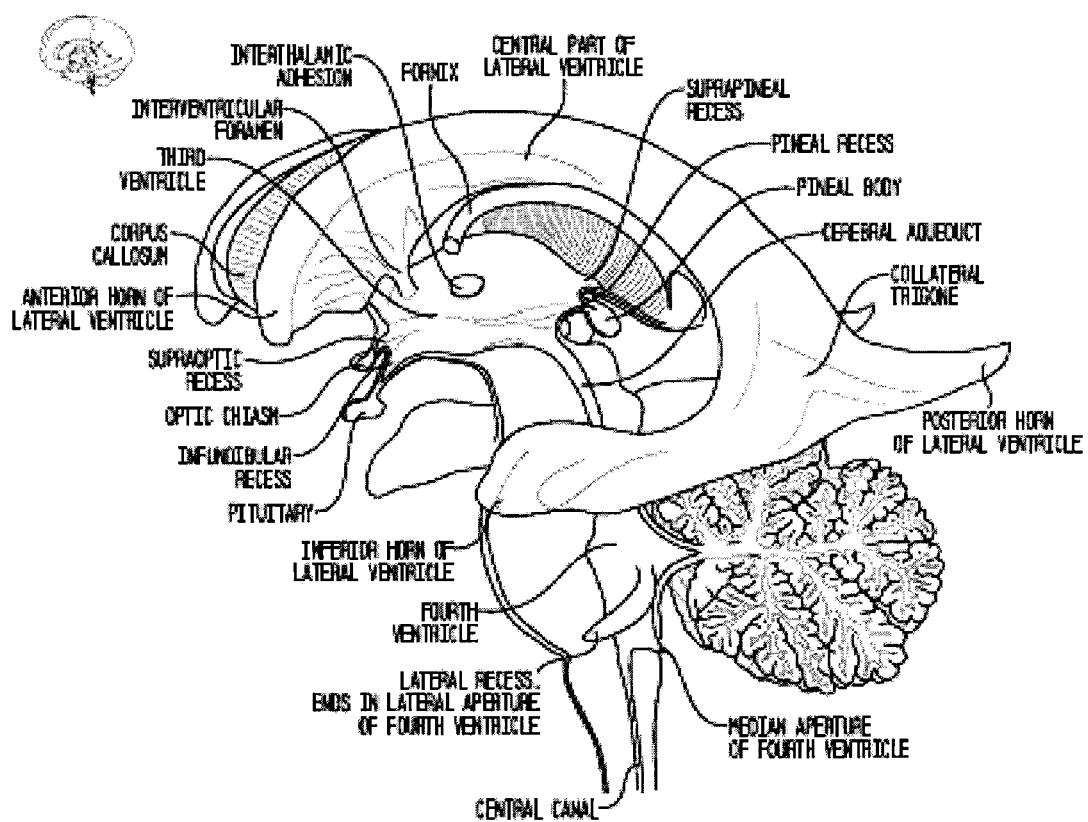
FIG. 9 shows an illustrative view of the cerebral ventricles (page 192, Ross L M, Lamperti E D, Taub E (eds), Schuenke M, Schulte E, Schumacher U. Thieme Atlas of Anatomy. Georg Thieme Verlag: Stuttgart. 2006).
Figure 10:
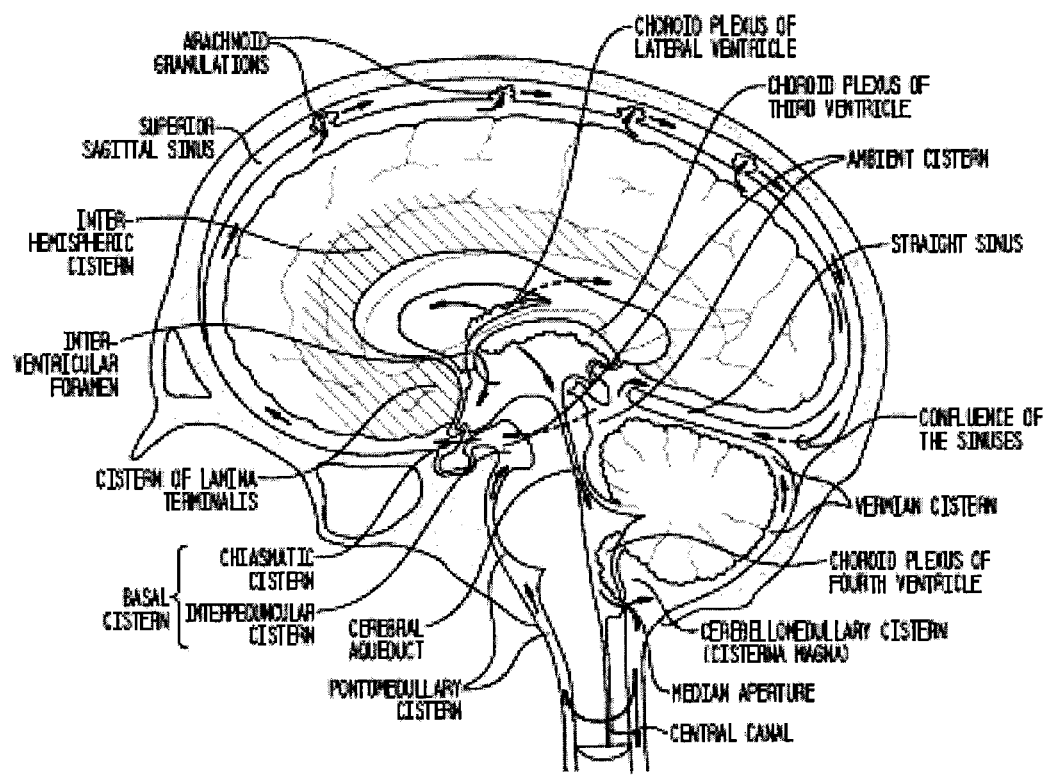
FIG. 10 shows an illustrative view of the CSF flow from the ventricles to the subarachnoid space (page 194, Ross L M, Lamperti E D, Taub E (eds), Schuenke M, Schulte E, Schumacher U. Thieme Atlas of Anatomy. Georg Thieme Verlag: Stuttgart. 2006).
Figure 11A:
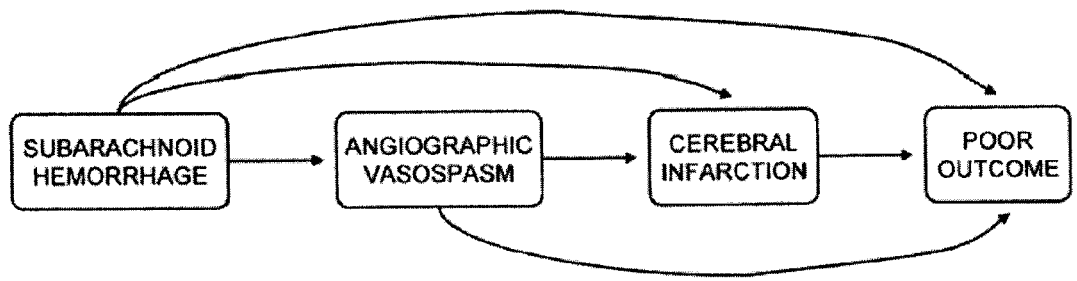
FIG. 11A shows a simple flow diagram for prognosis following SAH.
Figure 11B:
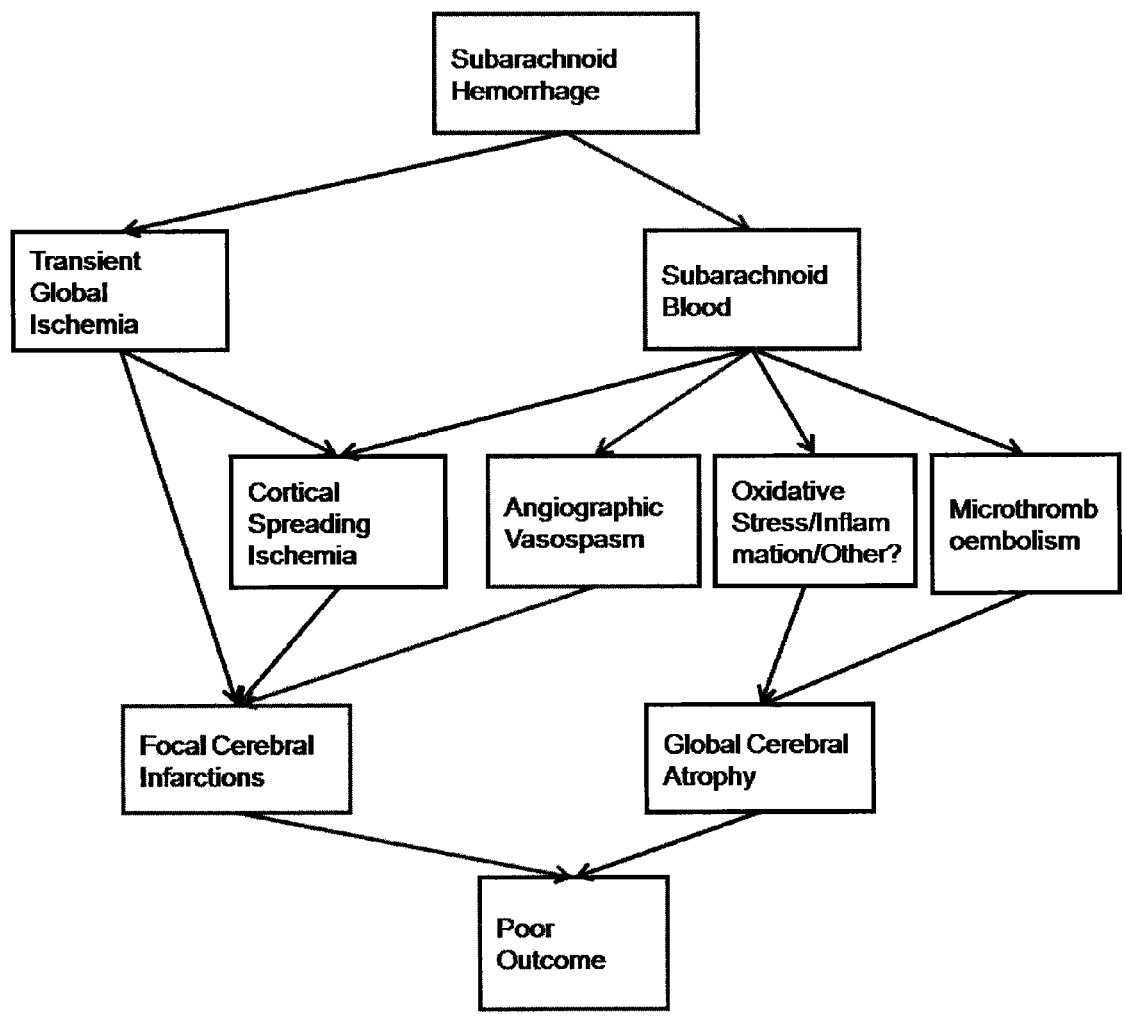
FIG. 11B shows a flow diagram of pathways proposed to be involved in delayed complications after SAH.
Figure 12:
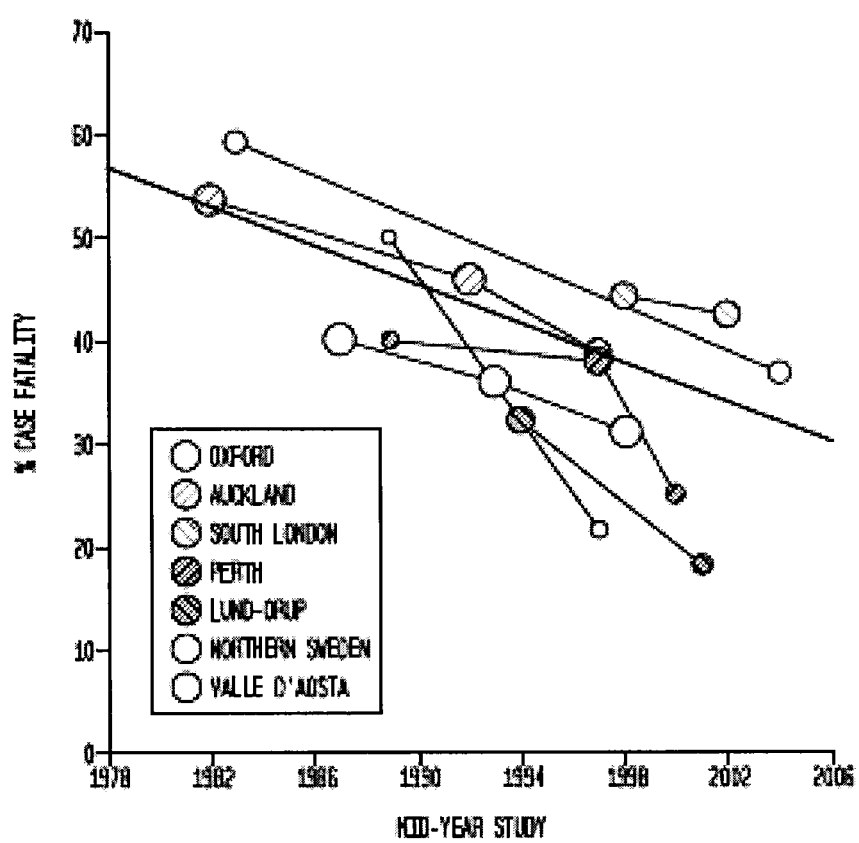
FIG. 12 shows time trends in outcome of subarachnoid hemorrhage in seven population-based studies of SAH, which shows 50% decrease in mortality over 20 years.

The term "active" as used herein refers to the ingredient, component or constituent of the composition of the present invention responsible for the intended therapeutic effect.

The terms "acute lethal dose" or "LD50" as used herein refers to the amount of a drug that when administered kills 50% of subjects.

The term "additive effect", as used herein, refers to a combined effect of two chemicals that is equal to the sum of the effect of each agent given alone.

The term "administer" as used herein means to give or to apply. The term "administering" as used herein includes in vivo administration, as well as administration directly to tissue ex vivo. Generally, compositions may be administered systemically either orally, buccally, parenterally, topically, by inhalation or insufflation (i.e., through the mouth or through the nose), administered rectally in dosage unit formulations containing conventional nontoxic pharmaceutically acceptable carriers, adjuvants, and vehicles as desired, or administered locally by means such as, but not limited to, injection, implantation, grafting, topical application, or parenterally.

The term "adverse event" (AE), as used herein, refers to any undesirable change from a patient's baseline condition associated with the use of a medical product in a patient. An undesirable change refers to any unfavorable or unintended sign including, but are not limited to, an abnormal laboratory finding, symptom or disease that occurs during the course of a study, whether or not considered related to the study drug, etc. The term "treatment-emergent AE" as used herein refers to any AE temporally associated with the use of a study drug, whether or not considered related to the study drug.

Exemplary adverse events include but are not limited to, any unfavorable and unintended sign including an abnormal laboratory finding, symptom or disease that occurs during the course of the study, whether or not considered related to the study drug; exacerbation of pre-existing disease; increase in frequency or intensity of a pre-existing episodic disease or medical condition; a disease or medical condition detected or diagnosed after study drug administration even though it may have been present prior to the start of the study; continuous persistent disease or symptoms present at baseline that worsen following the start of the study; lack of efficacy in the acute treatment of a life threatening disease; events considered by the investigator to be related to study mandated procedure; abnormal assessments, e.g., electrocardiographic findings if representing a clinically significant finding not present at baseline or worsened during the course of the study; laboratory test abnormalities if representing a clinically significant finding not present at baseline or worsened during the course of the study or that led to dose reduction, interruption or permanent discontinuation of study drug. Adverse events do not include: a medical or surgical procedure, e.g., surgery, endoscopy, tooth extraction, transfusion; pre-existing disease or a medical condition that does not worsen; or situations in which an adverse change did not occur, e.g., hospitalizations for cosmetic elective surgery.

Adverse events are assessed by the investigators as to whether or not there is a reasonable possibility of causal relationship to the study drug and reported as either related or unrelated. The term "adverse drug reactions related to the study drug" can apply to any adverse event (including serious adverse event) that appears to have a reasonable possibility of a causal relationship to the use of the study drug. The term "adverse drug reactions unrelated to the study drug" applies to any adverse event (including serious adverse event) that does not appear to have a reasonable relationship to the use of the study drug.

The intensity of clinical adverse events is graded on a three-point scale: mild, moderate, severe. If the intensity of an adverse event worsens during study drug administration, only the worst intensity is reported. If the adverse event lessens in intensity, no change in the severity is required. A mild adverse event is one noticeable to subject, but that does not influence daily activities, and usually does not require intervention. A moderate adverse event is one that may make the subject uncomfortable, may influence performance of daily activities, and may require intervention. A severe adverse event is one that may cause noticeable discomfort, usually interferes with daily activities, a result of which a subject may not be able to continue in the study, and for which treatment or intervention is usually needed.

The term "agonist" as used herein refers to a chemical substance capable of activating a receptor to induce a full or partial pharmacological response. Receptors can be activated or inactivated by either endogenous or exogenous agonists and antagonists, resulting in stimulating or inhibiting a biological response. A physiological agonist is a substance that creates the same bodily responses, but does not bind to the same receptor. An endogenous agonist for a particular receptor is a compound naturally produced by the body which binds to and activates that receptor. A superagonist is a compound that is capable of producing a greater maximal response than the endogenous agonist for the target receptor, and thus an efficiency greater than 100%. This does not necessarily mean that it is more potent than the endogenous agonist, but is rather a comparison of the maximum possible response that can be produced inside a cell following receptor binding. Full agonists bind and activate a receptor, displaying full efficacy at that receptor. Partial agonists also bind and activate a given receptor, but have only partial efficacy at the receptor relative to a full agonist. An inverse agonist is an agent which binds to the same receptor binding-site as an agonist for that receptor and reverses constitutive activity of receptors. Inverse agonists exert the opposite pharmacological effect of a receptor agonist. An irreversible agonist is a type of agonist that binds permanently to a receptor in such a manner that the receptor is permanently activated. It is distinct from a mere agonist in that the association of an agonist to a receptor is reversible, whereas the binding of an irreversible agonist to a receptor is believed to be irreversible. This causes the compound to produce a brief burst of agonist activity, followed by desensitization and internalization of the receptor, which with long-term treatment produces an effect more like an antagonist. A selective agonist is specific for one certain type of receptor.

The terms "anastomosis" and "anastomoses" are used interchangeably to refer to interconnections between blood vessels. These interconnections protect the brain when part of its vascular supply is compromised. At the circle of Willis, the two anterior cerebral arteries are connected by the anterior communicating artery and the posterior cerebral arteries are connected to the internal carotid arteries by the posterior communicating arteries. Other important anastomoses include connections between the ophthalmic artery and branches of the external carotid artery through the orbit, and connections at the brain surface between branches of the middle, anterior, and posterior cerebral arteries (Principles of Neural Sciences, 2d Ed., Eric R. Kandel and James H. Schwartz, Elsevier Science Publishing Co., Inc., New York, pp. 854-56 (1985)).

The term "angina pectoris" as used herein refers to a severe constricting chest pain, often radiating from the shoulder to the arm.

The term "angiographic vasospasm" as used herein refers to the reduction of vessel size that can be detected on angiographic exams, including, but not limited to, computed tomographic, magnetic resonance or catheter angiography, occurring in approximately 67% of patients following SAH. On the other hand, the term "clinical vasospasm" as used herein refers to the syndrome of confusion and decreased level of consciousness associated with reduced blood flow to the brain parenchyma, occurring in approximately 30% of patients, and is now defined as DCI.

The term "antagonist" as used herein refers to a substance that interferes with the effects of another substance. Functional or physiological antagonism occurs when two substances produce opposite effects on the same physiological function. Chemical antagonism or inactivation is a reaction between two substances to neutralize their effects. Dispositional antagonism is the alteration of the disposition of a substance (its absorption, biotransformation, distribution, or excretion) so that less of the agent reaches the target or its persistence there is reduced. Antagonism at the receptor for a substance entails the blockade of the effect of an antagonist with an appropriate antagonist that competes for the same site.

The term "anti-inflammatory agent" as used herein refers to an agent that prevents or reduces symptoms associated with inflammation.

The term "anti-coagulant" as used herein refers to an agent that prevents formation of a blood clot.

The term "anti-fibrinolytic agent" as used herein refers to an agent used to prevent dissolution of a fibrin clot.

The term "ataxia" as used herein refers to an inability to coordinate muscle activity during voluntary movement.

The term "biocompatible" as used herein refers to that which causes no clinically relevant tissue irritation, injury, toxic reaction, or immunological reaction to living tissue.

The term "biodegradable", as used herein, refers to material that will break down actively or passively over time by simple chemical processes, by action of body enzymes or by other similar biological activity mechanisms.

The term "blood vessel", as used herein, refers to a structure, e.g. a tube or a duct conveying or containing blood. Exemplary blood vessels include, but are not limited to, arteries, arterioles, capillaries, veins, and venules.

The term "carrier" as used herein describes a material that does not cause significant irritation to an organism and does not abrogate the biological activity and properties of the active compound of the composition of the described invention. Carriers must be of sufficiently high purity and of sufficiently low toxicity to render them suitable for administration to the mammal being treated. The carrier can be inert, or it can possess pharmaceutical benefits, cosmetic benefits or both. The terms "excipient", "carrier", or "vehicle" are used interchangeably to refer to carrier materials suitable for formulation and administration of pharmaceutically acceptable compositions described herein. Carriers and vehicles useful herein include any such materials know in the art which are nontoxic and do not interact with other components.

As shown in FIG. 1, the term "cerebral artery" or its numerous grammatical forms refers to the anterior communication artery, middle cerebral artery, internal carotid artery, anterior cerebral artery, ophthalmic artery, anterior choroidal artery, posterior communicating artery, basilar artery, and vertebral artery, among others.

The term "cerebral vasospasm" as used herein refers to the delayed occurrence of narrowing of large capacitance arteries at the base of the brain after SAH, often associated with diminished perfusion in the territory distal to the affected vessel. Cerebral vasospasm may occur any time after rupture of an aneurysm but most commonly peaks at seven days following the hemorrhage and often resolves within 14 days when the blood has been absorbed by the body.

The term "complication" as used herein refers to a pathological process or event during a disorder that is not an essential part of the disease, although it may result from it or from independent causes. A delayed complication is one that occurs some time after a triggering effect. Complications associated with SAH include, but are not limited to, angiographic vasospasm, microthromboemboli, and cortical spreading ischemia.

The term "composition" as used herein refers to a material formed of two or more substances.

The term "condition", as used herein, refers to a variety of health states and is meant to include disorders or diseases caused by any underlying mechanism, disorder, or injury.

The term "contact" and all its grammatical forms as used herein refers to a state or condition of touching or of immediate or local proximity.

The term "controlled release" as used herein refers to any drug-containing formulation in which the manner and profile of drug release from the formulation are regulated. This refers to immediate as well as non-immediate release formulations, with non-immediate release formulations including, but not limited to, sustained release and delayed release formulations.

The term "cortical spreading depolarization" or "CSD" as used herein refers to a wave of near-complete neuronal depolarization and neuronal swelling in the brain that is ignited when passive cation influx across the cellular membrane exceeds ATP-dependent sodium and calcium pump activity. The cation influx is followed by water influx and shrinkage of the extracellular space by about 70%. If normal ion homoeostasis is not restored through additional recruitment of sodium and calcium pump activity, the cell swelling is maintained—a process then termed "cytotoxic edema," since it potentially leads to cell death through a protracted intracellular calcium surge and mitochondrial depolarization. CSD induces dilation of resistance vessels in healthy tissue; hence regional cerebral blood flow increases during the neuronal depolarization phase. (Dreier, J. P. et al., Brain 132: 1866-81 (2009).

The term "cortical spreading ischemia" or "CSI," or "inverse hemodynamic response" refers to a severe microvascular spasm that is coupled to the neuronal depolarization phase. The resulting spreading perfusion deficit prolongs neuronal depolarization [as reflected by a prolonged negative shift of the extracellular direct current (DC) potential] and the intracellular sodium and calcium surge. The hypoperfusion is significant enough to produce a mismatch between neuronal energy demand and supply. (Id.).

The term "delayed cerebral ischemia" or "DCI" as used herein refers to the occurrence of focal neurological impairment (such as hemiparesis, aphasia, apraxia, hemianopia, or neglect), or a decrease in the Glasgow coma scale (either on the total score or on one of its individual components [eye, motor on either side, verbal]). This may or may not last for at least one hour, is not apparent immediately after aneurysm occlusion, and cannot be attributed to other causes by means of clinical assessment, CT or magnetic resonance imaging (MRI) scanning of the brain, and appropriate laboratory studies. Angiographic cerebral vasospasm is a description of a radiological test (either CT angiography [CTA], MR angiography [MRA] MRA or catheter angiography [CA]), and may be a cause of DCI.

The term "delayed release" is used herein in its conventional sense to refer to a drug formulation in which there is a time delay between administration of the formulation and the release of the drug there from. "Delayed release" may or may not involve gradual release of drug over an extended period of time, and thus may or may not be "sustained release."

The term "diffuse pharmacologic effect", as used herein, refers to a pharmacologic effect that spreads, disperses or scatters widely over a space or surface.

The term "disease" or "disorder", as used herein, refers to an impairment of health or a condition of abnormal functioning.

The term "dispersion", as used herein, refers to a two-phase system, in which one phase is distributed as particles or droplets in the second, or continuous phase. In these systems, the dispersed phase frequently is referred to as the discontinuous or internal phase, and the continuous phase is called the external phase or dispersion medium. For example, in coarse dispersions, the particle size is 0.5 µm. In colloidal dispersions, size of the dispersed particle is in the range of approximately 1 nm to 0.5 µm. A molecular dispersion is a dispersion in which the dispersed phase consists of individual molecules; if the molecules are less than colloidal size, the result is a true solution.

The term "disposed", as used herein, refers to being placed, arranged or distributed in a particular fashion.

The term "drug" as used herein refers to a therapeutic agent or any substance, other than food, used in the prevention, diagnosis, alleviation, treatment, or cure of disease.

The term "effective amount" refers to the amount necessary or sufficient to realize a desired biologic effect.

The term "emulsion" as used herein refers to a two-phase system prepared by combining two immiscible liquid carriers, one of which is disbursed uniformly throughout the other and consists of globules that have diameters equal to or greater than those of the largest colloidal particles. The globule size is critical and must be such that the system achieves maximum stability. Usually, separation of the two phases will occur unless a third substance, an emulsifying agent, is incorporated. Thus, a basic emulsion contains at least three components, the two immiscible liquid carriers and the emulsifying agent, as well as the active ingredient. Most emulsions incorporate an aqueous phase into a non-aqueous phase (or vice versa). However, it is possible to prepare emulsions that are basically non-aqueous, for example, anionic and cationic surfactants of the non-aqueous immiscible system glycerin and olive oil.

The term "flowable", as used herein, refers to that which is capable of movement in, or as if in, a stream by continuous change of relative position.

The term "formulation" as used herein refers to a mixture prepared according to a formula, recipe or procedure.

The term "granulomatous inflammation" as used herein refers to an inflammation reaction characterized by a predominance of regular to epithelioid macrophages with or without multinucleated giant cells and connective tissue.

The term "hemostatic agent" as used herein refers to an agent that arrests the flow of blood within the vessels.

The term "histamine type-2 blocking agent" as used herein refers to an agent that blocks the action of histamine on parietal cells in the stomach by blocking the histamine 2 receptor, decreasing the production of acid by these cells.

The term "hydrocephalus" as used herein refers to a condition marked by an excessive accumulation of cerebrospinal fluid (CSF) resulting in dilation of the cerebral ventricles, with or without raised intracranial pressure.

The term "hydrogel" as used herein refers to a substance resulting in a solid, semisolid, pseudoplastic, or plastic structure containing a necessary aqueous component to produce a gelatinous or jelly-like mass.

The term "hypersensitivity reaction" as used herein refers to an exaggerated response of the body to a foreign agent. A hypersensitivity reaction can be delayed or immediate. A delayed hypersensitivity reaction is a cell mediated response that occurs in immune individuals peaking at about 24-48 hours after challenge with the same antigen used in an initial challenge. The interaction of T-helper I lymphocytes (Th-I) with MHC Class II positive antigen presenting cells initiates the delayed hypersensitivity reaction. This interaction induces T-helper 1 lymphocytes and macrophages at the site to secrete cytokines. An immediate hypersensitivity reaction is an exaggerated immune response mediated by antibodies occurring within minutes after exposing a sensitized individual to the approximate antigen.

The term "hypertension" as used herein refers to high systemic blood pressure, a transitory or sustained elevation of systemic blood pressure to a level likely to induce cardiovascular damage or other adverse consequences.

The term "hypotension" as used herein refers to subnormal systemic arterial blood pressure; or a reduced pressure or tension of any kind The term "implanting" as used herein refers to grafting, embedding or inserting a substance, composition, or device into a pre-determined location within a tissue or space.

The term "impregnate", as used herein in its various grammatical forms refers to causing to be infused or permeated throughout; or to fill interstices with a substance.

The phrase "in proximity" as used herein refers to being in the subarachnoid space within less than 10 mm, less than 9.9 mm, less than 9.8 mm, less than 9.7 mm, less than 9.6 mm, less than 9.5 mm, less than 9.4 mm, less than 9.3 mm, less than 9.2 mm, less than 9.1 mm, less than 9.0 mm, less than 8.9 mm, less than 8.8 mm, less than 8.7 mm, less than 8.6 mm, less than 8.5 mm, less than 8.4 mm, less than 8.3 mm, less than 8.2 mm, less than 8.1 mm, less than 8.0 mm, less than 7.9 mm, less than 7.8 mm, less than 7.7 mm, less than 7.6 mm, less than 7.5 mm, less than 7.4 mm, less than 7.3 mm, less than 7.2 mm, less than 7.1 mm, less than 7.0 mm, less than 6.9 mm, less than 6.8 mm, less than 6.7 mm, less than 6.6 mm, less than 6.5 mm, less than 6.4 mm, less than 6.3 mm, less than 6.2 mm, less than 6.1 mm, less than 6.0 mm, less than 5.9 mm, less than 5.8 mm, less than 5.7 mm, less than 5.6 mm, less than 5.5 mm, less than 5.4 mm, less than 5.3 mm, less than 5.2 mm, less than 5.1 mm, less than 5.0 mm, less than 4.9 mm, less than 4.8 mm, less than 4.7 mm, less than 4.6 mm, less than 4.5 mm, less than 4.4 mm, less than 4.3 mm, less than 4.2 mm, less than 4.1 mm, less than 4.0 mm, less than 3.9 mm, less than 3.8 mm, less than 3.7 mm, less than 3.6 mm, less than 3.5 mm, less than 3.4 mm, less than 3.3 mm, less than 3.2 mm, less than 3.1 mm, less than 3.0 mm, less than 2.9 mm, less than 2.8 mm, less than 2.7 mm, less than 2.6 mm, less than 2.5 mm, less than 2.4 mm, less than 2.3 mm, less than 2.2 mm, less than 2.1 mm, less than 2.0 mm, less than 1.9 mm, less than 1.8 mm, less than 1.7 mm, less than 1.6 mm, less than 1.5 mm, less than 1.4 mm, less than 1.3 mm, less than 1.2 mm, less than 1.1 mm, less than 1.0 mm, less than 0.9 mm, less than 0.8 mm, less than 0.7 mm, less than 0.6 mm, less than 0.5 mm, less than 0.4 mm, less than 0.3 mm, less than 0.2 mm, less than 0.1 mm, less than 0.09 mm, less than 0.08 mm, less than 0.07 mm, less than 0.06 mm, less than 0.05 mm, less than 0.04 mm, less than 0.03 mm, less than 0.02 mm, less than 0.01 mm, less than 0.009 mm, less than 0.008 mm, less than 0.007 mm, less than 0.006 mm, less than 0.005 mm, less than 0.004 mm, less than 0.003 mm, less than 0.002 mm, less than 0.001 mm from a blood vessel at risk of interruption, including without limitation, that caused by a brain injury.

The term "infarction" as used herein refers to a sudden insufficiency of arterial or venous blood supply due to emboli, thrombi, mechanical factors, or pressure that produces a macroscopic area of necrosis. The term "cerebral infarction" as used herein refers to s loss of brain tissue subsequent to the transient or permanent loss of circulation and/or oxygen delivery to the cerebrum region of the brain. The term "infarct" as used herein refers to an area of necrosis resulting from a sudden insufficiency of arterial or venous blood supply.

The term "inflammation" as used herein refers to the physiologic process by which vascularized tissues respond to injury. See, e.g., FUNDAMENTAL IMMUNOLOGY, 4th Ed., William E. Paul, ed. Lippincott-Raven Publishers, Philadelphia (1999) at 1051-1053, incorporated herein by reference. During the inflammatory process, cells involved in detoxification and repair are mobilized to the compromised site by inflammatory mediators. Inflammation is often characterized by a strong infiltration of leukocytes at the site of inflammation, particularly neutrophils (polymorphonuclear cells). These cells promote tissue damage by releasing toxic substances at the vascular wall or in uninjured tissue. Traditionally, inflammation has been divided into acute and chronic responses.

The term "injection", as used herein, refers to introduction into subcutaneous tissue, or muscular tissue, a vein, an artery, or other canals or cavities in the body by force.

The term "injury," as used herein, refers to damage or harm to a structure or function of the body caused by an outside agent or force, which may be physical or chemical.

The term "interruption" and its various grammatical forms, as used herein, refers to an alteration in the continuity of blood flow through a blood vessel that is caused by dilation or constriction of the blood vessel induced by chemical, mechanical, and/or physical effects.

The terms "intracisternal administration", "intracisternal site", and "intracisternal site of administration" are used interchangeably to refer to administration of a substance, for example a drug formulation, into a subarachnoid cistern of the brain.

The terms "intraventricular administration", "intraventricular site" and "intraventricular site of administration" are used interchangeably to refer to administration of a substance, for example a drug formulation, into a cerebral ventricle.

The terms "intrathecal administration", "intrathecal site", or "intrathecal site of administration" are used interchangeably to refer to administration of a substance, for example a drug formulation, into the spinal subarachnoid space.

The term "ischemia" as used herein refers to a lack of blood supply and oxygen that occurs when reduced perfusion pressure distal to an abnormal narrowing (stenosis) of a blood vessel is not compensated by autoregulatory dilation of the resistance vessels.

The term "isolated molecule" as used herein refers to a molecule that is substantially pure and is free of other substances with which it is ordinarily found in nature or in vivo systems to an extent practical and appropriate for its intended use.

The terms "in the body", "void volume", "resection pocket", "excavation", "injection site", "deposition site" or "implant site" or "site of delivery" as used herein are meant to include all tissues of the body without limit, and may refer to spaces formed therein from injections, surgical incisions, tumor or tissue removal, tissue injuries, abscess formation, or any other similar cavity, space, or pocket formed thus by action of clinical assessment, treatment or physiologic response to disease or pathology as non-limiting examples thereof The term "lipophilic agent" as used herein refers to an agent that is capable of dissolving, of being dissolved in, or of absorbing lipids.

The phrase "localized administration", as used herein, refers to administration of a therapeutic agent in a particular location in the body.

The phrase "localized pharmacologic effect", as used herein, refers to a pharmacologic effect limited to a certain location, i.e. in proximity to a certain location, place, area or site. The phrase "predominantly localized pharmacologic effect", as used herein, refers to a pharmacologic effect of a drug limited to a certain location by at least 1 to 3 orders of magnitude, which is achieved by a localized administration as compared to a systemic administration.

The term "long-term" release, as used herein, refers to delivery of therapeutic levels of the active ingredient for at least 7 days, and potentially up to about 30 to about 60 days. Terms such as "long-acting", "sustained-release" or "controlled release" are used generally to describe a formulation, dosage form, device or other type of technologies used, such as, for example, in the art to achieve the prolonged or extended release or bioavailability of a bioactive agent to a subject; it may refer to technologies that provide prolonged or extended release or bioavailability of a bioactive agent to the general systemic circulation or a subject or to local sites of action in a subject including (but not limited to) cells, tissues, organs, joints, regions, and the like. Furthermore, these terms may refer to a technology that is used to prolong or extend the release of a bioactive agent from a formulation or dosage form or they may refer to a technology used to extend or prolong the bioavailability or the pharmacokinetics or the duration of action of a bioactive agent to a subject or they may refer to a technology that is used to extend or prolong the pharmacodynamic effect elicited by a formulation. A "long-acting formulation," a "sustained release formulation," or a "controlled release formulation" (and the like) is a pharmaceutical formulation, dosage form, or other technology that is used to provide long-acting release of a bioactive agent to a subject.

Generally, long-acting or sustained release formulations comprise a bioactive agent or agents (including, for example, an antibody or nucleic acid, steroid, or nimodipine) that is/are incorporated or associated with a biocompatible polymer in one manner or another. The polymers typically used in the preparation of long-acting formulations include, but are not limited, to biodegradable polymers (such as the polyesters poly(lactide), poly(lactide-co-glycolide), poly(caprolactone), poly(hydroxybutyrates), and the like) and non-degradable polymers (such as ethylenevinyl acetate (EVA), silicone polymers, and the like). The agent may be blended homogeneously throughout the polymer or polymer matrix or the agent may be distributed unevenly (or discontinuously or heterogeneously) throughout the polymer or polymer matrix (as in the case of a bioactive agent-loaded core that is surrounded by a polymer-rich coating or polymer wall forming material as in the case of a microcapsule, nanocapsule, a coated or encapsulated implant, and the like). The dosage form may be in the physical form of particles, film, a fiber, a filament, a sheet, a thread, a cylindrical implant, a asymmetrically-shaped implant, or a fibrous mesh (such as a woven or non-woven material; felt; gauze, sponge, and the like). When in the form of particles, the formulation may be in the form of microparticles, nanoparticles, microspheres, nanospheres, microcapsules or nanocapsules, and particles, in general, and combinations thereof. As such, the long-acting (or sustained-release) formulations of the present invention may include any variety of types or designs that are described, used or practiced in the art.

Long-acting formulations containing bioactive agents can be used to deliver those agents to the systemic circulation or they can be used to achieve local or site-specific delivery to cells, tissues, organs, bones and the like that are located nearby the site of administration. Further, formulations can be used to achieve systemic delivery of the bioactive agent and/or local delivery of the bioactive agent. Formulations can be delivered by injection (through, for example, a needle, a syringe, a trocar, a cannula, and the like) or by implantation. Delivery can be made via any variety of routes of administration commonly used for medical, clinical, surgical purposes including, but not limited to, intravenous, intraarterial, intramuscular, intraperitoneal, subcutaneous, intradermal, infusion and intracatheter delivery (and the like) in addition to delivery to specific locations (such as local delivery) including intrathecal, intracardiac, intraosseous (bone marrow), stereotactic-guided delivery, infusion delivery, CNS delivery, stereo-tactically administered delivery, orthopedic delivery (for example, delivery to joints, into bone, into bone defects and the like), cardiovascular delivery, inter-, intra-, and para-ocular (including intravitreal and scleral and retrobulbar and sub-tenons delivery and the like) delivery, and any delivery to any multitude of other sites, locations, organs, tissues, etc.

The term "maximum tolerated dose" as used herein in the context of a toxicity study refers to the highest dose of a drug that does not produce unacceptable toxicity.

The term "meningitis" as used herein refers to an inflammation of the meninges of the brain and spinal cord.

The term "microparticle composition", as used herein, refers to a composition comprising a microparticle formulation and a pharmaceutically acceptable carrier, where the microparticle formulation comprises a therapeutic agent and a plurality of microparticles.

The term "microthromboembolus" (or plural "microthromboemboli") as used herein refers to a small fragment of blood clot that causes obstruction or occlusion of a blood vessel.

The term "modulate" as used herein means to regulate, alter, adapt, or adjust to a certain measure or proportion.

The term "muscle relaxant" as used herein refers to an agent that reduces muscle tension or produces skeletal muscle paralysis.

The term "myocardial infarction" refers to a sudden insufficiency of arterial or venous blood supply to the heart due to emboli, thrombi, mechanical factors, or pressure that produces a macroscopic area of necrosis.

The term "onset of a delayed complication", as used herein, refers to the start or beginning of symptoms associated with the delayed complication.

The term "parenteral" as used herein refers to introduction into the body by way of an injection (i.e., administration by injection) outside the gastrointestinal tract, including, for example, subcutaneously (i.e., an injection beneath the skin), intramuscularly (i.e., an injection into a muscle); intravenously (i.e., an injection into a vein), intrathecally (i.e., an injection into the subarachnoid space of the spine), intracisternally, intraventricularly, or by infusion techniques. A parenterally administered composition is delivered using a needle, e.g., a surgical needle. The term "surgical needle" as used herein, refers to any needle adapted for delivery of fluid (i.e., those capable of flow) compositions into a selected anatomical structure. Injectable preparations, such as sterile injectable aqueous or oleaginous suspensions, may be formulated according to the known art using suitable dispersing or wetting agents and suspending agents.

The term "paresis" as used herein refers to partial or incomplete paralysis.

The terms "particles", as used herein, refer to extremely small constituents, e.g., femoparticles ($10^{-15}$ m), picoparticles ($10^{-12}$), nanoparticles ($10^{-9}$ m), microparticles ($10^{-6}$ m), milliparticles ($10^{-3}$ m)) that may contain in whole or in part at least one therapeutic agent as described herein. The particles may contain therapeutic agent(s) in a core surrounded by a coating. Therapeutic agent(s) also may be dispersed throughout the particles. Therapeutic agent(s) also may be adsorbed into the particles. The particles may be of any order release kinetics, including zero order release, first order release, second order release, delayed release, sustained release, immediate release, etc., and any combination thereof. The particle may include, in addition to therapeutic agent(s), any of those materials routinely used in the art of pharmacy and medicine, including, but not limited to, erodible, nonerodible, biodegradable, or nonbiodegradable material or combinations thereof. The particles may be microcapsules that contain the voltage-gated calcium channel antagonist in a solution or in a semi-solid state. The particles may be of virtually any shape.

The term "pharmaceutically acceptable carrier" as used herein refers to one or more compatible solid or liquid filler, diluent or encapsulating substance which is/are suitable for administration to a human or other vertebrate animal. The components of the pharmaceutical compositions also are capable of being commingled in a manner such that there is no interaction which would substantially impair the desired pharmaceutical efficiency.

The term "pharmaceutical composition" is used herein to refer to a composition that is employed to prevent, reduce in intensity, cure or otherwise treat a target condition or disease.

The term "pharmacologic effect", as used herein, refers to a result or consequence of exposure to an active agent.

The term "positive end expiratory pressure" or "PEEP" as used herein refers to an elevation of transpulmonary pressure at the end of expiration.

The term "prognosis" as used herein refers to an expected future cause and outcome of a disease or disorder, based on medical knowledge.

The term "proton pump inhibitor" as used herein refers to a compound that suppresses gastric acid secretion leading to relief of acid related symptoms. (McDonagh, E. M. et al., "From pharmacogenomic knowledge acquisition to clinical applications: the PharmGKB as a clinical pharmacogenomic biomarker resource," Biomarkers in Medicine (2011) December; 5(6):795-806).

The term "pulsatile release" as used herein refers to any drug-containing formulation in which a burst of the drug is released at one or more predetermined time intervals.

The term "release" and its various grammatical forms, refers to dissolution of an active drug component and diffusion of the dissolved or solubilized species by a combination of the following processes: (1) hydration of a matrix, (2) diffusion of a solution into the matrix; (3) dissolution of the drug; and (4) diffusion of the dissolved drug out of the matrix.

The term "reduce" or "reducing" as used herein refers to a diminution, a decrease, an attenuation, limitation or abatement of the degree, intensity, extent, size, amount, density, number or occurrence of disorder in individuals at risk of developing the disorder.

The term "serious adverse event" as used herein refers to an adverse event that has one or more of the following patient outcomes, or, based on reasonable medical judgment, requires a medical or surgical intervention to prevent one of the following patient outcomes: death, a life-threatening experience, inpatient hospitalization, prolongation of existing hospitalization, a persistent or significant disability or incapacity; a congenital anomaly or birth defect. The term "life-threatening experience" refers to an event in which the subject/patient was at risk of death at the time of the event. It does not refer to an event that hypothetically might have caused death if it were more severe. Important medical events that may not immediately result in death, be life-threatening, or require hospitalization may be considered as a serious adverse event when, based upon appropriate medical judgment, they may jeopardize the patient and may require medical or surgical intervention to prevent one of the outcomes listed in the definitions above. The term "inpatient hospitalization" as used herein refers to an overnight stay in a hospital unit and/or emergency room due to an adverse event. The term "prolongation of existing hospitalization" as used herein refers to at least one overnight stay in the hospital unit and/or emergency room due to the adverse event in addition to the initial inpatient hospitalization. The treatment on an emergency or outpatient basis for an event not fulfilling the definition of seriousness given above and not resulting in hospitalization is not considered a serious adverse event and is reported as an adverse event only. The following reasons for hospitalizations are not considered adverse events or serious adverse events: hospitalizations for cosmetic elective surgery, social and/or convenience reasons; standard monitoring of a pre-existing disease or medical condition that did not worsen, e.g., hospitalization for coronary angiography in a patient with stable angina pectoris; elective treatment of a pre-existing disease or medical condition that did not worsen.

The term "statin" as used herein refers to a cholesterol-lowering agent that inhibits the enzyme 3-hydroxy-3-methylglutaryl-coenzyme (HMG-CoA) reductase.

The term "subacute inflammation" as used herein refers to a tissue reaction typically seen subsequent to the early inflammatory process characterized by a mixture of neutrophils, lymphocytes, and occasionally macrophages and/or plasma cells.

The term "subarachnoid hemorrhage" or "SAH" is used herein to refer to a condition in which blood collects beneath the arachnoid mater. This area, called the subarachnoid space, normally contains cerebrospinal fluid. The accumulation of blood in the subarachnoid space may lead to stroke, seizures, and other complications. Additionally, SAH may cause permanent brain damage and a number of harmful biochemical events in the brain. Causes of SAH include bleeding from a cerebral aneurysm, vascular anomaly, trauma and extension into the subarachnoid space from a primary intracerebral hemorrhage. Symptoms of SAH include, for example, sudden and severe headache, nausea and/or vomiting, symptoms of meningeal irritation (e.g., neck stiffness, low back pain, bilateral leg pain), photophobia and visual changes, and/or loss of consciousness. SAH is often secondary to a head injury or a blood vessel defect known as an aneurysm. In some instances, SAH can induce angiographic vasospasm that may in turn lead to an ischemic stroke or DCI. A common manifestation of SAH is the presence of blood in the CSF. Subjects having a SAH may be identified by a number of symptoms. For example, a subject having a SAH will present with blood in the subarachnoid space. Subjects having a SAH can also be identified by an intracranial pressure that approximates mean arterial pressure, by a fall in cerebral perfusion pressure, or by the sudden transient loss of consciousness (sometimes preceded by a painful headache). In about half of cases, subjects present with a severe headache which may be associated with physical exertion. Other symptoms associated with SAH include nausea, vomiting, memory loss, temporary or prolonged loss of consciousness, hemiparesis and aphasia. Subjects having a SAH also may be identified by the presence of creatine kinase-BB isoenzyme activity in their CSF. This enzyme is enriched in the brain but normally is not present in the CSF. Thus, its presence in the CSF is indicative of "leak" from the brain into the subarachnoid space. Assay of creatine-kinase BB isoenzyme activity in the CSF is described by Coplin et al. (Coplin et al 1999 Arch Neurol 56, 1348-1352), which is incorporated herein by reference. Additionally, a spinal tap or lumbar puncture may be used to demonstrate whether blood is present in the CSF, a strong indication of a SAH. A cranial CT scan or an MRI also may be used to identify blood in the subarachnoid region. Angiography also may be used to determine not only whether a hemorrhage has occurred, but also the location of the hemorrhage. SAH commonly results from rupture of an intracranial saccular aneurysm or from malformation of the arteriovenous system in the brain. Accordingly, a subject at risk of having a SAH includes a subject having a saccular aneurysm as well as a subject having a malformation of the arteriovenous system. Common sites of saccular aneurysms are the anterior communicating artery, posterior communicating artery, middle cerebral artery, internal carotid artery, top of the basilar artery and the junction of the basilar artery with the superior cerebellar or the anterior inferior cerebellar artery. A subject with a saccular aneurysm may be identified through routine medical imaging techniques, such as CT and MRI. A saccular or cerebral aneurysm forms a mushroom-like or berry-like shape (sometimes referred to as "a dome with a neck" shape). When the SAH is caused by an aneurysm, it is termed an "aneurysmal SAH" (aSAH).

The terms "subject" or "individual" or "patient" are used interchangeably to refer to a member of an animal species of mammalian origin, including humans.

The phrase "a subject having cerebral vasospasm" as used herein refers to one who has symptoms of or has been diagnosed with cerebral vasospasm and/or presents with diagnostic markers with angiographic vasospasm. A "subject at risk of cerebral vasospasm" is one who has one or more predisposing factors to the development of cerebral vasospasm. A predisposing factor includes, but is not limited to, existence of a SAH. A subject who has experienced a recent SAH is at significantly higher risk of developing cerebral vasospasm than a subject who has not had a recent SAH. MR angiography, CT angiography and catheter angiography can be used to diagnose cerebral vasospasm Angiography is a technique in which a contrast agent is introduced into the blood stream in order to view blood flow and/or arteries. A contrast agent is required because blood flow and/or arteries sometimes are only weakly apparent in a regular MR scan, CT scan or radiographic film for catheter angiography. Appropriate contrast agents will vary depending upon the imaging technique used. For example, gadolinium is commonly used as a contrast agent used in MR scans. Other MR appropriate contrast agents are known in the art. Diagnostic markers include, but are not limited to, the presence of blood in the CSF, a recent history of a SAH and/or reduction in the lumen diameter of cerebral arteries observed on a catheter, computed tomographic or magnetic resonance angiogram one to 14 days after an SAH or TBI. Presence of blood in the CSF may be detected using CT scans. However, in some instances where the amount of blood is so small as to not be detected by CT, a lumbar puncture is warranted.

The phrase "a subject having delayed cerebral ischemia" or "DCI" as used herein refers to a subject who presents with diagnostic markers associated with DCI. Diagnostic markers include, but are not limited to, the presence of blood in the CSF and/or a recent history of a SAH and/or development of neurological deterioration one to 14 days after SAH when the neurological deterioration is not due to another cause that can be diagnosed, including but not limited to seizures, hydrocephalus, increased intracranial pressure, infection, intracranial hemorrhage or other systemic factors. DCI-associated symptoms include, but are not limited to, paralysis on one side of the body, inability to vocalize the words or to understand spoken or written words, and inability to perform tasks requiring spatial analysis. Such symptoms may develop over a few days, or they may fluctuate in their appearance, or they may present abruptly.

The phrase "a subject having microthromboemboli" as used herein refers to a subject who presents with diagnostic markers associated with microthromboemboli. Such diagnostic markers include, but are not limited to, the presence of blood in the CSF and/or a recent history of a SAH and/or development of neurological deterioration one to 14 days after SAH when the neurological deterioration is not due to another cause that can be diagnosed, including, but not limited to, seizures, hydrocephalus, increased intracranial pressure, infection, intracranial hemorrhage or other systemic factors, and embolic signals detected on transcranial Doppler ultrasound of large conducting cerebral arteries. Microthromboemboli-associated symptoms include, but are not limited to, paralysis on one side of the body, inability to vocalize the words or to understand spoken or written words, and inability to perform tasks requiring spatial analysis. Such symptoms may develop over a few days, or they may fluctuate in their appearance, or they may present abruptly.

The phrase "a subject having cortical spreading ischemia" as used herein refers to a subject who presents with diagnostic markers associated with cortical spreading ischemia. Such diagnostic markers include, but are not limited to, the presence of blood in the CSF and/or a recent history of a SAH and/or development of neurological deterioration one to 14 days after SAH when the neurological deterioration is not due to another cause that can be diagnosed, including but not limited to seizures, hydrocephalus, increased intracranial pressure, infection, intracranial hemorrhage or other systemic factors and detection of propagating waves of depolarization with vasoconstriction detected by electrocorticography. Cortical spreading ischemia-associated symptoms include, but are not limited to, paralysis on one side of the body, inability to vocalize the words or to understand spoken or written words, and inability to perform tasks requiring spatial analysis. Such symptoms may develop over a few days, or they may fluctuate in their appearance, or they may present abruptly.

The term "a subject at risk of DCI, microthromboemboli, cortical spreading ischemia, or angiographic vasospasm" as used herein refers to a subject who has one or more predisposing factors to the development of these conditions. A predisposing factor includes, but is not limited to, existence of a SAH. A subject who has experienced a recent SAH is at significantly higher risk of developing angiographic vasospasm and DCI than a subject who has not had a recent SAH. MR angiography, CT angiography and catheter angiography can be used to diagnose at least one of DCI, microthromboemboli, cortical spreading ischemia or angiographic vasospasm. Angiography is a technique in which a contrast agent is introduced into the blood stream in order to view blood flow and/or arteries. A contrast agent is required because blood flow and/or arteries sometimes are only weakly apparent in a regular MR scan, CT scan or radiographic film for catheter angiography. Appropriate contrast agents will vary depending upon the imaging technique used. For example, gadolinium is commonly used as a contrast agent used in MR scans. Other MR appropriate contrast agents are known in the art.

The term "suitable for delivery", as used herein, refers to being apt, appropriate for, designed for, or proper for release only in a subarachnoid space.

The term "substantially pure", as used herein, refers to a condition of a therapeutic agent such that it has been substantially separated from the substances with which it may be associated in living systems or during synthesis. According to some embodiments, a substantially pure therapeutic agent is at least 70% pure, at least 75% pure, at least 80% pure, at least 85% pure, at least 90% pure, at least 95% pure, at least 96% pure, at least 97% pure, at least 98% pure, or at least 99% pure.

The term "sustained release" (also referred to as "extended release") is used herein in its conventional sense to refer to a drug formulation that provides for gradual release of a drug over an extended period of time, and that preferably, although not necessarily, results in substantially constant blood levels of a drug over an extended time period. Alternatively, delayed absorption of a parenterally administered drug form is accomplished by dissolving or suspending the drug in an oil vehicle. Nonlimiting examples of sustained release biodegradable polymers include polyesters, polyester polyethylene glycol copolymers, polyamino-derived biopolymers, polyanhydrides, polyorthoesters, polyphosphazenes, sucrose acetate isobutyrate (SAIB), photopolymerizable biopolymers, protein polymers, collagen, polysaccharides, chitosans, and alginates.

The term "syndrome," as used herein, refers to a pattern of symptoms indicative of some disease or condition.

The term "synergistic effect", as used herein, refers to a combined effect of two chemicals, which is greater than the sum of the effects of each agent given alone.

The phrase "systemic administration", as used herein, refers to administration of a therapeutic agent with a pharmacologic effect on the entire body. Systemic administration includes enteral administration (e.g. oral) through the gastrointestinal tract and parenteral administration (e.g. intravenous, intramuscular, etc.) outside the gastrointestinal tract.

The terms "therapeutic amount", "therapeutic effective amount" or an "amount effective" of one or more of the therapeutic agents is an amount that is sufficient to provide the intended benefit of treatment. Combined with the teachings provided herein, by choosing among the various active compounds and weighing factors such as potency, relative bioavailability, patient body weight, severity of adverse side-effects and preferred mode of administration, an effective prophylactic or therapeutic treatment regimen may be planned which does not cause substantial toxicity and yet is effective to treat the particular subject. A therapeutic effective amount of the therapeutic agents that can be employed ranges from generally 0.1 mg/kg body weight and about 50 mg/kg body weight. A therapeutic effective amount for any particular application may vary depending on such factors as the disease or condition being treated, the particular therapeutic agent being administered, the size of the subject, or the severity of the disease or condition. One of ordinary skill in the art may determine empirically the effective amount of a particular inhibitor and/or other therapeutic agent without necessitating undue experimentation. It is preferred generally that a maximum dose be used, that is, the highest safe dose according to some medical judgment. However, dosage levels are based on a variety of factors, including the type of injury, the age, weight, sex, medical condition of the patient, the severity of the condition, the route of administration, and the particular therapeutic agent employed. Thus the dosage regimen may vary widely, but can be determined routinely by a surgeon using standard methods. "Dose" and "dosage" are used interchangeably herein.

The term "therapeutic agent" as used herein refers to a drug, molecule, nucleic acid, protein, composition or other substance that provides a therapeutic effect. The terms "therapeutic agent" and "active agent" are used interchangeably. The term "first therapeutic agent" as used herein includes a calcium channel antagonist, an endothelin antagonist, or a transient receptor potential (TRP) protein antagonist. The term "second therapeutic agent" as used herein may include a hemostatic agent, a proton pump inhibitor, a histamine type-2 blocking agent, an anticoagulant, a vasodilator, a statin, an anti-inflammatory agent, a muscle relaxant, etc.

The term "therapeutic component" as used herein refers to a therapeutically effective dosage (i.e., dose and frequency of administration) that eliminates, reduces, or prevents the progression of a particular disease manifestation in a percentage of a population. An example of a commonly used therapeutic component is the $ED_{50}$ which describes the dose in a particular dosage that is therapeutically effective for a particular disease manifestation in 50% of a population.

The term "therapeutic effect" as used herein refers to a consequence of treatment, the results of which are judged to be desirable and beneficial. A therapeutic effect may include, directly or indirectly, the arrest, reduction, or elimination of a disease manifestation. A therapeutic effect may also include, directly or indirectly, the arrest reduction or elimination of the progression of a disease manifestation.

The term "thrombocytopenia" as used herein refers to a condition in which the number of platelets circulating in the blood is below the normal range of platelets.

The term "topical" refers to administration of a composition at, or immediately beneath, the point of application. The phrase "topically applying" describes application onto one or more surfaces(s) including epithelial surfaces. Topical administration, in contrast to transdermal administration, generally provides a local rather than a systemic effect.

The term "transient receptor potential (TRP) protein antagonist" as used herein refers to a protein that is structurally distinct from other calcium channel antagonist and that blocks or antagonizes intracellular calcium increases in cells due to receptor-mediated calcium influx. Transient receptor potential (TRP) protein antagonists include, but are not limited to, SK&F 96365 (1-(beta-[3-(4-methoxy-phenyl) propoxy]-4-methoxyphenethyl)-1H-imidazole hydrochloride) and LOE 908 (RS)-(3,4-dihydro-6,7-dimethoxyisoquinoline-1-gamma 1)-2-phenyl-N, N-dit2-(2,3,4-trimethoxyphenyl)ethyl]acetamide).

The term "treat" or "treating" includes abrogating, substantially inhibiting, slowing or reversing the progression of a disease, condition or disorder, substantially ameliorating clinical or esthetical symptoms of a condition, substantially preventing the appearance of clinical or esthetical symptoms of a disease, condition, or disorder, and protecting from harmful or annoying symptoms. Treating further refers to accomplishing one or more of the following: (a) reducing the severity of the disorder; (b) limiting development of symptoms characteristic of the disorder(s) being treated; (c) limiting worsening of symptoms characteristic of the disorder(s) being treated; (d) limiting recurrence of the disorder(s) in patients that have previously had the disorder(s); and (e) limiting recurrence of symptoms in patients that were previously asymptomatic for the disorder(s).

The term "vasoconstriction" as used herein refers to the narrowing of the blood vessels resulting from contracting of the muscular wall of the vessels. When blood vessels constrict, the flow of blood is restricted or slowed. The terms "vasoconstrictors," "vasopressors," or "pressors" as used herein refer to factors or agents causing vasoconstriction.

The term "vasodilation" which is the opposite of vasoconstriction as used herein refers to the widening of blood vessels. The term "vasodilators" as used herein refers to factors or agents that cause vasodilation. Examples of vasodilators include for example calcium channel antagonists, endothelin receptor antagonists, TRP protein antagonists, etc.

The term "vasospasm" as used herein refers to a decrease in the internal diameter of a cerebral artery that results from contraction of smooth muscle within the wall of the artery which causes a decrease in blood flow, but generally without an increase in systemic vascular resistance. Vasospasm results in decreased cerebral blood flow and increased cerebral vascular resistance. Without being limited by theory, it generally is believed that vasospasm is caused by local injury to vessels, such as that which results from traumatic head injury, aneurysmal SAH and other causes of SAH. Cerebral vasospasm is a naturally occurring vasoconstriction that also may be triggered by the presence of blood in the CSF, a common occurrence after rupture of an aneurysm or following traumatic head injury. Cerebral vasospasm ultimately can lead to brain cell damage, in the form of cerebral ischemia and infarction, due to interrupted blood supply. The term "cerebral vasospasm" as used herein further refers to the delayed occurrence of narrowing of large capacitance arteries at the base of the brain after SAH, often associated with diminished perfusion in the territory distal to the affected vessel. Cerebral vasospasm may occur any time after rupture of an aneurysm but most commonly peaks at seven days following the hemorrhage and often resolves within 14 days when the blood has been absorbed by the body. Angiographic vasospasm is a consequence of SAH, but also can occur after any condition that deposits blood in the subarachnoid space. More specifically, the term "angiographic cerebral vasospasm" refers to the narrowing of the large capacitance arteries at the base of the brain (i.e., cerebral arteries) following hemorrhage into the subarachnoid space, and leads to reduced perfusion of distal brain regions.

The term "ventriculitis", as used herein refers to inflammation of the ventricles of the brain.

The term "ventriculocranial ratio" as used herein refers to the ratio of the average size of the cerebral ventricles, where the ventricular width is measured at the level of the foramen of Monroe, and compared to the width of the cranium at the same level.

The term "viscosity", as used herein refers to the property of a fluid that resists the force tending to cause the fluid to flow. Viscosity is a measure of the fluid's resistance to flow. The resistance is caused by intermolecular friction exerted when layers of fluids attempt to slide by one another. Viscosity can be of two types: dynamic (or absolute) viscosity and kinematic viscosity. Absolute viscosity or the coefficient of absolute viscosity is a measure of the internal resistance. Dynamic (or absolute) viscosity is the tangential force per unit area required to move one horizontal plane with respect to the other at unit velocity when maintained a unit distance apart by the fluid. Dynamic viscosity is usually denoted in poise (P) or centipoise (cP), wherein 1 poise=1 g/cm$^2$, and 1 cP=0.01 P. Kinematic viscosity is the ratio of absolute or dynamic viscosity to density. Kinematic viscosity is usually denoted in Stoke (St) or Centistokes (cSt), wherein 1 St=$10^{-4}$ m$^2$/s, and 1 cSt=0.01 St.

Anatomical Terms

When referring to animals, that typically have one end with a head and mouth, with the opposite end often having the anus and tail, the head end is referred to as the cranial end, while the tail end is referred to as the caudal end. Within the head itself, rostral refers to the direction toward the end of the nose, and caudal is used to refer to the tail direction. The surface or side of an animal's body that is normally oriented upwards, away from the pull of gravity, is the dorsal side; the opposite side, typically the one closest to the ground when walking on all legs, swimming or flying, is the ventral side. On the limbs or other appendages, a point closer to the main body is "proximal"; a point farther away is "distal". Three basic reference planes are used in zoological anatomy. A "sagittal" plane divides the body into left and right portions. The "midsagittal" plane is in the midline, i.e. it would pass through midline structures such as the spine, and all other sagittal planes are parallel to it. A "coronal" plane divides the body into dorsal and ventral portions. A "transverse" plane divides the body into cranial and caudal portions. When referring to humans, the body and its parts are always described using the assumption that the body is standing upright. Portions of the body which are closer to the head end are "superior" (corresponding to cranial in animals), while those farther away are "inferior" (corresponding to caudal in animals). Objects near the front of the body are referred to as "anterior" (corresponding to ventral in animals); those near the rear of the body are referred to as "posterior" (corresponding to dorsal in animals). A transverse, axial, or horizontal plane is an X-Y plane, parallel to the ground, which separates the superior/head from the inferior/feet. A coronal or frontal plane is an Y-Z plane, perpendicular to the ground, which separates the anterior from the posterior. A sagittal plane is an X-Z plane, perpendicular to the ground and to the coronal plane, which separates left from right. The midsagittal plane is the specific sagittal plane that is exactly in the middle of the body.

Structures near the midline are called medial and those near the sides of animals are called lateral. Therefore, medial structures are closer to the midsagittal plane, lateral structures are further from the midsagittal plane. Structures in the midline of the body are median. For example, the tip of a human subject's nose is in the median line.

Ipsilateral means on the same side, contralateral means on the other side and bilateral means on both sides. Structures that are close to the center of the body are proximal or central, while ones more distant are distal or peripheral. For example, the hands are at the distal end of the arms, while the shoulders are at the proximal ends.

I. Method of Treating

According to one aspect, the present invention provides a method for treating at least one cerebral artery at risk of interruption due to a brain injury in a human subject, comprising:

a) providing a flowable sustained release particulate composition comprising:
    (i) a particulate formulation comprising a plurality of particles of uniform size distribution, and a therapeutic amount of at least one first therapeutic agent, wherein the first therapeutic agent is dispersed throughout each particle, adsorbed onto the particles, or in a core surrounded by a coating; and
    (ii) a pharmaceutical carrier; and
    b) administering the flowable sustained release particulate composition locally, via an injection apparatus, so as to contact the at least one artery of the subarachnoid space at risk of interruption due to the brain injury, without the first therapeutic agent entering systemic circulation in an amount to cause unwanted side effects,
    wherein interruption of the cerebral artery is associated with at least one delayed complication of the brain injury.

According to one embodiment, the particulate formulation comprises microparticles. According to another embodiment, the particulate formulation comprises nanoparticles. According to another embodiment, the particulate formulation comprises milliparticles, femtoparticles, or picoparticles.

According to some embodiments, the delayed complication is an angiographic vasospasm, microthromboemboli, a cortical spreading ischemia, a delayed cerebral ischemia (DCI), or a combination thereof. According to one embodiment, the delayed complication is an angiographic vasospasm. According to another embodiment, the delayed complication is a plurality of microthromboemboli. According to another embodiment, the delayed complication is a cortical spreading ischemia. According to another embodiment, the delayed complication is a delayed cerebral ischemia (DCI).

According to some embodiments, the brain injury is a result of an underlying condition. Exemplary underlying conditions include, but are not limited to, aneurysm, sudden traumatic head injury, subarachnoid hemorrhage (SAH), or a combination thereof. According to one embodiment, the underlying condition is an aneurysm. According to another embodiment, the underlying condition is a traumatic head injury. According to another embodiment, the underlying condition is a subarachnoid hemorrhage (SAH). According to another embodiment, the underlying condition is a combination of an aneurysm, a sudden traumatic head injury, and a subarachnoid hemorrhage (SAH).

According to some embodiments, the cerebral artery is an anterior cerebral artery, a middle cerebral artery, an internal carotid artery, a basilar artery, a vertebral artery, or a combination thereof. According to one embodiment, the cerebral artery is an anterior cerebral artery. According to another embodiment, the cerebral artery is a middle cerebral artery. According to another embodiment, the cerebral artery is an internal carotid artery. According to another embodiment, the cerebral artery is a basilar artery. According to another embodiment, the cerebral artery is a vertebral artery.

Optional Rescue Therapy Step

According to some embodiments, the method further comprises a rescue therapy step comprising administering: (a) a vasopressor, (b) a vasodilator, (c) balloon angioplasty, or a combination thereof.

According to one embodiment, the method further comprises a rescue therapy step comprising administering a vasopressor. According to one embodiment, the vasopressor is administered by intravenous injection. According to one embodiment, the rescue therapy step comprises initiating or increasing the dose of the vasopressor administered intravenously, with or without fluid therapy. Exemplary vasopressors for use in rescue therapy can include, but are not limited to, dopamine, dobutamine, phenylephrine, epinephrine, norepinephrine, etc.

According to another embodiment, the method further comprises a rescue therapy step comprising administering a vasodilator. According to one embodiment, the vasodilator is administered by intraarterial infusion. According to one embodiment, the rescue therapy step comprises initiating or increasing dose of the vasodilator administered by intraarterial infusion, with or without fluid therapy. Exemplary vasodilators drug for use in rescue therapy can include, but are not limited to, nicardipine, nimodipine, verapamil, papaverine, etc.

Characteristics of the Flowable Sustained Release Particulate Composition

The viscosity of the flowable pharmaceutical composition according to the present invention can be measured using a viscometer. According to one embodiment, the viscosity of the flowable pharmaceutical composition at 20° C., when administered intracisternally, intrathecally or intraventricularly, is from about 0.1 cP to about 0.5 cp. According to another embodiment, the viscosity of the flowable pharmaceutical composition at 20° C., when administered intrathecally is from about 0.5 cP to about 50 cp. According to another embodiment, the viscosity of the flowable pharmaceutical composition at 20° C., when administered intracisternally is from about 0.5 cP to about 50 cp. According to another embodiment, the viscosity of the flowable pharmaceutical composition at 20° C., when administered inrtaventricularly is from about 0.5 cP to about 50 cp. According to another embodiment, the viscosity of the flowable pharmaceutical composition at 20° C., when administered intracisternally, intrathecally or intraventricularly, is from about 50 cP to about 100 cP. According to another embodiment, the viscosity of the flowable pharmaceutical composition at 20° C., when administered intracisternally, is from about 50 cP to about 100 cP. According to another embodiment, the viscosity of the flowable pharmaceutical composition at 20° C., when administered intrathecally, is from about 50 cP to about 100 cP. According to another embodiment, the viscosity of the flowable pharmaceutical composition at 20° C., when administered intraventricularly, is from about 50 cP to about 100 cP. According to another embodiment, the viscosity of the flowable pharmaceutical composition at 20° C., when administered intracisternally, intrathecally or intraventricularly, is from about 100 cP to about 1,000 cP. According to another embodiment, the viscosity of the flowable pharmaceutical composition at 20° C., when administered intracisternally, is from about 100 cP to about 1,000 cP. According to another embodiment, the viscosity of the flowable pharmaceutical composition at 20° C., when administered intrathecally, is from about 100 cP to about 1,000 cP. According to another embodiment, the viscosity of the flowable pharmaceutical composition at 20° C., when administered intraventricularly, is from about 100 cP to about 1,000 cP.

According to another embodiment, the composition is administered via injection into the subarachnoid space in a cistern closest to the cerebral artery at risk for interruption, wherein the viscosity of the flowable pharmaceutical composition at 20° C. is from about 100 cP to about 1,000 cP. According to some such embodiments, the viscosity of the flowable pharmaceutical composition at 20° C. is at least about 100 cP, at least about 150 cP, at least about 200 cP, at least about 250 cP, at least about 300 cP, at least about 350 cP, at least about 400 cP, at least about 450 cP, at least about 500 cP, at least about 550 cP, at least about 600 cP, at least about 650 cP, at least about 700 cP, at least about 750 cP, at least about 800 cP, at least about 850 cP, at least about 900 cP, at least about 950 cP, or at least about 1000 cP.

According to another embodiment, the composition is administered intraventricularly so that the pharmaceutical composition is carried by cerebrospinal flow to contact the at least one artery of the subarachnoid space at risk of interruption, wherein the viscosity of the flowable pharmaceutical composition at 20° C. is from about 0.5 cP to about 50 cP. According to some such embodiments, the viscosity of the flowable pharmaceutical composition at 20° C. is at least about 0.5 cP, at least about 1 cP, at least about 5 cP, at least about 10 cP, at least about 20 cP, at least about 30 cP, at least about 40 cP, at least about 50 cP, at least about 60 cP, at least about 70 cP, at least about 80 cP, at least about 90 cP, or at least about 100 cP.

According to another embodiment, the composition is administered intrathecally into the spinal subarachnoid space so that the pharmaceutical composition is carried by cerebrospinal flow to contact the at least one artery of the subarachnoid space at risk of interruption, wherein the viscosity of the flowable pharmaceutical composition at 20° C. is from about 0.5 cP to about 50 cp. According to some such embodiments, the viscosity of the flowable pharmaceutical composition at 20° C. is at least about 0.5 cP, at least about 1 cP, at least about 5 cP, at least about 10 cP, at least about 15 cP, at least about 20 cP, at least about 25 cP, at least about 30 cP, at least about 35 cP, at least about 40 cP, at least about 45 cP, or at least about 50 cP.

According to some embodiments, the pH of the flowable sustained release particulate composition is pH 6.8, 6.9, 7.0, 7.1, 7.2, 7.3, 7.4, 7.5, or 7.6.

According to some embodiments, the osmolarity of the flowable sustained release particulate composition is about 250 mOsm/kg, about 258 mOsm/kg, about 275 mOsm/kg, about 300 mOsm/kg, about 325 mOsm/kg, about 350 mOsm/kg, about 375 mOsm/kg, or about 381 mOsm/kg.

According to some embodiments, the flowable sustained release particulate composition, upon delivery via the injection apparatus so as to contact the at least one artery of the subarachnoid space, at risk of interruption, is capable of sustained release of the therapeutic amount of the at least one first therapeutic agent. According to some embodiments, the flowable sustained release particulate composition, upon delivery via an injection apparatus so as to contact the at least one artery of the subarachnoid space, at risk of interruption, is capable of sustained release of about 50-100% of the first therapeutic agent within 1 day to 30 days. According to some embodiments, the flowable sustained release particulate composition, upon delivery via an injection apparatus so as to contact the at least one artery of the subarachnoid space, at risk of interruption, is capable of sustained release of about 50-100% of the first therapeutic agent within 6 days to 14 days.

According to some embodiments, the composition, upon delivery via an injection apparatus so as to contact the at least one artery in the subarachnoid space, at risk of interruption, is capable of sustained release of the at least one first therapeutic agent, such that upon release, the concentration of the first therapeutic agent in the plasma ranges from about 0.200 ng/ml to about 200 g/ml. According to some such embodiments, the concentration of the first therapeutic agent in the plasma is measured every 6 hours after administration for 4 days. According to some such embodiments, the concentration of the first therapeutic agent in the plasma is measured every 6 hours after administration for 4 days and then daily until hospital discharge. According to some such embodiments, the concentration of the first therapeutic agent in the plasma is measured every 6 hours after administration for 4 days, then daily for 14 days. According to some such embodiments, the concentration of the first therapeutic agent in the plasma is measured every 6 hours after administration for 4 days and then daily until hospital discharge of for 14 days, with a follow-up at week 6.

According to some embodiments, the composition, upon delivery via an injection apparatus so as to contact the at least one artery in the subarachnoid space, at risk of interruption, is capable of sustained release of the first therapeutic agent, such that upon release, the concentration of the first therapeutic agent in the plasma is less than about 30-40 ng/mL. According to one embodiment, upon release, the average concentration of the first therapeutic agent in the plasma (PLASMA-$C_{av}$) is less than about 30-40 ng/mL. According to one embodiment, the area under the plot of plasma concentration of drug against time after drug administration (AUC), which is the overall amount of drug in the bloodstream after a dose, for the first therapeutic agent at 24 hours (PLASMA-$AUC_{24}$) is less than about 960 ng/mL hour.

According to some embodiments, the composition, upon delivery via an injection apparatus so as to contact the at least one artery of the subarachnoid space at risk of interruption is capable of sustained release of the first therapeutic agent, such that upon release, the concentration of the first therapeutic agent in the cerebrospinal fluid (CSF) (CSF-$C_{av}$) ranges from 5 ng/mL to about 5000 mg/mL. According to some such embodiments, the composition, upon delivery via an injection apparatus so as to contact the at least one artery of the subarachnoid space at risk of interruption is capable of sustained release of the first therapeutic agent, such that upon release, the concentration of the first therapeutic agent in the cerebrospinal fluid (CSF) (CSF-$C_{av}$) is about 5 ng/mL, about 10 ng/mL, about 15 ng/mL, about 20 ng/mL, about 25 ng/mL, about 30 ng/mL, about 35 ng/mL, about 40 ng/mL, about 45 ng/mL, about 50 ng/mL, about 55 ng/mL, about 60 ng/mL, about 65 ng/mL, about 70 ng/mL, about 75 ng/mL, about 80 ng/mL, about 85 ng/mL, about 90 ng/mL, about 95 ng/mL, about 100 ng/mL, about 200 ng/mL, about 300 ng/mL, about 400 ng/mL, about 500 ng/mL, about 600 ng/mL, about 700 ng/mL, about 800 ng/mL, about 900 ng/mL, about 1 µg/mL, about 5 µg/mL, about 10 µg/mL, about 15 µg/mL, about 20 µg/mL, about 25 µg/mL, about 30 µg/mL, about 35 µg/mL, about 40 µg/mL, about 45 µg/mL, about 50 µg/mL, about 55 µg/mL, about 60 µg/mL, about 65 µg/mL, about 70 µg/mL, about 75 µg/mL, about 80 µg/mL, about 85 µg/mL, about 90 µg/mL, about 95 µg/mL, about 100 µg/mL, about 200 µg/mL, about 300 µg/mL, about 400 µg/mL, about 500 µg/mL, about 600 µg/mL, about 700 µg/mL, about 800 µg/mL, about 900 µg/mL, about 1 mg/mL, about 5 mg/mL, about 10 mg/mL, about 15 mg/mL, about 20 mg/mL, about 25 mg/mL, about 30 mg/mL, about 35 mg/mL, about 40 mg/mL, about 45 mg/mL, about 50 mg/mL, about 55 mg/mL, about 60 mg/mL, about 65 mg/mL, about 70 mg/mL, about 75 mg/mL, about 80 mg/mL, about 85 mg/mL, about 90 mg/mL, about 95 mg/mL, about 100 mg/mL, about 200 mg/mL, about 300 mg/mL, about 400 mg/mL, about 500 mg/mL, about 600 mg/mL, about 700 mg/mL, about 800 mg/mL, about 900 mg/mL, about 1000 mg/mL, about 1100 mg/mL, about 1200 mg/mL, about 1300 mg/mL, about 1400 mg/mL, about 1500 mg/mL, about 1600 mg/mL, about 1700 mg/mL, about 1800 mg/mL, about 1900 mg/mL, about 2000 mg/mL, about 2100 mg/mL, about 2200 mg/mL, about 2300 mg/mL, about 2400 mg/mL, about 2500 mg/mL, about 2600 mg/mL, about 2700 mg/mL, about 2800 mg/mL, about 2900 mg/mL, about 3000 mg/mL, about 33100 mg/mL, about 200 mg/mL, about 3300 mg/mL, about 3400 mg/mL, about 3500 mg/mL, about 3600 mg/mL, about 3700 mg/mL, about 3800 mg/mL, about 3900 mg/mL, about 4000 mg/mL, about 4100 mg/mL, about 4200 mg/mL, about 4300 mg/mL, about 4400 mg/mL, about 4500 mg/mL, about 4600 mg/mL, about 4700 mg/mL, about 4800 mg/mL, about 4900 mg/mL, or about 5000 mg/mL.

According to some embodiments, the injection apparatus is a ventricular catheter. According to some such embodiments, the concentration of the first therapeutic agent in the cerebrospinal fluid (CSF) is measured daily until the catheter is removed. According to some embodiments, the concentration of the first therapeutic agent in the CSF is measured until 14 days. According to one embodiment, the average concentration of the first therapeutic agent in the cerebrospinal fluid (CSF) (CSF-$C_{av}$) is at least about 5 ng/mL, at least about 50 ng/mL, at least about 500 ng/mL; or at least about 5000 ng/mL. According to one embodiment, the area under the plot of CSF concentration of drug against time after drug administration ($AUC_{CSF}$) for the first therapeutic agent at 14 days ($CSF\text{-}AUC_{14}$) is at least about 1,000 ng/mL day, at least about 5,000 ng/mL day, at least 15,000 ng/mL day, at least about 10,000 ng/mL day.

According to one embodiment, the injection apparatus is a catheter inserted into the spinal canal. According to one such embodiment, the concentration of the first therapeutic agent in the cerebrospinal fluid (CSF) is measured daily until the catheter is removed. According to one such embodiment, the concentration of the first therapeutic agent in the CSF is measured until 14 days. According to one embodiment, the average concentration of the first therapeutic agent in the cerebrospinal fluid (CSF) ($CSF\text{-}C_{av}$) is at least about 5 ng/mL, at least about 50 ng/mL, at least about 500 ng/mL; or at least about 5000 ng/mL. According to one embodiment, the area under the plot of CSF concentration of drug against time after drug administration ($AUC_{CSF}$) for the first therapeutic agent at 14 days ($CSF\text{-}AUC_{14}$) is at least about 1,000 ng/mL day, at least about 5,000 ng/mL day, at least 15,000 ng/mL day, at least about 10,000 ng/mL day.

According to some such embodiments, the flowable sustained release particulate composition is capable of sustained release of a therapeutic amount of the first therapeutic agent within a half-life ($t_{1/2}$) ranging from 1 day to 30 days. According to one embodiment, the flowable sustained release particulate composition is capable of sustained release of the therapeutic amount of the first therapeutic agent within a half-life of 1 day. According to another embodiment, the flowable sustained release particulate composition is capable of sustained release of the therapeutic amount of the first therapeutic agent within a half-life of 2 days. According to another embodiment, the flowable sustained release particulate composition is capable of sustained release of the therapeutic amount of the first therapeutic agent within a half-life of 3 days. According to another embodiment, the flowable sustained release particulate composition is capable of sustained release of the therapeutic amount of the first therapeutic agent within a half-life of 4 days. According to another embodiment, the flowable sustained release particulate composition is capable of sustained release of the therapeutic amount of the first therapeutic agent within a half-life of 5 days. According to another embodiment, the flowable sustained release particulate composition is capable of sustained release of the therapeutic amount of the first therapeutic agent within a half-life of 6 days. According to another embodiment, the flowable sustained release particulate composition is capable of sustained release of the therapeutic amount of the first therapeutic agent within a half-life of 7 days. According to another embodiment, the flowable sustained release particulate composition is capable of sustained release of the therapeutic amount of the first therapeutic agent within a half-life of 8 days. According to another embodiment, the flowable sustained release particulate composition is capable of sustained release of the therapeutic amount of the first therapeutic agent within a half-life of 9 days. According to another embodiment, the flowable sustained release particulate composition is capable of sustained release of the therapeutic amount of the first therapeutic agent within a half-life of 10 days. According to another embodiment, the flowable sustained release particulate composition is capable of sustained release of the therapeutic amount of the first therapeutic agent within a half-life of 12 days. According to another embodiment, the flowable sustained release particulate composition is capable of sustained release of the therapeutic amount of the first therapeutic agent within a half-life of 14 days. According to another embodiment, the flowable sustained release particulate composition is capable of sustained release of the therapeutic amount of the first therapeutic agent within a half-life of 16 days. According to another embodiment, the flowable sustained release particulate composition is capable of sustained release of the therapeutic amount of the first therapeutic agent within a half-life of 18 days. According to another embodiment, the flowable sustained release particulate composition is capable of sustained release of the therapeutic amount of the first therapeutic agent within a half-life of 20 days. According to another embodiment, the flowable sustained release particulate composition is capable of sustained release of the therapeutic amount of the first therapeutic agent within a half-life of 22 days. According to another embodiment, the flowable sustained release particulate composition is capable of sustained release of the therapeutic amount of the first therapeutic agent within a half-life of 24 days. According to another embodiment, the flowable sustained release particulate composition is capable of sustained release of the therapeutic amount of the first therapeutic agent within a half-life of 26 days. According to another embodiment, the flowable sustained release particulate composition is capable of sustained release of the therapeutic amount of the first therapeutic agent within a half-life of 28 days. According to another embodiment, the flowable sustained release particulate composition is capable of sustained release of the therapeutic amount of the first therapeutic agent within a half-life of 30 days.

According to one embodiment, the sustained release of the therapeutic amount of the first therapeutic agent in contact with the cerebral artery in the subarachnoid space can produce a predominantly localized pharmacologic effect over a desired amount of time. According to one embodiment, the release of the therapeutic amount of the first therapeutic agent in contact with the cerebral artery in the subarachnoid space produces a predominantly localized pharmacologic effect for 1 day. According to another embodiment, the release of the therapeutic amount of the first therapeutic agent in contact with the cerebral artery in the subarachnoid space produces a predominantly localized pharmacologic effect for 2 days. According to another embodiment, the release of the therapeutic amount of the first therapeutic agent in contact with the cerebral artery in the subarachnoid space produces a predominantly localized pharmacologic effect for 3 days. According to another embodiment, the release of the therapeutic amount of the first therapeutic agent in contact with the cerebral artery in the subarachnoid space produces a predominantly localized pharmacologic effect for 4 days. According to another embodiment, the release of the therapeutic amount of the first therapeutic agent in contact with the cerebral artery in the subarachnoid space produces a predominantly localized pharmacologic effect for 5 days. According to another embodiment, the release of the therapeutic amount of the first therapeutic agent in contact with the cerebral artery in the subarachnoid space produces a predominantly localized pharmacologic effect for 6 days. According to another embodiment, the release of the therapeutic amount of the first therapeutic agent in contact with the cerebral artery in the subarachnoid space produces a predominantly localized pharmacologic effect for 7 days. According to another embodiment, the release of the therapeutic amount of the first therapeutic agent in contact with the cerebral artery in the subarachnoid space produces a predominantly localized pharmacologic effect for 8 days. According to another embodiment, the release of the therapeutic amount of the first therapeutic agent in contact with the cerebral artery in the subarachnoid space produces a predominantly localized pharmacologic effect for 15 days. According to another embodiment, the release of the therapeutic amount of the first therapeutic agent in contact with the cerebral artery in the subarachnoid space produces a predominantly localized pharmacologic effect for 30 days.

According to some embodiments, the therapeutic amount of the flowable sustained release particulate composition, upon release in contact with the cerebral artery in the subarachnoid space at risk of interruption, is effective in preventing or reducing the incidence or severity of the delayed complication associated with the interruption of the cerebral artery caused by the brain injury, wherein the delayed complication is selected from the group consisting of an angiographic vasospasm, a plurality of microthromboemboli, a cortical spreading ischemia, a delayed cerebral ischemia (DCI), or a combination thereof. According to some such embodiments, the therapeutic amount of the flowable sustained release particulate composition, upon release in contact with the cerebral artery in the subarachnoid space at risk of interruption, is effective in preventing or reducing the incidence or severity of the delayed complication associated with the interruption of the cerebral artery caused by the brain injury, within at least 7 days, 14 days, or 28 days of the brain injury. According to some such embodiments, the brain injury is a result of an underlying condition. Exemplary underlying conditions include, but are not limited to, aneurysm, sudden traumatic head injury, subarachnoid hemorrhage (SAH), or a combination thereof. According to one embodiment, the underlying condition is an aneurysm. According to another embodiment, the underlying condition is a traumatic head injury. According to another embodiment, the underlying condition is a subarachnoid hemorrhage (SAH). According to another embodiment, the underlying condition is a combination of an aneurysm, a sudden traumatic head injury, and a subarachnoid hemorrhage (SAH).

Reducing Angiographic Vasospasm

According to one embodiment, the therapeutic amount of the flowable sustained release particulate composition, upon release in contact with the cerebral artery in the subarachnoid space at risk of interruption, is effective in preventing or reducing the incidence or severity of an angiographic vasospasm.

According to some embodiments, the therapeutic amount of the flowable sustained release particulate composition, upon release of the therapeutic amount of the first therapeutic agent in contact with the cerebral artery in the subarachnoid space at risk of interruption caused by brain injury, is effective in reducing angiographic vasospasm such that the angiographic diameter of the at least one cerebral artery is increased, compared to an untreated control. According to some embodiments, the percent change in the angiographic diameter of the at least one cerebral artery is at least about 10%, at least about 20%, at least about 30%, at least about 40%, or at least about 50%, compared to an untreated control. According to some embodiments, the cerebral artery is selected from the group consisting of an anterior cerebral artery, a middle cerebral artery, an internal carotid artery, a basilar artery, a vertebral artery, or a combination thereof. According to one embodiment, the cerebral artery is an anterior cerebral artery. According to another embodiment, the cerebral artery is a middle cerebral artery. According to another embodiment, the cerebral artery is an internal carotid artery. According to another embodiment, the cerebral artery is a basilar artery. According to another embodiment, the cerebral artery is a vertebral cerebral artery.

According to one embodiment, the predominantly localized pharmacologic effect is a reduction of angiographic vasospasm such that the angiographic diameter of at least one cerebral artery in the subarachnoid space at risk of interruption is increased, compared to an untreated control. According to one embodiment, the therapeutic amount of the flowable sustained release particulate composition is effective to reduce angiographic vasospasm such that the angiographic diameter of at least one cerebral artery in the subarachnoid space at risk of interruption is increased, compared to an untreated control.

According to one embodiment, the therapeutic amount of the first therapeutic agent in in contact with the cerebral artery in subarachnoid space can produce a predominantly localized pharmacologic effect. According to some embodiments, the first therapeutic agent is a lipophilic agent capable of binding to blood in the cerebrospinal fluid (CSF).

According to some embodiments, the predominantly localized pharmacologic effect is a reduction of angiographic vasospasm such that the internal diameter of the at least one cerebral artery in subarachnoid space at risk of interruption is increased, compared to an untreated control, wherein the at least one cerebral artery is at least 10 mm, at least 9.9 mm, at least 9.8 mm, at least 9.7 mm, at least 9.6 mm, at least 9.5 mm, at least 9.4 mm, at least 9.3 mm, at least 9.2 mm, at least 9.1 mm, at least 9.0 mm, at least 8.9 mm, at least 8.8 mm, at least 8.7 mm, at least 8.6 mm, at least 8.5 mm, at least 8.4 mm, at least 8.3 mm, at least 8.2 mm, at least 8.1 mm, at least 8.0 mm, at least 7.9 mm, at least 7.8 mm, at least 7.7 mm, at least 7.6 mm, at least 7.5 mm, at least 7.4 mm, at least 7.3 mm, at least 7.2 mm, at least 7.1 mm, at least 7.0 mm, at least 6.9 mm, at least 6.8 mm, at least 6.7 mm, at least 6.6 mm, at least 6.5 mm, at least 6.4 mm, at least 6.3 mm, at least 6.2 mm, at least 6.1 mm, at least 6.0 mm, at least 5.9 mm, at least 5.8 mm, at least 5.7 mm, at least 5.6 mm, at least 5.5 mm, at least 5.4 mm, at least 5.3 mm, at least 5.2 mm, at least 5.1 mm, at least 5.0 mm from the site of release in the subarachnoid space.

According to one embodiment, the predominantly localized pharmacologic effect is a reduction of angiographic vasospasm such that the angiographic diameter of the cerebral artery that is at least 10 mm from the site of release in the subarachnoid space is increased, compared to an untreated control. According to another embodiment, the predominantly localized pharmacologic effect is a reduction of angiographic vasospasm such that the angiographic diameter of the cerebral artery that is at least 9.9 mm from the site of release in the subarachnoid space is increased, compared to an untreated control. According to another embodiment, the predominantly localized pharmacologic effect is a reduction of angiographic vasospasm such that the angiographic diameter of the cerebral artery that is at least 9.8 mm from the site of release in the subarachnoid space is increased, compared to an untreated control. According to another embodiment, the predominantly localized pharmacologic effect is a reduction of angiographic vasospasm such that the angiographic diameter of the cerebral artery that is at least 9.7 mm from the site of release in the subarachnoid space is increased, compared to an untreated control. According to another embodiment, the predominantly localized pharmacologic effect is a reduction of angiographic vasospasm such that the angiographic diameter of the cerebral artery that is at least 9.6 mm from the site of release in the subarachnoid space is increased, compared to an untreated control. According to another embodiment, the predominantly localized pharmacologic effect is a reduction of angiographic vasospasm such that the angiographic diameter of the cerebral artery that is at least 9.5 mm from the site of release in the subarachnoid space is increased, compared to an untreated control. According to another embodiment, the predominantly localized pharmacologic effect is a reduction of angiographic vasospasm such that the angiographic diameter of the cerebral artery that is at least 9.4 mm from the site of release in the subarachnoid space is increased, compared to an untreated control. According to another embodiment, the predominantly localized pharmacologic effect is a reduction of angiographic vasospasm such that the angiographic diameter of the cerebral artery that is at least 9.3 mm from the site of release in the subarachnoid space is increased, compared to an untreated control. According to another embodiment, the predominantly localized pharmacologic effect is a reduction of angiographic vasospasm such that the angiographic diameter of the cerebral artery that is at least 9.2 mm from the site of release in the subarachnoid space is increased, compared to an untreated control. According to another embodiment, the predominantly localized pharmacologic effect is a reduction of angiographic vasospasm such that the angiographic diameter of the cerebral artery that is at least 9.1 mm from the site of release in the subarachnoid space is increased, compared to an untreated control. According to another embodiment, the predominantly localized pharmacologic effect is a reduction of angiographic vasospasm such that the angiographic diameter of the cerebral artery that is at least 9.0 mm from the site of release in the subarachnoid space is increased, compared to an untreated control. According to another embodiment, the predominantly localized pharmacologic effect is a reduction of angiographic vasospasm such that the angiographic diameter of the, cerebral artery that is at least 8.9 mm from the site of release in the subarachnoid space is increased, compared to an untreated control. According to another embodiment, the predominantly localized pharmacologic effect is a reduction of angiographic vasospasm such that the angiographic diameter of the cerebral artery that is at least 8.8 mm from the site of release in the subarachnoid space is increased, compared to an untreated control. According to another embodiment, the predominantly localized pharmacologic effect is a reduction of angiographic vasospasm such that the angiographic diameter of the cerebral artery that is at least 8.7 mm from the site of release in the subarachnoid space is increased, compared to an untreated control. According to another embodiment, the predominantly localized pharmacologic effect is a reduction of angiographic vasospasm such that the angiographic diameter of the cerebral artery that is at least 8.6 mm from the site of release in the subarachnoid space is increased, compared to an untreated control. According to another embodiment, the predominantly localized pharmacologic effect is a reduction of angiographic vasospasm such that the angiographic diameter of the cerebral artery that is at least 8.5 mm from the site of release in the subarachnoid space is increased, compared to an untreated control. According to another embodiment, the predominantly localized pharmacologic effect is a reduction of angiographic vasospasm such that the angiographic diameter of the cerebral artery that is at least 8.4 mm from the site of release in the subarachnoid space is increased, compared to another embodiment. According to another embodiment, the predominantly localized pharmacologic effect is a reduction of angiographic vasospasm such that the angiographic diameter of the cerebral artery that is at least 8.3 mm from the site of release in the subarachnoid space is increased, compared to an untreated control. According to another embodiment, the predominantly localized pharmacologic effect is a reduction of angiographic vasospasm such that the angiographic diameter of the cerebral artery that is at least 8.2 mm from the site of release in the subarachnoid space is increased, compared to an untreated control. According to another embodiment, the predominantly localized pharmacologic effect is a reduction of angiographic vasospasm such that the angiographic diameter of the cerebral artery that is at least 8.1 mm from the site of release in the subarachnoid space is increased, compared to an untreated control. According to another embodiment, the predominantly localized pharmacologic effect is a reduction of angiographic vasospasm such that the angiographic diameter of the cerebral artery that is at least 8.0 mm from the site of release in the subarachnoid space is increased, compared to an untreated control. According to another embodiment, the predominantly localized pharmacologic effect is a reduction of angiographic vasospasm such that the angiographic diameter of the cerebral artery that is at least 7.9 mm from the site of release in the subarachnoid space is increased, compared to an untreated control. According to another embodiment, the predominantly localized pharmacologic effect is a reduction of angiographic vasospasm such that the angiographic diameter of the cerebral artery that is at least 7.8 mm from the site of release in the subarachnoid space is increased, compared to an untreated control. According to another embodiment, the predominantly localized pharmacologic effect is a reduction of angiographic vasospasm such that the angiographic diameter of the cerebral artery that is at least 7.7 mm from the site of release in the subarachnoid space is increased, compared to an untreated control. According to another embodiment, the predominantly localized pharmacologic effect is a reduction of angiographic vasospasm such that the angiographic diameter of the cerebral artery that is at least 7.6 mm from the site of release in the subarachnoid space is increased, compared to an untreated control. According to another embodiment, the predominantly localized pharmacologic effect is a reduction of angiographic vasospasm such that the angiographic diameter of the cerebral artery that is at least 7.5 mm from the site of release in the subarachnoid space is increased, compared to an untreated control. According to another embodiment, the predominantly localized pharmacologic effect is a reduction of angiographic vasospasm such that the angiographic diameter of the cerebral artery that is at least 7.4 mm from the site of release in the subarachnoid space is increased, compared to another embodiment. According to another embodiment, the predominantly localized pharmacologic effect is a reduction of angiographic vasospasm such that the angiographic diameter of the cerebral artery that is at least 7.3 mm from the site of release in the subarachnoid space is increased, compared to an untreated control. According to another embodiment, the predominantly localized pharmacologic effect is a reduction of angiographic vasospasm such that the angiographic diameter of the cerebral artery that is at least 7.2 mm from the site of release in the subarachnoid space is increased, compared to an untreated control. According to another embodiment, the predominantly localized pharmacologic effect is a reduction of angiographic vasospasm such that the angiographic diameter of the cerebral artery that is at least 7.1 mm from the site of release in the subarachnoid space is increased, compared to an untreated control. According to another embodiment, the predominantly localized pharmacologic effect is a reduction of angiographic vasospasm such that the angiographic diameter of the cerebral artery that is at least 7.0 mm from the site of release in the subarachnoid space is increased, compared to an untreated control. According to another embodiment, the predominantly localized pharmacologic effect is a reduction of angiographic vasospasm such that the angiographic diameter of the cerebral artery that is at least 6.9 mm from the site of release in the subarachnoid space is increased, compared to an untreated control. According to another embodiment, the predominantly localized pharmacologic effect is a reduction of angiographic vasospasm such that the angiographic diameter of the cerebral artery that is at least 6.8 mm from the site of release in the subarachnoid space is increased, compared to an untreated control. According to another embodiment, the predominantly localized pharmacologic effect is a reduction of angiographic vasospasm such that the angiographic diameter of the cerebral artery that is at least 6.7 mm from the site of release in the subarachnoid space is increased, compared to an untreated control. According to another embodiment, the predominantly localized pharmacologic effect is a reduction of angiographic vasospasm such that the angiographic diameter of the cerebral artery that is at least 6.6 mm from the site of release in the subarachnoid space is increased, compared to an untreated control. According to another embodiment, the predominantly localized pharmacologic effect is a reduction of angiographic vasospasm such that the angiographic diameter of the cerebral artery that is at least 6.5 mm from the site of release in the subarachnoid space is increased, compared to an untreated control. According to another embodiment, the predominantly localized pharmacologic effect is a reduction of angiographic vasospasm such that the angiographic diameter of the cerebral artery that is at least 6.4 mm from the site of release in the subarachnoid space is increased, compared to an untreated control. According to another embodiment, the predominantly localized pharmacologic effect is a reduction of angiographic vasospasm such that the angiographic diameter of the cerebral artery that is at least 6.3 mm from the site of release in the subarachnoid space is increased, compared to an untreated control. According to another embodiment, the predominantly localized pharmacologic effect is a reduction of angiographic vasospasm such that the angiographic diameter of the cerebral artery that is at least 6.2 mm from the site of release in the subarachnoid space is increased, compared to an untreated control. According to another embodiment, the predominantly localized pharmacologic effect is a reduction of angiographic vasospasm such that the angiographic diameter of the cerebral artery that is at least 6.1 mm from the site of release in the subarachnoid space is increased, compared to an untreated control. According to another embodiment, the predominantly localized pharmacologic effect is a reduction of angiographic vasospasm such that the angiographic diameter of the cerebral artery that is at least 6.0 mm from the site of release in the subarachnoid space is increased, compared to an untreated control. According to another embodiment, the predominantly localized pharmacologic effect is a reduction of angiographic vasospasm such that the angiographic diameter of the cerebral artery that is at least 5.9 mm from the site of release in the subarachnoid space is increased, compared to an untreated control. According to another embodiment, the predominantly localized pharmacologic effect is a reduction of angiographic vasospasm such that the angiographic diameter of the cerebral artery that is at least 5.8 mm from the site of release in the subarachnoid space is increased, compared to another embodiment, the predominantly localized pharmacologic effect is a reduction of angiographic vasospasm such that the angiographic diameter of the cerebral artery that is at least 5.7 mm from the site of release in the subarachnoid space is increased, compared to an untreated control. According to another embodiment, the predominantly localized pharmacologic effect is a reduction of angiographic vasospasm such that the angiographic diameter of the cerebral artery that is at least 5.6 mm from the site of release in the subarachnoid space is increased, compared to an untreated control. According to another embodiment, the predominantly localized pharmacologic effect is a reduction of angiographic vasospasm such that the angiographic diameter of the cerebral artery that is at least 5.5 mm from the site of release in the subarachnoid space is increased, compared to an untreated control. According to another embodiment, the predominantly localized pharmacologic effect is a reduction of angiographic vasospasm such that the angiographic diameter of the cerebral artery that is at least 5.4 mm from the site of release in the subarachnoid space is increased, compared to an untreated control. According to another embodiment, the predominantly localized pharmacologic effect is a reduction of angiographic vasospasm such that the angiographic diameter of the cerebral artery that is at least 5.3 mm from the site of release in the subarachnoid space is increased, compared to an untreated control. According to another embodiment, the predominantly localized pharmacologic effect is a reduction of angiographic vasospasm such that the angiographic diameter of the cerebral artery that is at least 5.2 mm from the site of release in the subarachnoid space is increased, compared to an untreated control. According to another embodiment, the predominantly localized pharmacologic effect is a reduction of angiographic vasospasm such that the angiographic diameter of the cerebral artery that is at least 5.1 mm from the site of release in the subarachnoid space is increased, compared to an untreated control. According to another embodiment, the predominantly localized pharmacologic effect is a reduction of angiographic vasospasm such that the angiographic diameter of the cerebral artery that is at least 5.0 mm from the site of release in the subarachnoid space is increased, compared to an untreated control.

Reducing Plurality of Microthromboemboli

According to another embodiment, the therapeutic amount of the flowable sustained release particulate composition, upon release of the first therapeutic agent in proximity to at least one cerebral artery in the subarachnoid space at risk of interruption, is effective in preventing or in reducing the incidence or severity of a plurality of microthromboemboli. According to some embodiments, the therapeutic amount of the composition is effective in preventing or in reducing the incidence or severity of the occurrence of microthromboemboli, such that the occurrence of at least one of the following symptoms is reduced within at least 7 days, 14 days, or within 28 days of the subarachnoid hemorrhage (SAH): neurological deterioration, a seizure, or a combination thereof. Neurological deterioration can be assessed, for example, by a decrease of at least 2 points on the Glasgow Coma Scale (GCS), the National Institute of Health Stroke Scale (NIHSS), or a combination hereof.

Reducing Cortical Spreading Ischemia

According to another embodiment, the therapeutic amount of the flowable sustained release particulate composition, upon release of the first therapeutic agent in proximity to at least one cerebral artery in the subarachnoid space at risk of interruption, is effective in preventing or in reducing the incidence or severity of a cortical spreading ischemia.

According to some embodiments, the therapeutic amount of the composition is effective in preventing or in reducing the incidence or severity of the cortical spreading ischemia such that the occurrence of at least one of the following symptoms is reduced within at least 7 days, 14 days, or within 28 days of the subarachnoid hemorrhage (SAH): presence of blood in the cerebrospinal fluid (CSF), neurological deterioration, a seizure, or a combination thereof. Neurological deterioration can be assessed, for example, by a decrease of at least 2 points on the Glasgow Coma Scale (GCS), the National Institute of Health Stroke Scale (NIHSS), or a combination hereof.

Reducing Delayed Cerebral Ischemia (DCI)

According to another embodiment, the therapeutic amount of the flowable sustained release particulate composition, upon release of the first therapeutic agent in proximity to at least one cerebral artery in the subarachnoid space at risk of interruption, is effective in preventing or reducing the incidence or severity of a delayed cerebral ischemia (DCI).

According to another embodiment, the therapeutic amount of the flowable sustained release particulate composition, upon release of the first therapeutic agent in proximity to at least one cerebral artery in the subarachnoid space at risk of interruption, is effective in reducing the occurrence of delayed cerebral infarction on a Computed Tomography (CT) scan within 7 days, 15 days, or within 30 days of subarachnoid hemorrhage (SAH). According to another embodiment, the therapeutic amount of the flowable sustained release particulate composition, upon release of the first therapeutic agent in proximity to at least one cerebral artery in the subarachnoid space at risk of interruption, is effective in reducing the occurrence of delayed cerebral ischemia assessable as a decrease of at least 2 points on the modified Glasgow Coma Score or an increase of at least 2 points on the abbreviated National Institutes of Health Stroke Scale lasting for at least 2 hours.

Reducing Occurrence of Adverse Events

According to another embodiment, the therapeutic amount of the flowable sustained release particulate composition, upon release of the first therapeutic agent in proximity to at least one cerebral artery in the subarachnoid space at risk of interruption, is effective in reducing the occurrence of adverse events, within at least 7 days, 14 days, or within 30 days of the subarachnoid hemorrhage (SAH). According to some such embodiments, the adverse event is selected from the group consisting of hypotension, occurrence of new cerebral infarcts, seizures, cerebral infarction, increased intracranial pressure, hypersensitivity reaction, paralytic ileus, elevated liver enzymes, thrombocytopenia, cardiac rhythm disturbances, angina pectoris, myocardial infarction, or a combination thereof.

According to another embodiment, the therapeutic amount of the flowable sustained release particulate composition, upon release of the first therapeutic agent in proximity to at least one cerebral artery in the subarachnoid space at risk of interruption, is effective in reducing the occurrence of hypotension, defined as mean arterial pressure<60 mm Hg for 15 minutes.

According to another embodiment, the therapeutic amount of the flowable sustained release particulate composition, upon release of the first therapeutic agent in proximity to at least one cerebral artery in the subarachnoid space at risk of interruption, is effective in reducing the occurrence of new cerebral infarcts within at least 7 days, 14 days, or within 30 days of the subarachnoid hemorrhage (SAH).

According to another embodiment, elevated liver enzymes can be detected by a measurement of the level of enzyme(s) in the blood serum or plasma. Exemplary liver enzymes that can be measured for occurrence of adverse events include, but are not limited to, transminase (ALT), aspartate transaminase (AST), etc.

Reducing Occurrence of Serious Adverse Events

According to another embodiment, the therapeutic amount of the flowable sustained release particulate composition, upon release of the first therapeutic agent in proximity to at least one cerebral artery in the subarachnoid space at risk of interruption, is effective in reducing the occurrence of serious adverse events up to 28 days after study drug administration.

Restoring Cerebral Metabolism

According to another embodiment, the therapeutic amount of the flowable sustained release particulate composition, upon release of the first therapeutic agent in proximity to at least one cerebral artery in the subarachnoid space at risk of interruption, is effective in restoring cerebral metabolism, as measured by jugular bulb oxygen saturation, intracerebral microdialysis measurements of lactate, pyruvate and glutamate, brain tissue oxygen, or a combination thereof, as compared to an untreated control. According to another embodiment, the therapeutic amount of the flowable sustained release particulate composition, upon release of the first therapeutic agent in proximity to at least one cerebral artery in the subarachnoid space at risk of interruption, is effective in restoring the integrity of the blood brain barrier.

Reducing Need for Rescue Therapy

According to another embodiment, the therapeutic amount of the flowable sustained release particulate composition, upon release of the first therapeutic agent in proximity to at least one cerebral artery in the subarachnoid space at risk of interruption, is effective in reducing a need for rescue therapy.

According to some embodiments, the rescue therapy comprises further administering: (a) a vasopressor, (b) a vasodilator, (c) balloon angioplasty, or a combination thereof.

Effects on Clinical Outcome

According to some embodiments, the therapeutic amount of the flowable sustained release particulate composition, upon release of the first therapeutic agent in proximity to at least one cerebral artery in the subarachnoid space at risk of interruption, is effective to improve outcome, as measured on the Glasgow outcome score (GOS), extended GOS, modified Rankin scale (mRS), or other clinical outcome measure (Montreal cognitive assessment, neurocognitive assessment) compared to the outcome expected or in patients treated with a placebo particulate composition. According to one embodiment, the therapeutic amount of the flowable sustained release particulate composition, upon release of the first therapeutic agent in proximity to at least one cerebral artery in the subarachnoid space at risk of interruption, is effective to improve outcome on the Glasgow outcome score (GOS) by at least 2 points as compared to the outcome in a patient treated with a placebo particulate composition. According to another embodiment, the therapeutic amount of the flowable sustained release particulate composition, upon release of the first therapeutic agent in proximity to at least one cerebral artery in the subarachnoid space at risk of interruption, is effective to improve outcome on the extended Glasgow outcome score by at least 2 points as compared to the outcome in a patient treated with a placebo particulate composition. According to another embodiment, the therapeutic amount of the flowable sustained release particulate composition, upon release of the first therapeutic agent in proximity to at least one cerebral artery in the subarachnoid space at risk of interruption, is effective to improve outcome on the modified Rankin scale (mRS) by at least 2 points as compared to the outcome in a patient treated with a placebo particulate composition.

According to another embodiment, the therapeutic amount of the flowable sustained release particulate composition, upon release of the first therapeutic agent in proximity to at least one cerebral artery in the subarachnoid space at risk of interruption, is effective to reduce the occurrence of poor outcome 90 days after subarachnoid hemorrhage (SAH). According to some embodiments, the therapeutic amount of the flowable sustained release particulate composition, upon release of the first therapeutic agent in proximity to at least one cerebral artery in the subarachnoid space at risk of interruption, is effective to reduce the occurrence of poor outcome, as measured on the Glasgow outcome score (GOS), extended GOS, modified Rankin scale (mRS), or other clinical outcome measure (Montreal cognitive assessment, neurocognitive assessment) compared to the outcome expected or in patients treated with a placebo particulate composition. According to one embodiment, the therapeutic amount of the flowable sustained release particulate composition, upon release of the first therapeutic agent in proximity to at least one cerebral artery in the subarachnoid space at risk of interruption, is effective to reduce the occurrence of poor outcome on the Glasgow outcome score (GOS) by at least 2 points as compared to the outcome in a patient treated with a placebo microparticle composition. According to another embodiment, the therapeutic amount of the flowable sustained release particulate composition, upon release of the first therapeutic agent in proximity to at least one cerebral artery in the subarachnoid space at risk of interruption, is effective to reduce the occurrence of poor outcome on the extended Glasgow outcome score by at least 2 points as compared to the outcome in a patient treated with a placebo particulate composition. According to another embodiment, the therapeutic amount of the flowable sustained release particulate composition, upon release of the first therapeutic agent in proximity to at least one cerebral artery in the subarachnoid space at risk of interruption, is effective to reduce the occurrence of poor outcome on the modified Rankin scale (mRS) by at least 2 points as compared to the outcome in a patient treated with a placebo particulate composition.

Administering Step

According to one embodiment, the composition is administered via injection into the subarachnoid space in a cistern closest to the cerebral artery at risk for interruption. According to another embodiment, the composition is administered intraventricularly so that the pharmaceutical composition is carried by CSF flow to contact the at least one artery of the subarachnoid space at risk of interruption. According to another embodiment, the composition is administered intrathecally so that the pharmaceutical composition is carried by CSF flow to contact the at least one artery of the subarachnoid space at risk of interruption. According to another embodiment, the composition is administered intrathecally into the spinal subarachnoid space so that the pharmaceutical composition is carried by CSF flow to contact the at least one artery of the subarachnoid space at risk of interruption.

According to some embodiments, the flowable sustained release particulate composition is administered parenterally using an injection apparatus. According to some such embodiments, the injection apparatus is a needle, a cannula, a catheter, or a combination thereof According to some embodiments, administering is by passage through a catheter or catheterization. The term "catheterization" refers to a minimally invasive procedure by which the flowable sustained release particulate composition can access the desired areas of the brain, which can mean less risk of complications and a shorter recovery. According to some embodiments, the catheter is a silicone catheter. According to some embodiments, the catheter is a soft catheter. According to some embodiments, the catheter is a flexible catheter. According to some embodiments, the catheter is a pliable catheter.

According to some embodiments, the site of delivery in the central nervous system (CNS) is a site selected from the group consisting of an intracisternal site, an intraventricular site, an intrathecal site, or a combination thereof According to another embodiment, the site of delivery in the central nervous system (CNS) is an intraventricular site. According to one embodiment, the intraventricular site is into a cerebral ventricle such that the flowable sustained release particulate composition comprising the at least one first therapeutic agent is carried by CSF circulation to the subarachnoid space so as to contact the at least one cerebral artery at risk of interruption due to the brain injury. According to some embodiments, the cerebral ventricle is selected from the group consisting of a lateral ventricle, a third ventricle, a fourth ventricle, or a combination thereof. According to one embodiment, the cerebral ventricle is a lateral ventricle. According to another embodiment, the cerebral ventricle is a third ventricle. According to another embodiment, the cerebral ventricle is a fourth ventricle.

According to another embodiment, the flowable sustained release particulate composition comprising the at least one first therapeutic agent is administered parenterally via the injection apparatus locally into a cerebral ventricle so that the composition is carried by CSF circulation so as to contact and flow around the cerebral artery in the subarachnoid space at risk of interruption without the first therapeutic agent entering the systemic circulation in an amount to cause unwanted side effects.

According to some embodiments, the cerebral ventricle is at least 0.001 mm to at least 10 cm from the at least one cerebral artery in the subarachnoid space at risk of interruption caused by a brain injury. According to one embodiment, the cerebral ventricle is at least 0.001 mm from the at least one cerebral artery in the subarachnoid space at risk of interruption caused by the brain injury. According to another embodiment, the cerebral ventricle is at least 0.005 mm from the at least one cerebral artery in the subarachnoid space at risk of interruption caused by the brain injury. According to another embodiment, the cerebral ventricle is at least 0.01 mm from the at least one cerebral artery in the subarachnoid space at risk of interruption caused by the brain injury. According to another embodiment, the cerebral ventricle is at least 0.05 mm from the at least one cerebral artery in the subarachnoid space at risk of interruption caused by the brain injury. According to another embodiment, the cerebral ventricle is at least 0.1 mm from the at least one cerebral artery in the subarachnoid space at risk of interruption caused by the brain injury. According to another embodiment, the cerebral ventricle is at least 0.5 mm from the at least one cerebral artery in the subarachnoid space at risk of interruption caused by the brain injury. According to another embodiment, the cerebral ventricle is at least 1.0 mm from the at least one cerebral artery in the subarachnoid space at risk of interruption caused by the brain injury. According to another embodiment, the cerebral ventricle is at least 1.5 mm from the at least one cerebral artery in the subarachnoid space at risk of interruption caused by the brain injury. According to another embodiment, the cerebral ventricle is at least 2.0 mm from the at least one cerebral artery in the subarachnoid space at risk of interruption caused by the brain injury. According to another embodiment, the cerebral ventricle is at least 2.5 mm from the at least one cerebral artery in the subarachnoid space at risk of interruption caused by the brain injury. According to another embodiment, the cerebral ventricle is at least 3.0 mm from the at least one cerebral artery in the subarachnoid space at risk of interruption caused by the brain injury. According to another embodiment, the cerebral ventricle is at least 3.5 mm from the at least one cerebral artery in the subarachnoid space at risk of interruption caused by the brain injury. According to another embodiment, the cerebral ventricle is at least 4.0 mm from the at least one cerebral artery in the subarachnoid space at risk of interruption caused by the brain injury. According to another embodiment, the cerebral ventricle is at least 4.5 mm from the at least one cerebral artery in the subarachnoid space at risk of interruption caused by the brain injury. According to another embodiment, the cerebral ventricle is at least 5.0 mm from the at least one cerebral artery in the subarachnoid space at risk of interruption caused by the brain injury. According to another embodiment, the cerebral ventricle is at least 5.5 mm from the at least one cerebral artery in the subarachnoid space at risk of interruption caused by the brain injury. According to another embodiment, the cerebral ventricle is at least 6.0 mm from the at least one cerebral artery in the subarachnoid space at risk of interruption caused by the brain injury. According to another embodiment, the cerebral ventricle is at least 6.5 mm from the at least one cerebral artery in the subarachnoid space at risk of interruption caused by the brain injury. According to another embodiment, the cerebral ventricle is at least 7.0 mm from the at least one cerebral artery in the subarachnoid space at risk of interruption caused by the brain injury. According to another embodiment, the cerebral ventricle is at least 7.5 mm from the at least one cerebral artery in the subarachnoid space at risk of interruption caused by the brain injury. According to another embodiment, the cerebral ventricle is at least 8.0 mm from the at least one cerebral artery in the subarachnoid space at risk of interruption caused by the brain injury. According to another embodiment, the cerebral ventricle is at least 8.5 mm from the at least one cerebral artery in the subarachnoid space at risk of interruption caused by the brain injury. According to another embodiment, the cerebral ventricle is at least 9.0 mm from the at least one cerebral artery in the subarachnoid space at risk of interruption caused by the brain injury. According to another embodiment, the cerebral ventricle is at least 9.5 mm from the at least one cerebral artery in the subarachnoid space at risk of interruption caused by the brain injury. According to another embodiment, the cerebral ventricle is at least 1 cm from the at least one cerebral artery in the subarachnoid space at risk of interruption caused by the brain injury. According to another embodiment, the cerebral ventricle is at least 1.5 cm from the at least one cerebral artery in the subarachnoid space at risk of interruption caused by the brain injury. According to another embodiment, the cerebral ventricle is at least 2.0 cm from the at least one cerebral artery in the subarachnoid space at risk of interruption caused by the brain injury. According to another embodiment, the cerebral ventricle is at least 2.5 cm from the at least one cerebral artery in the subarachnoid space at risk of interruption caused by the brain injury. According to another embodiment, the cerebral ventricle is at least 3.0 cm from the at least one cerebral artery in the subarachnoid space at risk of interruption caused by the brain injury. According to another embodiment, the cerebral ventricle is at least 3.5 cm from the at least one cerebral artery in the subarachnoid space at risk of interruption caused by the brain injury. According to another embodiment, the cerebral ventricle is at least 4.0 cm from the at least one cerebral artery in the subarachnoid space at risk of interruption caused by the brain injury. According to another embodiment, the cerebral ventricle is at least 4.5 cm from the at least one cerebral artery in the subarachnoid space at risk of interruption caused by the brain injury. According to another embodiment, the cerebral ventricle is at least 5.0 cm from the at least one cerebral artery in the subarachnoid space at risk of interruption caused by the brain injury. According to another embodiment, the cerebral ventricle is at least 5.5 cm from the at least one cerebral artery in the subarachnoid space at risk of interruption caused by the brain injury. According to another embodiment, the cerebral ventricle is at least 6.0 cm from the at least one cerebral artery in the subarachnoid space at risk of interruption caused by the brain injury. According to another embodiment, the cerebral ventricle is at least 6.5 cm from the at least one cerebral artery in the subarachnoid space at risk of interruption caused by the brain injury. According to another embodiment, the cerebral ventricle is at least 7.0 cm from the at least one cerebral artery in the subarachnoid space at risk of interruption caused by the brain injury. According to another embodiment, the cerebral ventricle is at least 7.5 cm from the at least one cerebral artery in the subarachnoid space at risk of interruption caused by the brain injury. According to another embodiment, the cerebral ventricle is at least 8.0 cm from the at least one cerebral artery in the subarachnoid space at risk of interruption caused by the brain injury. According to another embodiment, the cerebral ventricle is at least 8.5 cm from the at least one cerebral artery in the subarachnoid space at risk of interruption caused by the brain injury. According to another embodiment, the cerebral ventricle is at least 9.0 cm from the at least one cerebral artery in the subarachnoid space at risk of interruption caused by the brain injury. According to another embodiment, the cerebral ventricle is at least 9.5 cm from the at least one cerebral artery in the subarachnoid space at risk of interruption caused by the brain injury. According to another embodiment, the cerebral ventricle is at least 10 cm from the at least one cerebral artery in the subarachnoid space at risk of interruption caused by the brain injury.

Figure 15:
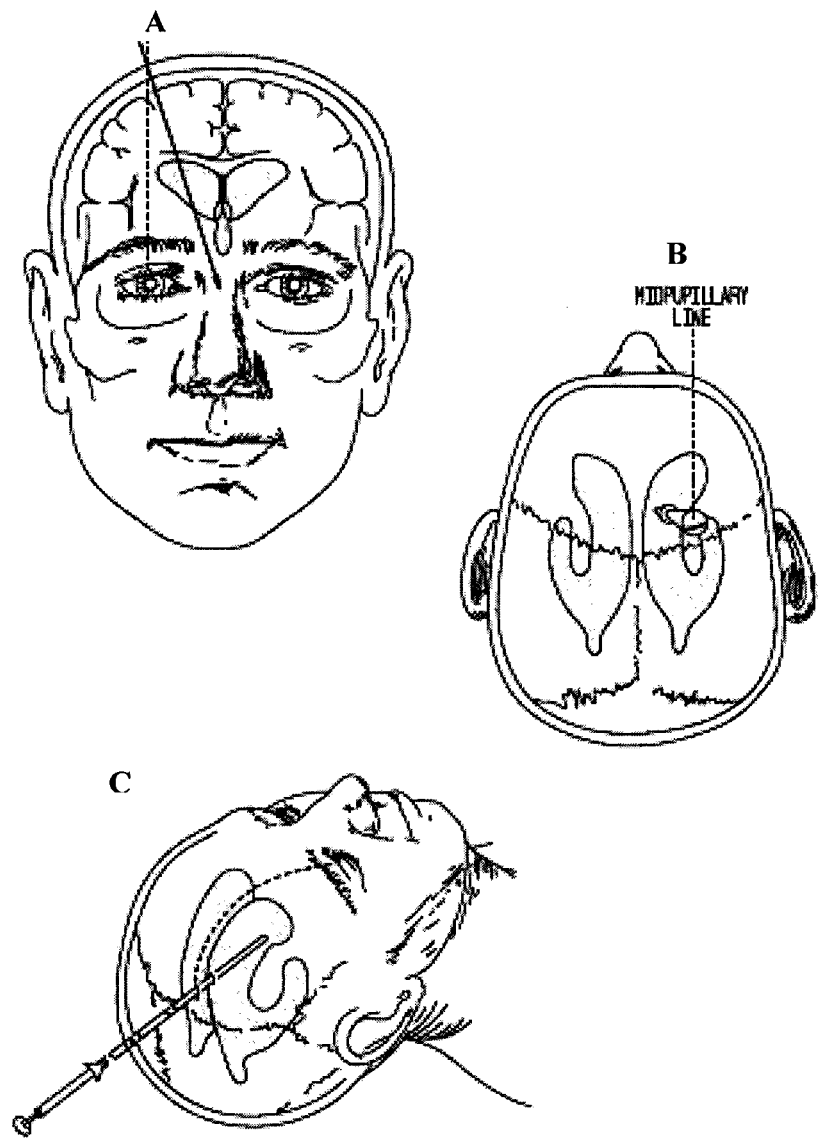
FIG. 15 shows an exemplary view of the application of a particulate composition of the described invention containing a calcium channel antagonist, an endothelin receptor antagonist, a TRP protein antagonist, or a combination thereof, to the cerebral ventricles through an intraventricular catheter (Figure from Mccomb J G: Techniques of CSF diversion. In: Scott R M (ed). Hydrocephalus. Vol. 3. Williams & Wilkins: Baltimore. 1990. page 48, pp. 128).
Figure 16:
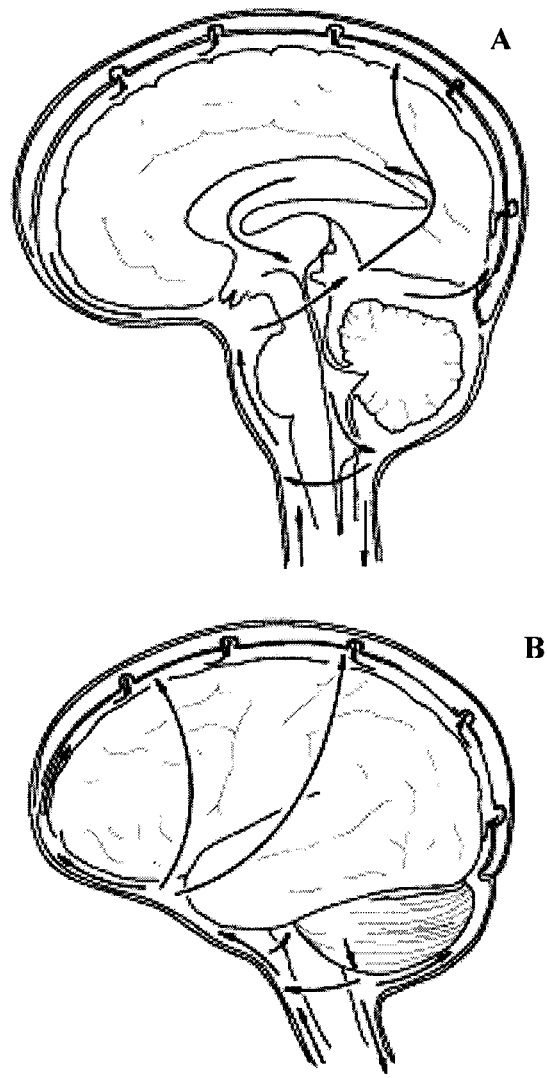
FIG. 16 is a schematic depicting a particulate composition of the described invention comprising a calcium channel antagonist, an endothelin receptor antagonist, a TRP protein antagonist, or a combination thereof, in or on particles being carried by CSF flow from the ventricles to the arteries of the subarachnoid space. (Pollay M: Cerebrospinal fluid. In: Tindall G T, Cooper P R, Barrow D L (eds). The Practice of Neurosurgery. Vol. 1. Williams & Wilkins: Baltimore. 1996. page 36, pp. 1381).

The cerebral ventricles may be cannulated or catheterized as is well-known in the art and as described in various neurosurgical textbooks. This is called insertion of a ventricular catheter or drain or ventriculostomy. According to some embodiments, a hole of varying size can be drilled in the skull and the outer dura mater covering the brain incised. The pia mater is incised and a catheter (a hollow tube generally made of silicone elastomer or some other biocompatible, nonabsorbable compound) is inserted through the brain into the ventricle of choice. This usually is the lateral ventricle but any ventricle could be catheterized. The catheter can be used to monitor the pressure inside the head, to drain CSF or to administer substances into the CSF. FIG. 15 shows an exemplary view of the application of a particulate composition of the described invention containing a calcium channel antagonist, an endothelin receptor antagonist, a TRP protein antagonist, or a combination thereof, to the cerebral ventricles through an intraventricular catheter (Figure from Mccomb J G: Techniques of CSF diversion. In: Scott R M (ed). Hydrocephalus. Vol. 3. Williams & Wilkins: Baltimore. 1990. page 48, pp. 128). FIG. 16 is a schematic depicting a particulate composition of the described invention comprising a calcium channel antagonist, an endothelin receptor antagonist, a TRP protein antagonist, or a combination thereof, in or on microparticles being carried by CSF flow from the ventricles to the arteries of the subarachnoid space (Pollay M: Cerebrospinal fluid. In: Tindall G T, Cooper P R, Barrow D L (eds). The Practice of Neurosurgery. Vol. 1. Williams & Wilkins: Baltimore. 1996. page 36, pp. 1381).

According to one embodiment, release of the first therapeutic agent from the particulate formulation occurs in the CSF of the subarachnoid space. The circulation of CSF is often slowed after SAH due to the presence of blood clots in the subarachnoid space. Thus, the flowable sustained release particulate composition can become trapped in the blood clots, thereby facilitating localized release of the pharmacological agent(s) from the particulate formulation where a pharmacological effect to the adjacent arteries and brain is achieved.

According to one embodiment, the flowable sustained release particulate composition comprising the at least one first therapeutic agent can be delivered by inserting a catheter into the ventricle and injecting the flowable sustained release particulate composition through the catheter such that the composition emanates from the end of the catheter locally into the ventricle.

According to another embodiment, the flowable sustained release particulate composition is administered as a single bolus injection. According to another embodiment, the injection is repeated after a pre-determined time period. According to some such embodiments, the pre-determined time period ranges from 1 minute or more to 10 days or more. For example, a repeat injection can be given if monitoring of the patient shows that the patient still had evidence of an interruption of a cerebral artery.

According to one embodiment, the site of delivery in the central nervous system (CNS) is an intracisternal site. According to one embodiment, the intracisternal site is a cerebral cistern closest to the at least one cerebral artery at risk of interruption due to the brain injury, such that the composition comprising the at least one first therapeutic agent flows around the at least one cerebral artery at risk of interruption due to the brain injury without the first therapeutic agent entering the systemic circulation in an amount to cause unwanted side effects.

According to some embodiments, the cerebral cistern is at least one of a cisterna magna, a carotid cistern, a chiasmatic cistern, a Sylvian cistern, an interhemispheric cistern, an ambient cistern, a crural cistern, an interpeduncular cistern, a prepontine cistern, and a lateral medullary cistern. According to one embodiment, the cerebral cistern is a cisterna magna. According to another embodiment, the cerebral cistern is a a carotid cistern. According to another embodiment, the cerebral cistern is a a chiasmatic cistern. According to another embodiment, the cerebral cistern is a Sylvian cistern. According to another embodiment, the cerebral cistern is an interhemispheric cistern. According to another embodiment, the cerebral cistern is an ambient cistern. According to another embodiment, the cerebral cistern is a crural cistern. According to another embodiment, the cerebral cistern is an interpeduncular cistern. According to another embodiment, the cerebral cistern is a prepontine cistern. According to another embodiment, the cerebral cistern is a lateral medullary cistern.

According to another embodiment, the flowable sustained release particulate composition comprising the at least one first therapeutic agent can be delivered by inserting a catheter into the cerebral cistern closest to the at least one cerebral artery at risk of interruption due to the brain injury.

According to some embodiments, the cerebral cistern is at least 0.001 mm to at least 10 cm from the at least one cerebral artery in the subarachnoid space at risk of interruption caused by a brain injury. According to one embodiment, the cerebral cistern is at least 0.001 mm from the at least one cerebral artery in the subarachnoid space at risk of interruption caused by the brain injury. According to another embodiment, the cerebral cistern is at least 0.005 mm from the at least one cerebral artery in the subarachnoid space at risk of interruption caused by the brain injury. According to another embodiment, the cerebral cistern is at least 0.01 mm from the at least one cerebral artery in the subarachnoid space at risk of interruption caused by the brain injury. According to another embodiment, the cerebral cistern is at least 0.05 mm from the at least one cerebral artery in the subarachnoid space at risk of interruption caused by the brain injury. According to another embodiment, the cerebral cistern is at least 0.1 mm from the at least one cerebral artery in the subarachnoid space at risk of interruption caused by the brain injury. According to another embodiment, the cerebral cistern is at least 0.5 mm from the at least one cerebral artery in the subarachnoid space at risk of interruption caused by the brain injury. According to another embodiment, the cerebral cistern is at least 1.0 mm from the at least one cerebral artery in the subarachnoid space at risk of interruption caused by the brain injury. According to another embodiment, cerebral cistern is at least 1.5 mm from the at least one cerebral artery in the subarachnoid space at risk of interruption caused by the brain injury. According to another embodiment, the cerebral cistern is at least 2.0 mm from the at least one cerebral artery in the subarachnoid space at risk of interruption caused by the brain injury. According to another embodiment, the cerebral cistern is at least 2.5 mm from the at least one cerebral artery in the subarachnoid space at risk of interruption caused by the brain injury. According to another embodiment, the cerebral cistern is at least 3.0 mm from the at least one cerebral artery in the subarachnoid space at risk of interruption caused by the brain injury. According to another embodiment, the cerebral cistern is at least 3.5 mm from the at least one cerebral artery in the subarachnoid space at risk of interruption caused by the brain injury. According to another embodiment, the cerebral cistern is at least 4.0 mm from the at least one cerebral artery in the subarachnoid space at risk of interruption caused by the brain injury. According to another embodiment, the cerebral cistern is at least 4.5 mm from the at least one cerebral artery in the subarachnoid space at risk of interruption caused by the brain injury. According to another embodiment, the cerebral cistern is at least 5.0 mm from the at least one cerebral artery in the subarachnoid space at risk of interruption caused by the brain injury. According to another embodiment, the cerebral cistern is at least 5.5 mm from the at least one cerebral artery in the subarachnoid space at risk of interruption caused by the brain injury. According to another embodiment, the cerebral cistern is at least 6.0 mm from the at least one cerebral artery in the subarachnoid space at risk of interruption caused by the brain injury. According to another embodiment, the cerebral cistern is at least 6.5 mm from the at least one cerebral artery in the subarachnoid space at risk of interruption caused by the brain injury. According to another embodiment, the cerebral cistern is at least 7.0 mm from the at least one cerebral artery in the subarachnoid space at risk of interruption caused by the brain injury. According to another embodiment, the cerebral cistern is at least 7.5 mm from the at least one cerebral artery in the subarachnoid space at risk of interruption caused by the brain injury. According to another embodiment, the cerebral cistern is at least 8.0 mm from the at least one cerebral artery in the subarachnoid space at risk of interruption caused by the brain injury. According to another embodiment, the cerebral cistern is at least 8.5 mm from the at least one cerebral artery in the subarachnoid space at risk of interruption caused by the brain injury. According to another embodiment, the cerebral cistern is at least 9.0 mm from the at least one cerebral artery in the subarachnoid space at risk of interruption caused by the brain injury. According to another embodiment, the cerebral cistern is at least 9.5 mm from the at least one cerebral artery in the subarachnoid space at risk of interruption caused by the brain injury. According to another embodiment, the cerebral cistern is at least 1 cm from the at least one cerebral artery in the subarachnoid space at risk of interruption caused by the brain injury According to another embodiment, the site of delivery in the central nervous system (CNS) is an intrathecal site. According to one embodiment, the intrathecal site is into the subarachnoid space of the spinal canal, such that the flowable sustained release particulate composition comprising the at least one first therapeutic agent is capable of flowing from the CSF of the spinal canal to the CSF in the subarachnoid space of the brain to contact the at least one cerebral artery at risk of interruption due to the brain injury without the first therapeutic agent entering the systemic circulation in an amount to cause unwanted side effects.

According to another embodiment, the intrathecal site is at least 1.5 cm from the at least one cerebral artery in the subarachnoid space of the brain at risk of interruption caused by the brain injury. According to another embodiment, the intrathecal site is at least 2.0 cm from the at least one cerebral artery in the subarachnoid space of the brain at risk of interruption caused by the brain injury. According to another embodiment, the intrathecal site is at least 2.5 cm from the at least one cerebral artery in the subarachnoid space of the brain at risk of interruption caused by the brain injury. According to another embodiment, the intrathecal site is at least 3.0 cm from the at least one cerebral artery in the subarachnoid space of the brain at risk of interruption caused by the brain injury. According to another embodiment, the intrathecal site is at least 3.5 cm from the at least one cerebral artery in the subarachnoid space of the brain at risk of interruption caused by the brain injury. According to another embodiment, the intrathecal site is at least 4.0 cm from the at least one cerebral artery in the subarachnoid space of the brain at risk of interruption caused by the brain injury. According to another embodiment, the intrathecal site is at least 4.5 cm from the at least one cerebral artery in the subarachnoid space of the brain at risk of interruption caused by the brain injury. According to another embodiment, the intrathecal site is at least 5.0 cm from the at least one cerebral artery in the subarachnoid space of the brain at risk of interruption caused by the brain injury. According to another embodiment, the intrathecal site is at least 5.5 cm from the at least one cerebral artery in the subarachnoid space of the brain at risk of interruption caused by the brain injury. According to another embodiment, the intrathecal site is at least 6.0 cm from the at least one cerebral artery in the subarachnoid space of the brain at risk of interruption caused by the brain injury. According to another embodiment, the intrathecal site is at least 6.5 cm from the at least one cerebral artery in the subarachnoid space of the brain at risk of interruption caused by the brain injury. According to another embodiment, the intrathecal site is at least 7.0 cm from the at least one cerebral artery in the subarachnoid space of the brain at risk of interruption caused by the brain injury. According to another embodiment, the intrathecal site is at least 7.5 cm from the at least one cerebral artery in the subarachnoid space of the brain at risk of interruption caused by the brain injury. According to another embodiment, the intrathecal site is at least 8.0 cm from the at least one cerebral artery in the subarachnoid space of the brain at risk of interruption caused by the brain injury. According to another embodiment, the intrathecal site is at least 8.5 cm from the at least one cerebral artery in the subarachnoid space of the brain at risk of interruption caused by the brain injury. According to another embodiment, the intrathecal site is at least 9.0 cm from the at least one cerebral artery in the subarachnoid space of the brain at risk of interruption caused by the brain injury. According to another embodiment, the intrathecal site is at least 9.5 cm from the at least one cerebral artery in the subarachnoid space of the brain at risk of interruption caused by the brain injury. According to another embodiment, the intrathecal site is at least 10 cm from the at least one cerebral artery in the subarachnoid space of the brain at risk of interruption caused by the brain injury.

First Therapeutic Agent

According to some embodiments, the first therapeutic agent is a calcium channel antagonist, an endothelin antagonist, a transient receptor potential (TRP) protein antagonist, or a combination thereof.

According to one embodiment, the first therapeutic agent is a calcium channel antagonist. According to some embodiments, the calcium channel antagonist is selected from the group consisting of an L-type voltage dependent calcium channel inhibitor, an R-type voltage dependent calcium channel inhibitor, an N-type voltage dependent calcium channel inhibitor, a P/Q-type voltage dependent calcium channel inhibitor, a T-type voltage dependent calcium channel inhibitor, or a combination thereof. According to one embodiment, the calcium channel antagonist is an L-type voltage dependent calcium channel inhibitor. According to another embodiment, the calcium channel antagonist is an R-type voltage dependent calcium channel inhibitor. According to another embodiment, the calcium channel antagonist is an N-type voltage dependent calcium channel inhibitor. According to another embodiment, the calcium channel antagonist is a P/Q-type voltage dependent calcium channel inhibitor. According to another embodiment, the calcium channel antagonist is a T-type voltage dependent calcium channel inhibitor.

For example, L-type voltage dependent calcium channel inhibitor include, but are not limited to: dihydropyridine L-type antagonists such as nimodipine, nisoldipine, nicardipine and nifedipine, AHF (such as 4aR,9aS)-(+)-4a-Amino-1,2,3,4,4a,9a-hexahydro-4aH-fluorene, HCl), isradipine (such as 4-(4-Benzofurazanyl)-1,-4-dihydro-2,6-dimethyl-3,5-pyridinedicarboxylic acid methyl 1-methylethyl ester), calciseptine/calciseptin (such as isolated from (*Dendroaspis polylepis ploylepis*), H-Arg-Ile-Cys-Tyr-Ile-His-Lys-Ala-Ser-Leu-Pro-Arg -Ala-Thr-Lys-Thr-Cys-Val-Glu-Asn-Thr-Cys-Tyr-Lys-Met-Phe-Ile-Arg-Thr-Gln-Arg-Glu-Tyr -Ile-Ser-Glu-Arg-Gly-Cys-Gly-Cys-Pro-Thr-Ala-Met-Trp-Pro-Tyr-Gln-Thr-Glu-Cys-Cys-Lys -Gly-Asp-Arg-Cys-Asn-Lys-OH (SEQ ID NO. 1), Calciclu-dine (such as isolated from *Dendroaspis angusticeps* (eastern green mamba)), (H-Trp-Gln-Pro-Pro-Trp-Tyr-Cys-Lys-Glu -Pro-Val-Arg-Ile-Gly-Ser-Cys-Lys-Lys-Gln-Phe-Ser-Ser-Phe-Tyr-Phe-Lys-Trp-Thr-Ala-Lys -Lys-Cys-Leu-Pro- Phe-Leu-Phe-Ser-Gly-Cys-Gly-Gly-Asn-Ala-Asn-Arg-Phe-Gln-Thr-Ile-Gly -Glu-Cys-Arg-Lys-Lys-Cys-Leu-Gly-Lys-OH (SEQ ID NO. 2), Cilnidipine (such as also FRP-8653, a dihydropyridine-type inhibitor), Dilantizem (such as (2S, 3S)-(+)-cis-3-Acetoxy-5-(2-dimethylaminoethyl)-2,3-dihydro-2-(4-methoxyphenyl)-1,5-benzothiazepin-4(5H)-one hydrochloride), diltiazem (such as benzothiazepin-4(5H)-one, 3-(acetyloxy)-5-[2-(dimethylamino)ethyl]-2,3-dihydro-2-(4-methoxyphenyl)-, (+)-cis-, monohydrochloride), Felodipine (such as 4-(2,3-Dichlorophenyl)-1,4-dihydro-2,6-dimethyl-3,5-pyridinecarboxylic acid ethyl methyl ester), FS-2 (such as an isolate from *Dendroaspis polylepis polylepis* venom), FTX-3.3 (such as an isolate from *Agelenopsis aperta*), Neomycin sulfate (such as $C_{23}H_{46}N_6O_{13} \cdot 3H_2SO_4$), Nicardipine (such as 1,4-Dihydro-2,6-dimethyl-4-(3-nitrophenylmethyl-2-[methyl(phenylmethylamino]-3,5-pyridinedicarboxylic acid ethyl ester hydrochloride, also YC-93, Nifedipine (such as 1,4-Dihydro-2,6-dimethyl-4-(2-nitrophenyl)-3,5-pyridinedicarboxylic acid dimethyl ester), Nimodipine (such as 4-Dihydro-2,6-dimethyl-4-(3-nitrophenyl)-3,5-pyridinedicarboxylic acid 2-methoxyethyl 1-methylethyl ester) or (Isopropyl 2-methoxyethyl 1,4-dihydro-2,6-dimethyl-4-(m-nitrophenyl)-3,5-pyridinedicarboxylate), Nitrendipine (such as 1,4-Dihydro-2,6-dimethyl-4-(3-nitrophenyl)-3,5-pyridinedicarboxylic acid ethyl methyl ester), S-Petasin (such as (3S,4aR,5R,6R)-[2,3,4,4a,5,6,7,8-Octahydro-3-(2-propenyl)-4-a,5-dimethyl-2-o-xo-6-naphthyl]Z-3'-methylthio-1'-propenoate), Phloretin (such as 2',4',6'-Trihydroxy-3-(4-hydroxyphenyl)propiophenone, also 3-(4-Hydroxyphenyl)-1-(2,4,6-trihydroxyphenyl)-1-propanone, also b-(4-Hydroxyphenyl)-2,4,6-trihydroxypropiophenone), Protopine (such as $C_{20}H_{19}NO_5Cl$), SKF-96365 (such as 1-[b-[3-(4-Methoxyphenyl)propoxy]-4-methoxyphenethyl]-1H-imidazole, HCl), Tetrandine (such as 6,6',7,12-Tetramethoxy-2,2'-dimethylberbaman), (+/−)-Methoxyverapamil or (+)-Verapamil (such as 54N-(3,4-Dimethoxyphenylethyl)methylamino]-2-(3,4-dimethoxyphenyl)-2-iso-propylvaleronitrile hydrochloride), and (R)-(+)-Bay K8644 (such as R-(+)-1,4-Dihydro-2,6-dimethyl-5-nitro-442-(trifluoromethyl)phenyl]-3-pyridinecarboxylic acid methyl ester). The foregoing examples may be specific to L-type voltage-gated calcium channels or may inhibit a broader range of voltage-gated calcium channels, e.g. N, P/Q, R, and T-type.

According to some embodiments, the L-type voltage dependent calcium channel inhibitor is a dihydropyridine. Exemplary dihydropyridines include, but are not limited to, amlodipine, aranidipine, azelnidipine, bamidipine, benidipine, cinaldipine, efonidipine, felodipine, isradipine, lacidipine, lemildipine, lercanidipine, nicardipine, nifedipine, nilvadipine, nimodipine, nisoldipine, nitrendipine, manidipine, pranidipine, etc. According to one embodiment, the dihydropyridine is nimodipine. According to one embodiment, the nimodipine has a half life of 7-10 days when formulated as described herein, and appropriate lipid solubility.

According to some embodiments, the L-type voltage dependent calcium channel inhibitor is a phenylalkylamine. Exemplary phenylalkylamines include, but are not limited to, gallopamil, verapamil, etc. According to some embodiments, the L-type voltage dependent calcium channel inhibitor is a 1-4 benzothiazepine. According to one embodiment, the 1-4 benzothiazepine is diltiazem. According to one embodiment, the L-type voltage dependent calcium channel inhibitor is bepridil. According to another embodiment, the L-type voltage dependent calcium channel inhibitor is nimodipine.

According to another embodiment, the first therapeutic agent is an endothelin antagonist. Exemplary endothelin antagonists include, but are not limited to, A-127722, ABT-627, BMS 182874, BQ-123, BQ-153, BQ-162, BQ-485, BQ-518, BQ-610, EMD-122946, FR 139317, IPI-725, L-744453, LU 127043, LU 135252, PABSA, PD 147953, PD 151242, PD 155080, PD 156707, RO 611790, SB-247083, clazosentan, atrasentan, sitaxsentan sodium, TA-0201, TBC 11251, TTA-386, WS-7338B, ZD-1611, aspirin, A-182086, CGS 27830, CP 170687, J-104132, L-751281, L-754142, LU 224332, LU 302872, PD 142893, PD 145065, PD 160672, RO-470203, bosentan, RO 462005, RO 470203, SB 209670, SB 217242, TAK-044, A-192621, A-308165, BQ-788, BQ-017, IRL 1038, IRL 2500, PD-161721, RES 701-1, RO 468443, etc.

According to another embodiment, the first therapeutic agent is a transient receptor potential (TRP) protein antagonist. Exemplary transient receptor potential (TRP) protein antagonists include, but are not limited to, gadolinium chloride, lanthanum chloride, SKF 96365 (1-(beta-[3-(4-methoxy-phenyl)propoxy]-4-methoxyphenethyl)-1H-imidazole hydrochloride), and LOE 908 ((RS)-(3,4-dihydro-6,7-dimethoxyisoquinoline-1-gamma 1)-2-phenyl-N, N-di-[2-(2,3,4-trimethoxyphenyl)ethyl]acetamide).

According to some embodiments, the first therapeutic agent is an isolated molecule. According to some embodiments, the first therapeutic agent is substantially pure.

According to some embodiments, the therapeutic amount of the first therapeutic agent constitutes from about 0.000001 mg/ml of the particulate formulation to about 1,000 mg/ml of the particulate formulation. According to one embodiment, the therapeutic amount of the first therapeutic agent constitutes about 0.000001 mg/ml of the particulate formulation. According to another embodiment, the therapeutic amount of the first therapeutic agent constitutes about 0.00001 mg/ml of the particulate formulation. According to another embodiment, the therapeutic amount of the first therapeutic agent constitutes about 0.0001 mg/ml of the particulate formulation. According to another embodiment, the therapeutic amount of the first therapeutic agent constitutes about 0.001 mg/ml of the particulate formulation. According to another embodiment, the therapeutic amount of the first therapeutic agent constitutes about 0.01 mg/ml of the particulate formulation. According to another embodiment, the therapeutic amount of the first therapeutic agent constitutes about 0.1 mg/ml of the particulate formulation. According to another embodiment, the therapeutic amount of the first therapeutic agent constitutes about 1 mg/ml of the particulate formulation. According to another embodiment, the therapeutic amount of the at least one first therapeutic agent constitutes about 10 mg/ml of the particulate formulation. According to another embodiment, the therapeutic amount of the first therapeutic agent constitutes about 20 mg/ml of the particulate formulation. According to another embodiment, the therapeutic amount of the first therapeutic agent constitutes about 30 mg/ml of the particulate formulation. According to another embodiment, the therapeutic amount of the first therapeutic agent constitutes about 40 mg/ml of the particulate formulation. According to another embodiment, the therapeutic amount of the first therapeutic agent constitutes about 50 mg/ml of the particulate formulation. According to another embodiment, the therapeutic amount of the first therapeutic agent constitutes about 60 mg/ml of the particulate formulation. According to another embodiment, the therapeutic amount of the first therapeutic agent constitutes about 70 mg/ml of the particulate formulation. According to another embodiment, the therapeutic amount of the first therapeutic agent constitutes about 80 mg/ml of the particulate formulation. According to another embodiment, the therapeutic amount of the first therapeutic agent constitutes about 90 mg/ml of the particulate formulation. According to another embodiment, the therapeutic amount of the first therapeutic agent constitutes about 100 mg/ml of the particulate formulation. According to another embodiment, the therapeutic amount of the first therapeutic agent constitutes about 150 mg/ml of the particulate formulation. According to another embodiment, the therapeutic amount of the first therapeutic agent constitutes about 200 mg/ml of the particulate formulation. According to another embodiment, the therapeutic amount of the first therapeutic agent constitutes about 250 mg/ml of the particulate formulation. According to another embodiment, the therapeutic amount of the first therapeutic agent constitutes about 300 mg/ml of the particulate formulation. According to another embodiment, the therapeutic amount of the first therapeutic agent constitutes about 350 mg/ml of the particulate formulation. According to another embodiment, the therapeutic amount of the first therapeutic agent constitutes about 400 mg/ml of the particulate formulation. According to another embodiment, the therapeutic amount of the first therapeutic agent constitutes about 450 mg/ml of the particulate formulation. According to another embodiment, the therapeutic amount of the first therapeutic agent constitutes about 500 mg/ml of the particulate formulation. According to another embodiment, the therapeutic amount of the first therapeutic agent constitutes about 550 mg/ml of the particulate formulation. According to another embodiment, the therapeutic amount of the first therapeutic agent constitutes about 600 mg/ml of the particulate formulation. According to another embodiment, the therapeutic amount of the first therapeutic agent constitutes about 650 mg/ml of the particulate formulation. According to another embodiment, the therapeutic amount of the therapeutic agent constitutes about 700 mg/ml of the particulate formulation. According to another embodiment, the therapeutic amount of the first therapeutic agent constitutes about 750 mg/ml of the particulate formulation. According to another embodiment, the therapeutic amount of the first therapeutic agent constitutes about 800 mg/ml of the particulate formulation. According to another embodiment, the therapeutic amount of the first therapeutic agent constitutes about 850 mg/ml of the particulate formulation. According to another embodiment, the therapeutic amount of the first therapeutic agent constitutes about 900 mg/ml of the particulate formulation. According to another embodiment, the therapeutic amount of the first therapeutic agent constitutes about 950 mg/ml of the particulate formulation. According to another embodiment, the therapeutic amount of the first therapeutic agent constitutes about 1,000 mg/ml of the particulate formulation.

According to some embodiments, the therapeutic amount of the first therapeutic agent is at least about 40 mg, at least about 50 mg, at least about 60 mg, at least about 70 mg, at least about 80 mg, at least about 90 mg, at least about 100 mg, at least about 120 mg, at least about 140 mg, at least about 160 mg, at least about 180 mg, at least about 200 mg, at least about 220 mg, at least about 240 mg, at least about 260 mg, at least about 280 mg, at least about 300 mg, at least about 320 mg, at least about 340 mg, at least about 360 mg, at least about 380 mg, at least about 400 mg, at least about 420 mg, at least about 440 mg, at least about 460 mg, at least about 480 mg, at least about 500 mg, at least about 520 mg, at least about 540 mg, at least about 560 mg, at least about 580 mg, at least about 600 mg, at least about 620 mg, at least about 640 mg, at least about 660 mg, at least about 680 mg, at least about 700 mg, at least about 720 mg, at least about 740 mg, at least about 760 mg, at least about 780 mg, at least about 800 mg, at least about 820 mg, at least about 840 mg, at least about 860 mg, at least about 880 mg, at least about 900 mg, at least about 920 mg, at least about 940 mg, at least about 960 mg, at least about 980 mg, or at least about 1,000 mg or more.

According to some embodiments, the flowable sustained release particulate composition is administered in at least 1 administered dose, at least 2 administered doses, at least 3 administered doses, at least 4 administered doses, at least 5 administered doses, at least 6 administered doses, at least 7 administered doses, at least 8 administered doses, at least 9 administered doses, at least 10 administered doses, at least 11 administered doses, at least 12 administered doses, at least 13 administered doses, at least 14 administered doses, at least 15 administered doses, at least 16 administered doses, at least 17 administered doses, at least 18 administered doses, at least 19 administered doses, at least 20 administered doses or more.

According to some embodiments, the administered dose contains at least about 40 mg, at least about 50 mg, at least about 60 mg, at least about 70 mg, at least about 80 mg, at least about 90 mg, at least about 100 mg, at least about 120 mg, at least about 140 mg, at least about 160 mg, at least about 180 mg, at least about 200 mg, at least about 220 mg, at least about 240 mg, at least about 260 mg, at least about 280 mg, at least about 300 mg, at least about 320 mg, at least about 340 mg, at least about 360 mg, at least about 380 mg, at least about 400 mg, at least about 420 mg, at least about 440 mg, at least about 460 mg, at least about 480 mg, at least about 500 mg, at least about 520 mg, at least about 540 mg, at least about 560 mg, at least about 580 mg, at least about 600 mg, at least about 620 mg, at least about 640 mg, at least about 660 mg, at least about 680 mg, at least about 700 mg, at least about 720 mg, at least about 740 mg, at least about 760 mg, at least about 780 mg, at least about 800 mg, at least about 820 mg, at least about 840 mg, at least about 860 mg, at least about 880 mg, at least about 900 mg, at least about 920 mg, at least about 940 mg, at least about 960 mg, at least about 980 mg, or at least about 1,000 mg or more of the first therapeutic agent.

According to some embodiments, the flowable sustained release particulate composition is administered at least 2 administered doses at least 1 hour apart, at least 2 hours apart, at least 4 hours apart, at least 6 hours apart, at least 8 hours apart, at least 10 hours apart, at least 12 hours apart, at least 14 hours apart, at least 16 hours apart, at least 18 hours apart, at least 20 hours apart, at least 22 hours apart, at least 24 hours apart, at least 2 days apart, at least 3 days apart, at least 4 days apart, at least 5 days apart, at least 6 days apart, at least 7 days apart, at least 14 days apart, at least one month apart, or at least 2 months apart.

According to some embodiments, the flowable sustained release particulate composition is administered at least 3 administered doses each at least 1 hour apart, at least 2 hours apart, at least 4 hours apart, at least 6 hours apart, at least 8 hours apart, at least 10 hours apart, at least 12 hours apart, at least 14 hours apart, at least 16 hours apart, at least 18 hours apart, at least 20 hours apart, at least 22 hours apart, at least 24 hours apart, at least 2 days apart, at least 3 days apart, at least 4 days apart, at least 5 days apart, at least 6 days apart, at least 7 days apart, at least 14 days apart, at least one month apart, or at least 2 months apart.

According to some embodiments, the flowable sustained release particulate composition is administered at least 4 administered doses each at least 1 hour apart, at least 2 hours apart, at least 4 hours apart, at least 6 hours apart, at least 8 hours apart, at least 10 hours apart, at least 12 hours apart, at least 14 hours apart, at least 16 hours apart, at least 18 hours apart, at least 20 hours apart, at least 22 hours apart, at least 24 hours apart, at least 2 days apart, at least 3 days apart, at least 4 days apart, at least 5 days apart, at least 6 days apart, at least 7 days apart, at least 14 days apart, at least one month apart, or at least 2 months apart.

According to some embodiments, the flowable sustained release particulate composition is administered at least 5 administered doses each at least 1 hour apart, at least 2 hours apart, at least 4 hours apart, at least 6 hours apart, at least 8 hours apart, at least 10 hours apart, at least 12 hours apart, at least 14 hours apart, at least 16 hours apart, at least 18 hours apart, at least 20 hours apart, at least 22 hours apart, at least 24 hours apart, at least 2 days apart, at least 3 days apart, at least 4 days apart, at least 5 days apart, at least 6 days apart, at least 7 days apart, at least 14 days apart, at least one month apart, or at least 2 months apart.

According to some embodiments, the flowable sustained release particulate composition is administered at least 6 administered doses each at least 1 hour apart, at least 2 hours apart, at least 4 hours apart, at least 6 hours apart, at least 8 hours apart, at least 10 hours apart, at least 12 hours apart, at least 14 hours apart, at least 16 hours apart, at least 18 hours apart, at least 20 hours apart, at least 22 hours apart, at least 24 hours apart, at least 2 days apart, at least 3 days apart, at least 4 days apart, at least 5 days apart, at least 6 days apart, at least 7 days apart, at least 14 days apart, at least one month apart, or at least 2 months apart.

According to some embodiments, the flowable sustained release particulate composition is administered at least 7 administered doses each at least 1 hour apart, at least 2 hours apart, at least 4 hours apart, at least 6 hours apart, at least 8 hours apart, at least 10 hours apart, at least 12 hours apart, at least 14 hours apart, at least 16 hours apart, at least 18 hours apart, at least 20 hours apart, at least 22 hours apart, at least 24 hours apart, at least 2 days apart, at least 3 days apart, at least 4 days apart, at least 5 days apart, at least 6 days apart, at least 7 days apart, at least 14 days apart, at least one month apart, or at least 2 months apart.

According to some embodiments, the flowable sustained release particulate composition is administered at least 8 administered doses each at least 1 hour apart, at least 2 hours apart, at least 4 hours apart, at least 6 hours apart, at least 8 hours apart, at least 10 hours apart, at least 12 hours apart, at least 14 hours apart, at least 16 hours apart, at least 18 hours apart, at least 20 hours apart, at least 22 hours apart, at least 24 hours apart, at least 2 days apart, at least 3 days apart, at least 4 days apart, at least 5 days apart, at least 6 days apart, at least 7 days apart, at least 14 days apart, at least one month apart, or at least 2 months apart.

According to some embodiments, the flowable sustained release particulate composition is administered at least 9 administered doses each at least 1 hour apart, at least 2 hours apart, at least 4 hours apart, at least 6 hours apart, at least 8 hours apart, at least 10 hours apart, at least 12 hours apart, at least 14 hours apart, at least 16 hours apart, at least 18 hours apart, at least 20 hours apart, at least 22 hours apart, at least 24 hours apart, at least 2 days apart, at least 3 days apart, at least 4 days apart, at least 5 days apart, at least 6 days apart, at least 7 days apart, at least 14 days apart, at least one month apart, or at least 2 months apart.

According to some embodiments, the flowable sustained release particulate composition is administered at least 10 administered doses each at least 1 hour apart, at least 2 hours apart, at least 4 hours apart, at least 6 hours apart, at least 8 hours apart, at least 10 hours apart, at least 12 hours apart, at least 14 hours apart, at least 16 hours apart, at least 18 hours apart, at least 20 hours apart, at least 22 hours apart, at least 24 hours apart, at least 2 days apart, at least 3 days apart, at least 4 days apart, at least 5 days apart, at least 6 days apart, at least 7 days apart, at least 14 days apart, at least one month apart, or at least 2 months apart.

According to some embodiments, the flowable sustained release particulate composition is administered at least 11 administered doses each at least 1 hour apart, at least 2 hours apart, at least 4 hours apart, at least 6 hours apart, at least 8 hours apart, at least 10 hours apart, at least 12 hours apart, at least 14 hours apart, at least 16 hours apart, at least 18 hours apart, at least 20 hours apart, at least 22 hours apart, at least 24 hours apart, at least 2 days apart, at least 3 days apart, at least 4 days apart, at least 5 days apart, at least 6 days apart, at least 7 days apart, at least 14 days apart, at least one month apart, or at least 2 months apart.

According to some embodiments, the flowable sustained release particulate composition is administered at least 12 administered doses each at least 1 hour apart, at least 2 hours apart, at least 4 hours apart, at least 6 hours apart, at least 8 hours apart, at least 10 hours apart, at least 12 hours apart, at least 14 hours apart, at least 16 hours apart, at least 18 hours apart, at least 20 hours apart, at least 22 hours apart, at least 24 hours apart, at least 2 days apart, at least 3 days apart, at least 4 days apart, at least 5 days apart, at least 6 days apart, at least 7 days apart, at least 14 days apart, at least one month apart, or at least 2 months apart.

According to some embodiments, the flowable sustained release particulate composition is administered at least 13 administered doses each at least 1 hour apart, at least 2 hours apart, at least 4 hours apart, at least 6 hours apart, at least 8 hours apart, at least 10 hours apart, at least 12 hours apart, at least 14 hours apart, at least 16 hours apart, at least 18 hours apart, at least 20 hours apart, at least 22 hours apart, at least 24 hours apart, at least 2 days apart, at least 3 days apart, at least 4 days apart, at least 5 days apart, at least 6 days apart, at least 7 days apart, at least 14 days apart, at least one month apart, or at least 2 months apart.

According to some embodiments, the flowable sustained release particulate composition is administered at least 14 administered doses each at least 1 hour apart, at least 2 hours apart, at least 4 hours apart, at least 6 hours apart, at least 8 hours apart, at least 10 hours apart, at least 12 hours apart, at least 14 hours apart, at least 16 hours apart, at least 18 hours apart, at least 20 hours apart, at least 22 hours apart, at least 24 hours apart, at least 2 days apart, at least 3 days apart, at least 4 days apart, at least 5 days apart, at least 6 days apart, at least 7 days apart, at least 14 days apart, at least one month apart, or at least 2 months apart.

According to some embodiments, the flowable sustained release particulate composition is administered at least 15 administered doses each at least 1 hour apart, at least 2 hours apart, at least 4 hours apart, at least 6 hours apart, at least 8 hours apart, at least 10 hours apart, at least 12 hours apart, at least 14 hours apart, at least 16 hours apart, at least 18 hours apart, at least 20 hours apart, at least 22 hours apart, at least 24 hours apart, at least 2 days apart, at least 3 days apart, at least 4 days apart, at least 5 days apart, at least 6 days apart, at least 7 days apart, at least 14 days apart, at least one month apart, or at least 2 months apart.

According to some embodiments, the flowable sustained release particulate composition is administered at least 16 administered doses each at least 1 hour apart, at least 2 hours apart, at least 4 hours apart, at least 6 hours apart, at least 8 hours apart, at least 10 hours apart, at least 12 hours apart, at least 14 hours apart, at least 16 hours apart, at least 18 hours apart, at least 20 hours apart, at least 22 hours apart, at least 24 hours apart, at least 2 days apart, at least 3 days apart, at least 4 days apart, at least 5 days apart, at least 6 days apart, at least 7 days apart, at least 14 days apart, at least one month apart, or at least 2 months apart.

According to some embodiments, the flowable sustained release particulate composition is administered at least 17 administered doses each at least 1 hour apart, at least 2 hours apart, at least 4 hours apart, at least 6 hours apart, at least 8 hours apart, at least 10 hours apart, at least 12 hours apart, at least 14 hours apart, at least 16 hours apart, at least 18 hours apart, at least 20 hours apart, at least 22 hours apart, at least 24 hours apart, at least 2 days apart, at least 3 days apart, at least 4 days apart, at least 5 days apart, at least 6 days apart, at least 7 days apart, at least 14 days apart, at least one month apart, or at least 2 months apart.

According to some embodiments, the flowable sustained release particulate composition is administered at least 18 administered doses each at least 1 hour apart, at least 2 hours apart, at least 4 hours apart, at least 6 hours apart, at least 8 hours apart, at least 10 hours apart, at least 12 hours apart, at least 14 hours apart, at least 16 hours apart, at least 18 hours apart, at least 20 hours apart, at least 22 hours apart, at least 24 hours apart, at least 2 days apart, at least 3 days apart, at least 4 days apart, at least 5 days apart, at least 6 days apart, at least 7 days apart, at least 14 days apart, at least one month apart, or at least 2 months apart.

According to some embodiments, the flowable sustained release particulate composition is administered at least 19 administered doses each at least 1 hour apart, at least 2 hours apart, at least 4 hours apart, at least 6 hours apart, at least 8 hours apart, at least 10 hours apart, at least 12 hours apart, at least 14 hours apart, at least 16 hours apart, at least 18 hours apart, at least 20 hours apart, at least 22 hours apart, at least 24 hours apart, at least 2 days apart, at least 3 days apart, at least 4 days apart, at least 5 days apart, at least 6 days apart, at least 7 days apart, at least 14 days apart, at least one month apart, or at least 2 months apart.

According to some embodiments, the flowable sustained release particulate composition is administered at least 20 administered doses each at least 1 hour apart, at least 2 hours apart, at least 4 hours apart, at least 6 hours apart, at least 8 hours apart, at least 10 hours apart, at least 12 hours apart, at least 14 hours apart, at least 16 hours apart, at least 18 hours apart, at least 20 hours apart, at least 22 hours apart, at least 24 hours apart, at least 2 days apart, at least 3 days apart, at least 4 days apart, at least 5 days apart, at least 6 days apart, at least 7 days apart, at least 14 days apart, at least one month apart, or at least 2 months apart.

According to some embodiments, the maximum tolerated dose of the first therapeutic agent by oral administration is from 1 mg/kg to about 10 mg/kg. According to some embodiments, the maximum tolerated dose of the first therapeutic agent by intravenous administration is from 14 mg/kg to about 20 mg/kg. According to some embodiments, the maximum tolerated dose of the first therapeutic agent by intracisternal administration is from 0.14 mg/kg to about 20 mg/kg. According to some embodiments, the maximum tolerated dose of the first therapeutic agent by intraventricular administration is from 0.14 mg/kg to about 20 mg/kg. According to some embodiments, the maximum tolerated dose of the first therapeutic agent by intrathecal administration is from 0.14 mg/kg to about 20 mg/kg.

According to some embodiments, the maximum tolerated dose of the first therapeutic agent by oral administration is from 1 mg to about 1,000 mg/kg. According to some embodiments, the maximum tolerated dose of the first therapeutic agent by intravenous administration is from 40 mg to about 1,000 mg. According to some embodiments, the maximum tolerated dose of the first therapeutic agent by intracisternal administration is from 40 mg to about 1,000 mg. According to some embodiments, the maximum tolerated dose of the first therapeutic agent by intraventricular administration is from 40 mg to about 1,000 mg. According to some embodiments, the maximum tolerated dose of the first therapeutic agent by intrathecal administration is from 40 mg to about 1,000 mg.

Optional Combination Therapy

According to one embodiment, the flowable sustained release microparticulate composition further comprises a second therapeutic agent. According to some embodiments, the second therapeutic agent is in an amount of 0.000001 mg/kg body weight to about 10 g/kg body weight.

According to another embodiment, the second therapeutic agent is a vasodilator. Exemplary vasodilators include, but are not limited to, calcium channel antagonists, endothelin receptor antagonists, TRP protein antagonists, magnesium salts, nitric oxide donors (such as diethylenetriamine (DETA)-NO and sodium nitrite), fasudil, vasoactive peptides (such as calcitonin gene related peptide (CGRP), neuropeptide Y), papaverine, milrinone, etc. According to one embodiment, the vasodilator is a magnesium salt. According to one embodiment, the magnesium salt is magnesium sulfate.

According to another embodiment, the second therapeutic agent is a statin. Exemplary statins include, but are not limited to, atorvastatin, fluvastatin, lovastatin, pravastatin, rosuvastatin, simvastatin, etc.

According to another embodiment, the second therapeutic agent is an anti-inflammatory agent. Exemplary anti-inflammatory agents include, but are not limited to, ibuprofen, etc.

Particulate Formulation

According to one embodiment, the flowable sustained release particulate composition comprises a plurality of particles. According to another embodiment, the flowable sustained release particulate composition comprises a plurality of particles comprising at least one first therapeutic agent. According to another embodiment, the flowable sustained release particulate composition further comprises a plurality of particles comprising a second therapeutic agent.

According to one embodiment, the particulate formulation comprises a plurality of milliparticles of uniform size distribution, and a therapeutic amount of at least one first therapeutic agent, wherein the first therapeutic agent is dispersed throughout each milliparticle, adsorbed onto the milliparticles, or in a core surrounded by a coating. According to another embodiment, the particulate formulation comprises a plurality of microparticles of uniform size distribution, and a therapeutic amount of at least one first therapeutic agent, wherein the first therapeutic agent is dispersed throughout each microparticle, adsorbed onto the microparticles, or in a core surrounded by a coating. According to another embodiment, the particulate formulation comprises a plurality of nanoparticles of uniform size distribution, and a therapeutic amount of at least one first therapeutic agent, wherein the first therapeutic agent is dispersed throughout each nanoparticle, adsorbed onto the nanoparticles, or in a core surrounded by a coating. According to another embodiment, the particulate formulation comprises a plurality of picoparticles of uniform size distribution, and a therapeutic amount of at least one first therapeutic agent, wherein the first therapeutic agent is dispersed throughout each picoparticle, adsorbed onto the picoparticles, or in a core surrounded by a coating. According to another embodiment, the particulate formulation comprises a plurality of femtoparticles of uniform size distribution, and a therapeutic amount of at least one first therapeutic agent, wherein the first therapeutic agent is dispersed throughout each femtoparticle, adsorbed onto the femtoparticles, or in a core surrounded by a coating.

According to some embodiments, the first therapeutic agent is provided in the form of a microparticle. According to another embodiment, the therapeutic agent is disposed on or in the microparticle. According to one embodiment, the first therapeutic agent is dispersed throughout each microparticle. According to some embodiments, the first therapeutic agent is impregnated on the surface of each microparticle. According to another embodiment, the first therapeutic agent is contained within a core of the microparticle surrounded by a coating. According to another embodiment, the therapeutic agent is adsorbed into each microparticle.

According to some embodiments, the second therapeutic agent is provided in the form of a microparticle. According to another embodiment, the second agent is disposed on or in the microparticle. According to one embodiment, the second therapeutic agent is dispersed throughout each microparticle. According to some embodiments, the second therapeutic agent is impregnated on the surface of each microparticle. According to another embodiment, the second therapeutic agent is contained within a core of the microparticle surrounded by a coating. According to another embodiment, the second agent is adsorbed into each microparticle.

According to some embodiments, the microparticle can be of any order release kinetics, including a zero order release, first order release, second order release, delayed release, sustained release, immediate release, and a combination thereof. The microparticles can include, in addition to therapeutic agent(s), any of those materials routinely used in the art of pharmacy and medicine, including, but not limited to, erodible, nonerodible, biodegradable, or nonbiodegradable material or combinations thereof.

According to some embodiments, the microparticle is a microcapsule that contains the therapeutic agent in a solution or in a semi-solid state. According to some embodiments, the microparticle contains the therapeutic agent, in whole or in part. According to some embodiments, the microparticles can be of virtually any shape.

According to some embodiments, each microparticle is loaded with at least 40% by weight to at least 100% by weight of the therapeutic agent. According to one embodiment, each microparticle is loaded with at least 40% by weight of the therapeutic agent. According to another embodiment, each microparticle is loaded with at least 45% by weight of the therapeutic agent. According to another embodiment, each microparticle is loaded with at least 50% by weight of the therapeutic agent. According to another embodiment, each microparticle is loaded with at least 55% by weight of the therapeutic agent. According to another embodiment, each microparticle is loaded with at least 60% by weight of the therapeutic agent. According to another embodiment, each microparticle is loaded with at least 63% by weight of the therapeutic agent. According to another embodiment, each microparticle is loaded with at least 65% by weight of the therapeutic agent. According to another embodiment, each microparticle is loaded with at least 70% by weight of the therapeutic agent. According to another embodiment, each microparticle is loaded with at least 75% by weight of the therapeutic agent. According to another embodiment, each microparticle is loaded with at least 80% by weight of the therapeutic agent. According to another embodiment, each microparticle is loaded with at least 85% by weight of the therapeutic agent. According to another embodiment, each microparticle is loaded with at least 90% by weight of the therapeutic agent. According to another embodiment, each microparticle is loaded with at least 95% by weight of the therapeutic agent. According to another embodiment, each microparticle is loaded with at least 100% by weight of the therapeutic agent.

According to some such embodiments, the microparticles are of uniform size distribution. According to some embodiments, the uniform distribution of microparticle size is achieved by a homogenization process to form a uniform emulsion comprising microparticles. According to some such embodiments, each microparticle comprises a matrix. According to some embodiments, the matrix comprises the least one therapeutic agent.

According to some embodiments, the microparticle formulation comprises a uniform distribution of microparticles from about 40 μm to about 100 μm in particle size. According to another embodiment, the particle size is at least about 40 μm. According to another embodiment, the particle size is at least about 45 μm. According to another embodiment, the particle size is at least about 50 μm. According to another embodiment, the particle size is at least about 55 μm. According to another embodiment, the particle size is at least about 60 μm. According to another embodiment, the particle size is at least about 65 μm. According to another embodiment, the particle size is at least about 70 μm. According to another embodiment, the particle size is at least about 75 μm. According to another embodiment, the particle size is at least about 80 μm. According to another embodiment, the particle size is at least about 85 μm. According to another embodiment, the particle size is at least about 90 μm. According to another embodiment, the particle size is at least about 95 μm. According to another embodiment, the particle size is at least about 100 μm.

According to another embodiment, the therapeutic agent can be provided as at least one string. The string can contain the therapeutic agent in a core surrounded by a coating, or the therapeutic agent can be dispersed throughout the string, or the therapeutic agent can be absorbed into the string. The string can be of any order release kinetics, including zero order release, first order release, second order release, delayed release, sustained release, immediate release, etc., and any combination thereof. The string can include, in addition to therapeutic agent(s), any of those materials routinely used in the art of pharmacy and medicine, including, but not limited to, erodible, nonerodible, biodegradable, or nonbiodegradable material or combinations thereof According to another embodiment, the therapeutic agent can be provided as at least one sheet. The sheet can contain the first therapeutic agent and additional therapeutic agent in a core surrounded by a coating, the first therapeutic agent and additional therapeutic agent can be dispersed throughout the sheet, or the first therapeutic agent can be absorbed into the sheet. The sheet can be of any order release kinetics, including zero order release, first order release, second order release, delayed release, sustained release, immediate release, etc., and any combination thereof. The sheet can include, in addition to the first therapeutic agent and additional therapeutic agent, any of those materials routinely used in the art of pharmacy and medicine, including, but not limited to, erodible, nonerodible, biodegradable, or nonbiodegradable material or combinations thereof.

According to some embodiments, the particulate formulation comprises a suspension of microparticles. According to one embodiment, the particulate formulation comprises a powder suspension of microparticles. According to some embodiments, the particulate formulation further comprises at least one of a suspending agent, a stabilizing agent and a dispersing agent. According to some such embodiments, the particulate formulation is presented as a dispersion. According to some such embodiments, the particulate formulation is presented as a suspension. According to some such embodiments, the particulate formulation is presented as a solution. According to some such embodiments, the particulate formulation is presented as an emulsion.

According to some embodiments, the particulate formulation comprises an aqueous solution of the therapeutic agent in water-soluble form. According to some embodiments, the particulate formulation comprises an oily suspension of the at least one first therapeutic agent. An oily suspension of the at least one first therapeutic agent can be prepared using suitable lipophilic solvents. Exemplary lipophilic solvents or vehicles include, but are not limited to, fatty oils such as sesame oil, or synthetic fatty acid esters, such as ethyl oleate or triglycerides. According to some embodiments, the particulate formulation comprises an aqueous suspension of the therapeutic agent. Aqueous injection suspensions can contain substances which increase the viscosity of the suspension, such as sodium carboxymethyl cellulose, sorbitol, hyaluronic acid, or dextran. Optionally, the suspension can also contain suitable stabilizers or agents which increase the solubility of the compounds to allow for the preparation of highly concentrated solutions. Alternatively, the therapeutic agent can be in powder form for constitution with a suitable vehicle, e.g., sterile pyrogen-free water, before use. According to some embodiments, the particulate formulation is dispersed in a vehicle to form a dispersion, with the microparticles as the dispersed phase, and the vehicle as the dispersion medium.

The particulate formulation can include, for example, microencapsulated dosage forms, and if appropriate, with one or more excipients, encochleated, coated onto microscopic gold particles, contained in liposomes, pellets for implantation into the tissue, or dried onto an object to be rubbed into the tissue. As used herein, the term "microencapsulation" refers to a process in which very tiny droplets or particles are surrounded or coated with a continuous film of biocompatible, biodegradable, polymeric or non-polymeric material to produce solid structures including, but not limited to, nonpareils, pellets, crystals, agglomerates, microspheres, or nanoparticles. The particulate formulation can be in the form of granules, beads, powders, tablets, coated tablets, (micro)capsules, suppositories, syrups, emulsions, suspensions, creams, drops or preparations with protracted release of active compounds, in whose preparation excipients and additives and/or auxiliaries such as disintegrants, binders, coating agents, swelling agents, lubricants, or solubilizers are customarily used as described above. The particulate formulations are suitable for use in a variety of drug delivery systems. For a brief review of methods for drug delivery, see Langer (1990) Science 249, 1527-1533, which is incorporated herein by reference.

Particle Polymer Matrix

According to one embodiment, the particles comprise a matrix. According to some embodiments, the therapeutic agent is impregnated in or on a naturally occurring biopolymer matrix, a synthetic polymer matrix, or a combination thereof. According to one embodiment, the particulate composition comprises a polymer matrix, wherein the therapeutic agent is impregnated in the polymer matrix. According to one embodiment, the polymer is a slow release compound. According to one embodiment, the polymer is a biodegradable polymer. According to one embodiment, the polymer is poly (D, L-Lactide-co-glycolide). According to another embodiment, the polymer is poly(orthoester). According to another embodiment, the polymer is poly(anhydride). According to another embodiment, the polymer is polylactide-polyglycolide.

Both non-biodegradable and biodegradable polymeric materials can be used in the manufacture of particles for delivering the therapeutic agents. Such polymers can be natural or synthetic polymers. The polymer is selected based on the period of time over which release is desired. Bioadhesive polymers of particular interest include, but are not limited to, bioerodible hydrogels as described by Sawhney et al in Macromolecules (1993) 26, 581-587, the teachings of which are incorporated herein. Exemplary bioerodible hydrogels include, but are not limited to, polyhyaluronic acids, casein, gelatin, glutin, polyanhydrides, polyacrylic acid, alginate, chitosan, poly(methyl methacrylates), poly(ethyl methacrylates), poly(butylmethacrylate), poly(isobutyl methacrylate), poly(hexylmethacrylate), poly(isodecyl methacrylate), poly(lauryl methacrylate), poly(phenyl methacrylate), poly(methyl acrylate), poly(isopropyl acrylate), poly(isobutyl acrylate), and poly(octadecyl acrylate). According to one embodiment, the bioadhesive polymer is hyaluronic acid. According to some such embodiments, the bioadhesive polymer includes less than about 2.3% of hyaluronic acid.

According to another embodiment, the polymer enhances aqueous solubility of the particulate formulation. Examples of suitable polymers include but are not limited to polyethylene glycol, poly-(d-glutamic acid), poly-(1-glutamic acid), poly-(d-aspartic acid), poly-(1-aspartic acid) and copolymers thereof. Polyglutamic acids having molecular weights between about 5,000 to about 100,000, with molecular weights between about 20,000 and about 80,000, and with molecular weights between about 30,000 and about 60,000 may also be used. The polymer is conjugated via an ester linkage to one or more hydroxyls of an inventive epothilone using a protocol as essentially described by U.S. Pat. No. 5,977,163 which is incorporated herein by reference. Particular conjugation sites include the hydroxyl off carbon-21 in the case of 21-hydroxy-derivatives of the present invention. Other conjugation sites include, but are not limited to, the hydroxyl off carbon 3 and/or the hydroxyl off carbon 7.

According to some embodiments, the therapeutic agent is impregnated in or on a polyglycolide (PGA) matrix. PGA is a linear aliphatic polyester developed for use in sutures. Studies have reported PGA copolymers formed with trimethylene carbonate, polylactic acid (PLA), and polycaprolactone. Some of these copolymers may be formulated as microparticles for sustained drug release.

According to some embodiments, the therapeutic agent is impregnated in or on a polyester-polyethylene glycol matrix. Polyester-polyethylene glycol compounds can be synthesized; these are soft and may be used for drug delivery.

According to some embodiments, the therapeutic agent is impregnated in or on a poly (amino)-derived biopolymer matrix. Poly (amino)-derived biopolymers can include, but are not limited to, those containing lactic acid and lysine as the aliphatic diamine (see, for example, U.S. Pat. No. 5,399,665), and tyrosine-derived polycarbonates and polyacrylates. Modifications of polycarbonates may alter the length of the alkyl chain of the ester (ethyl to octyl), while modifications of polyarylates may further include altering the length of the alkyl chain of the diacid (for example, succinic to sebasic), which allows for a large permutation of polymers and great flexibility in polymer properties.

According to some embodiments, the therapeutic agent is impregnated in or on a polyanhydride matrix. Polyanhydrides are prepared by the dehydration of two diacid molecules by melt polymerization (see, for example, U.S. Pat. No. 4,757,128). These polymers degrade by surface erosion (as compared to polyesters that degrade by bulk erosion). The release of the drug can be controlled by the hydrophilicity of the monomers chosen.

According to some embodiments, the therapeutic agent is impregnated in or on a photopolymerizable biopolymer matrix. Photopolymerizable biopolymers include, but are not limited to, lactic acid/polyethylene glycol/acrylate copolymers.

According to some embodiments, the therapeutic agent is impregnated in or on a hydrogel matrix. The term "hydrogel" refers to a substance resulting in a solid, semisolid, pseudoplastic or plastic structure containing a necessary aqueous component to produce a gelatinous or jelly-like mass. Hydrogels generally comprise a variety of polymers, including hydrophilic polymers, acrylic acid, acrylamide and 2-hydroxyethylmethacrylate (HEMA).

According to some embodiments, the therapeutic agent is impregnated in or on a naturally-occurring biopolymer matrix. Naturally-occurring biopolymers include, but are not limited to, protein polymers, collagen, polysaccharides, and photopolymerizable compounds.

According to some embodiments, the therapeutic agent is impregnated in or on a protein polymer matrix. Protein polymers have been synthesized from self-assembling protein polymers such as, for example, silk fibroin, elastin, collagen, and combinations thereof According to some embodiments, the therapeutic agent is impregnated in or on a naturally-occurring polysaccharide matrix. Naturally-occurring polysaccharides include, but are not limited to, chitin and its derivatives, hyaluronic acid, dextran and cellulosics (which generally are not biodegradable without modification), and sucrose acetate isobutyrate (SAIB).

According to some embodiments, the therapeutic agent is impregnated in or on a chitin matrix. Chitin is composed predominantly of 2-acetamido-2-deoxy-D-glucose groups and is found in yeasts, fungi and marine invertebrates (shrimp, crustaceous) where it is a principal component of the exoskeleton. Chitin is not water soluble and the deacetylated chitin, chitosan, only is soluble in acidic solutions (such as, for example, acetic acid). Studies have reported chitin derivatives that are water soluble, very high molecular weight (greater than 2 million Daltons), viscoelastic, non-toxic, biocompatible and capable of crosslinking with peroxides, gluteraldehyde, glyoxal and other aldehydes and carbodiamides, to form gels.

According to some embodiments, the therapeutic agent is impregnated in or on a hyaluronic acid (HA) matrix. Hyaluronic acid (HA), which is composed of alternating glucuronidic and glucosaminidic bonds and is found in mammalian vitreous humor, extracellular matrix of the brain, synovial fluid, umbilical cords and rooster combs from which it is isolated and purified, also can be produced by fermentation processes.

Microencapsulation Process

Examples of microencapsulation processes and products; methods for the production of emulsion-based microparticles; emulsion-based microparticles and methods for the production thereof; solvent extraction microencapsulation with tunable extraction rates; microencapsulation process with solvent and salt; a continuous double emulsion process for making microparticles; drying methods for tuning microparticle properties, controlled release systems from polymer blends; polymer mixtures comprising polymers having different non-repeating units and methods for making and using the same; and an emulsion based process for preparing microparticles and workhead assembly for use with same are disclosed and described in, but not limited to U.S. Pat. No. 5,407,609 (entitled Microencapsulation Process and Products Thereof), U.S. Application Publication No. US 2007-0190154 A1 (entitled Method for the production of emulsion-based microparticles), U.S. Application Publication No. US 2007-0207211 A1 (entitled Emulsion-based microparticles and methods for the production thereof), U.S. Application Publication No. US 2010-0063179 A1 (entitled Solvent Extraction Microencapsulation With Tunable Extraction Rates), U.S. Application Publication No. US 2010-0291027 A1 (entitled Hyaluronic Acid (HA) Injection Vehicle), U.S. Application Publication No. US 2010-0069602 A1 entitled Microencapsulation Process With Solvent And Salt), U.S. Application No. US 2009-0162407 A1 (entitled Process For Preparing Microparticles Having A Low Residual Solvent Volume); U.S. Application Publication No. US 2010-0189763 A1 (entitled Controlled Release Systems From Polymer Blends); U.S. Application Publication No. US 2010-0216948 A1 (entitled Polymer Mixtures Comprising Polymers Having Different Non-Repeating Units And Methods For Making And Using Same); U.S. Application Publication No. US 2007-0092574 A1 (entitled "Controlled release compositions"); U.S. application Ser. No. 12/692,029 (entitled "Drying Methods for Tuning Microparticle Properties); U.S. Application Publication No. US 2011-0204533 A1 (entitled "Emulsion Based Process for Preparing Microparticles and Workhead for Use with Same); and U.S. Application Publication No. US 2011-0236497 A1 (entitled Composition and Methods for Improved Retention of a Pharmaceutical Composition at a Local Administration Site"). The contents of each of these patents and patent application publications are incorporated herein by reference in its entirety.

According to some embodiments, delivery of the active therapeutic agent(s) using microparticle technology involves bioresorbable, polymeric particles that encapsulate the first therapeutic agent and additional therapeutic agent.

The particulate formulation containing a uniform distribution of microparticle size can be prepared by an emulsion based process, for example as described in U.S. Pat. No. 5,407,609, the entire content of which is incorporated herein by reference.

According to one embodiment a process for producing a a bioactive agent encapsulated into particles comprises: (a) providing a substantially pure crystalline form of the bioactive agent; (b) adding the substantially pure crystalline form of the bioactive agent to a polymer solution, thereby creating a mixture of the bioactive agent and the polymer solution; (c) homogenizing the mixture to form a disperse phase; (d) mixing the disperse phase with a continuous phase comprising a continuous process medium, thereby forming an emulsion comprising the bioactive agent; (e) forming and extracting the particles comprising the substantially pure bioactive agent; and (f) drying the particles.

It is understood and herein contemplated that where a polymer solution comprises a polymer in an organic solvent forming a oil/water emulsion in the disperse phase, mixing the disperse phase with the continuous phase results in a double emulsion (i.e., a water/oil/water emulsion). Where the polymer solution comprises a polymer in an aqueous solvent such as water, only a single emulsion is formed upon mixing the dispersed phase with the continuous phase.

According to one embodiment, the continuous process medium comprises a surfactant and the bioactive agent saturated with the solvent used in the polymer solution.

According to a another embodiment, the polymer solutions of the aforementioned processes comprise a polymer and a solvent. It is understood and herein contemplated that the disclosed polymers comprise in one aspect polylactide, polylactide-co-glycolide, poly(orthoester), and poly(anhydride). According to some embodiments, the polylactide co-glycolide can be in a 85:15, 75:25, 65:35, or 50:50 ratio of lactide to glycolide. In a further aspect, the polymer comprises 8515 DLG 6A, 8515 DLG 5A, 8515 DLG 4.5E, 88515 DLG 5E, 515 DLG 7A, 7525 DLG 7A, 7525 DLG 7E, 7525 DLG 5E, 6535DLG 5E, 6353 DLG 2E, 6535 DLG 4A, 5050DLG 4A, 5050 DLG2A, and 2000 MW DLPL. In another aspect, the solvent can comprise ethyl acetate or dichloromethane.

According to another aspect, the processes disclosed herein comprise drying the particles over a 10 to 48 hour period.

Pharmaceutical Carrier

According to some embodiments, the flowable sustained release particulate composition comprises (ii) a pharmaceutical carrier. According to some such embodiments, the particulate formulation comprising a plurality of particles and a therapeutic amount of the therapeutic agent(s) is combined with the pharmaceutical carrier to form the flowable sustained release particulate composition.

According to one embodiment, the pharmaceutically acceptable carrier is a solid carrier or excipient. According to another embodiment, the pharmaceutically acceptable carrier is a gel-phase carrier or excipient. Examples of carriers or excipients include, but are not limited to, calcium carbonate, calcium phosphate, various monomeric and polymeric sugars (including without limitation hyaluronic acid), starches, cellulose derivatives, gelatin, and polymers. An exemplary carrier can also include saline vehicle, e.g. hydroxyl propyl methyl cellulose (HPMC) in phosphate buffered saline (PBS). According to another embodiment, the pharmaceutically acceptable carrier is a buffer solution. Exemplary buffer solutions can include without limitation a phosphate buffered saline (PBS) solution.

Suitable injection vehicles for use in the present invention can be found in U.S. Pat. No. 6,495,164, U.S. Patent Application Publication No. 2010/0303900, U.S. Patent Application Publication No. 2010/0330184, and U.S. Patent Application Publication No. 2010/0291027, the entire disclosures of which are incorporated herein by reference. Exemplary injection vehicles suitable for use in the present invention include, but are not limited to, water, saline (sodium chloride solution, hydroxyl propyl methyl cellulose (HPMC) in phosphate buffered saline (PBS)), and hyaluronic acid and hyaluronic acid derivatives, or a combination thereof. Exemplary hyaluronic acid derivatives can include, but are not limited to, salts, esters, amides, and lactide derivatives. Exemplary hyaluronic acid derivatives suitable for use in the present invention are provided in U.S. Pat. No. 5,527,893, U.S. Pat. No. 5,017,229, and U.S. Pat. No. 4,937,270, the entire disclosures of which are incorporated herein by reference. According to one embodiment, the injection vehicle can be combined with a suitable surfactant. Exemplary surfactants can include, but are not limited to, poly(vinyl alcohol), carboxymethyl cellulose, gelatin, poly (vinyl pyrrolidone), Tween 80, Tween 20, or a combination thereof According to one embodiment, the pharmaceutical carrier comprises a hyaluronic acid or a hyaluronic acid derivative. According to some embodiments, the hyaluronic acid or the hyaluronic acid derivative thereof has an average molecular weight ranging between about 5 KDa to about 20,000 KDa. According to some embodiments, the hyaluronic acid or the hyaluronic acid derivative thereof has an average molecular weight of about 5 KDa, 10 KDa, 20 KDa, 30 KDa, 40 KDa, 50 KDa, 60 KDa, 70 KDa, 80 KDa, 90 KDa, 100 KDa, 200 KDa, 300 KDa, 400 KDa, 500 KDa, 600 KDa, 700 KDa, 800 KDa, 900 KDa, 1,000 KDa, 2,000 KDa, 3,000 KDa, 4,000 KDa, 5,000 KDa, 6,000 KDa, 7,000 KDa, 8,000 KDa, 9,000 KDa, 10,000 KDa, 11,000 KDa, 12,000 KDa, 13,000 KDa, 14,000 KDa, 15,000 KDa, 16,000 KDa, 17,000 KDa, 18,000 KDa, 19,000 KDa, or 20,000 KDa. According to one embodiment, the hyaluronic acid or the hyaluronic acid derivative thereof has an average molecular weight of about 500 KDa.

According to some embodiments, the pharmaceutically acceptable carrier imparts stickiness to the composition. According to one embodiment, the pharmaceutically acceptable carrier comprises hyaluronic acid. According to some embodiments, the pharmaceutically acceptable carrier comprises 0% to 5% by weight hyaluronic acid or the hyaluronic acid derivative. According to one embodiment, the pharmaceutically acceptable carrier comprises less than 0.01% by weight hyaluronic acid or the hyaluronic acid derivative. According to another embodiment, the pharmaceutically acceptable carrier comprises less than 0.05% by weight hyaluronic acid or the hyaluronic acid derivative. According to another embodiment, the pharmaceutically acceptable carrier comprises less than 0.1% by weight hyaluronic acid or the hyaluronic acid derivative. According to another embodiment, the pharmaceutically acceptable carrier comprises less than 0.2% by weight hyaluronic acid or the hyaluronic acid derivative. According to another embodiment, the pharmaceutically acceptable carrier comprises less than 0.3% by weight hyaluronic acid or the hyaluronic acid derivative. According to another embodiment, the pharmaceutically acceptable carrier comprises less than 0.4% by weight hyaluronic acid or the hyaluronic acid derivative. According to another embodiment, the pharmaceutically acceptable carrier comprises less than 0.5% by weight hyaluronic acid or the hyaluronic acid derivative. According to another embodiment, the pharmaceutically acceptable carrier comprises less than 0.6% by weight hyaluronic acid or the hyaluronic acid derivative. According to another embodiment, the pharmaceutically acceptable carrier comprises less than 0.7% by weight hyaluronic acid or the hyaluronic acid derivative. According to another embodiment, the pharmaceutically acceptable carrier comprises less than 0.8% by weight hyaluronic acid or the hyaluronic acid derivative. According to another embodiment, the pharmaceutically acceptable carrier comprises less than 0.9% by weight hyaluronic acid or the hyaluronic acid derivative. According to another embodiment, the pharmaceutically acceptable carrier comprises less than 1.0% by weight hyaluronic acid or the hyaluronic acid derivative. According to another embodiment, the pharmaceutically acceptable carrier comprises less than 1.1% by weight hyaluronic acid or the hyaluronic acid derivative. According to another embodiment, the pharmaceutically acceptable carrier comprises less than 1.2% by weight hyaluronic acid or the hyaluronic acid derivative. According to another embodiment, the pharmaceutically acceptable carrier comprises less than 1.3% by weight hyaluronic acid or the hyaluronic acid derivative. According to another embodiment, the pharmaceutically acceptable carrier comprises less than 1.4% by weight hyaluronic acid or the hyaluronic acid derivative According to another embodiment, the pharmaceutically acceptable carrier comprises less than 1.5% by weight hyaluronic acid or the hyaluronic acid derivative. According to another embodiment, the pharmaceutically acceptable carrier comprises less than 1.6% by weight hyaluronic acid or the hyaluronic acid derivative. According to another embodiment, the pharmaceutically acceptable carrier comprises less than 1.7% by weight hyaluronic acid or the hyaluronic acid derivative. According to another embodiment, the pharmaceutically acceptable carrier comprises less than 1.8% by weight hyaluronic acid or the hyaluronic acid derivative. According to another embodiment, the pharmaceutically acceptable carrier comprises less than 1.9% by weight hyaluronic acid or the hyaluronic acid derivative. According to another embodiment, the pharmaceutically acceptable carrier comprises less than 2.0% by weight hyaluronic acid or the hyaluronic acid derivative. According to another embodiment, the pharmaceutically acceptable carrier comprises less than 2.1% by weight hyaluronic acid or the hyaluronic acid derivative. According to another embodiment, the pharmaceutically acceptable carrier comprises less than 2.2% by weight hyaluronic acid or the hyaluronic acid derivative. According to another embodiment, the pharmaceutically acceptable carrier comprises less than 2.3% by weight hyaluronic acid or the hyaluronic acid derivative. According to another embodiment, the pharmaceutically acceptable carrier comprises less than 2.4% by weight hyaluronic acid or the hyaluronic acid derivative. According to another embodiment, the pharmaceutically acceptable carrier comprises less than 2.5% by weight hyaluronic acid or the hyaluronic acid derivative. According to another embodiment, the pharmaceutically acceptable carrier comprises less than 2.6% by weight hyaluronic acid or the hyaluronic acid derivative. According to another embodiment, the pharmaceutically acceptable carrier comprises less than 2.7% by weight hyaluronic acid or the hyaluronic acid derivative. According to another embodiment, the pharmaceutically acceptable carrier comprises less than 2.8% by weight hyaluronic acid or the hyaluronic acid derivative. According to another embodiment, the pharmaceutically acceptable carrier comprises less than 2.9% by weight hyaluronic acid or the hyaluronic acid derivative. According to another embodiment, the pharmaceutically acceptable carrier comprises less than 3.0% by weight hyaluronic acid or the hyaluronic acid derivative. According to another embodiment, the pharmaceutically acceptable carrier comprises less than 3.5% by weight hyaluronic acid or the hyaluronic acid derivative. According to another embodiment, the pharmaceutically acceptable carrier comprises less than 4.0% by weight hyaluronic acid or the hyaluronic acid derivative. According to another embodiment, the pharmaceutically acceptable carrier comprises less than 4.5% by weight hyaluronic acid or the hyaluronic acid derivative. According to another embodiment, the pharmaceutically acceptable carrier comprises less than 5.0% by weight hyaluronic acid or the hyaluronic acid derivative.

According to some embodiments, the pH of the hyaluronic acid or the hyaluronic acid derivative thereof is 6.8, 6.9, 7.0, 7.1, 7.2, 7.3, 7.4, 7.5, or 7.6.

According to some embodiments, the osmolarity of the hyaluronic acid or the hyaluronic acid derivative thereof is about 250 mOsm/kg, about 258 mOsm/kg, about 275 mOsm/kg, about 300 mOsm/kg, about 325 mOsm/kg, about 350 mOsm/kg, about 375 mOsm/kg, or about 381 mOsm/kg.

Exemplary hyaluronic acid derivatives can include, but are not limited to, salts, esters, amides, and lactide derivatives. Exemplary hyaluronic acid derivatives suitable for use in the present invention are provided in U.S. Pat. No. 5,527,893, U.S. Pat. No. 5,017,229, and U.S. Pat. No. 4,937,270, the entire disclosures of which are incorporated herein by reference. According to one embodiment, the injection vehicle can be combined with a suitable surfactant. Exemplary surfactants can include, but are not limited to, poly(vinyl alcohol), carboxymethyl cellulose, gelatin, poly (vinyl pyrrolidone), Tween 80, Tween 20, or a combination thereof Hyaluronic acid (hyaluronate sodium salt, "HA") is a naturally occurring glycosaminoglycan found in the extracellular matrix and is an abundant component of the extracellular space of the brain. (Laurent T C et al., "The structure and function of hyaluronan: An overview," Immunol. Cell. Biol., (1996) 74:A1-A7). It is found normally in synovial joints where it is believed to function as a lubricant, among other functions. Normal CSF also contains HA. It is composed of repeated nonsulfated disaccharide units of D-glucuronic acid and N-acetyl-D-glucosamine linked by β(1-3) and β(1-4) glycoside linkages, respectively. HA can be assembled in varying molecular weights and lyophilized or etherified to alter the rate of degradation. The HA derivatives used in most human products are synthesized by fermentation in bacteria, overcoming problems with toxicity, immunological reactions and allergies due to contaminants associated with naturally derived HA from avian sources. HA is formulated for injection into joints to treat pain from osteoarthritis (Orthovisc®, Nuflexxa®, Hyalgan® and others), for injection into the eye during ophthalmic surgery (Healon®, Viscoat®, Biolon®), as epidural injection films (Seprafilm®) and for use in otolaryngology (Merogel®). Sodium hyaluronate is listed in the FDA's inactive ingredients list for administration via several parenteral routes including intravitreal, intraarticular and intramuscular.

According to one embodiment, the nimodipine particulate formulation of the described invention can be mixed with a <2.3 w/w % bacterial-derived sodium hyaluronate solution in PBS with 0.1% polysorbate 20. According to some embodiments, the pH is 6.8, or 6.9, or 7.0, or 7.1, or 7.2, or 7.3, or 7.4, or 7.5, or 7.6. According to some embodiments, the osmolarity is about 250 mOsm/kg, or about 258 mOsm/kg, or about 275 mOsm/kg, or about 300 mOsm/kg, or about 325 mOsm/kg, or about 350 mOsm/kg, or about 375 mOsm/kg, or about 381 mOsm/kg. The average molecular weight of the sodium hyaluronate is approximately 500 kDa. The 2.3 w/w % solution is approved for use. Injection volumes of 1% HA into joints are typically 2 ml. The maximum volume of a nimodipine particulate formulation of the invention (6 ml total) contains a similar amount of HA.

The biocompatibility and non-immunogenicity of HA have been attributed to its relatively simple structure, which is conserved throughout all mammals, and its poor interaction with blood components. (Amarnath L P et al., "In vitro hemocompatibility testing of UV-modified hyaluronan hydrogels," Biomaterials, 27:1416-1424 (2006)). HA is degraded in mammals by 3 types of enzymes: hyaluronase, β-D-glucuronidase, and β-N-acetyl-hexosaminidase. Generally, hyaluronase acts on the high molecular weight species to reduce the polysaccharide to oligosaccharides. β-D-glucuronidase, and β-N-acetyl-hexosaminidase in turn degrade the oligosaccharides by removing the nonreducing terminal sugars. (Chen W Y, and Abatangelo G, "Functions of hyaluronan in wound repair," Wound Repair Regen., 7:79-89 (1999); Leach J B et al., "Development of photocrosslinkable hyaluronic acid-polyethylene glycol-peptide composite hydrogels for soft tissue engineering," J. Biomed. Mater. Res. A, 70:74-82 (2004)).

Hyaluronate has been shown to be non-mutagenic, non-cytotoxic, and non-neurotoxic. Jansen, et al., found that HA was not cytotoxic when used as a conduit for peripheral nerve repair. (Jansen K et al., "A hyaluronan-based nerve guide: in vitro cytotoxicity, subcutaneous tissue reactions, and degradation in the rat," Biomaterials, 25:483-489 (2004)). Product information for Orthovisc® (high molecular weight hyaluronate) shows that HA is not mutagenic in several assays including the Sister chromatid exchange assay, the chromosomal aberration assay, and the Ames Salmonella/Mammalian Microsome mutagenicity assay. (Orthovisc®, High Molecular Weight Hyaluronan, Package insert, Anika Therapeutics, Inc., Distributed by DePuy Mitek, a Johnson and Johnson Company). Chronic administration of HA did not result in reproduction toxicity in rats and rabbit at doses up to 1.43 mg/kg per treatment cycle.

Hyaluronic acid was reported to have anti-inflammatory and bacteriostatic effects. (Burns J W et al., "Preclinical evaluation of Seprafilm bioresorbable membrane," Eur. J. Surg. Suppl., 40-48 (1997)) Injection of 0.2 ml/kg of HA (10 mg/ml, molecular weight 1100 kDa, pH 6.3-8.3) into the epidural space of 10 rabbits did not produce any clinically detectable abnormalities or neurotoxicity. (Lim Y J et al., "The neurotoxicity of epidural hyaluronic acid in rabbits: a light and electron microscopic examination," Anesth. Analg., 97:1716-1720 (2003)).

According to some embodiments, the pharmaceutically acceptable carrier includes, but is not limited to, a gel, slow-release solid or semisolid compound, optionally as a sustained release gel. In some such embodiments, the at least one first therapeutic agent is embedded into the pharmaceutically acceptable carrier. In some embodiments, the at least one first therapeutic agent is coated on the pharmaceutically acceptable carrier. The coating can be of any desired material, preferably a polymer or mixture of different polymers. Optionally, the polymer can be utilized during the granulation stage to form a matrix with the active ingredient so as to obtain a desired release pattern of the active ingredient. The gel, slow-release solid or semisolid compound is capable of releasing the active agent over a desired period of time. The gel, slow-release solid or semisolid compound can be implanted in a tissue within the parenchyma of human brain, including, but not limited to, in proximity to a blood vessel, such as a cerebral artery.

According to another embodiment, the pharmaceutically acceptable carrier comprises a slow-release solid compound. According to one such embodiment, the at least one first therapeutic agent is embedded in the slow-release solid compound or coated on the slow-release solid compound. According to yet another embodiment, the pharmaceutically acceptable carrier comprises a slow-release microparticle containing the at least one first therapeutic agent.

According to another embodiment, the pharmaceutically acceptable carrier is a gel compound, such as a biodegradable hydrogel.

Additional Components

According to some embodiments, the flowable sustained release particulate composition further comprises a surfactant. Exemplary surfactants can include, but are not limited to, poly(vinyl alcohol), carboxymethyl cellulose, gelatin, poly(vinyl pyrrolidone), Tween 80, Tween 20, or a combination thereof According to some embodiments, the flowable sustained release particulate composition further comprises a preservative agent. According to some such embodiments, the flowable sustained release particulate composition is presented in a unit dosage form. Exemplary unit dosage forms include, but are not limited to, ampoules or multi-dose containers.

The flowable sustained release particulate compositions for parenteral administration include aqueous and non-aqueous sterile injection solutions that can contain anti-oxidants, buffers, bacteriostats and solutes, which render the formulation isotonic with the blood or CSF of the intended recipient; and aqueous and non-aqueous sterile suspensions, which can include suspending agents and thickening agents.

According to some embodiments, the flowable sustained release particulate composition is formulated for local injection, parenteral injection, implantation, or a combination thereof. According to some such embodiments, the flowable sustained release particulate composition is in the form of a pharmaceutically acceptable sterile aqueous or nonaqueous solution, dispersion, suspension, emulsion or a sterile powder for reconstitution into a sterile injectable solution or dispersion. Examples of suitable aqueous and nonaqueous carriers, diluents, solvents or vehicles include, but are not limited to, water, ethanol, dichloromethane, acetonitrile, ethyl acetate, polyols (propylene glycol, polyethylene glycol, glycerol, and the like), suitable mixtures thereof, vegetable oils (such as olive oil) and injectable organic esters such as ethyl oleate. Proper fluidity can be maintained, for example, by the use of a coating such as lecithin, by the maintenance of the required particle size in the case of dispersions, and by the use of surfactants. Suspensions can further contain suspending agents, as, for example, ethoxylated isostearyl alcohols, polyoxyethylene sorbitol and sorbitan esters, microcrystalline cellulose, aluminum metahydroxide, bentonite, agar-agar, tragacanth, and mixtures thereof According to some embodiments, the flowable sustained release particulate composition is formulated in an injectable depot form. Injectable depot forms are made by forming microencapsulated matrices of the therapeutic agent in a biodegradable polymer. Depending upon the ratio of drug to polymer and the nature of the particular polymer employed, the rate of drug release may be controlled. Such long acting formulations can be formulated with suitable polymeric or hydrophobic materials (for example as an emulsion in an acceptable oil) or ion exchange resins, or as sparingly soluble derivatives, for example, as a sparingly soluble salt. Examples of biodegradable polymers include, but are not limited to, polylactide-polyglycolide, poly(orthoesters) and poly(anhydrides). Depot injectable formulations are also prepared by entrapping the drug in liposomes or microemulsions which are compatible with body tissues.

According to some embodiments, the flowable sustained release particulate composition further comprises an adjuvant. Exemplary adjuvants include, but are not limited to, preservative agents, wetting agents, emulsifying agents, and dispersing agents. Prevention of the action of microorganisms can be ensured by various antibacterial and antifungal agents, for example, parabens, chlorobutanol, phenol, sorbic acid, and the like. Isotonic agents, for example, sugars, sodium chloride and the like, can also be included. Prolonged absorption of the injectable pharmaceutical form can be brought about by the use of agents delaying absorption, for example, aluminum monostearate and gelatin.

The flowable sustained release particulate compositions can be sterilized, for example, by terminal gamma irradiation, filtration through a bacterial-retaining filter or by incorporating sterilizing agents in the form of sterile solid compositions that may be dissolved or dispersed in sterile water or other sterile injectable medium just prior to use. Injectable preparations, for example, sterile injectable aqueous or oleaginous suspensions may be formulated according to the known art using suitable dispersing or wetting agents and suspending agents. The sterile injectable preparation also may be a sterile injectable solution, suspension or emulsion in a nontoxic, parenterally acceptable diluent or solvent such as a solution in 1,3-butanediol, dichloromethane, ethyl acetate, acetonitrile, etc. Among the acceptable vehicles and solvents that may be employed are water, Ringer's solution, U.S.P. and isotonic sodium chloride solution. In addition, sterile, fixed oils conventionally are employed or as a solvent or suspending medium. For this purpose any bland fixed oil may be employed including synthetic mono- or diglycerides. In addition, fatty acids such as oleic acid are used in the preparation of injectables.

Exemplary buffering agents include: acetic acid and a salt (1-2% w/v); citric acid and a salt (1-3% w/v); boric acid and a salt (0.5-2.5% w/v); and phosphoric acid and a salt (0.8-2% w/v). Exemplary preservatives include benzalkonium chloride (0.003-0.03% w/v); chlorobutanol (0.3-0.9% w/v); parabens (0.01-0.25% w/v) and thimerosal (0.004-0.02% w/v).

As used herein, the singular forms "a", "an" and "the" include plural referents unless the context clearly dictates otherwise. For example, reference to a "polypeptide" means one or more polypeptides.

Where a range of values is provided, it is understood that each intervening value, to the tenth of the unit of the lower limit unless the context clearly dictates otherwise, between the upper and lower limit of that range and any other stated or intervening value in that stated range is encompassed within the invention. The upper and lower limits of these smaller ranges which may independently be included in the smaller ranges is also encompassed within the invention, subject to any specifically excluded limit in the stated range. Where the stated range includes one or both of the limits, ranges excluding either both of those included limits are also included in the invention.

Unless defined otherwise, all technical and scientific terms used herein have the same meaning as commonly understood by one of ordinary skill in the art to which this invention belongs. Although any methods and materials similar or equivalent to those described herein can also be used in the practice or testing of the present invention, the preferred methods and materials are now described. All publications mentioned herein are incorporated by reference to disclose and describe the methods and/or materials in connection with which the publications are cited.

The publications discussed herein are provided solely for their disclosure prior to the filing date of the present application. Nothing herein is to be construed as an admission that the present invention is not entitled to antedate such publication by virtue of prior invention. Further, the dates of publication provided may be different from the actual publication dates which may need to be independently confirmed.

EXAMPLES

The following examples are put forth so as to provide those of ordinary skill in the art with a complete disclosure and description of how to make and use the present invention, and are not intended to limit the scope of what the inventors regard as their invention nor are they intended to represent that the experiments below are all or the only experiments performed. Efforts have been made to ensure accuracy with respect to numbers used (e.g., amounts, temperature, etc.) but some experimental errors and deviations should be accounted for. Unless indicated otherwise, parts are parts by weight, molecular weight is weight average molecular weight, temperature is in degrees Centigrade, and pressure is at or near atmospheric.

Example 1

Exemplary Nimodipine Microparticle Formulation

A microparticle nimodipine formulation containing a uniform size distribution of microparticles was prepared by combining a polymer solution (e.g., a 50-50 glycolide-lactide blend) with a solvent in the presence of nimodipine and suspended in a buffer. The mixture was added to a surfactant containing aqueous solution to form an emulsion and the solvent extracted to produce the flowable microparticle nimodipine formulation.

Nimodipine dispersed throughout each microparticles comprising a 50-50 glycolide-lactide (PLGA) blend had an initial drug load of 65%, i.e., 65% nimodipine and 35% polymer. An exemplary nimodipine microparticle formulation comprises 63.2 wt. % of nimodipine and 36.8 wt. % of PLGA.

Figure 13:
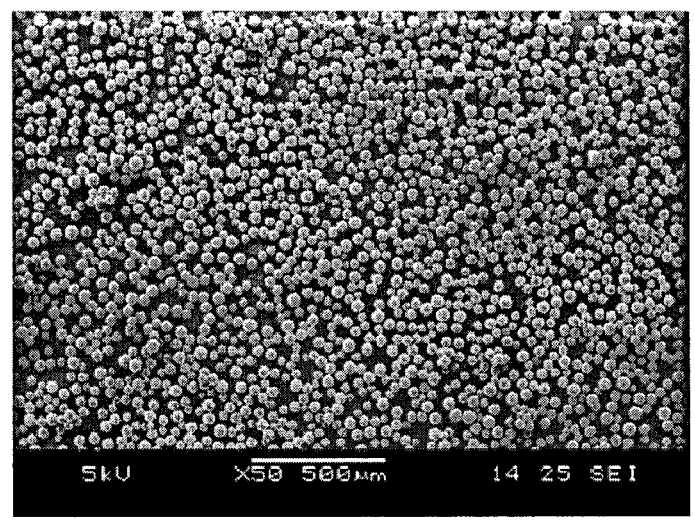
FIG. 13 shows a scanning electron micrograph (SEM) image of a particulate nimodipine formulation according to the present invention.

The mean particle diameter was about 70 μm, ranging between 40 μm-100 μm. FIG. 13 shows a scanning electron micrograph (SEM) image of a microparticle nimodipine formulation according to the present invention.

Example 2

In Vitro Release Kinetic Analysis

Figure 14:
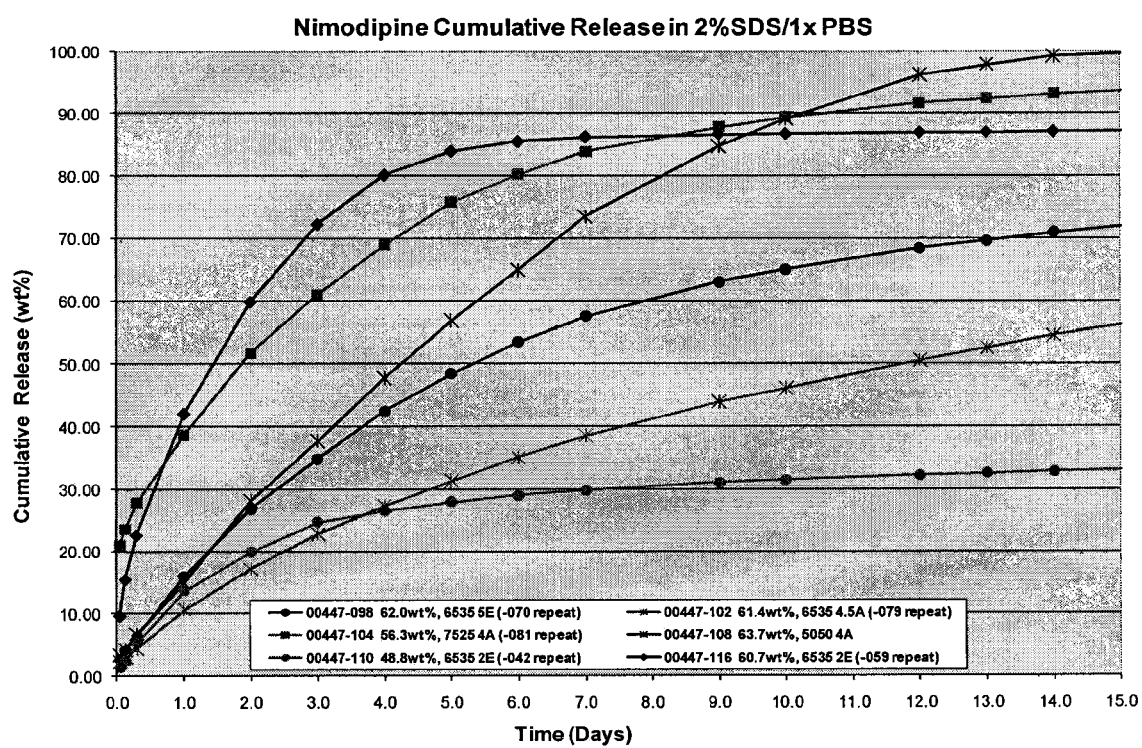
FIG. 14 shows the in vitro cumulative release of exemplary particulate nimodipine formulations expressed as weight % of the over time.

For measuring in vitro release profiles, samples of microparticle nimodipine formulations were analyzed for nimodipine content by high performance liquid chromatography (HPLC) at specific time points (1 hr, 2 hrs, 6 hrs, 24 hrs and then each day for 14 days). The release characteristics in vitro were assessed by mixing nimodipine PLGA microparticles, 10 mg, with 20 ml PBS/sodium dodecyl sulfate. The supernatant fluid (10 ml) was removed and assayed at the specified times. At each time the supernatant fluid removed was replaced with an equal volume of the buffer solution. The assay was optimized to meet regulatory requirements for sink conditions. Exemplary microparticle formulations are capable of releasing in vitro about 50% to 100% of nimodipine within a time frame of 6 to 14 days in vitro. FIG. 14 shows the in vitro cumulative release of exemplary microparticle nimodipine formulations expressed as weight % of the over time.

Example 3

Local Delivery of the Microparticle Nimodipine Formulation

The microparticle nimodipine formulation was combined with a pharmaceutical carrier or an injection vehicle to form the flowable pharmaceutical composition of the described invention. The placebo formulation contained the microparticles created without nimodipine plus vehicle. For example, a vehicle (e.g. water, saline (hydroxyl propyl methyl cellulose (HPMC) in PBS, sodium hyaluronate, etc.) can be mixed with the microparticle nimodipine formulation to form a flowable suspension.

The microparticle nimodipine formulation was filled into a 10 mL syringe (sterile, latex-free) and closed with a polyprolyene cap. The syringe/cap was then packaged within a laminated foil pouch to protect from light.

Example 4

Preclinical Study 1—Effect of Nimodipine Formulation on Cerebral Vasospasm in a Subarachnoid Hemorrhage (SAH) Model in Dogs Materials and Methods The formulation comprised nimodipine encapsulated in PLGA microparticles for sustained release. The excipient used in the exemplary nimodipine microparticle formulation was a poly(DL-lactide-co-glycolide), also referred to as PLGA, with equivalent ratios of lactide and glycolide with acid end groups. PLGA, is a non-toxic, well-tolerated, biocompatible and biodegradable polymer used as a controlled release agent for prolonged release/depot type formulations. The initial drug load was 65%, i.e., 65% nimodipine and 35% polymer. The mean particle diameter was about 70 μm, ranging between 40 μm-100 μm.

Treatment Groups

Six mongrel dogs weighing between 15-17 kg were randomly allocated to receive microparticle placebo formulation (n=2) or microparticle nimodipine formulation (10 mg [n=2] or 30 mg [n=2], Table 4).

TABLE 4

Treatment group assignments
Table 4. Group Assignments (Study 1)

| Group Number | Treatment | Number of Male Animals |
| --- | --- | --- |
| 1 | Microparticle placebo formulation (Placebo) | 2 |
| 2 | 10 mg of microparticle nimodipine formulation (Low dose) | 2 |
| 3 | 30 mg of microparticle nimodipine formulation (High dose) | 2 |

Administration

FIG. 15 shows an exemplary view of the application of a composition of the described invention containing a microparticle formulation of a calcium channel antagonist, an endothelin receptor antagonist, a TRP protein antagonist, or a combination thereof, into a cerebral ventricle via an intraventricular catheter (Figure from Mccomb J G: Techniques of CSF diversion. In: Scott R M (ed). Hydrocephalus. Vol. 3. Williams & Wilkins: Baltimore. 1990. page 48, pp. 128). FIG. 16 is a schematic depicting a composition of the described invention comprising a microparticle formulation of a calcium channel antagonist, an endothelin receptor antagonist, a TRP protein antagonist, or a combination thereof, in or on microparticles being carried by CSF flow from the ventricle to the cerebral arteries of the subarachnoid space (Pollay M: Cerebrospinal fluid. In: Tindall G T, Cooper P R, Barrow D L (eds). The Practice of Neurosurgery. Vol. 1. Williams & Wilkins: Baltimore. 1996. page 36, pp. 1381).

The microparticle placebo and microparticle nimodipine formulations were combined with a pharmaceutical carrier to form the flowable pharmaceutical compositions of the described invention prior to administration. For each treatment group, a saline injection vehicle (e.g. hydroxyl propyl methyl cellulose (HPMC) in PBS) was mixed with the microparticulate formulations prior to administration. The microparticle placebo formulation contained the microparticles created without nimodipine plus the saline vehicle. The microparticle nimodipine formulations contained the microparticles created with nimodipine at low or high doses plus the saline vehicle. Each flowable pharmaceutical compositions was administered to each respective treatment group once during surgery on Day 1 via injection into the cisterna magna (the enlarged subarachnoid space between the caudal surface of the cerebellum and the dorsal surface of the medulla oblongata). The dose levels for the treated groups were 10 mg or 30 mg at a fixed dose volume of 0.25 mL (microparticle placebo formulation), 0.17 mL or 0.18 mL (microparticle nimodipine formulation at low dose), or 0.46 mL (microparticle nimodipine formulation at high dose). The syringes provided were loaded with 16 and 40 mg of microparticle nimodipine formulation at low dose and microparticle nimodipine formulation at high dose, respectively; this took into account the overfill needed to fill the dead volume in the delivery system. As the materials were administered per the reconstitution/injection procedure, the delivered doses were approximately 10 mg and 30 mg. The control group received the control article (microparticle placebo formulation) in the same manner as the treated groups.

For reconstitution/injection, a syringe comprising diluent was attached via a connector to a syringe comprising the microparticle nimodipine formulation. A plunger is cycled to draw the vehicle into the microparticle formulation. The resulting pharmaceutical composition is then pushed into the left syringe, which is disconnected from the connector. For delivery, the composition is injectable either through a surgical needle or can be fitted with or injected through a cannula or catheter of any appropriate size.

Surgical Procedures

On Day 1, the dogs were weighed and sedated with acepromazine, 0.1 mg/kg subcutaneously. They then received atropine, 0.05 mg/kg subcutaneously and propofol, 6 mg/kg intravenously, after which they were intubated and ventilated on air and isoflurane, 1-3%. Baseline blood was collected and blood pressure, temperature, heart rate, oxygen saturation, and arterial blood gases (eg. $CO_2$ pressure ($pCO_2$)) were monitored throughout the surgical procedure.

Cerebral angiography was performed through a 5F catheter inserted into one vertebral artery (e.g the right femoral artery). The catheter with 0.035 inch guidewire was advanced under fluoroscopic guidance into the proximal portion of one vertebral artery. An anteroposterior angiogram was obtained by injection of 8 ml of radiopaque dye (diatrizoate meglumine United States Pharmacopeia, 60%). Video images were captured using identical exposure factors and magnification for every angiogram (General Electric OEC 9800 fluoroscopy unit, Waukesha, Wis.). An internal magnification standard was included in every angiogram.

Following angiography, the animals were turned prone and the cisterna magna was punctured percutaneously with an 18 gauge 3.5 inch spinal needle. A targeted volume of 0.3 mL/kg CSF was allowed to drain spontaneously, after which 0.5 mL/kg of fresh, autologous, arterial, non-heparinized blood was withdrawn from the femoral catheter and injected into the cisterna magna at a rate of approximately 5 mL/minute. Approximately one half of the blood volume was injected, then the placebo or nimodipine formulation was administered at a rate of approximately 5 mL/minute. Upon completion of administration of microparticle placebo or microparticle nimodipine formulations (low dose and high dose), the remaining blood was injected. The needle was withdrawn immediately after the injection. The animal was tilted 30° head down during cisternal blood injection and remained in that position for 15 minutes following completion of injection. The animal was then turned supine, the femoral catheter was removed, and the femoral artery was ligated. The incision was closed in a standard fashion.

On day 3, the dogs were placed under general anesthesia and the cisternal blood injection was repeated. On days 8 and 15, the animals were anesthetized, and angiography and removal of CSF from the cistern magna was repeated. After angiography on day 15, animals were not recovered from anesthesia. They were euthanized under anesthesia, perfused with PBS and then neutral buffered formalin, and the brains subjected to histological analysis as described above.

Physiological Observations

There were no significant differences in physiologic parameters within groups of dogs at each time or between groups over time. Table 5 summarizes the physiological parameters by group for days 0, 7 and 14.

For statistical analysis, paired t-tests were used to compare values within a group over time or by analysis of variance (ANOVA) if there were more than 2 times (Sigmaplot, Chicago, Ill.). Post-hoc pairwise comparisons were done by the Holm-Sidak test. Unpaired t-tests were used to compare values between groups. In t-tests, the Mann-Whitney Rank Sum test was used if the normality test failed. P<0.05 was considered significant. All data are means V standard error of the mean.

Figure 17:
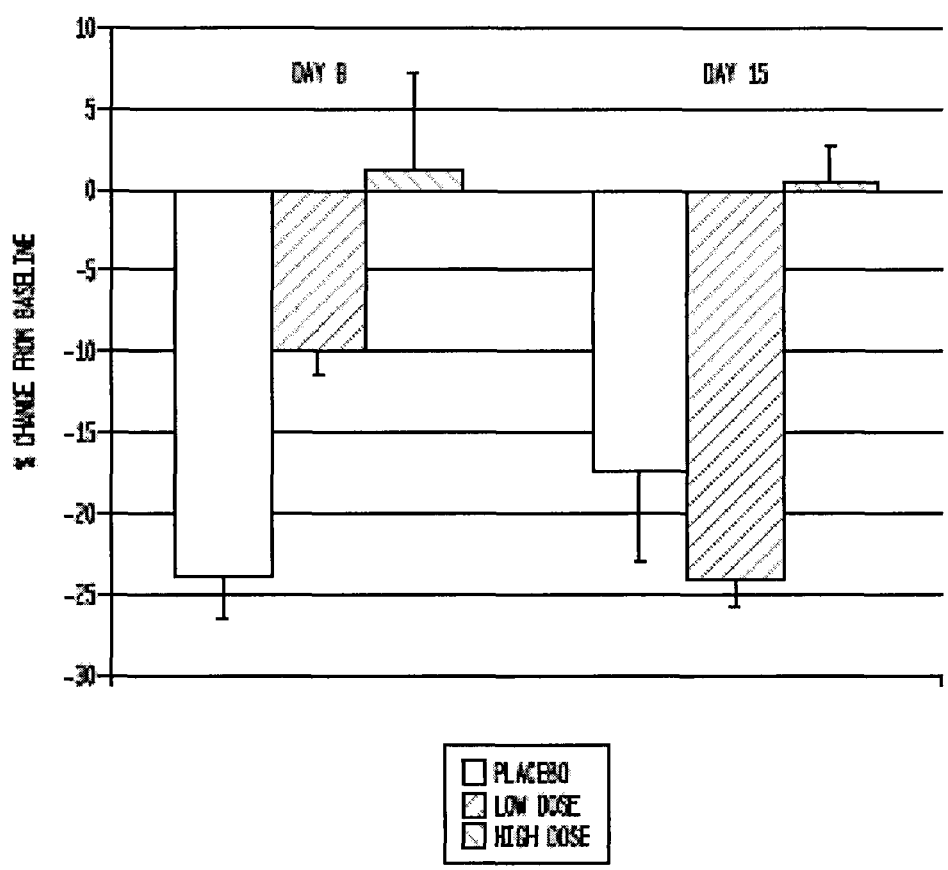
FIG. 17 shows percent (%) changes in mean basilar arterial diameters from baseline following treatment (administration into the cisterna magna of the subarachnoid space) with a low dose (10 mg) nimodipine formulation, a high dose (30 mg) formulation, and a placebo. (Preclinical Study 1)

Average percent vasospasm for Days 8 and 15 was also determined for each group. FIG. 17 shows percent (%) changes in mean basilar arterial diameters from baseline following treatment in the cisterna magna of the subarachnoid space with a low dose (10 mg) nimodipine formulation, a high dose (30 mg) formulation, and a placebo. Table 6 summarizes the mean, standard error, median and standard deviation for percent angiographic vasospasm.

TABLE 5

Physiological parameters for dogs by group for days 0, 7, and 14

| Parameter | Placebo (n = 2) | | | Nimodipine 10 mg (n = 2) | | | Nimodipine 30 mg (n = 2) | | |
| --- | --- | --- | --- | --- | --- | --- | --- | --- | --- |
| | Day 0 | Day 7 | Day 14 | Day 0 | Day 7 | Day 14 | Day 0 | Day 7 | Day 14 |
| Weight (kg) | 17.8 ± 0.8 | 17.8 ± 0.3 | 17.8 ± 1.3 | 16.8 ± 0.3 | 17.0 ± 1.0 | 15.5 ± 1.0 | 16.0 ± 0.5 | 16.5 ± 0 | 16.8 ± 0.3 |
| Heart rate | 117 ± 1 | 124 ± 1 | 130 ± 4 | 107 ± 7 | 123 ± 18 | 107 ± 13 | 105 ± 2 | 102 ± 4 | 109 ± 5 |
| $PCO_2$ (mmHg) | 53.8 ± 0.4 | 55.5 ± 0.0 | 73.5 ± 0.0 | 58.2 ± 0.4 | 60.6 ± 1.0 | 66.0 ± 1.0 | 47.4 ± 0.1 | 43.0 ± 0.0 | 52.7 ± 1.3 |
| $O_2$ saturation | 97 ± 1 | 99 ± 1 | 97 ± 1 | 97 ± 1 | 98 ± 2 | 98 ± 2 | 95 ± 1 | 97 ± 2 | 97 ± 2 |

Angiographic Vasospasm

Angiographic vasospasm was assessed by comparing the diameters of the basilar arteries on days 1, 8, and 15. The diameter of the basilar artery was measured from digital angiograms using catheter angiography at predetermined locations using computer software (Adobe Photoshop CS4 with image processing tool kit, Adobe Systems, San Jose, Calif.). Quantification of fibrinogen staining was performed on 5 fixed symmetrical areas for cerebral cortex on a coronal section of the dog brain including regions of anterior, middle and posterior cerebral artery territories. One image from each fixed area (5 from each hemisphere for a total of 10) was photographed and all microthrombi in the section were counted. All counting was done by blinded researchers using stereologic principles. The angiographic data was independently analyzed by four reviewers who were blinded to the animal group. The five averaged lumen diameters for each animal were then averaged to obtain a mean lumen diameter for each animal at each time point. Individual percent vasospasm was determined for each animal for Days 8 and 15 using formula (1):

$$\frac{[\text{Follow-up}(Day8or15)MeanLumenDiameter] - [Baseline(Day1)MeanLumenDiameter]}{BaselineMeanLumenDiameter} \times 100 \quad (1)$$

TABLE 6

Summary of percent vasospasm data from review of angiograms (Preclinical Study 1)

| | Placebo Day 8 | Low Dose Day 8 | High Dose Day 8 | Placebo Day 15 | Low Dose Day 15 | High Dose Day 15 |
| --- | --- | --- | --- | --- | --- | --- |
| Mean | −24 | −9.9 | 1.2 | −17.3 | −24 | 0.6 |
| Standard Error | 2.5 | 1.6 | 6.0 | 5.7 | 1.8 | 2.1 |
| Median | −25.0 | −10.6 | −3.2 | −13.8 | −25.6 | −1.2 |
| Standard Deviation | 5.1 | 3.1 | 12.0 | 11.5 | 3.6 | 4.2 |

At day 8, the mean basilar artery diameter decreased 24% in control animals when compared to baseline. Animals treated with low dose of nimodipine microparticles had a −9.9% mean decrease in basilar artery diameter when compared to baseline. Animals treated with the high dose of nimodipine microparticles had a mean basilar artery diameter increase of 1.2% when compared to baseline.

At day 15, the mean basilar artery diameter decrease for the control animals (placebo-treated) was −17.3% when compared to baseline. Animals treated with the low dose of nimodipine microparticles had a −24% mean decrease in basilar artery diameter when compared to baseline. Animals treated with the high dose of nimodipine microparticles had a mean basilar artery diameter increase of 0.7% when compared to baseline. Statistical analysis was not performed due to the small number of animals studied.

This Example shows that: (1) at day 8, narrowing of basilar artery was highest for the control group, followed by the low dose group and lowest for the high dose group; and (2) at day 15, narrowing of basilar artery was highest the control, low dose groups and lowest for the high dose group. Due to a small number of animals in the study, the change in basilar artery in the lose dose group at day 15 was within expected statistical variation.

Clinical findings that were considered to be associated with the study procedures were limited to observations of decreased activity and inappetence. Decreased activity was noted in all 6 animals during the first week of the study and in one placebo treated and one low dose nimodipine microparticle treated animal during the second week. Inappetence was noted in 5 of 6 animals during the first week and 4 of 6 animals during the second week. These findings were present in animals from all dose groups and therefore considered to be study procedure related.

Behavioral Observations

Behavior was assessed on a 6-point scale that has been used to determine effects of SAH and drug treatment on SAH in dogs as described in Zhou, C. et al., "Role of p53 and apoptosis in cerebral vasospasm after experimental subarachnoid hemorrhage," J. Cereb. Blood Flow Metab. 25:572-582 (2005). Observations for morbidity, mortality, injury, and the availability of food and water were conducted twice daily for all animals. Body weights were measured and recorded prior to randomization and weekly during the study. A complete physical examination was conducted on all animals by a staff veterinarian pretest.

Behavioral observations were conducted by a staff veterinarian on a daily basis for each animal enrolled on study. Behavior of each animal was examined by a staff veterinarian daily. Behavior pertaining to behavior categories of apetite, activity and neurological deficit were given behavioral scores according to Tables 7-9.

Table 7 provides behavioral scores given for appetite.

TABLE 7

Behavioral Score for Appetite
Appetite

| Score | Observation |
|---|---|
| 2 | Finished meal |
| 1 | Left meal unfinished |
| 0 | Scarcely ate |

Table 8 provides behavioral scores for activity.

TABLE 8

Behavioral scores for Activity
Activity

| Score | Observation |
|---|---|
| 2 | Active, barking or standing |
| 1 | Lying down, will stand and walk with some stimulation |
| 0 | Almost always lying down |

Table 9 provides behavioral scores for neurological deficits. Neurological deficit scored was ability to walk because of ataxia or paresis.

TABLE 9

Behavioral scores for neurological deficits
Neurological Deficits

| Score | Observation |
|---|---|
| 2 | No deficit |
| 1 | Unable to walk because of ataxia or paresis |
| 0 | Impossible to walk or stand because of ataxia or paresis |

Figure 18:
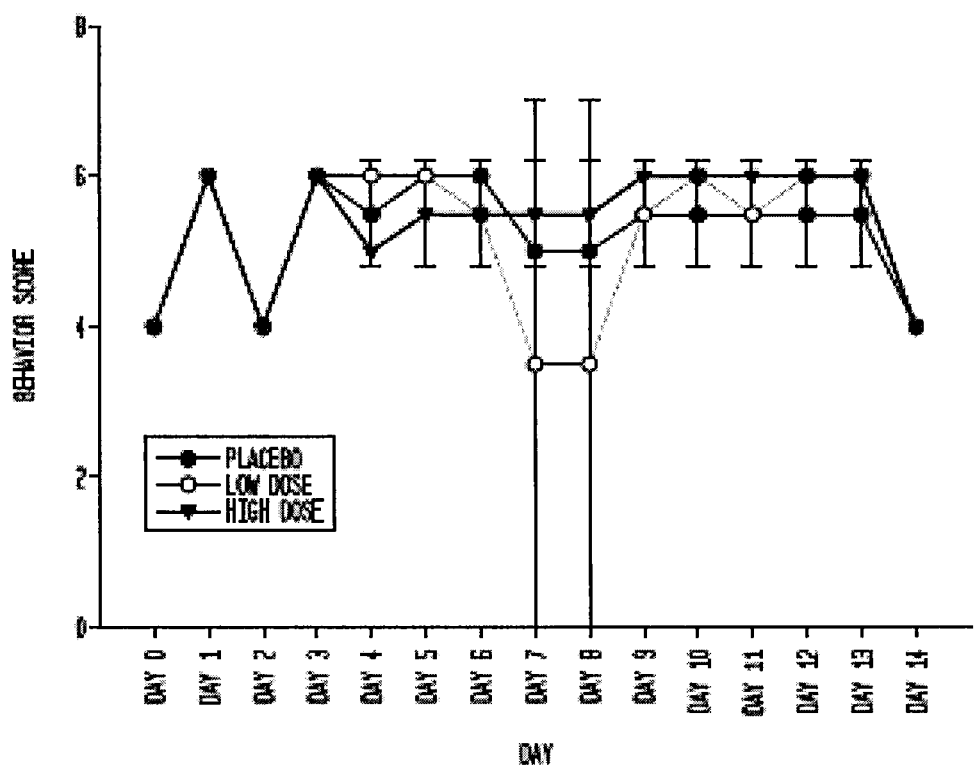
FIG. 18 shows a plot of averaged behavioral scores of dogs subjected to SAH, following treatment (administration into the cisterna magna of the subarachnoid space) with a placebo, a low dose (10 mg) of the microparticle nimodipine formulation, or a high dose (30 mg) of the microparticle nimodipine formulation. (Preclinical Study 1)

FIG. 18 shows a plot of averaged behavioral scores of dogs subjected to SAH, which are treated with a placebo, a low dose (10 mg) of the microparticle nimodipine formulation, or a high dose (30 mg) of the microparticle nimodipine formulation.

There were no consistent or marked changes in appetite or activity and no changes in neurological function.

Neither the study procedures nor treatment with placebo or nimodipine microparticles was associated with any substantial change in body weight. There were no apparent differences in hematology parameters between either nimodipine microparticle dose and placebo.

Serum Analysis

Nimodipine concentrations were measured in serum using the United States Pharmacopeia liquid chromatography mass spectrometry/mass spectrometry (LC-MS/MS) method. (USP Monograph, Nimodipine, USP 30-NF 25, First Supplement, p. 1535, Published February 2007). Standards used were a reference standard (50 µg/mL dismicronized nimodipine dissolved in methanol and diluted to various concentrations to be used as calibration standards) and a working internal standard (WIS) (400 ng/mL nitrendipine dissolved in methanol). The LC-MS/MS assay method was developed for the analysis of nimodipine in mongrel dog plasma with $K_2$EDTA at nimodipine concentrations ranging from 0.200-200 ng/mL using a Shimadzu LC-20AD HPLC system fitted with a Phenomenex, Luna C18 column (3 µM, 100 Å, 2×50 mm) and Applied Biosystems/MDS SCIEX API 4000 LC-MS/MS system. Samples with concentrations above the upper limit of quantitation (ULOQ) were diluted within the range of the calibration curve, processed, and then analyzed. For HPLC, 0.1% formic acid (v/v/) was used as mobile phase A, methanol/formic acid (1000:1, v/v) as mobile phase B, methanol/$NH_4OH$ (500:25 v/v) as wash 1, and methanol/$H_2O$ (350:150, v/v) as wash 2. For MS/MS, the mass/charge (m/z) ratio for precursor to product ion for nimodipine was 419 to 343, respectively and for nitrendipine was 361 to 315, respectively.

In brief, each plasma sample (mongrel dog plasma with $K_2$ EDTA), standard or blank (methanol) was transferred to a solid phase extraction plate in 2% ammonia (v/v), processed with methyl tert-butyl ether (MTBE) in minimal vacuum or positive pressure until all disks appeared dry. The eluate was then evaporated under a stream of $N_2$, heated to about 35° C. The dried residue was reconstituted with methanol/water (350:150 v/v) and transferred to a 96-well autosampler plater and analyzed by LC-MS/MS. The calibration curve for each run was determined from the peak response ratio versus the concentration of analyte by least square analysis, using the peak area ratio of the calibration standards to the internal standard versus the concentration of the calibration standards. The concentration of the analyte was calculated using the calibration curve and solving for the variable nimodipine concentration.

Figure 19:
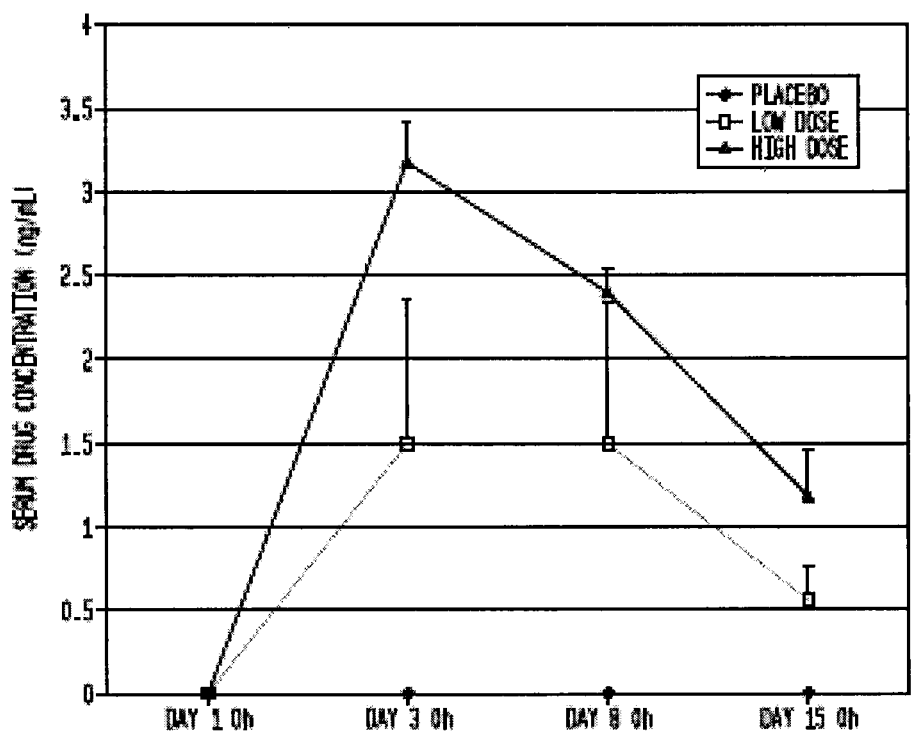
FIG. 19 shows a plot of serum drug concentrations (ng/mL) over time in dogs subjected to SAH, following treatment (administration into the cisterna magna of the subarachnoid space) with a placebo, a low dose (10 mg) microparticle nimodipine formulation or a high dose (30 mg) microparticle nimodipine formulation. (Preclinical Study 1)

Analysis of serum samples for nimodipine showed higher concentrations on day 3 with detectable levels of nimodipine still present on day 15. Table 10 lists the serum drug concentrations (ng/mL) in dogs subjected to SAH, when treated with placebo, low dose (10 mg) microparticle nimodipine formulation or a high dose (30 mg) microparticle nimodipine formulation. FIG. 19 shows a plot of the serum drug concentrations (ng/mL) over time in dogs subjected to SAH, when treated with placebo, a low dose (10 mg) microparticle nimodipine formulation or a high dose (30 mg) microparticle nimodipine formulation.

Serum concentrations of nimodipine were higher in animals treated with high-dose nimodipine microparticles. Nimodipine was not detected at any time point in the placebo animals.

TABLE 10

Serum drug concentrations (ng/mL)
Table 10: Serum Drug Concentrations (ng/mL) (Study 1)

| Group | | Day 1 0 h | Day 3 0 h | Day 8 0 h | Day 15 0 h |
|---|---|---|---|---|---|
| Placebo | Mean | 0 | 0 | 0 | 0 |
|  | SD | NA | NA | NA | NA |
| Formulation | Mean | 0 | 1.51 | 1.5 | 0.559 |
| Low Dose | SD | NA | 0.184 | 0.148 | 0.257 |
| Formulation | Mean | 0 | 3.18 | 2.4 | 1.19 |
| High Dose | SD | NA | 0.856 | 0.834 | 0.219 |

Below limit of quantitation <0.200 ng/mL
Above limit of quantitation >200 ng/mL
N = 2 per measurement Cerebrospinal Fluid (CSF) Analysis Nimodipine concentrations were measured in CSF using the United States Pharmacopeia liquid chromatography mass spectrometry/mass spectrometry (LC-MS/MS) method. (USP Monograph, Nimodipine, USP 30-NF 25, First Supplement, p. 1535, Published February 2007). Standards used were a reference standard (50 μg/mL dismicronized nimodipine dissolved in methanol and diluted to various concentrations to be used as calibration standards), and a working internal standard (WIS) (400 ng/mL nimodipine-d7 dissolved in methanol). The LC-MS/MS assay method was developed for the analysis of nimodipine in mongrel dog CSF at nimodipine concentrations ranging from 0.500-500 ng/mL using a Shimadzu LC-20AD HPLC system fitted with a Phenomenex, Luna C18 column (3 μM, 100 Å, 2×50 mm) and Applied Biosystems/MDS SCIEX API 4000 LC-MS/MS system. Samples with concentrations above the upper limit of quantitation (ULOQ) were diluted within the range of the calibration curve, processed, and then analyzed. For HPLC, 0.1% formic acid (v/v/) was used as mobile phase A, methanol/formic acid (1000:1, v/v) as mobile phase B, methanol/$NH_4OH$ (500:25 v/v) as wash 1, and methanol/$H_2O$ (350:150, v/v) as wash 2. For MS/MS, the mass/charge (m/z) ratio for precursor to product ion for nimodipine was 419 to 343, respectively and for nimodipine-d7 was 426.1 to 350, respectively.

In brief, each CSF sample in 1.5% octyl-β-glucopyranoside (OG), standard or blank (methanol) was transferred to a solid phase extraction plate in 2% ammonia (v/v), processed with methyl tert-butyl ether (MTBE) in minimal vacuum or positive pressure until all disks appear dry. The eluate was then evaporated under a stream of $N_2$, heated to about 35° C. The dried residue was reconstituted with methanol/water (350:150 v/v) and transferred to a 96-well autosampler plate and analyzed by LC-MS/MS. The calibration curve for each run was determined using the peak response ratio versus the concentration of analyte by least square analysis; the peak area ratio of the calibration standards to the internal standard versus the concentration of the calibration standards was used. The concentration of the analyte was calculated using the calibration curve and solving for the variable nimodipine concentration.

Sustained high concentrations of nimodipine in CSF samples on days 3 and 8 were found after administration of the low dose of nimodipine microparticles with lower concentrations present on day 15. Table 11 lists the drug concentrations (ng/mL) in CSF from dogs subjected to SAH, when treated with placebo, a low dose (10 mg) microparticle nimodipine formulation or a high dose (30 mg) microparticle nimodipine formulation.

CSF nimodipine concentrations were significantly higher than serum concentrations with administration of low and high dose of nimodipine microparticles and detectable concentrations were still present at day 15. One of the high dose day 3 samples was above the limit of quantitation (>500 ng/mL) and was not re-testable due to lack of additional sample. Statistical significance could not be determined because of low sample number. Nimodipine was not detected at any time points in the Placebo animals.

TABLE 11

CSF nimodipine concentrations (ng/mL) for each treatment group
Table 11: CSF Nimodipine Concentrations (ng/mL) (Study 1)

| Group | | Day 1 0 h | Day 3 0 h | Day 8 0 h | Day 15 0 h |
|---|---|---|---|---|---|
| Placebo | Mean | 0 | 0 | 0 | 0 |
|  | SD | NA | NA | NA | NA |
| Formulation | Mean | 0 | 380 | 379 | 156 |
| Low Dose | SD | NA | 151 | NA | 132 |
| Formulation | Mean | 0 | 5.78* | 126 | 63.6 |
| High Dose | SD | NA | NA | 168 | 88.2 |

Figure 20:
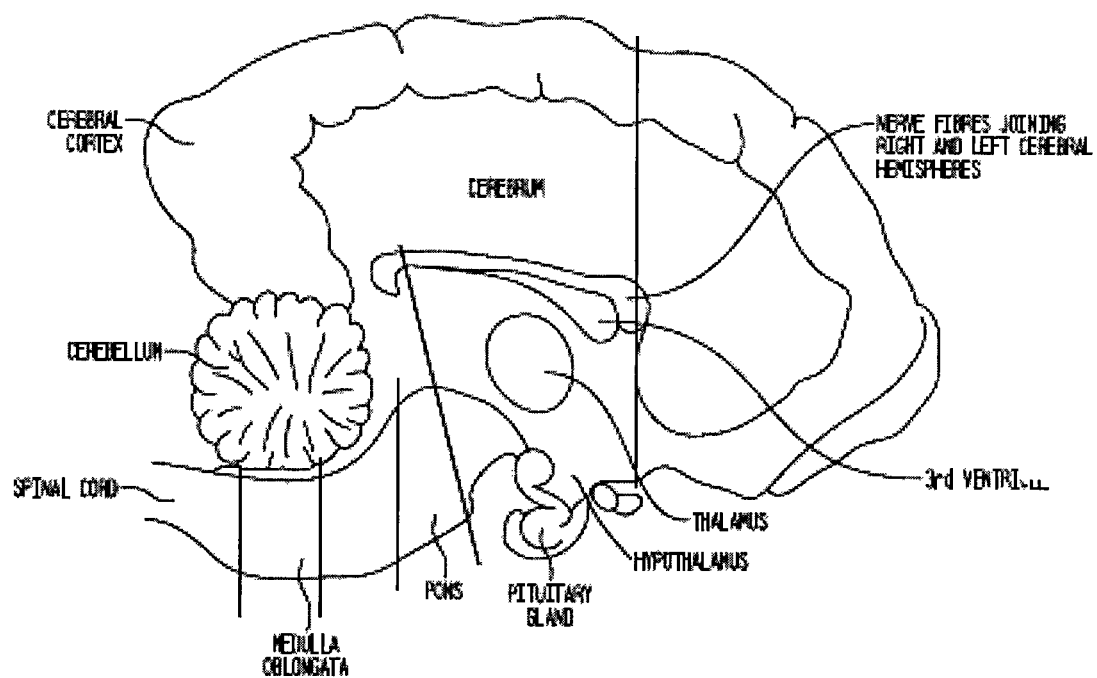
FIG. 20 shows sectional planes used in the dog model experiments.

Below limit of quantitation <0.500 ng/mL
Above limit of quantitation >500 ng/mL
*One of the two samples of the High Dose Formulation was above the limit of quantitation and not enough sample remained for additional testing
N = 2 per measurement Microscopic Analysis All animals were euthanized by perfusion through the left ventricle with 2 L ice-cold PBS at mean blood pressure. The brain was removed and sliced in 12 5 mm sections in the coronal plane. For dogs, the brainstem also was sectioned in the axial plane. FIG. 20 shows sectional planes used in canine model experiments. Sections of brain from the anterior cerebral (ACA), middle cerebral (MCA), posterior cerebral and basilar artery territories were placed in 10% buffered formalin and then processed for routine histology. Histological sections were cut, stained with hematoxylin and eosin and viewed under a light microscope by a blinded investigator.

Figure 21:
FIG. 21 shows histopathology of dogs subjected to SAH when treated with placebo (A) and when treated with the low dose microparticle nimodipine formulation (B).

FIG. 21 shows histopathology of dogs subjected to SAH when treated with placebo (A) and when treated with the low dose microparticle nimodipine formulation (B). The only microscopic findings consisted of minimal to mild granulomatous inflammation within the subarachnoid space of the pons and/or medulla in both animals from the low-dose microparticle nimodipine formulation group and one of 2 animals from the high-dose microparticle nimodipine formulation group. Inflammation was characterized by aggregates of giant cells that engulfed foreign material. Minimal subacute inflammation or lymphocytic perivascular infiltrate was also noted in a few animals across groups. The latter finding was closely associated with the granulomatous inflammation.

Minimal to mild degeneration was noted in one of two animals from the placebo group and both animals from the low-dose nimodipine microparticle group. Degeneration was present in the ventral portion of the pons and/or medulla and was characterized by cavitating spaces partially filled with hemorrhage, proliferating small vessels, and increased numbers of glial/astrocytic cells. Foamy vacuolated cells were occasionally present. Axonal swelling/degeneration was present in the adjacent brain tissue. This finding was considered related to the injection procedure and was not an effect of the injected composition.

Meningeal hemorrhage and/or fibroplasia were noted in most animals examined and were likely related to the necropsy and/or the injection procedure.

The microscopic studies showed minimal to mild granulomatous inflammation within the subarachnoid space, minimal to mild degeneration and meningeal hemorrhage and/or fibroplasia in all treatment groups, i.e., placebo, low dose (10 mg) microparticle nimodipine formulation and high dose (30 mg) microparticle nimodipine formulation.

Example 5

Preclinical Study 2: Pharmacokinetics and Efficacy of Nimodipine Formulations in Dogs A second preclinical study was undertaken to assess pharmacokinetics and efficacy in dogs.

Treatment Groups

A total of 40 mongrel dogs were randomly assigned to one of five groups as presented in Table 12.

TABLE 12

Treatment group assignments
Table 12. Group Assignments

| Group Number | Treatment | Number of Animals |
|---|---|---|
| 1 | Placebo: microparticle placebo formulation | 4 males + 4 females |
| 2 | Active Control: microparticle placebo formulation followed by oral nimodipine (0.86 mg/kg dose) | 4 males + 4 females |
| 3 | Intracisternal 40 mg: intracisternal administration of 40 mg of microparticle nimodipine formulation | 4 males + 4 females |
| 4 | Intracisternal 100 mg: intracisternal administration of 100 mg microparticle nimodipine formulation | 4 males + 4 females |
| 5 | Intraventricular 100 mg: intraventricular administration of 100 mg of microparticle nimodipine formulation | 4 males + 4 females |

Formulations

Placebo microparticles are PLGA microparticles without nimodipine. The test formulation of a microparticulate nimodipine formulation containing a uniform size distribution of microparticles was prepared by combining a polymer solution (e.g., a 50-50 glycolide-lactide blend) with a solvent in the presence of nimodipine and suspended in a buffer (0.24% sodium hyaluronate in 6.7 mmol/l phosphate-buffered saline+0.1% Tween 20). The mixture was added to a surfactant containing aqueous solution to form an emulsion and the solvent extracted to produce the flowable microparticulate nimodipine formulation. The particle size distribution for 63% nimodipine (wt %) and 1.3% water was 66 µm (mean), 95 µm ($95^{th}$ percentile) and 39 µm ($10^{th}$ percentile). The initial drug load was 65% nimodipine (weight per volume). The placebo microparticulate formulation containing a uniform size distribution of microparticles was prepared by combining a polymer solution (e.g., a 50-50 glycolide-lactide blend) with a solvent in the absence of nimodipine.

The dose of oral nimodipine is equivalent to 30 mg every 4 hours in humans when converting dose based on body surface area or to 60 mg every 4 hours when converting dose based on body weight. (Reagan-Shaw S et al., "Dose translation from animal to human studies revisited," FASEB J., (2008) 22:659-661). This dose was chosen since it is a dose that already is associated with decreased blood pressure in dogs. (Zabramski J et al., "Chronic cerebral vasospasm: effect of calcium antagonists," Neurosurgery, (1986) 18:129-135). The second group receiving placebo formulation was treated with oral nimodipine in order to determine the efficacy of the test microparticle nimodipine formulation as compared to oral nimodipine.

According to some embodiments, for intracisternal administration, the microparticle formulation is admixed with a pharmaceutically acceptable carrier.

Administration

On Day 1, all dogs underwent baseline assessment followed by angiography and injection of autologous blood, 0.5 ml/g, into the cisterna magna. Following blood injection, the microparticle nimodipine formulation (100 mg) was administered to treatment group 5 by syringe through a catheter (14 gauge to 18 gauge) into a cerebral ventricle. The microparticle placebo composition was administered to treatment group 1 (Placebo), treatment group 2 (Oral Nimodipine), treatment groups 3 and 4 (40 mg and 100 mg microparticle nimodipine formulation) with a vehicle (e.g. hyaluronic acid) by injection within the cisterna magna of the subarachnoid space. Following administration of microparticle placebo composition on day 1, treatment group 2 (Oral Nimodipine) then received oral nimodipine capsules (0.86 mg/kg) six times per day till day 21. The syringes were loaded taking into account the overfill needed to fill the dead volume in the delivery system. The oral control and placebo groups received the control article in the same manner as the treated group. The dose of oral nimodipine is equivalent to 30 mg every 4 hours in humans when converting dose based on body surface area, or to 60 mg every 4 hours when converting dose based on body weight (Reagan-Shaw, S. et al., "Dose translation from animal to human studies revisited," FASEB J., 22: 659-661 (2008)). This dose was chosen since it is a dose that has been associated with decreased blood pressure in dogs (Zabramski, J. et al., "Chronic cerebral vasospasm: effect of calcium antagonists," Neurosurgery, 18: 129-135 (1986)).

For reconstitution/injection, a syringe comprising diluent was attached via a connector to a syringe comprising the microparticle nimodipine formulation. In case of treatment groups 1, and 2, i.e., for intracisternal administration, a plunger is cycled to draw the vehicle into the microparticle formulation. The resulting microparticle composition is then pushed into the left syringe, which is disconnected from the connector. For delivery, the composition is injectable either through a surgical needle or the surgical needle can be fitted with and injected through a cannula or catheter of any appropriate size.

The animals were suspended prone and tilted 30° head down for 15 minutes following completion of injections. The animals were awakened and returned to their cages. On Day 3, the animals underwent repeat blood injection (0.5 ml/kg) into the cisterna magna.

Endpoints

On days 8 and 15, the animals were anesthetized, and angiography, removal of CSF from the cistern magna and collection of plasma, were repeated. Other endpoints included daily blood pressure measurements, behavior assessment, and brain and spinal cord pathology. Animals were euthanized under anesthesia on day 28 or 49, perfused with PBS and then neutral buffered formalin, and the brains subjected to histological analysis.

Angiographic Vasospasm

For angiographic measurements, a repeated measures analysis (mixed model) was conducted. The model tested for the effects of treatment, time, and the interaction of treatment and time (Littell, R. C. et al., "SAS System for Mixed Models. Cary (NC): SAS Institute Inc." (1996)).

If there was no significant (P>0.05) treatment*time interaction, the treatment and time main effects were evaluated. If the treatment effect was significant (P<0.05), pair-wise comparisons of treatments with Tukey's adjustment were performed. If the time effect was significant (P<0.05), pair-wise comparisons of time with Tukey's adjustment were performed. If both the treatment and time effect were not significant (P>0.05), the results were deemed not significant and no further analyses was conducted on the variable.

If the interaction was significant (P<0.05), pair-wise comparisons of treatments at each time were conducted. Furthermore, pair-wise comparisons of time for each treatment were conducted. Tukey's method was used to adjust for multiple comparisons. These simple effect pair-wise comparisons were obtained from the 'treatment by time' interaction. Results of all pair-wise comparisons are reported at the 0.05 and 0.01 significances.

For normally distributed data, pairwise comparisons were by the Holm-Sidak method for multiple comparisons. Individual percent vasospasm was determined for each animal for Days 8 and 15 using formula (1):

$$\frac{[\text{Follow-up}(Day8or15)MeanLumenDiameter] - [Baseline(Day1)MeanLumenDiameter]}{BaselineMeanLumenDiameter} \times 100 \quad (1)$$

Figure 22:
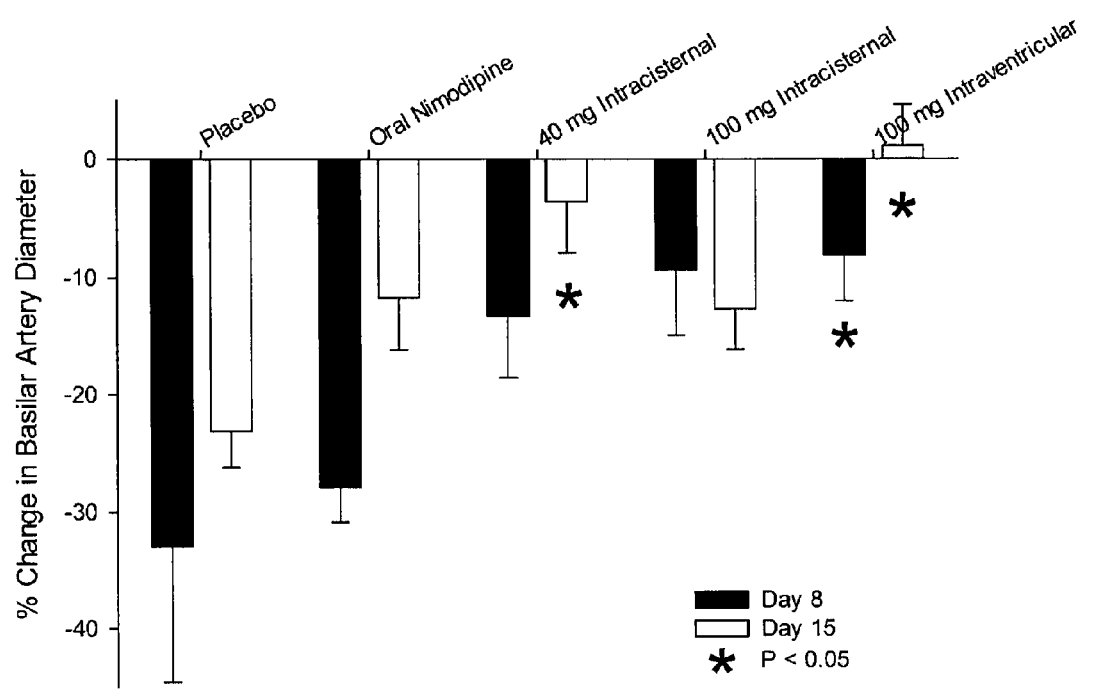
FIG. 22 is a bar graph showing percent change in angiographic diameter of the basilar artery 8 and 15 days after SAH in dogs treated by intracisternal administration of placebo microparticle composition (placebo, n=8), intracisternal administration of placebo microparticle composition followed by oral nimodipine (oral nimodipine, n=8), intracisternal administration of 40 mg nimodipine microparticles (40 mg intracisternal, n=8), intracisternal administration of 100 mg nimodipine microparticles (100 mg intracisternal, n=8) or intraventricular administration of 100 mg nimodipine microparticles (100 mg intraventricular, n=8). Analysis of variance showed significantly less angiographic vasospasm 8 and 15 days after SAH in dogs treated with intracisternal or intraventricular nimodipine microparticles (P<0.05, values are means±standard error of the mean).

Average percent vasospasm for Days 8 and 15 compared to diameter on day 1 was also determined for each group. FIG. 22 is a bar graph showing percent change in angiographic diameter of the basilar artery 8 and 15 days after SAH in dogs treated with placebo microparticle composition (placebo, n=8), oral nimodipine plus placebo microparticle composition (oral nimodipine, n=8), 40 mg intracisternal nimodipine microparticles (40 mg intracisternal, n=8), 100 mg intracisternal nimodipine microparticles (100 mg intracisternal, n=8) or 100 mg intraventricular nimodipine microparticles (100 mg intraventricular, n=8). Analysis of variance showed significantly less angiographic vasospasm 8 and 15 days after SAH in dogs treated with intraventricular nimodipine microparticles (P<0.05, values are means±standard error of the mean).

Angiography was measured by a blinded assessor and analyzed by repeated measures analysis of variance (ANOVA). The model tested for the effects of treatment, time, and the interaction of treatment and time. There was significantly less angiographic vasospasm in the groups treated with 40 or 100 mg intracisternal or 100 mg intraventricular nimodipine microparticles compared to those receiving oral nimodipine or placebo (P<0.05, FIG. 22). On day 15, there also was significantly less vasospasm in the groups treated with 40 mg intracisternal nimodipine microparticles and 100 mg intraventricular nimodipine microparticles compared to the oral nimodipine and placebo groups (P<0.05). Thus, these data show that (1) intracisternal or intraventricular sustained-release nimodipine microparticles reduce angiographic vasospasm, and (2) that there is no toxicity associated with intracisternal nimodipine microparticles containing 40 mg or 100 mg nimodipine or intraventricular nimodipine microparticles containing 100 mg nimodipine. There was a trend towards more effect on angiographic vasospasm after intraventricular delivery than with intracisternal delivery.

Behavioral Observations

Behavior was assessed on a 6-point scale that has been used to determine effects of SAH and drug treatment on SAH in dogs as described in Zhou, C. et al., "Role of p53 and apoptosis in cerebral vasospasm after experimental subarachnoid hemorrhage," J. Cereb. Blood Flow Metab. 25:572-582 (2005). Observations for morbidity, mortality, injury, and the availability of food and water were conducted twice daily for all animals. Body weights were measured and recorded prior to randomization and weekly during the study. A complete physical examination was conducted on all animals each day.

Behavioral observations were conducted daily for each animal enrolled on study. Behavior of each animal was examined daily. Behavior pertaining to behavior categories of appetite, activity and neurological defect were given behavioral scores according to Tables 7-9 above in Example 1.

Figure 23:
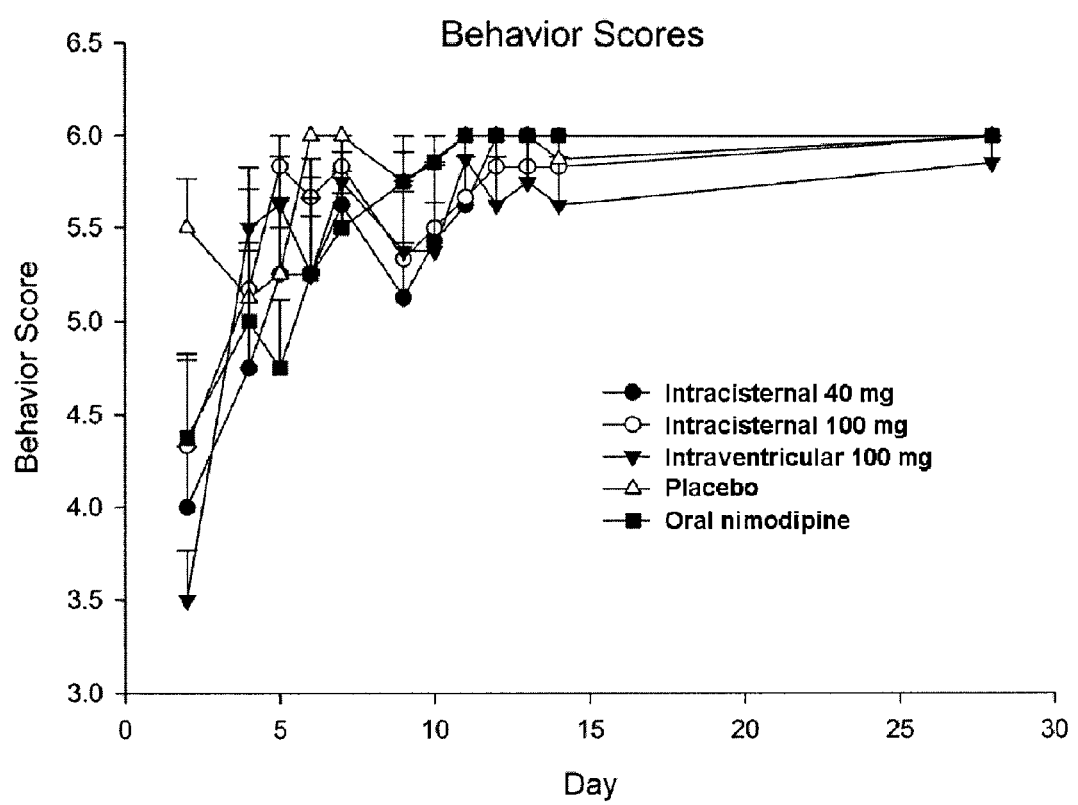
FIG. 23 shows a plot of averaged behavioral scores of dogs subjected to SAH and treated with placebo microparticle composition (placebo, n=8), oral nimodipine plus placebo microparticle composition (oral nimodipine, n=8), 40 mg intracisternal nimodipine microparticles (40 mg intracisternal, n=8), 100 mg intracisternal nimodipine microparticles (100 mg intracisternal, n=8) or 100 mg intraventricular nimodipine microparticles (100 mg intraventricular, n=8). Values are means±standard error of the mean (n=8 per measurement).

FIG. 23 shows a plot of averaged behavioral scores of dogs subjected to SAH and treated with placebo microparticle composition (placebo, n=8), oral nimodipine plus placebo microparticle composition (oral nimodipine, n=8), 40 mg intracisternal nimodipine microparticles (40 mg intracisternal, n=8), 100 mg intracisternal nimodipine microparticles (100 mg intracisternal, n=8) or 100 mg intraventricular nimodipine microparticles (100 mg intraventricular, n=8). Values are means±standard error of the mean (n=8 per measurement).

There were no significant differences in behavior between groups at any time after SAH (FIG. 23, ANOVA).

Plasma and Cerebrospinal Fluid (CSF) Analysis

Figure 24:
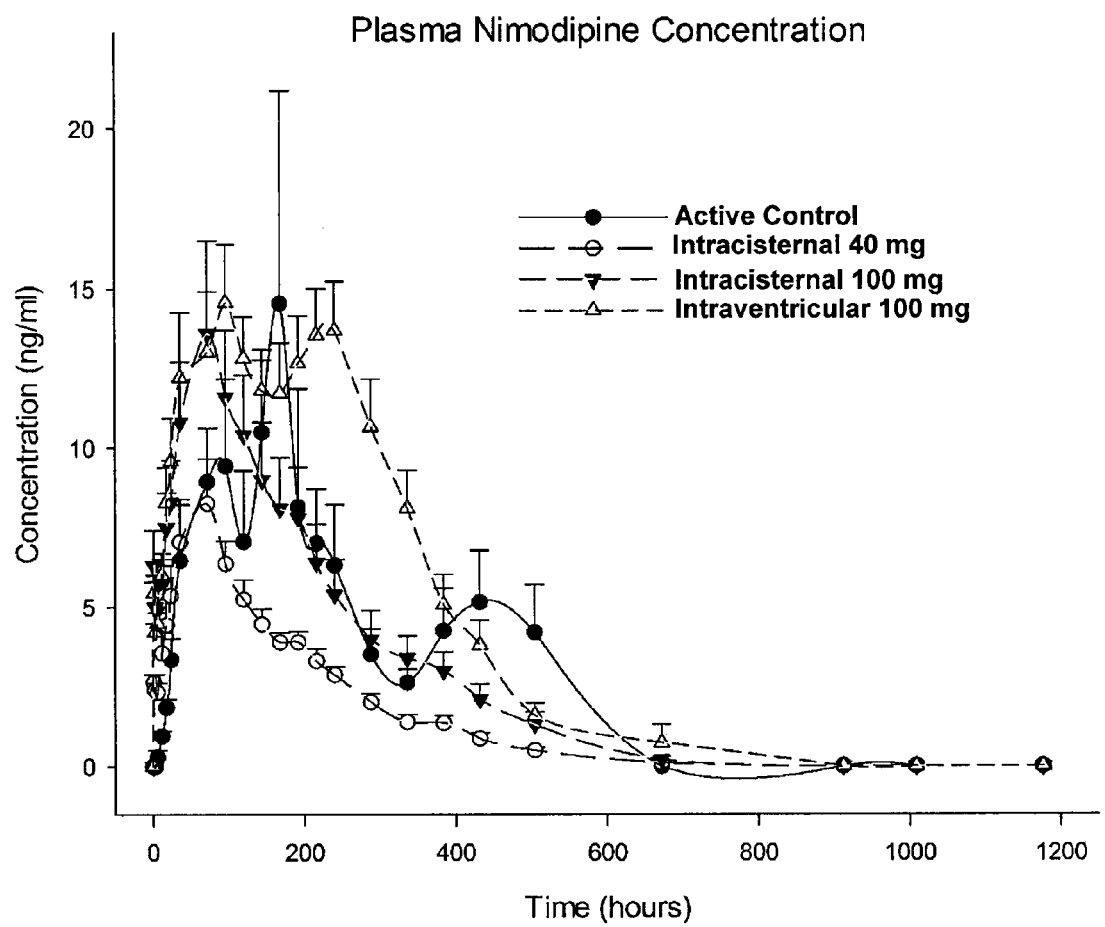
FIG. 24 shows a plot of the plasma concentration of nimodipine (ng/ml) in the 4 groups of dogs treated with oral nimodipine (administered for 21 days [504 hours]), 40 mg intracisternal nimodipine microparticles (40 mg intracisternal), 100 mg intracisternal nimodipine microparticles (100 mg intracisternal) or 100 mg intraventricular nimodipine microparticles (100 mg intraventricular). (Values are means±standard error of the mean [n=8 per measurement]).

FIG. 24 shows a plot of the plasma concentration of nimodipine (ng/ml) in the 4 groups treated with oral nimodipine (administered for 21 days [504 hours]), 40 mg intracisternal nimodipine microparticles (40 mg intracisternal), 100 mg intracisternal nimodipine microparticles (100 mg intracisternal) or 100 mg intraventricular nimodipine microparticles (100 mg intraventricular). The results show that there is systemic exposure to nimodipine after intracisternal or intraventricular nimodipine microparticle injection (values are means±standard error of the mean [n=8 per measurement]).

Figure 25:
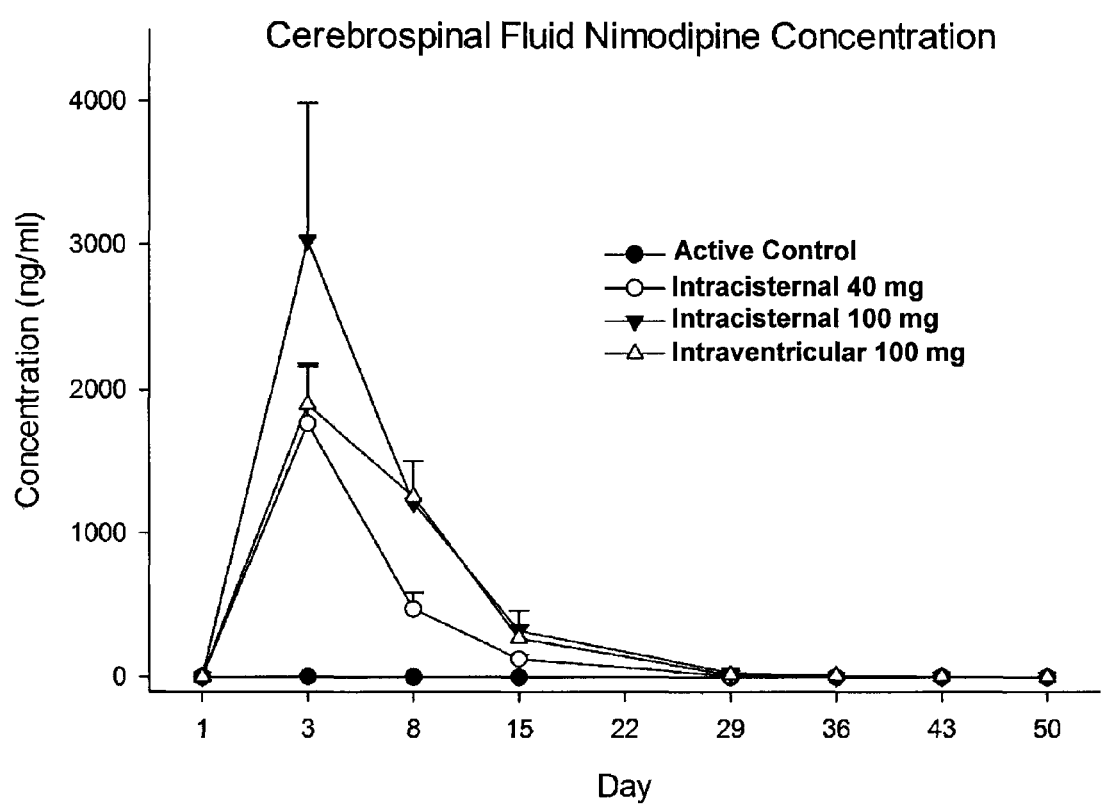
FIG. 25 shows a plot of concentration of nimodipine in cerebrospinal fluid (CSF) obtained from the cisterna magna in the 4 groups of dogs treated with oral nimodipine, 40 mg intracisternal nimodipine microparticles (40 mg intracisternal), 100 mg intracisternal nimodipine microparticles (100 mg intracisternal) or 100 mg intraventricular nimodipine microparticles (100 mg intraventricular). Values are means±standard error of the mean (n=8 per measurement).

FIG. 25 shows a plot of the cerebrospinal fluid (CSF) concentration of nimodipine in CSF obtained from cisterna magna in the 4 groups treated with oral nimodipine, 40 mg intracisternal nimodipine microparticles (40 mg intracisternal), 100 mg intracisternal nimodipine microparticles (100 mg intracisternal) or 100 mg intraventricular nimodipine microparticles (100 mg intraventricular). Values are means±standard error of the mean (n=8 per measurement). FIG. 25 shows peak nimodipine concentrations in CSF 3 to 4 days after administration of a nimodipine microparticle formulation of the invention.

Plasma and CSF concentrations of nimodipine demonstrated sustained release of nimodipine with concentrations that were higher in CSF than in plasma for the group treated with intracisternal and intraventricular nimodipine microparticles. CSF nimodipine concentrations were high and remained in a therapeutic range for up to 15 days after SAH, whereas CSF nimodipine concentrations were low or undetectable when oral nimodipine was administered (FIGS. 24 and 25).

Histological Observations

FIG. 20 shows the sectional planes used in the dog experiments. Table 13 provides a summary of macroscopic observations of the dogs subjected to SAH and treated with placebo microparticles (placebo), oral nimodipine plus placebo microparticles (oral nimodipine), or 100 mg intraventricular nimodipine microparticles euthanized at day 28 or day 49. The animals are grouped according to whether the animals died or were euthanized at an unscheduled time (DOS) or underwent scheduled necropsy (SNC).

TABLE 13

| | | | Placebo | | | | Oral | | | | Intraventricular Nimodipine | | | |
|---|---|---|---|---|---|---|---|---|---|---|---|---|---|---|
| | Day | | Male | | Female | | Male | | Female | | Male | | Female | |
| Tissue Observation | of Euthanasia | Severity | DOS | SNC | DOS | SNC | DOS | SNC | DOS | SNC | DOS | SNC | DOS | SNC |
| # of animals | | | 0 | 4 | 0 | 4 | 0 | 4 | 0 | 4 | 0 | 4 | 1 | 3 |
| All tissues Within normal limits Brain | 28 d | | 0 | 2 | 0 | 3 | 0 | 2 | 0 | 2 | 0 | 2 | 0 | 1 |
| | 49 d | | 0 | 0 | 0 | 0 | 0 | 2 | 0 | 2 | 0 | 2 | 0 | 2 |
| discoloration, red | 28 d | mild | 0 | 2 | 0 | 0 | 0 | 0 | 0 | 0 | 0 | 0 | 2 | 0 |
| | 49 d | | 0 | 0 | 0 | 0 | 0 | 0 | 0 | 0 | 0 | 0 | 0 | 0 |
| focus/foci, red | 28 d | mild | 0 | 0 | 0 | 1 | 0 | 0 | 0 | 0 | 0 | 0 | 0 | 0 |
| | 49 d | | 0 | 0 | 0 | 0 | 0 | 0 | 0 | 0 | 0 | 0 | 0 | 0 |
| nodule | 28 d | present | 0 | 0 | 0 | 0 | 0 | 0 | 0 | 0 | 0 | 0 | 1 | 0 |
| | 49 d | | 0 | 0 | 0 | 0 | 0 | 0 | 0 | 0 | 0 | 0 | 0 | 0 |

Table 14 provides a summary of microscopic observations of the dogs subjected to SAH and treated with placebo microparticles (placebo), oral nimodipine plus placebo microparticles (oral nimodipine), or 100 mg intraventricular nimodipine microparticles and euthanized at day 28 or day 49. The animals are grouped according to whether the animals died or were euthanized at an unscheduled time (DOS) or underwent scheduled necropsy (SNC).

TABLE 14

Summary of Microscopic Observations

| | | | Placebo | | | | Oral | | | | Intraventricular Nimodipine | | | |
|---|---|---|---|---|---|---|---|---|---|---|---|---|---|---|
| | Day of | | Male | | Female | | Male | | Female | | Male | | Female | |
| Tissue Observation | Euthanasia (day 28/day 49) | Severity | DOS | SNC | DOS | SNC | DOS | SNC | DOS | SNC | DOS | SNC | DOS | SNC |
| # of animals Brain | | | 0 | 4 | 0 | 4 | 0 | 4 | 0 | 3 | 0 | 4 | 1 | 3 |
| chromatolysis, central, neuronal | 28 d | minimal | 0 | 0 | 0 | 0 | 0 | 0 | 0 | 0 | 0 | 0 | 0 | 0 |
| | 49 d | | 0 | 0 | 0 | 0 | 0 | 0 | 0 | 0 | 0 | 0 | 0 | 0 |
| degeneration | 28 d | minimal | 0 | 0 | 0 | 0 | 0 | 0 | 0 | 0 | 0 | 0 | 0 | 0 |
| | 49 d | | 0 | 0 | 0 | 0 | 0 | 0 | 0 | 1 | 0 | 0 | 0 | 1 |
| | 28 d | mild | 0 | 0 | 0 | 0 | 0 | 0 | 0 | 0 | 0 | 0 | 1 | 0 |
| | 49 d | | 0 | 0 | 0 | 0 | 0 | 0 | 0 | 0 | 0 | 0 | 0 | 0 |
| degeneration, axonal/myelin | 28 d | minimal | 0 | 0 | 0 | 0 | 0 | 0 | 0 | 0 | 0 | 0 | 0 | 0 |
| | 49 d | | 0 | 0 | 0 | 0 | 0 | 0 | 0 | 0 | 0 | 0 | 0 | 0 |
| | 28 d | mild | 0 | 0 | 0 | 0 | 0 | 0 | 0 | 0 | 0 | 0 | 0 | 1 |
| | 49 d | | 0 | 0 | 0 | 0 | 0 | 0 | 0 | 0 | 0 | 0 | 0 | 0 |
| fibroplasia | 28 d | minimal | 0 | 0 | 0 | 0 | 0 | 1 | 0 | 0 | 0 | 2 | 0 | 0 |
| | 49 d | | 0 | 0 | 0 | 0 | 0 | 0 | 0 | 0 | 0 | 1 | 0 | 0 |
| | 28 d | mild | 0 | 0 | 0 | 0 | 0 | 1 | 0 | 0 | 0 | 0 | 0 | 0 |
| | 49 d | | 0 | 0 | 0 | 0 | 0 | 1 | 0 | 0 | 0 | 0 | 0 | 0 |
| granulation tissue | 28 d | minimal | 0 | 0 | 0 | 1 | 0 | 0 | 0 | 0 | 0 | 0 | 0 | 0 |
| | 49 d | | 0 | 0 | 0 | 0 | 0 | 0 | 0 | 0 | 0 | 1 | 0 | 1 |
| | 28 d | mild | 0 | 0 | 0 | 0 | 0 | 0 | 0 | 0 | 0 | 0 | 1 | 0 |
| | 49 d | | 0 | 0 | 0 | 0 | 0 | 0 | 0 | 0 | 0 | 0 | 0 | 0 |
| hemorrhage | 28 d | minimal | 0 | 0 | 0 | 1 | 0 | 0 | 0 | 0 | 0 | 0 | 0 | 0 |
| | 49 d | | 0 | 0 | 0 | 0 | 0 | 0 | 0 | 0 | 0 | 0 | 0 | 0 |
| | 28 d | mild | 0 | 0 | 0 | 1 | 0 | 0 | 0 | 1 | 0 | 0 | 0 | 0 |
| | 49 d | | 0 | 0 | 0 | 0 | 0 | 0 | 0 | 0 | 0 | 0 | 0 | 0 |
| | 28 d | moderate | 0 | 2 | 0 | 0 | 0 | 0 | 0 | 0 | 0 | 0 | 1 | 0 |
| | 49 d | | 0 | 0 | 0 | 0 | 0 | 0 | 0 | 0 | 0 | 0 | 0 | 0 |
| infiltration, lymphoid, perivascular | 28 d | minimal | 0 | 1 | 0 | 0 | 0 | 0 | 0 | 1 | 0 | 0 | 0 | 0 |
| | 49 d | | 0 | 0 | 0 | 0 | 0 | 0 | 0 | 0 | 0 | 0 | 0 | 0 |
| inflammation, granulomous | 28 d | minimal | 0 | 3 | 0 | 2 | 0 | 1 | 0 | 0 | 0 | 1 | 0 | 0 |
| | 49 d | | 0 | 0 | 0 | 0 | 0 | 1 | 0 | 0 | 0 | 0 | 0 | 0 |
| | 28 d | mild | 0 | 1 | 0 | 0 | 0 | 1 | 0 | 1 | 0 | 0 | 1 | 0 |
| | 49 d | | 0 | 0 | 0 | 0 | 0 | 0 | 0 | 0 | 0 | 0 | 0 | 0 |
| inflammation, meningeal | 28 d | minimal | 0 | 0 | 0 | 0 | 0 | 0 | 0 | 0 | 0 | 0 | 1 | 0 |
| | 49 d | | 0 | 0 | 0 | 0 | 0 | 0 | 0 | 0 | 0 | 0 | 0 | 0 |

TABLE 14-continued

Summary of Microscopic Observations

| Tissue Observation | Day of Euthanasia (day 28/day 49) | Severity | Placebo Male DOS | Placebo Male SNC | Placebo Female DOS | Placebo Female SNC | Oral Male DOS | Oral Male SNC | Oral Female DOS | Oral Female SNC | Intraventricular Nimodipine Male DOS | Intraventricular Nimodipine Male SNC | Intraventricular Nimodipine Female DOS | Intraventricular Nimodipine Female SNC |
|---|---|---|---|---|---|---|---|---|---|---|---|---|---|---|
| inflammation, subacute/chronic | 28 d | minimal | 0 | 1 | 0 | 1 | 0 | 0 | 0 | 2 | 0 | 1 | 0 | 1 |
| | 49 d | | 0 | 0 | 0 | 0 | 0 | 2 | 0 | 1 | 0 | 2 | 0 | 1 |
| | 28 d | mild | 0 | 1 | 0 | 0 | 0 | 0 | 0 | 0 | 0 | 0 | 0 | 0 |
| | 49 d | | 0 | 0 | 0 | 0 | 0 | 0 | 0 | 0 | 0 | 0 | 0 | 0 |
| macrophages, pigmented | 28 d | minimal | 0 | 0 | 0 | 1 | 0 | 0 | 0 | 0 | 0 | 2 | 1 | 0 |
| | 49 d | | 0 | 0 | 0 | 0 | 0 | 0 | 0 | 0 | 0 | 0 | 0 | 1 |
| | 28 d | mild | 0 | 1 | 0 | 0 | 0 | 2 | 0 | 0 | 0 | 0 | 0 | 0 |
| | 49 d | | 0 | 0 | 0 | 0 | 0 | 0 | 0 | 0 | 0 | 0 | 0 | 0 |
| mineralization, focal | 28 d | minimal | 0 | 0 | 0 | 0 | 0 | 0 | 0 | 0 | 0 | 0 | 0 | 0 |
| | 49 d | | 0 | 0 | 0 | 0 | 0 | 0 | 0 | 0 | 0 | 0 | 0 | 0 |
| neovascularization | 28 d | minimal | 0 | 0 | 0 | 0 | 0 | 0 | 0 | 0 | 0 | 1 | 0 | 0 |
| | 49 d | | 0 | 0 | 0 | 0 | 0 | 0 | 0 | 0 | 0 | 0 | 0 | 0 |
| within normal limits | 28 d | | 0 | 0 | 0 | 1 | 0 | 0 | 0 | 0 | 0 | 0 | 0 | 0 |
| | 49 d | | 0 | 0 | 0 | 0 | 0 | 0 | 0 | 0 | 0 | 0 | 0 | 0 |
| Spinal Cord, Cervical | | | | | | | | | | | | | | |
| degeneration, axonal/myelin | 28 d | minimal | 0 | 0 | 0 | 0 | 0 | 0 | 0 | 0 | 0 | 0 | 0 | 1 |
| | 49 d | | 0 | 0 | 0 | 0 | 0 | 0 | 0 | 0 | 0 | 0 | 0 | 0 |
| fibroplasia | 28 d | minimal | 0 | 1 | 0 | 1 | 0 | 0 | 0 | 0 | 0 | 0 | 0 | 0 |
| | 49 d | | 0 | 0 | 0 | 0 | 0 | 0 | 0 | 0 | 0 | 0 | 0 | 0 |
| | 28 d | mild | 0 | 3 | 0 | 1 | 0 | 1 | 0 | 2 | 0 | 2 | 1 | 1 |
| | 49 d | | 0 | 0 | 0 | 0 | 0 | 1 | 0 | 0 | 0 | 0 | 0 | 1 |
| | 28 d | moderate | 0 | 0 | 0 | 1 | 0 | 1 | 0 | 0 | 0 | 0 | 0 | 0 |
| | 49 d | | 0 | 0 | 0 | 0 | 0 | 0 | 0 | 0 | 0 | 0 | 0 | 0 |
| hemorrhage | 28 d | minimal | 0 | 1 | 0 | 1 | 0 | 2 | 0 | 1 | 0 | 1 | 0 | 0 |
| | 49 d | | 0 | 0 | 0 | 0 | 0 | 0 | 0 | 0 | 0 | 0 | 0 | 0 |
| inflammation, granulomatous | 28 d | minimal | 0 | 1 | 0 | 2 | 0 | 1 | 0 | 0 | 0 | 0 | 0 | 0 |
| | 49 d | | 0 | 0 | 0 | 0 | 0 | 0 | 0 | 0 | 0 | 0 | 0 | 0 |
| | 28 d | moderate | 0 | 0 | 0 | 0 | 0 | 0 | 0 | 1 | 0 | 0 | 0 | 0 |
| | 49 d | | 0 | 0 | 0 | 0 | 0 | 0 | 0 | 0 | 0 | 0 | 0 | 0 |
| inflammation, subacute/chronic | 28 d | minimal | 0 | 2 | 0 | 1 | 0 | 1 | 0 | 1 | 0 | 2 | 0 | 1 |
| | 49 d | | 0 | 0 | 0 | 0 | 0 | 1 | 0 | 1 | 0 | 2 | 0 | 0 |
| | 28 d | mild | 0 | 2 | 0 | 1 | 0 | 1 | 0 | 0 | 0 | 0 | 0 | 0 |
| | 49 d | | 0 | 0 | 0 | 0 | 0 | 0 | 0 | 0 | 0 | 0 | 0 | 0 |
| macrophages, pigmented | 28 d | minimal | 0 | 0 | 0 | 0 | 0 | 2 | 0 | 0 | 0 | 0 | 0 | 0 |
| | 49 d | | 0 | 0 | 0 | 0 | 0 | 0 | 0 | 0 | 0 | 0 | 0 | 0 |
| within normal limits | 28 d | | 0 | 0 | 0 | 0 | 0 | 0 | 0 | 0 | 0 | 0 | 0 | 0 |
| | 49 d | | 0 | 0 | 0 | 0 | 0 | 1 | 0 | 0 | 0 | 0 | 0 | 1 |
| Spinal Cord, Lumbar | | | | | | | | | | | | | | |
| fibroplasia | 28 d | minimal | 0 | 0 | 0 | 0 | 0 | 0 | 0 | 0 | 0 | 1 | 0 | 0 |
| | 49 d | | 0 | 0 | 0 | 0 | 0 | 0 | 0 | 0 | 0 | 0 | 0 | 0 |
| hemorrhage | 28 d | minimal | 0 | 1 | 0 | 0 | 0 | 0 | 0 | 0 | 0 | 0 | 0 | 0 |
| | 49 d | | 0 | 0 | 0 | 0 | 0 | 0 | 0 | 0 | 0 | 0 | 0 | 0 |
| mineralization | 28 d | minimal | 0 | 0 | 0 | 0 | 0 | 0 | 0 | 0 | 0 | 0 | 0 | 0 |
| | 49 d | | 0 | 0 | 0 | 0 | 0 | 0 | 0 | 0 | 0 | 0 | 0 | 0 |
| within normal limits | 28 d | | 0 | 3 | 0 | 4 | 0 | 0 | 0 | 0 | 0 | 0 | 0 | 0 |
| | 49 d | | 0 | 0 | 0 | 0 | 0 | 0 | 0 | 0 | 0 | 1 | 0 | 2 |
| Spinal Cord, Thoracic | | | | | | | | | | | | | | |
| fibroplasia | 28 d | minimal | 0 | 0 | 0 | 0 | 0 | 0 | 0 | 0 | 0 | 1 | 0 | 0 |
| | 49 d | | 0 | 0 | 0 | 0 | 0 | 0 | 0 | 0 | 0 | 0 | 0 | 0 |
| hemorrhage | 28 d | minimal | 0 | 1 | 0 | 0 | 0 | 0 | 0 | 0 | 0 | 0 | 0 | 1 |
| | 49 d | | 0 | 0 | 0 | 0 | 0 | 0 | 0 | 0 | 0 | 1 | 0 | 0 |
| inflammation, granulomatous | 28 d | minimal | 0 | 0 | 0 | 2 | 0 | 0 | 0 | 0 | 0 | 0 | 0 | 0 |
| | 49 d | | 0 | 0 | 0 | 0 | 0 | 0 | 0 | 0 | 0 | 0 | 0 | 0 |
| inflammation, subacute/chronic | 28 d | minimal | 0 | 0 | 0 | 0 | 0 | 0 | 0 | 0 | 0 | 1 | 0 | 0 |
| | 49 d | | 0 | 0 | 0 | 0 | 0 | 0 | 0 | 0 | 0 | 0 | 0 | 0 |
| macrophages, pigmented | 28 d | minimal | 0 | 0 | 0 | 0 | 0 | 0 | 0 | 0 | 0 | 1 | 0 | 0 |
| | 49 d | | 0 | 0 | 0 | 0 | 0 | 0 | 0 | 0 | 0 | 0 | 0 | 0 |
| within normal limits | 28 d | | 0 | 3 | 0 | 2 | 0 | 0 | 0 | 0 | 0 | 0 | 0 | 0 |
| | 49 d | | 0 | 0 | 0 | 0 | 0 | 0 | 0 | 0 | 0 | 0 | 0 | 1 |

Example 6

Toxicity Studies of Nimodipine Microparticle Formulations

All components of the nimodipine microparticle formulations used in these studies are approved for systemic use by the United States Food and Drug Administration (FDA) and European Medicines Agency.

Nimodipine Toxicity

Although treatment of nimodipine has not been associated with increases in intracranial pressure, close monitoring is recommended in such cases or when water content of the brain tissue is elevated. Caution is required in patients with hypotension (systolic blood pressure lower than 100 mm Hg). In patients with severely impaired liver function, dosage reduction may be required and discontinuation of treatment should be considered if hypotension persists. The side effects of oral or intravenous nimodipine (Nimotop®) include decrease in blood pressure, headache and edema. A transient rise in liver enzymes may occur during intravenous administration, usually reverting back to normal upon completion of treatment. Thrombocytopenia and ileus have also been reported. (Nimotop®, package insert, Updated February 2003, Bayer A G, Germany; Nimotop®, package insert, 1996, Bayer, USA).

Adverse reactions reported from published clinical trials of nimodipine, when administered orally or intravenously, for the treatment of aneurysmal SAH sorted by the Council for International Organizations of Medical Sciences (CIOMS) Group III categories of frequency (placebo-controlled trials: N=703 nimodipine, placebo N=692, non-controlled studies: nimodipine N=2496, placebo N=692 state) included thrombocytopenia, acute hypersensitivity reactions, allergic reactions, rash, nonspecific cerebrovascular symptoms, headache, nonspecific arrhythmias, tachycardia, bradycardia, non-specific cardiovascular symptoms, hypotension, vasodilatation, nausea, ileus, mild to moderate hepatic reactions, and reversible elevation of liver enzymes. (Allen, G. S. et al., "Cerebral arterial spasm—a controlled trial of nimodipine in patients with subarachnoid hemorrhage," N. Engl. J. Med., 308: 619-624 (1983); Jan, M. et al., "Therapeutic trial of intravenous nimodipine in patients with established cerebral vasospasm after rupture of intracranial aneurysms," Neurosurgery, 23: 154-157 (1988); Mee, E. et al., "Controlled study of nimodipine in aneurysm patients treated early after subarachnoid hemorrhage," Neurosurgery, 22:484-491 (1988); Neil-Dwyer, G. et al., "Early intervention with nimodipine in subarachnoid haemorrhage," Eur. Heart J., 8 Suppl K: 41-47 (1987); Ohman, J. et al., "Effect of nimodipine on the outcome of patients after aneurysmal subarachnoid hemorrhage and surgery," J. Neurosurg. 69: 683-686 (1988); Petruk, K. C. et al., "Nimodipine treatment in poor-grade aneurysm patients. Results of a multicenter double-blind placebo-controlled trial," J. Neurosurg., 68: 505-517 (1988); Philippon, J. et al., "Prevention of vasospasm in subarachnoid haemorrhage. A controlled study with nimodipine," Acta Neurochir., 82: 110-114 (1986); Pickard, J. D. et al., "Effect of oral nimodipine on cerebral infarction and outcome after subarachnoid haemorrhage: British aneurysm nimodipine trial," BMJ 298: 636-642 (1989)).

Attacks of angina pectoris, or an increase in frequency of such attacks in patients with a history of angina pectoris have been reported, especially when starting treatment or increasing the dose. There may be an increase in frequency, duration and severity of seizures. Myocardial infarction has also been reported. A causal relationship to therapy is not certain given the underlying disease for which nimodipine is administered here but causality cannot be excluded.

Preclinical data have revealed no special risks for humans based on data from conventional studies of toxicity after a single dose and after multiple doses, genotoxicity, carcinogenicity, and male and female fertility. (Nimotop®, 2007 package insert, Bayer USA; Scriabine, A. et al., "Nimodipine. New Drugs Annual," Cardiovascular Drugs 3:197-218 (1985)).

Acute $LD_{50}$ values have been reported (Table 15). (Scriabine A et al., "Nimodipine," New Drugs Annual: Cardiovascular Drugs 3:197-218 (1985)). The higher toxicity when given intravenously compared to orally is typical for dihydropyridines that antagonize calcium channels. The higher intravenous toxicity in rabbits and dogs compared to mice and rats also is typical for this class of drugs. Tonic-clonic seizures preceded death at lethal doses. Nimodipine was administered orally for 3 months to rats by gavage at 0, 10, 30 or 100 mg/kg/day. There were no adverse effects. In dogs, nimodipine was given orally at 0, 1, 3, or 10 mg/kg/day for 13 weeks to 3 male and 3 female dogs. The highest dose decreased the rate of weight gain, reduced appetite, produced salivation and sedation, and decreased hematocrit, hemoglobin, and erythrocyte count. The heart rate was increased 1 hour after starting nimodipine but decreased significantly at the end of the 13 weeks. This was associated with a prolonged PQ interval in electrocardiograms.

TABLE 15

Acute toxicity of nimodipine
Table 15: Acute toxicity of nimodipine

| Species | Sex | Route of administration | $LD_{50}$ (mg/kg) | 95% confidence interval |
|---|---|---|---|---|
| Mice | Male | Oral | 3562 | 2746-4417 |
| Mice | Male | Intravenous | 33 | 28-38 |
| Rats | Male | Oral | 6599 | 5118-10033 |
| Rats | Male | Intravenous | 16 | 14-18 |
| Rabbits | Female | Oral | 5000 | |
| Rabbits | Female | Intravenous | 2.5 | |
| Dogs | Male and female | Oral | 1000-2000 | |
| Dogs | Male and female | Intravenous | 4 | |

Nimodipine was given to rats at 0, 50, 300, or 1800 ppm in food for 2 years. The highest dose slowed growth rate, decreased food intake and increased water intake. The only histopathological change was observed at the highest dose and was hypertrophy of the zona glomerulosa and increased weight of the adrenal glands. (Scriabine A et al., "Nimodipine," New Drugs Annual: Cardiovascular Drugs 3:197-218 (1985)).

In dogs (4 male and 4 female), nimodipine was administered at 0, 1, 2.5, and 5.25 mg/kg/day for 52 weeks. Heart rate was decreased in animals given the highest dose at the end of the study, and this was associated with a slight increase in absolute and relative heart weight. In 2 animals that received the highest doses, depression of the ST segment in electrocardiograms was observed at various times although histopathology showed no myocardial lesions. (Scriabine A et al., "Nimodipine," New Drugs Annual: Cardiovascular Drugs 3:197-218 (1985)).

While there are some long-term effects of nimodipine, it is rapidly metabolized. The current indication involves a single administration of the drug.

Poly(lactic glycolic) Acid (PLGA) Toxicity

PLGA also has no or minimal toxicity in animals.

Biological degradation of PLGA microparticles depends largely on water uptake into the particles and hydrolysis of ester linkages, the rates of which are determined by the physical and chemical characteristics of the polymer. (Anderson J M, "Perspectives on the in vivo responses of biodegradable polymers," in Hollinger J O (ed): Biomedical Applications of Synthetic Polymers. New York: CRC Press, pp 223-233 (1995); Fournier E et al., "Biocompatibility of implantable synthetic polymeric drug carriers: focus on brain biocompatibility," Biomaterials, 24:3311-3331 (2003); Gopferich A, "Mechanisms of polymer degradation and erosion," Biomaterials, 17:103-114 (1996); Shive M S et al., "Biodegradation and biocompatibility of PLA and PLGA microspheres," Adv. Drug Deliv. Rev., 28:5-24 (1997)). Cellular and enzymatic mechanisms play a smaller role. (Devereux D F, and O'Connell S M, "Biomaterials used in hernia repair, abdominal wall replacement, and the intestinal sling procedure," in Greco R S (ed): Implantation Biology. The Host Response to Biomedical Devices. Boca Raton, Fla.: CRC Press, pp 229-314 (1994); Holland S J et al., "Polymers for biodegradable medical devices. 1. The potential of polyesters as controlled macromolecular release systems," Journal of Controlled Release, 4:155-180 (1986); Lewis D H, "Controlled release of bioactive agents from lactide/glycolide polymers," in Chasin M, Langer R (eds): Biodegradable Polymers as Drug Delivery Systems. New York, N.Y.: Marcel Dekker, pp 1-41 (1990)). Degradation rates of PLGA in vivo are inversely related to chain length, and lactide to glycolide ratio. For polymers of a given molecular weight, PLGAs with a carboxyl group at the end of the polymer degrade more rapidly than their ester-terminal counterparts. The ultimate degradation products are the monomers, lactic acid and glycolic acid. (Holland S J et al., "Polymers for biodegradable medical devices. 1. The potential of polyesters as controlled macromolecular release systems. Journal of Controlled Release, 4:155-180 (1986)). Experimental evidence suggests that microparticle degradation also is hastened by phagocytosis but the degree to which phagocytosis affects the degradation depends on the dimensions of the particle and the chemistry of the polymer. (Tabata Y, and Ikada Y, "Drug delivery systems for antitumor activation of macrophages," Crit. Rev. Ther. Drug Carrier Syst., 7:121-148 (1990); Visscher G E et al., "Effect of particle size on the in vitro and in vivo degradation rates of poly(DL-lactide-co-glycolide) microcapsules," J. Biomed. Mater. Res., 22:733-746 (1988)). Particles greater than 10 μm are not readily phagocytized. (Lemperle G et al., "Migration studies and histology of injectable microspheres of different sizes in mice," Plast. Reconstr. Surg., 113:1380-1390 (2004)) Since nimodipine microparticles of the described invention range in diameter from 40 to 100 μm with a mean diameter of 70 μm, they are not likely to undergo phagocytosis.

The amounts of L-lactate, D-lactate, D,L-lactate and glycolate resulting from the degradation of typical clinical doses of microparticles are well below those that have caused toxicological effects in humans and animals.

No systemic effects attributable to PLGA microparticles have been encountered in investigative and safety studies in laboratory animals. (Fournier E et al., "Biocompatibility of implantable synthetic polymeric drug carriers: focus on brain biocompatibility," Biomaterials, 24:3311-3331 (2003)).

Depending on the mode of use, studies of PLGA polymers have indicated that they are completely biodegradable and have no demonstrable antigenic or immunogenic potential.

PLGA Toxicity in the Brain

PLGA pellets and microparticles have been implanted in the subarachnoid space and brain without reported toxicity. (Camarata P J et al., "Sustained release of nerve growth factor from biodegradable polymer microspheres," Neurosurgery, 30:313-319 (1992); Fournier E et al., "Biocompatibility of implantable synthetic polymeric drug carriers: focus on brain biocompatibility," Biomaterials, 24:3311-3331 (2003); Shive M S, and Anderson J M, "Biodegradation and biocompatibility of PLA and PLGA microspheres," Adv. Drug Deliv. Rev., 28:5-24 (1997)).

Preliminary Safety Data—PLGA Combined with Nimodipine in Rats 44 male experimentally naïve Wistar rats with jugular vein cannulas, approximately 9 weeks of age at receipt, were used to study release of nimodipine from various formulations of nimodipine PLGA microparticles of the described invention injected into the subcutaneous space. The rats were divided into separate treatment groups: one control group for treatment with a nimodipine reference solution (control group) and several test groups for treatment with exemplary nimodipine formulations (microparticle test group) according to the described invention. The nimodipine reference solution or the exemplary nimodipine microparticle formulations were administered to the treatment groups via a single subcutaneous (bolus) injection between the skin and underlying layers of tissue in the left hind limb of each animal at a dose level of approximately 20 mg/kg or 200 mg/kg. The test article was reconstituted with an injection vehicle volume of 0.15 or 0.70 ml, and the entire volume of each reconstituted vial was drawn up immediately and administered individually to each animal. Blood samples were collected from two alternating cohorts of 2 or 3 animals per cohort in the microparticle formulation-injected groups. Collection was immediately before injection and then 1, 12, and 24 hours post dose, and on days 4, 8, 11, and 15. After the last blood sample collection interval, the surviving animals were euthanized via carbon dioxide inhalation. Euthanasia was confirmed by cervical dislocation and anesthesia.

There was no overt toxicity from the microparticle formulations. A positive finding of limb function impaired, forelimb/right was recorded for one animal in each of the control and microparticle test groups within 20 minutes of injection. This finding was transient and appeared across several groups, and did not appear to be dose dependent. It seemed to be unrelated to the nimodipine or microparticles. Two animals (nimodipine reference group and a 20 mg/kg low dose animal) were found dead on days 10 and 14 and one animal died (a 200 mg/kg dose animal) during blood collection on day 8. All 3 animals were submitted to necropsy for macroscopic postmortem evaluations. There were no findings in the animal that died during blood collection. The other 2 had nonspecific pathological changes.

Figure 26:
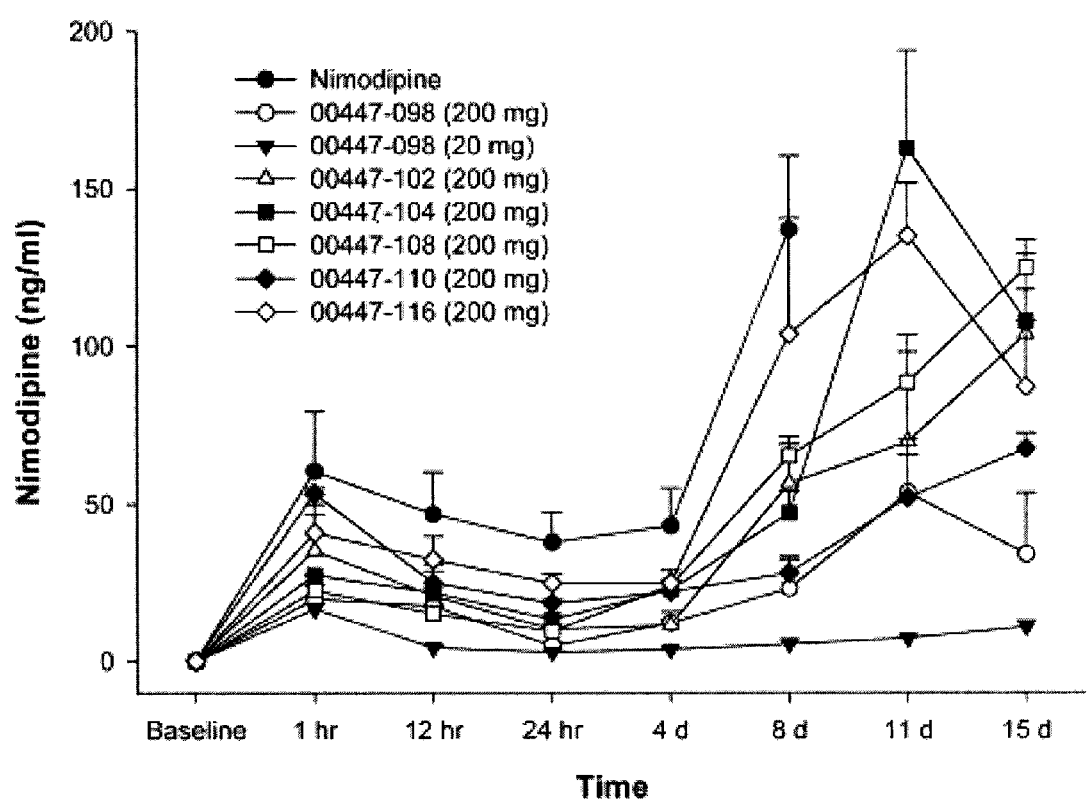
FIG. 26 shows a plot of concentration of nimodipine (ng/ml) in plasma over time in rats treated with subcutaneous injections of the nimodipine reference, 20 mg/kg low dose nimodipine microparticle formulation (#00447-098) and 200 mg/kg high dose nimodipine microparticle formulations (#00447-098, #00447-102, #00447-104, #00447-108, #00447-110, #00447-116). Values are means±standard error of the mean (n=8 per measurement).

The plasma nimodipine concentrations were analyzed over time and showed sustained release of nimodipine over time with all nimodipine microparticle formulations, as well as the nimodipine reference. FIG. 26 shows sustained release of nimodipine in the plasma (ng/ml) over time in the nimodipine reference group as well as in the 20 mg/kg low dose animal group and 200 mg/kg high dose animal group.

Hyaluronic Acid or Hyaluronate Sodium Salt

The microparticle nimodipine formulation was combined with a pharmaceutical carrier or an injection vehicle to form the flowable pharmaceutical composition of the described invention. The pharmaceutical carrier or the injection vehicle used comprises about 2.3% w/w bacterial-derived sodium hyaluronate in PBS with 0.1% polysorbate 20. The pH of the injection vehicle is 6.8-7.6 and the osmolarity is 258 mOsm/kg to 381 mOsm/kg. For intraventricular or intrathecal administration, the average molecular weight of the sodium hyaluronate is about 500 kDa and the viscosity of the injection vehicle is less than about 500 Poise. For intracisternal administration, the average molecular weight of the sodium hyaluronate is about 1,000 KDa to 2,000 KDa and the viscosity of the injection vehicle is above about 1,000 Poise. When combined with the microparticle nimodipine formulation, the viscosity of the resulting flowable pharmaceutical composition is less than about 500 Poise for intraventricular or intrathecal administration, and above about 1,000 Poise for intracisternal administration.

Example 7

Phase 1/2a Dose-Escalation Study to Assess Safety and Tolerability of Nimodipine Microparticle Formulation in Patients with Aneurysmal Subarachnoid Hemorrhage (aSAH) Undergoing Neurosurgical Clipping or Endovascular Coiling Study Objectives The primary objective of the phase I investigator-initiated study is to determine the safety and tolerability of nimodipine microparticle formulations in patients with aSAH.

Secondary objectives are as follows:

Measure plasma and cerebrospinal fluid (CSF) concentrations of nimodipine;

Assess safety and tolerability of microparticle nimodipine formulation based on:
  Hypotension (mean arterial blood pressure<60 mm Hg for 15 minutes after drug administration until 14 days later);
  Death and cause of death up to 90 days post-aSAH;
  Occurrence of adverse events of specific interest (i.e., hydrocephalus, meningitis, ventriculitis, hypotension, elevated liver enzymes [increase in alanine aminotransferase or alkaline phosphatase>2 times upper limit of normal], renal injury [increase in serum creatinine>2 times baseline]) within 28 days of study drug administration.
  Average daily change from baseline in systolic blood pressure, diastolic blood pressure, and heart rate over 14 days or until discharge.

Measure effect of microparticle nimodipine formulation on:
  Delayed cerebral infarction on computed tomography (CT) within 30 days of SAH, not present on baseline imaging and not due to catheter angiography or repair of the aneurysm, measured as number and volume of infarcts present on CT 28-42 (4-6 weeks) days after SAH that were not present on CT<24 hours after the aneurysm repair procedure;
  Delayed cerebral ischemia (DCI) in patients where other medical or surgical causes (e.g., hydrocephalus, seizure, etc.) are excluded;
  Rescue therapy defined as induced hypertension;

Measure effect of microparticle nimodipine formulation on clinical outcome 3 months (83-97 days) after aSAH, as measured by:
  the Barthel index
  modified Rankin scale (mRS)
  extended Glasgow outcome scale (GOS)
  telephone interview of cognitive status (TICS)
  Montreal cognitive assessment (MoCA).

Selection of Eligible Subjects for Phase I Study

A total of 15 patients, 3 per dose are enrolled in the study, with additional patients at the selected dose. Eligible subjects meet all of the following clinical criteria ("inclusion criteria"):
  (1) male or female aged 18 to 75 years;
  (2) World Federation of Neurological Surgeons (WFNS) Grades 2-4.
  (3) Ruptured saccular aneurysm confirmed by angiography (catheter or CTA) and treated by neurosurgical clipping or endovascular coiling.
  (4) SAH on admission CT scan is diffuse (clot present in both hemispheres) thick (>4 mm) or thin or local thick.
  (5) Able to be receive microparticle nimodipine formulation within 48 hours of aSAH.
  (6) Weight>45 kg.
  (7) Historical modified Rankin scale (mRS) of 0 or 1.
  (8) Hemodynamically stable after resuscitation (systolic blood pressure>100 mm Hg).
  (9) Informed consent from the patient or their surrogate or legal representative.

Subjects who satisfy any one of the following criteria are excluded from the study ("exclusion criteria"):
  (1) SAH due to causes other than saccular aneurysm (such as trauma or rupture of fusiform or infective aneurysm).
  (2) World Federation of Neurological Surgeons (WFNS) SAH grade 1.
  (3) Increase intracranial pressure>30 mm $H_2O$ in sedated patients greater than 4 hours during admission period.
  (4) Intraventricular or intracerebral hemorrhage, in the absence of SAH, or with only local, thin SAH.
  (6) Angiographic vasospasm prior to neurosurgical clipping procedure or endovascular coiling.
  (7) Major complication during neurosurgical clipping, such as massive intraoperative hemorrhage, brain swelling, arterial occlusion or inability to clip or coil the ruptured aneurysm.
  (8) Hemodynamically unstable prior to administration of study drug (eg. Requires >6 L colloid or crystalloid fluid resuscitation).
  (9) Cardiopulmonary resuscitation required following SAH.
  (10) Women with a positive urine pregnancy test at screening.
  (11) History within the past 6 months, and/or physical findings on admission of decompensated heart failure (New York Heart Association [NYHA] Class III and IV or heart failure requiring hospitalization).
  (12) Hospitalization for or diagnosis of acute myocardial infarction within the preceding 3 months.
  (13) Symptoms or electrocardiographic (ECG) signs of acute myocardial infarction or unstable angina pectoris on admission.
  (14) ECG evidence and/or physical findings compatible with second- or third-degree heart block, or of cardiac arrhythmia associated with hemodynamic instability.
  (15) Echocardiogram performed before treatment revealing a left ventricular ejection fraction<40%.

(16) Severe or unstable concomitant condition or disease (e.g., known significant neurologic deficit, cancer, hematologic, or coronary disease), or chronic condition (e.g., psychiatric disorder), which, in the opinion of the investigator, would affect the assessment of the safety of the nimodipine microparticle formulation.

(17) Patients who have received an investigational product or participated in another clinical trial within 28 days prior to randomization or those who have already participated in the current study.

(18) Patients taking β blockers/antagonists.

(19) Kidney and/or liver disease, as defined by plasma creatinine 2.5 mg/dl (221 μmol/l) and/or total bilirubin>3 mg/dl (51.3 μmol/l), and/or known diagnosis or clinical suspicion of liver cirrhosis.

(20) Patient already taking a calcium channel antagonist prior to SAH or known hypersensitivity to nimodipine or other dihydropyridine calcium channel antagonists or hypersensitivity to poly-D,L-lactide coglycolide or hyaluronic acid.

(21) Patients taking rifampin, cimetidine, phenyloin, carbamazepine, phenobarbital, fluoxetine, β blockers/antagonists, nephrotoxic substances, cephalosporins, haloperidol, zidovudine (AZT) or nortryptyline.

Pediatric patients are excluded because they comprise only about 1% of patients with aneurysmal SAH and there is limited knowledge about use of nimodipine in pediatric patients. (Proust F et al., "Pediatric cerebral aneurysms," J. Neurosurg., 94:733-739 (2001)). Patients in WFNS grade 5 are excluded considering the high mortality. Overall, 70% of 166 WFNS grade 4 and 5 patients died in one series. (Wilby M J et al., "Cost-effective outcome for treating poor-grade subarachnoid hemorrhage," Stroke 34:2508-2511 (2003)). Sixty percent of 83 Hunt and Hess grade 5 patients died in another series that already excluded an unspecified number of patients who were judged not eligible for treatment. Death is usually within 3 days of SAH and a median of 5 or less days after SAH. (Le R P et al., "Predicting outcome in poor-grade patients with subarachnoid hemorrhage: a retrospective review of 159 aggressively managed cases," J. Neurosurg. 85:39-49, (1996)). Inclusion of grade 5 patients would not permit collection of necessary data for this study and would impair the assessment of safety.

Patients with angiographic vasospasm on admission catheter angiography (CA) or computed tomographic angiography (CTA) are excluded to avoid confounding interpretation of study results with infarction unrelated to the second SAH. Patients with major complications during neurosurgical clipping or endovascular coiling of the ruptured aneurysm are also excluded since these may cause adverse events unrelated to the nimodipine microparticle formulations of the invention as well as infarction and other complications unrelated to the SAH or to nimodipine microparticle formulations of the invention.

Inclusion of patients with local thick, diffuse thin or diffuse thick SAH and exclusion of those with local thin or no SAH seen on admission CT scan is intended to target treatment to those at greatest risk for angiographic vasospasm and DCI.

The time limit of 48 hours has been chosen in order to maximize nimodipine concentrations prior to onset of delayed cerebral ischemia (DCI) following aneurysmal SAH. The onset of DCI generally is 3 or more days after aneurysmal SAH. (Vergouwen M D et al., "Definition of delayed cerebral ischemia after aneurysmal subarachnoid hemorrhage as an outcome event in clinical trials and observational studies: proposal of a multidisciplinary research group," Stroke 41:2391-2395 (2010)). Pharmacokinetic data in preclinical studies in dogs showed peak nimodipine concentrations in CSF 3 days after administration of a nimodipine microparticle formulation. (data shown in Example 5 above and FIG. 25.) Therefore, assuming a similar pharmacokinetic profile in humans, administration of a nimodipine microparticle formulation of the invention 48 hours after aSAH would be associated with high concentrations of nimodipine 5 days after SAH, i.e., at the time when angiographic vasospasm is beginning and before the peak day of onset of DCI. (Weir B et al., "Time course of vasospasm in man," J Neurosurg 48:173-178 (1978)).

Hemodynamic stability and absence of factors, such as cardio-pulmonary resuscitation, heart failure, recent myocardial infarction, acute myocardial infarction or cardiac injury, abnormal ECG, low ejection fraction, that may predispose to subsequent instability are required to minimize risk of hypotension. This is accomplished by excluding patients who are judged to be at increased risk of hypotension. The usual trend in blood pressure in patients with aneurysmal SAH is not well-documented although the overall incidence of hypotension is reported in several trials. (Haley E C J et al., "A randomized trial of two doses of nicardipine in aneurysmal subarachnoid hemorrhage. A report of the Cooperative Aneurysm Study," J. Neurosurg. 80:788-796 (1994); Macdonald R L et al., "Clazosentan to overcome neurological ischemia and infarction occurring after subarachnoid hemorrhage (CONSCIOUS-1): randomized, double-blind, placebo-controlled phase 2 dose-finding trial," Stroke 39:3015-3021 (2008)). Patients at risk of hypotension have also been excluded in studies where hypotension and a possible antecedent to hypotension, heart failure, are risk factors for DCI and poor outcome. For example, the Albumin in Subarachnoid Hemorrhage (ALISAH) trial funded by the National Institutes of Health excluded patients at risk for developing pulmonary complications and hypotension due to heart failure. (Suarez J I, and Martin R H, "Treatment of subarachnoid hemorrhage with human albumin: ALISAH study. rationale and design," Neurocrit. Care 13(2): 263-277 (2010)).

In this study, patients with a history in the past 6 months, and/or physical findings on admission of decompensated heart failure (NYHA Class III and IV or heart failure requiring hospitalization) are excluded. (Hunt S A et al., "ACC/AHA Guidelines for the Evaluation and Management of Chronic Heart Failure in the Adult: Executive Summary A Report of the American College of Cardiology/American Heart Association Task Force on Practice Guidelines (Committee to Revise the 1995 Guidelines for the Evaluation and Management of Heart Failure): Developed in Collaboration With the International Society for Heart and Lung Transplantation; Endorsed by the Heart Failure Society of America," Circulation 104:2996-3007 (2001)). Other exclusion criteria include hospitalization for, or diagnosis of, acute myocardial infarction within the preceding 3 months, symptoms or electrocardiographic signs indicative of acute myocardial infarction on admission, electrocardiographic evidence and/or physical findings compatible with second- or third-degree heart block, or of cardiac arrhythmia associated with hemodynamic instability and echocardiogram performed before treatment revealing a left ventricular ejection fraction≤40%. (Suarez J I, and Martin R H, "Treatment of subarachnoid hemorrhage with human albumin: ALISAH study. rationale and design," Neurocrit. Care 13(2): 263-277 (2010)).

Patients taking rifampin, cimetidine, phenyloin, carbamazepine, phenobarbital, fluoxetine, β blockers/antagoinists, nephrotoxic substances, cephalosporins, haloperidol, zidovudine (AZT) or nortryptyline, or other drugs that induce liver enzymes such as cytochrome P450 are excluded from this study in order to maximize plasma concentrations of nimodipine. Such drugs may increase the metabolism of nimodipine. While having no likely effect on CSF concentrations after intracranial delivery of the nimodipine microparticle formulation, this could reduce plasma concentrations and affect pharmacokinetic data.

Efficacy Endpoints

According to one embodiment, the primary safety endpoint of the study includes occurrence of hypotension, defined as mean arterial pressure<60 mm Hg for 15 minutes, developing after administration of nimodipine microparticles and occurring within 14 days of administration. The rate of hypotension is about 4% in cohorts of patients entered in other clinical trials. (Macdonald R L et al., "Clazosentan to overcome neurological ischemia and infarction occurring after subarachnoid hemorrhage (CONSCIOUS-1): randomized, double-blind, placebo-controlled phase 2 dose-finding trial," Stroke 39:3015-3021 (2008)).

Neurological deterioration is a secondary outcome and is defined by a decline in Glasgow Coma Scale from pre-treatment assessment by 2 points or greater that is not explained by the use of sedatives or hypnotics, lasting 2 hours, or a 2-point or more drop in NIH stroke scale (NIHSS) for 2 hours. The investigator will do a head CT scan to evaluate each episode of neurological deterioration and other tests as deemed appropriate. Neurological deterioration will be ascertained during the entire hospitalization after enrollment. Subjects are not expected to experience neurological deterioration as a result of administration of the nimodipine microparticle formulations. Other endpoints will be the incidence of various neurological complications, laboratory values, and the three-month functional outcome. The incidence of rebleeding, hydrocephalus, seizures, and delayed cerebral ischemia within 14 days of symptom onset will be determined. Angiographic vasospasm will be defined according to the investigator. Rebleeding will be defined as acute fresh SAH or intracranial hemorrhage adjacent to the treated aneurysm occurring on CT scan.

Hydrocephalus, given by ventricular dilatation, can be seen in 20-28% of SAH patients. The occurrence of hydrocephalus is related to the presence of intraventricular and subarachnoid blood and its presence increases mortality, particularly if left untreated. The increased mortality may be related to the presence of cerebral infarcts and decreased intravascular volume. Current treatment of hydrocephalus consists of insertion of an external ventricular catheter.

The secondary endpoints of the study include the following:

(1) Nimodipine concentration in plasma (4 ml whole blood every 6 hours for first 24 hours after administration of nimodipine microparticles; then 4 ml daily, from peripheral venous or arterial catheter) and CSF (5 ml daily) collected daily after injection of nimodipine microparticles for measurement of nimodipine concentrations.

(2) occurrence of death due to any cause within 30 days of SAH.

(3) Occurrence of adverse events of specific interest (i.e., hydrocephalus, meningitis, ventriculitis, hypotension, elevated liver enzymes [increase in alanine aminotransferase or alkaline phosphatase>2 times upper limit of normal], renal injury [increase in serum creatinine>2 times baseline]) within 28 days of study drug administration.

(4) Average daily change from baseline in systolic blood pressure, diastolic blood pressure, and heart rate over 14 days or until discharge. Baseline is the average of the 3 measurements performed before induction of anesthesia for aneurysm clipping or coiling.

(5) Exploratory efficacy endpoints. These are:

(a) Delayed cerebral infarction on CT within 30 days of SAH, not present on baseline imaging and not due to catheter angiography (CA) or neurosurgical clipping or endovascular coiling of the aneurysm, measured as number and volume of infarcts present on CT 28-42 (4-6 weeks) days after SAH that were not present on CT 24-48 hours after neurosurgical clipping or endovascular coiling.

(b) Delayed cerebral ischemia (DCI) in patients where other medical or surgical causes (e.g., hydrocephalus, seizure, etc.) are excluded. DCI is defined in patients in whom the neurologic scales are assessable as a decrease of at least 2 points on the modified Glasgow coma scale (GCS), or an increase of at least 2 points on the abbreviated National Institutes of Health stroke scale (NIHSS), lasting for at least 2 hours, and in patients in whom the neurologic scales are not assessable as investigator-initiated rescue therapy. A CT scan and catheter or CT angiography (CTA) should be performed whenever DCI is suspected.

(c) Rescue therapy including induced hypertension (intravenous vasopressor such as dopamine, dobutamine, phenylephrine, epinephrine, norepinephrine), superselective intraarterial infusion of vasodilator drugs (nicardipine, verapamil) or balloon angioplasty performed for DCI.

(6) Clinical outcome assessed about 12 weeks (74-104 days) after SAH, as measured by the Barthel index (Loewen S. C. et al., "Predictors of stroke outcome using objective measurement scales," Stroke, 21: 78-81 (1990);), modified Rankin scale (mRS) (Rankin, J. "Cerebral vascular accidents in patients over the age of 60. II. Prognosis," Scott Med. J. 2(5):200-215 (1957)), extended Glasgow Outcome Scale (eGOS) (Sander, A. (2002) "The Extended Glasgow Outcome Scale," The Center for Outcome Measurement in Brain Injury, accessible at the tbims.org/combi/gose website), telephone interview for cognitive status (TICS) and Montreal cognitive assessment (MoCA) (Ziad, S. et al., "The Montreal Cognitive Assessment, MoCA: a brief screening tool for mild cognitive impairment," Journal of American Geriatrics Society, 53(4): 695-699 (2005)).

(7) Hydrocephalus measured as the ventriculocranial ratio. Presence of hydrocephalus is identified as an increase of ventriculocranial ratio (VCR), where the ventricular width is measured at the level of the foramen of Monroe, over the values given in Table 16.

TABLE 16

Hydrocephalus guidelines for ventriculocranial ratio (VCR)

| Age (years) | Ratio (VCR) |
|---|---|
| <30 | >0.16 |
| <50 | >0.18 |
| <60 | >0.19 |
| <80 | >0.21 |

Trial Design

This is an open-label study. All patients will receive some dose of the exemplary nimodipine microparticle formulation. Unblinding is not necessary.

Each patient will undergo craniotomy and clipping or endovascular coiling of the ruptured aneurysm. If there are no events during the surgery that qualify as exclusion criteria, eligible patients will be treated within 48 hours of SAH with escalating doses of an exemplary nimodipine microparticle formulation, administered either as one intracisternal injection into the basal cisterns via the craniotomy site, or administered intraventricularly. Safety data will be collected until 30 days after SAH or up to at least 28 days from administration of nimodipine microparticle formulations. Cohorts of patients (n=3 per dose) will be treated with increasing doses of the nimodipine microparticulate formulation in a conventional 3+3 dose-escalation design, as presented in Table 17. (Le Tourneau et al., "Dose escalation methods in Phase I cancer clinical trials," J. Natl. Cancer Inst., 101: 708-720 (2009)) The 3+3 dose escalation design will allow estimation of maximum tolerated dose using a relatively small number of patients without the need for estimating parameters required in a continual reassessment method (CRM) of dose escalation. (Iasonos A et al., "A comprehensive comparison of the continual reassessment method to the standard 3+3 dose escalation scheme in Phase I dose-finding studies," Clin Trials 5:465-477 (2008)).

TABLE 17

Dose Escalation Schedule for Nimodipine microparticle formulation

| Cohort | N | Nimodipine Microparticle Formulation | |
|---|---|---|---|
| | | Dose | Volume |
| 1 | 3 | 200 mg | 1.54 ml |
| 2 | 3 | 400 mg | 3.08 ml |
| 3 | 3 | 600 mg | 4.62 ml |

Assessment Procedures

The primary adverse event of interest to be monitored will be hypotension. According to one embodiment, hypotension occurs when mean arterial pressure is <60 mm Hg for >15 minutes. Adverse interests will be recorded in case-report forms by a study coordinator. Additional patients will be entered at the maximum tolerated dose to a maximum of 15 patients.

Day 0 is the day of the aneurysm rupture and accompanying aSAH.

Following a screening period for eligibility criteria and selection of patients for the study, the nimodipine microparticle formulation is administered within 48 hours of aSAH during treatment of the ruptured aneurysm by neurosurgical clipping or after endovascular coiling of the aneurysm.

Daily data collection on clinical, radiological, pharmacokinetic and safety information continues for 14 days post aSAH. If patients are ready to discharged home earlier than 14 days, data collection will be limited to those components that can be obtained on outpatients. A follow-up period includes visits at 28-42 and 74-94 days post aSAH via retrospective review of the patient's medical chart.

A visits and assessment schedule is provided in Table 18. All study assessments are made by a qualified staff member including medical, nursing, or specialist technical staff. The investigator or designated physician will review laboratory reports, adverse events, and other safety data on the day of reception of this information.

The following data are entered into the clinical database:

(a) Specific unscheduled laboratory parameters (e.g., electrolytes, biochemistry, hematology, coagulation, liver function tests, arterial blood gases, microbiology cultures).

(b) Results of specific tests (e.g., electroencephalography, chest X-ray, transcranial Doppler, perfusion CT).

(c) Unscheduled vital signs assessments (i.e., SBP, DBP, heart rate, intracranial pressure [ICP]), body temperature.

(d) Dose and duration of administration for rescue medications, outcome of rescue therapy, effect on blood pressure (BP) during hemodynamic rescue therapy, presence or absence of a central venous line.

(e) Modified Glasgow coma scale (mGCS) and abbreviated NIH stroke scale (NIHSS) scores.

(f) Clinical status on arrival at hospital, baseline demographics and medications.

Additional information is provided in Table 18.

TABLE 18

Study Procedures

| | STUDY PERIOD | | |
|---|---|---|---|
| PROCEDURES | SCREENING (<48 HOURS FROM SAH) | TREATMENT (UNTIL 14 DAYS AFTER SAH) | FOLLOW-UP AT 4 WEEKS AND 12 WEEKS |
| Informed consent | X | | |
| Pregnancy test | X | | |
| Baseline demographics, height, weight, medical history, World Federation of Neurological Surgeons (WFNS) grade | X | | |
| Dose assignment | X | | |
| Electrocardiogram (ECG) | X | | |
| Concomitant medications | X | X (daily) | |
| Pharmacokinetic (PK) analysis of plasma & cerebrospinal fluid (CSF) | X | X | X (Plasma at week 4) |
| Hematology, blood gases, fraction of inspired oxygen (FiO$_2$), oxygen saturation (SpO$_2$) and biochemistry | X | X (daily) | |
| Fluid balance | X | X | |
| Perfusion computed tomography (PCT), angiogram (computed tomography angiogram (CTA), | X | X[4] (between days 7-11 and on | |

TABLE 18-continued

Study Procedures

| PROCEDURES | STUDY PERIOD | | |
|---|---|---|---|
| | SCREENING (<48 HOURS FROM SAH) | TREATMENT (UNTIL 14 DAYS AFTER SAH) | FOLLOW-UP AT 4 WEEKS AND 12 WEEKS |
| catheter angiogram) | | suspicion of DCI) | |
| Neurological worsening, rescue therapy | | X | |
| Vital signs (Blood pressure (BP), heart rate, temperature)$^B$, central venous pressure (CVP), intracranial pressure (ICP) if monitored | X | X (every 6 hours) | X |
| CT scan | X | X | X |
| Modified GCS, abbreviated NIHSS | X | X | |
| Barthel, extended GOS, mRS, TICS, MoCA | | | X |

$^A$CTA/PCT is performed 12-24 hours after neurosurgical clipping or endovascular coiling, and between days 7-11 post-SAH. CT scan and CTA/PCT or catheter angiogram is also performed for neurological worsening (up to 4 weeks post-aSAH). Angiogram is performed for clinical signs suggestive of DCI (unexplained fever, unexplained high white blood cell count, confusion, drowsiness) or suspicion of cerebral infarction (up to 4 weeks post-aSAH). If CTA or MRA are performed and results are inconclusive or poor quality, then a catheter angiogram is performed. Patients who require uninterrupted sedation or are unconscious from Day 7 post-aSAH onwards must have an angiogram 9 ± 2 days post-aSAH. If a patient dies prior to 4 weeks, the last CT scan performed (irrespective of CT findings) is retained.
$^B$Systolic BP (SBP) and diastolic BP (DBP) are measured in the supine position, using either a BP cuff (sphygmomanometer) or an arterial line. The same measuring method is used consistently for all measurements. ICP and CVP (if monitored) are measured at the same time. The admission BP is also measured. Within 30 minutes prior to the injection of microparticle nimodipine formulation, the SBP and DBP and heart rate are measured, as obtained from the anesthetic record. If hemodynamic rescue therapy is initiated at any time up to 4 weeks, then vital signs, central venous pressure (CVP), and ICP (if measured) are recorded every 6 hours in the case report form (CRF) for the duration of the rescue therapy.

The primary adverse event of interest is hypotension since this is the main known, common side effect of nimodipine. Other side effects noted in clinical trials may include increased intracranial pressure, hypersensitivity reaction, paralytic ileus, elevated liver enzymes, thrombocytopenia, cardiac rhythm disturbances, angina pectoris and myocardial infarction. There are no known, common side effects related to systemic administration of the other components of the nimodipine microparticle formulations. Injection of HA into joints is associated with pain, erythema and edema. HA is injected into the eye to prevent intraocular hypotension, which does not mean that it causes systemic hypotension. Intracranial exposure theoretically could lead to hydrocephalus, meningitis and ventriculitis so these will be looked for as well. There is some systemic exposure to nimodipine after subarachnoid or intraventricular administration of the nimodipine microparticle formulation but the plasma concentrations should be <30-40 ng/ml in order to avoid hypotension. The investigator will report all other adverse events (AEs). AEs of specific interest (i.e., hydrocephalus, meningitis, ventriculitis, hypotension, elevated liver enzymes, renal failure) within 28 days of study drug administration will be collected. (Laursen J et al., "Nimodipine treatment of subarachnoid hemorrhage," Clinical Neurology & Neurosurgery 90:329-337 (1988)).

Management includes avoidance of hypotension, hypoxia and other factors that adversely affect cerebral blood flow, maintaining adequate hematocrit, normovolemia, controlling increased intracranial pressure (ICP) with intravenous boluses of mannitol, 20%, 0.25 g/kg, maintenance of normothermia, appropriate use of antibiotics, mechanical and pharmacological prophylaxis for venous thromboembolism, maintenance of ICP below 20 mm Hg and cerebral perfusion pressure between 50 and 70 mm Hg, institution of early enteral feeding if possible, no routine anti-seizure prophylaxis, no corticosteroids and no infusion of long-acting sedatives unless required to reduce increased ICP and maintain cerebral perfusion pressure. Other management includes not administering drugs that induce liver enzymes such as cytochrome P450, as well as other drugs (rifampin, cimetidine, phenyloin, carbamazepine, phenobarbital, fluoxetine, β blockers/antagonists, nephrotoxic substances, cephalosporins, haloperidol, zidovudine (AZT) or nortryptyline). If the investigator believes anti-seizure prophylaxis is indicated, intravenous or oral levetiracetam is administered because it does not induce the cytochrome P450 system and has no known drug-drug interactions.

Concomitant medications, including but not limited to routine anti-seizure prophylaxis and corticosteroid prophylaxis, are not recommended. Concomitant medications including nimodipine, nicardipine, or other dihydropyridines by any method of administration, intravenous administration of magnesium for the prevention of angiographic vasospasm and/or DCI, thrombolytics and antifibrinolytics, e.g. tranexamic acid, and other investigational drugs are forbidden.

Concomitant oral or intravenous administration of nimodipine is not allowed to avoid confounding of plasma nimodipine concentrations. If angiographic vasospasm and/or DCI are diagnosed during the study, the site can initiate its standard treatment for angiographic vasospasm and/or DCI, including hemodynamic therapy, intra-arterial vasodilators, and/or endovascular balloon dilatation.

Example 8

Pharmacodynamics and Pharmacokinetics in Human Patients

The plasma and cerebrospinal (CSF) concentrations of nimodipine will be measured for pharmacokinetic (PK) and pharmacodynamic (PD) analysis.

Plasma for measuring plasma nimodipine concentration will be collected every 6 hours for 24 hours after administration, then daily after injection for 14 days or until discharge from hospital, and then at 18-20 days, and at week 4 follow-up. Plasma will be collected at the follow-up visit at week 6. About 4 mL of blood will be collected in tubes containing K$_2$EDTA, via either direct venipuncture or a catheter placed in an antecubital vein in the arm contra-lateral to the study drug infusion. CSF will be obtained for measurement of nimodipine concentration daily in patients with a ventricular catheter until the catheter is removed or until 14 days.

The concentration of nimodipine in plasma will be determined using a validated liquid chromatographic (LC-MS/MS) assay. The analytical range for nimodipine is from 0.200 ng/mL (lower limit of quantitation) to 200 ng/mL (upper limit of quantitation) for plasma. The concentration of nimodipine in CSF will be determined using a validated liquid chromatographic (LC-MS/MS) assay. The analytical range for nimodipine is from 5.00 ng/mL (lower limit of quantitation) to 5,000 ng/mL (upper limit of quantitation). Concentrations will be calculated by interpolation from a calibration curve. Quality control samples will be analyzed throughout the study; their measured concentrations will be used to determine between-run and overall precision and accuracy of the analysis.

Pharmacodynamic evaluations will use the pharmacokinetic data to evaluate the relationships between exposure and measures of safety and/or efficacy including effects of nimodipine exposure on blood pressure (the primary safety endpoint), other serious adverse events, other secondary endpoints, probability of occurrence of adverse events of specific interest (i.e., hydrocephalus, meningitis, ventriculitis, hypotension, elevated liver enzymes [increase in alanine aminotransferase or alkaline phosphatase>2 times upper limit of normal], and renal injury [increase in serum creatinine>2 times baseline]).

Exposure will be determined based on the following parameters: nimodipine average concentration ($C_{av}$), area under the curve from study drug administration to Day 14 ($AUC_{end}$), area under the curve from study drug administration to infinity ($AUC_{inf}$) over the complete treatment duration, and $C_{av}$ and AUC over 24 hours on each treatment day, as appropriate, depending on evaluations available, and conducted based on plasma and CSF values.

The pharmacokinetic analysis use mixed effects population PK modeling using commercially available software.

PK evaluations include, but are not necessarily be limited to, $C_{max}$, $T_{max}$, AUC from study drug administration to day 14 ($AUC_{end}$) and until last measurement ($AUC_{inf}$), apparent total body clearance of drug from plasma, half life and mean residence time in plasma and CSF where appropriate. The models used employ four basic components:

(1) The structural PK model component, which predicts the plasma concentration of nimodipine as a function of time, or the structural PK/PD model component, which predicts the clinical response as a function of exposure to nimodipine, and baseline characteristics. Categorical efficacy and safety endpoints (present or absent) follow a binomial distribution and will be analyzed by means of logistic regression. Continuous safety endpoints (BP), which follow normal distribution will be analyzed using the appropriate linear, log linear, or Fill functions of nimodipine concentrations and covariates. The modeling analysis will explore the influence of covariates on the PK and PK/PD relationships. These will be determined by exploratory analysis of the entire study dataset.

(2) The covariate model component, which describes the influence of fixed effects (demographic characteristics, concomitant medications on PK or PK/PD model population parameters.

(3) The between-subject variance component, which describes the inter-individual variation in PK or PK/PD parameters (after correcting for fixed effects).

(4) The residual error model component, which describes the underlying distribution of the error in the measured PK or PK/PD variables.

Analysis is done on patients in each dose group.

Example 9

Pilot Clinical Study

In an initial pilot clinical study, ten patients with World Federation of Neurological Surgeons (WFNS) grades 2-4 and Fisher grade 3 or 4 (diffuse thick SAH) underwent craniotomy and clipping of ruptured aneurysms. The patients were treated in 4 cohorts: (1) administration of nimodipine microparticle formulation 40 mg (n=1) into the basal cisterns at the time of surgery, and within 48 hours of SAH ("40 mg IC"); (2) administration of nimodipine microparticle formulation 100 mg (n=5) into the basal cisterns at the time of surgery, and within 48 hours of SAH ("100 mg IC"); (3) administration of nimodipine microparticle formulation 100 mg (n=3) into the cerebral ventricle at the time of surgery, and within 48 hours of SAH ("100 mg IVC"); and (4) administration of nimodipine microparticle formulation 200 mg (n=1) into a cerebral ventricle at the time of surgery, and within 48 hours of SAH ("200 mg IVC"). All patients underwent baseline and follow-up angiography as well as pharmacokinetic studies of plasma and CSF. Plasma for measuring plasma nimodipine concentration were collected every 6 hours for 24 hours after administration and then daily after injection for 14 days. About 4 mL of blood was collected in tubes containing K$_2$EDTA, via either direct venipuncture or a catheter placed in an antecubital vein in the arm contra-lateral to the study drug infusion. CSF was obtained for measurement of nimodipine concentration daily in patients with a ventricular catheter until 14 days. Some patients received 1 mg/kg intravenous (IV) nimodipine for the first day before administration of nimodipine microparticle formulation according to the schedule in Table 19.

TABLE 19

Schedule of Administration in Pilot Clinical Study

| Patient # | Pre-treatment: IV nimodipine | Dose of Nimodipine Microparticle Formulation | Route of Administration |
|---|---|---|---|
| Patient 1 | Day 0 only | 40 mg | Intracisternal (IC) |
| Patient 2 | Day 0 only | 100 mg | Intracisternal (IC) |
| Patient 3 | NO | 100 mg | Intracisternal (IC) |
| Patient 4 | NO | 100 mg | Intracisternal (IC) |
| Patient 5 | NO | 100 mg | Intracisternal (IC) |
| Patient 6 | NO | 100 mg | Intraventricular (IVC) |
| Patient 7 | Day 0; Rescue Therapy (Day 5, 7) | 100 mg | Intraventricular (IVC) |
| Patient 8 | Day 0; Rescue Therapy (Day 5, 6, 7) | 100 mg | Intraventricular (IVC) |
| Patient 9 | Day 0 and Day 1 | 100 mg | Intracisternal (IC) |
| Patient 10 | Day 0 and Day 1 | 200 mg | Intraventricular (IVC) |

Results

To date, 10 patients have received therapy with a nimodipine microparticle formulation on protocol. Patient 1 who received 40 mg of the nimodipine microparticle formulation had no angiographic vasospasm at the site of delivery but did develop asymptomatic angiographic vasospasm at remote sites. Patients 2-9 were treated with 100 mg of the nimodipine microparticle formulation either intraventricularly or intracisternally. Patient 10 received 200 mg nimodipine microparticle formulation intraventricularly. None of the 5 patients treated with 100 mg nimodipine microparticle formulation intracisternally developed angiographic vasospasm, DCI or delayed infarctions. Both patients treated with 100 mg nimodipine microparticle formulation intraventricularly developed some angiographic vasospasm and DCI but neither developed cerebral infarctions. The patient treated with 200 mg nimodipine microparticle formulation intraventricularly did not develop angiographic vasospasm, DCI or infarction. There were no side effects such as hypotension, unexpected intracranial complications, delayed hydrocephalus, or seizures over the three groups. All patients have been classified as good recovery on the Glasgow outcome scale 30 days after SAH. By using historical controls from a clinical trial database, and comparing patients like those studied so far with nimodipine microparticle formulation, the predicted outcome would be that 53% of these patients would be dead, in a vegetative state or severely disabled and 47% would be good recovery or moderate disability. The chance of 9 random patients being in the 47% better outcome group would be about 5%. Thus, the calculations based on historical data suggest that the nimodipine microparticle formulation is effective.

Table 20 provides the plasma concentrations of nimodipine (ng/ml) of Patients 1-9. Data from day(s) on which a patient received IV nimodipine and from patient 10 are not shown.

to the schedule in Table 20. Plasma nimodipine concentrations in patients receiving 100 mg were about two times higher than the patient receiving 40 mg. Plasma nimodipine concentrations in patients receiving 100 mg were less than 5 ng/ml for 14 days with the highest concentrations occurring 2 to 4 days after administration irrespective of the route of administration. The average plasma concentration achieved with the 100 mg dose is 6 ng/ml to 7 ng/ml, which is below 30-40 ng/ml, the level known to cause hypotension.

CSF nimodipine concentrations for these 9 patients have been below the limit of quantification (<5 ng/ml) because ventricular CSF is sampled, which is upstream of the site of administration of the nimodipine microparticle formulation.

EQUIVALENTS

While the present invention has been described with reference to the specific embodiments thereof it should be understood by those skilled in the art that various changes may be made and equivalents may be substituted without departing from the true spirit and scope of the invention. In addition, many modifications may be made to adopt a particular situation, material, composition of matter, process, process step or steps, to the objective spirit and scope of the present invention. All such modifications are intended to be within the scope of the claims appended hereto.

What is claimed is:

1. A method for treating a delayed complication of a brain injury that deposits blood in a subarachnoid space of the brain, wherein the brain injury is mediated by decreased cerebral perfusion, comprising:
   a) providing a flowable particulate composition comprising:
      (i) a microparticle suspension comprising a plurality of particles of a uniform distribution of microparticle size, and a therapeutic amount of at least one therapeutic agent, wherein each microparticle comprises a matrix, and wherein the at least one therapeutic agent is a calcium channel antagonist; and

TABLE 20

Plasma concentration of nimodipine (ng/ml) in Patient 1-9

| Patient #/Dose/Route | Days after Administration | | | | | | | | | | | | | | |
|---|---|---|---|---|---|---|---|---|---|---|---|---|---|---|---|
| | 0 | 1 | 2 | 3 | 4 | 5 | 6 | 7 | 8 | 9 | 10 | 11 | 12 | 13 | 14 |
| Patient 1 40 mg Intracisternal (IC) | * | * | 6.0 | 3.0 | 2.0 | 1.5 | 1.4 | 2.1 | 3.0 | 1.0 | 0.6 | 0.5 | 0.4 | 0.4 | 0.4 |
| Patient 2 100 mg IC | * | * | 4.8 | 2.7 | 3.1 | 2.9 | 3.0 | 2.7 | 3.4 | 2.5 | 3.4 | 2.8 | 2.2 | 2.1 | |
| Patient 3 100 mg IC | 7.3 | 9.6 | 7.3 | 8.2 | 7.4 | 4.2 | 5.4 | 6.0 | 3.0 | 3.9 | 4.4 | 4.0 | 3.0 | 3.0 | 2.7 |
| Patient 4 100 mg IC | 0.4 | 3.6 | 5.1 | 5.5 | 5.6 | 5.6 | 4.3 | 3.5 | 3.5 | 2.7 | 2.9 | 3.3 | 3.3 | 3.2 | 2.4 |
| Patient 5 100 mg IC | 6.5 | 4.5 | 2.7 | 1.9 | 2.0 | 1.9 | 2.1 | 2.3 | 1.8 | 2.3 | 2.2 | 2.2 | 2.4 | 2.2 | 2.6 |
| Patient 6 100 mg Intraventricular (IVC) | 0.9 | 4.6 | 5.6 | 4.8 | 6.5 | 5.5 | 4.4 | 2.8 | 3.1 | 2.5 | 2.4 | 2.4 | 2.3 | * | |
| Patient 7 100 mg IVC | * | 2.4 | * | * | * | 8.5 | 5.8 | 3.8 | 3.7 | 4.4 | 3.6 | 2.9 | 2.1 | 2.5 | |
| Patient 8 100 mg IVC | 3.2 | 3.6 | 6.3 | 7.0 | 10.3 | * | * | * | 3.9 | | | | | | |
| Patient 9 100 mg IC | * | * | 3.1 | 2.6 | 2.1 | 2.9 | 3.2 | 2.4 | 2.1 | | | | | | |

* Patient treated with oral or IV/intra-arterial nimodipine; data excluded.

Figure 27:
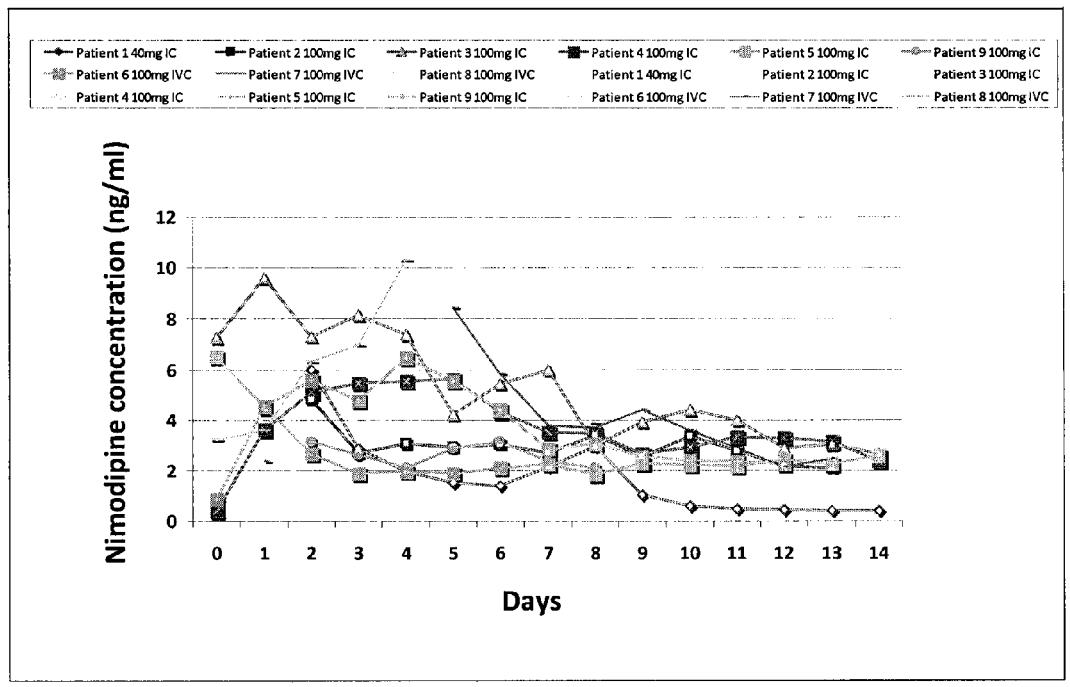
FIG. 27 shows a plot of the concentration of nimodipine (ng/ml) in plasma in 3 groups of human patients: 1 patient treated intracisternally (IC) with 40 mg nimodipine microparticle formulation (Patient 1: 40 mg IC); 5 patients treated intracisternally (IC) with 100 mg nimodipine microparticle formulation (Avg. 100 mg IC); and 3 patients treated intraventricularly (IVC) with 100 mg nimodipine microparticle formulation (Avg. 100 mg IVC). (Values are means±standard error of the mean [n=3-4 per measurement]).

FIG. 27 shows a plot of the plasma concentration of nimodipine (ng/ml) from Patients 1 to 9 treated with the nimodipine microparticle formulation over time according (ii) a pharmaceutical carrier comprising an agent that affects viscosity of the suspension, the pharmaceutical composition being characterized by:
  A) dispersal of the at least one therapeutic agent throughout each particle;
  B) a drug load of at least 40% (wt/wt) of the at least one therapeutic agent;
  C) as a dispersion, its fluidity around at least one cerebral artery in the subarachnoid space;
  D) release characteristics as follows:
    (1) gradual release of the therapeutic agent from the composition over an extended period of time such that release of about 50%-100% of the therapeutic agent is within 6 days to 14 days;
    (2) upon release, the concentration of the therapeutic agent in plasma (PLASMA-$C_{av}$) is less than about 15 ng/mL; and
    (3) upon release, the concentration of the therapeutic agent in cerebrospinal fluid (CSF) (CSF-$C_{av}$) is greater than 0 ng/mL to about 2000 ng/mL, and
  E) a local therapeutic effect; and
b) administering the flowable particulate composition locally, via an injection apparatus, either
  intracisternally into the subarachnoid space in a cistern;
  intraventricularly; or
  intrathecally into the spinal subarachnoid space;
so that the microparticulate suspension releases the at least one therapeutic agent in the subarachnoid space to contact the at least one cerebral artery in the subarachnoid space, without entering systemic circulation in an amount to cause unwanted side effects, wherein the therapeutic amount is effective to improve perfusion and to treat the delayed complication comprising a delayed cerebral ischemia (DCI) comprising an angiographic vasospasm, formation of a plurality of microthromboemboli, a cortical spreading ischemia, or a combination thereof.

2. The method according to claim 1, wherein the cerebral artery is an anterior cerebral artery, a middle cerebral artery, an internal carotid artery, a basilar cerebral artery, a vertebral cerebral artery, or a combination thereof.

3. The method according to claim 1, wherein each microparticle is of a particle size from about 40 mm to about 100 mm.

4. The method according to claim 3, wherein the mean size distribution is about 70 mm.

5. The method according to claim 1, wherein each microparticle is loaded with at least 65% (wt/wt) of the at least one therapeutic agent.

6. The method according to claim 1, wherein the calcium channel antagonist is selected from the group consisting of an L-type voltage dependent calcium channel inhibitor, an R-type voltage dependent calcium channel inhibitor, an N-type voltage dependent calcium channel inhibitor, a P/Q-type voltage dependent calcium channel inhibitor, a T-type voltage dependent calcium channel inhibitor, or a combination thereof.

7. The method according to claim 6, wherein the L-type voltage dependent calcium channel inhibitor is a dihydropyridine, selected from the group consisting of amlodipine, aranidipine, azelnidipine, bamidipine, benidipine, cinaldipine, efonidipine, felodipine, isradipine, lacidipine, lemildipine, lercanidipine, nicardipine, nifedipine, nilvadipine, nimodipine, nisoldipine, nitrendipine, manidipine, pranidipine, or a combination thereof.

8. The method according to claim 7, wherein the dihydropyridine is nimodipine.

9. The method according to claim 1, wherein the agent that affects viscosity of the suspension comprises between 0% to 5% by weight hyaluronic acid or a derivative thereof, wherein the hyaluronic acid has an average molecular weight of about 500 kDa.

10. The method according to claim 1, wherein the injection apparatus is a needle, a cannula, a catheter, or a combination thereof.

11. The method according to claim 1, wherein the viscosity of the suspension at 20° C., when administered intracisternally, is from about 100 cP to about 1,000 cp.

12. The method according to claim 1, wherein the viscosity of the suspension at 20° C., when administered intraventricularly, is from about 0.5 cP to about 50 cp.

13. The method according to claim 1, wherein the viscosity of the suspension at 20° C., when administered intrathecally into the spinal subarachnoid space, is from about 0.5 cP to about 50 cp.

14. The method according to claim 1, wherein maximum tolerated dose of the therapeutic agent when administered intracisternally is from 40 mg to about 1,000 mg.

15. The method according to claim 1, wherein maximum tolerated dose of the therapeutic agent when administered intraventricularly is from 40 mg to about 1,000 mg.

16. The method according to claim 1, wherein maximum tolerated dose of the therapeutic agent when administered intrathecally is from 40 mg to about 1,000 mg.

17. The method according to claim 1, wherein the the flowable particulate composition is administered intraventricularly in a lateral ventricle, a third ventricle, a fourth ventricle, or a combination thereof.

18. The method according to claim 1, wherein the cerebral cistern is a carotid cistern, a chiasmatic cistern, a Sylvian cistern, an interhemispheric cistern, an ambient cistern, a crural cistern, an interpeduncular cistern, a prepontine cistern, a lateral medullary cistern, a cisterna magna, or a combination thereof.

19. The method according to claim 1, wherein the particulate formulation comprises a femtoparticle, a picoparticle, a microparticle, or a nanoparticle.

20. The method according to claim 1, wherein the matrix comprises a biodegradable polymer.

21. The method according to claim 20, wherein the biodegradable polymer is a poly(lactide-co-glycolide) (PLGA) polymer, wherein the lactide to glycolide ratio is 65:35 or 50:50.

22. The method according to claim 1, wherein the pharmaceutically acceptable carrier comprises a matrix.

23. The method according to claim 1, wherein the pharmaceutically acceptable carrier comprises nanoparticles.

24. The method according to claim 23, wherein the therapeutic agent is dispersed throughout the nanoparticles, adsorbed into the nanoparticles, in a core of the nanoparticles surrounded by a coating, or a combination thereof.

25. The method according to claim 1, wherein the pharmaceutically acceptable carrier is a slow release carrier.

26. The method according to claim 1, wherein the pharmaceutically acceptable carrier is a localized release carrier.

27. The method according to claim 1, wherein the pharmaceutically acceptable carrier is a depot release carrier.

28. The method according to claim 1, wherein the pharmaceutically acceptable carrier is a delayed release carrier.

29. The method according to claim 1, wherein the pharmaceutically acceptable carrier is a long-term release carrier.

30. The method according to claim 1, wherein the pharmaceutically acceptable carrier is a biphasic release carrier.

31. The method according to claim 1, wherein the pharmaceutically acceptable carrier is an extended release carrier.

32. The method according to claim 1, wherein the concentration of the therapeutic agent in plasma (PLASMA-Cav) is from 0.200 ng/ml/day to 30 mg/ml/day for at least 4 days after administration.

33. The method according to claim 1, wherein the concentration of the therapeutic agent in plasma (PLASMA-Cav) is less than 5 ng/ml/day for at least 14 days after administration.

34. The method according to claim 1, wherein the concentration of the therapeutic agent in cerebrospinal fluid (CSF) (CSF-Cav) is from 5 ng/ml/day to 30 mg/ml/day for at least 14 days after administration.

35. The method according to claim 1, wherein the therapeutic amount of the therapeutic agent is effective to decrease angiographic diameter of the cerebral artery at risk of interruption such that percent change in angiographic diameter of at least one cerebral artery is less than 50% compared to baseline.

36. The method according to claim 1, wherein the therapeutic amount of the therapeutic agent is effective to decrease occurrence of delayed cerebral ischemia (DCI) within 14 days of symptom onset of subarachnoid hemorrhage (SAH).

37. The method according to claim 1, wherein the therapeutic amount of the therapeutic agent is effective to decrease occurrence of delayed cerebral infarction on CT within 30 days of symptom onset of subarachnoid hemorrhage (SAH).

38. The method according to claim 1, wherein the therapeutic amount of the therapeutic agent is effective to decrease occurrence of delayed cerebral ischemia.

39. The method according to claim 38, wherein occurrence of delayed cerebral ischemia is assessable as a decrease of at least 2 points on the modified glasgow coma score or an increase of at least 2 points on the abbreviated National Institutes of Health Stroke Scale lasting for at least 2 hours.

40. The method according to claim 1, wherein the therapeutic amount of the therapeutic agent is effective to reduce need for rescue therapy.

* * * * *